(12) United States Patent
De Maagd et al.

(10) Patent No.: US 11,034,971 B2
(45) Date of Patent: Jun. 15, 2021

(54) INHIBITION OF BOLTING AND FLOWERING OF A BETA VULGARIS PLANT

(71) Applicant: KWS SAAT SE & Co. KGaA, Einbeck (DE)

(72) Inventors: Rudolf Aart De Maagd, Wageningen (NL); Jeroen Van Arkel, Renkum (NL); Gerrit Cornelis Angenent, Wageningen (NL); David Wurbs, Einbeck (DE); Josef Kraus, Einbeck (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 121 days.

(21) Appl. No.: 15/771,873

(22) PCT Filed: Oct. 28, 2016

(86) PCT No.: PCT/EP2016/076090
§ 371 (c)(1),
(2) Date: Apr. 27, 2018

(87) PCT Pub. No.: WO2017/072304
PCT Pub. Date: May 4, 2017

(65) Prior Publication Data
US 2019/0127750 A1    May 2, 2019

(30) Foreign Application Priority Data
Oct. 30, 2015    (EP) .................................... 15003108

(51) Int. Cl.
| C12N 15/82 | (2006.01) |
| C07K 14/415 | (2006.01) |
| A01H 5/04 | (2018.01) |
| A01H 1/00 | (2006.01) |
| A01H 6/02 | (2018.01) |

(52) U.S. Cl.
CPC ....... *C12N 15/8265* (2013.01); *A01H 1/1215* (2021.01); *A01H 5/04* (2013.01); *A01H 6/024* (2018.05); *C07K 14/415* (2013.01); *C12N 15/827* (2013.01); *C12N 15/8222* (2013.01); *C12N 15/8267* (2013.01)

(58) Field of Classification Search
None
See application file for complete search history.

(56) References Cited

U.S. PATENT DOCUMENTS 9,222,101 B2    12/2015    Tojo et al.

FOREIGN PATENT DOCUMENTS

| WO | 2007122086 | 11/2007 |
| WO | 2010025888 | 3/2010 |
| WO | 2011032537 | 3/2011 |

OTHER PUBLICATIONS

Mandel et al (2005, NCBI Accession No. Z16421).*
Abou-Elwafa et al (2012, "Genetic Identification of a Novel Bolting Locus in blue Which Promotes Annuality Independently of the Bolting Gene B", Molecular Breeding 29:989-998).*
Bowie et al, (1990, "Deciphering the Message in Protein Sequences: Tolerance to Amino Acid Substitutions", Science 247:1306-1310).*
McConnell et al, (2001, "Radial Patterning of *Arabidopsis* Shoots By Class III HD-ZIP and KANADI Genes", Nature 411 (6838)709-713).*
Abou-Elwafa et al (2012, "Genetic Identification of a Novel Bolting Locus in blue Which Promotes Annuality Independently of the Bolting Gene B", Molecular Breeding 29:989-998) (Year: 2012).*
Ferrandiz, C. et al., "Redundant regulation of meristem identity and plant architecture by Fruitfull, APETALA1 and Cauliflower", Development, The Company of Biologists Ltd, GB, Feb. 1, 2000, vol. 127, No. 4, pp. 725-734.
Database UniProt [online]; Oct. 14, 2015; "SubName: Full=Uncharacterized protein {ECO:0000313 EMBL: KMT08699.1};", retrieved from EBI accession No. UNIPROT:A0A0J8C8W8.
Database UniProt [online]; Sep. 2, 2008; "SubName: Full=APETALA1-1 {ECO:0000313 EMBL:ACE75943.2};", XP002753817, retrieved from EBI accession No. UNIPROT:B3VA96.
Database UniProt [online]; Oct. 14, 2015; "SubName: Full=Uncharacterized protein {ECO:0000313 EMBL:KMT10844.1}", retrived from EBI accession No. UNIPROT:A0A0J8CFD5.
Database UniProt [online]; Sep. 2, 2008; "SubName: Full=Fruitfull {ECO:0000313 EMBL:ACE75945.2};", retrieved from EBI accession No. UNIPROT:B3VA98.
Database EMBL [online]; Jun. 19, 2008; "Spinacia oleracea APETALA1-1 (AP1-1) mRNA, complete cds.", retrieved from EBI accession No. EM_STD:EU726484.
International Search report dated Feb. 2, 2017 in connection with PCT/EP2016/076090.
Written Opinion dated Feb. 2, 2017 in connection with PCT/EP2016/076090.
Database EMBL [online]; Jun. 19, 2008; "Spinacia oleracea Fruitfull (Ful) mRNA, complete cds.", retrieved from EBI accession No. EM_STD:EU726486.

* cited by examiner

*Primary Examiner* — Lee A Visone
(74) *Attorney, Agent, or Firm* — Troutman Pepper Hamilton Sanders LLP

(57) ABSTRACT

The present invention provides means for inhibiting the bolting and flowering of a *Beta vulgaris* plant, including an isolated nucleic acid, which can be used to produce a transgenic *Beta vulgaris* plant, where bolting and flowering is inhibited after vernalization. Furthermore, the invention discloses vectors, transgenic and non-transgenic, non-bolting plants and parts thereof, and methods for producing such plants.

3 Claims, 7 Drawing Sheets

Specification includes a Sequence Listing.

BvAp1
(SEQ ID NO: 5)   1 mgrgrvelkrienkinrqvtfskrrsglivkkaheisvlcdaevallifsh      50
                   |||||||::||||||||||||||||:|||||||||||||||||:||:||||
AtAp1
(SEQ ID NO: 41)  1 mgrgrvqlkrienkinrqvtfskrraglikkaheisvlcdaevalvvfsh      50

51 rgklfeyssdssmekileryerysyaerrlasndpdsqvnwtfdfaklka     100
                   :|||||||:||:||||||||||||||||||:|:::|:|||||:||:|||
                51 kgklfeystdscmekileryerysyaerqliapesdvntnwsmeynrlka     100

101 kiellqrnhrhylggeldslnmkelqsleqqldtalknvsrknqlmhes      150
                   |:|||||:|:|||||||:|:|:|||:|||||||||||||:|:|:||:||
               101 kiellerngrhylgedlqamspkelqnleqqldtalkhirtkknqlmyes     150

151 iselqkkeramqehnnilskkilkergknleqvqgmqwqnqhqhqqpp       200
                   .|||.||.     ::||.  |.|.|||..:|||....:|.   |::.||
               151 lnelqkkekalgeqnsmlskqlkerekil-raggeqwdqgnq-ghnmppp     198

201 pppqmhqvppdasnfmlp-ppipslntgg-yqggfggevrrndidltlep     248
                   .|||.|:      ::::||.  ...:|:|| || |||:||||||:||:|||||
               199 lppqqhqi---qhpymlshqpspflnmgglyqeddpmamrrndleltlep     245

249 lyschmgcftt*                                          260
                   ::|:|::|||..
               246 vyncnlgcfaa*                                          257

Figure 6

```
BvFUL
(SEQ ID NO: 6)    1  mgrgrvqlkrienkinrqvtfskrrigllkkaheisilcdadvaliifst   50
                     ||||||||||||||||||||||||||||||||||||||||*||:||:||::
AtFUL
(SEQ ID NO: 42)   1  mgrgrvqlkrienkinrqvtfskrrsgllkkaheisvlcdaevalivfss   50

51  kgklfeyasdtcmerilleryerhsyaerqltapdgshvsltlehaklka  100
                     |||||||||:|:||||||||||||*:|::|::.:.:||||||||||||
                 51  kgklfeystdscmerilleryerydrylysdkqlvgrdvsqsenwvlehaklka  100

101  rldilqknqrhymgeeldtlslkelqnlehqidsalkhirskknqlmhes  150
                     |:*:|||||||::|||:*:||||||||||:|||:|||*:||||*:|||
                101  rvevleknkrnfmgedldslkelqslehqldaaiksirsrknqamfes  150

151  isqlqrkdkalkehnmllskkvkerekvlaqqaeldqqnhdnnssgfvms  200
                     ||*:|||||*:||||:*:||:::|||::*:|:||::*:*::::.*.:.:|
                151  isalqkkdkalqdhnnsllkkikerekktgqqe---gglvqcsnsssvllp  198

201  qalpsln------tggtssaavedeatqppnlnsnsaqipswmlqhiqe  243
                     |:::*.::     ::|||::*||::|:::*
                199  qycvtssrdgfvervggengga---ssltepnsl------lpawmlrptt  240

INHIBITION OF BOLTING AND FLOWERING OF A BETA VULGARIS PLANT

CROSS-REFERENCE TO RELATED PATENT APPLICATIONS

This application is a National Stage of International Application No. PCT/EP2016/076090, filed Oct. 28, 2016, which claims priority of European Patent Application No. 15003108.6, filed Oct. 30, 2015, the contents of each of which are herein fully incorporated by reference into this application.

SEQUENCE LISTING

This application contains a Sequence Listing which has been submitted in ASCII format via EFS-Web and is hereby incorporated by reference herein in its entirety. The ASCII text file was created on Apr. 17, 2018, is named Sequence Listing_ST25.txt and is 246,431 bytes in size.

The present invention relates to an isolated nucleic acid for inhibiting bolting (the first visible sign of reproductive transition in beets) and flowering of a *Beta vulgaris* plant, as well as the use thereof, a method for producing a transgenic *Beta vulgaris* plant or an non-transgenic *Beta vulgaris* plant in which bolting and flowering is inhibited after vernalization, vectors or mobile genetic elements, as well as a transgenic or non-transgenic *Beta vulgaris* in which bolting and flowering is inhibited after vernalization, and seeds as well as their parts.

It is possible to use molecular biological techniques or mutagenesis techniques to genetically modify crops in order to change their properties and thus to improve them. One property of importance in the cultivation and use of biennial plants such as *Beta vulgaris* is that bolting and subsequent flowering requires an induction by a longer period of cold weather, as regularly occurs in temperate latitudes in winter. This transition from the vegetative to the generative phase induced by a prolonged period of low temperature is referred to as vernalization.

There are several metabolic pathways by which flowering is controlled. These include inter alia the photoperiodic metabolic pathway, an autonomous pathway, a gibberellic acid and a vernalization dependent pathway. A large number of genes involved in the regulation of flowering have been identified in recent years in model plants. In particular the control of the timing of flowering was extensively explored in the model plant *Arabidopsis* (Boss, P K, Bastow R M, Mylne, J S, and Dean, C. (2004) Multiple pathways in the decision to flower: enabling, promoting, and resetting, Plant Cell 16 Suppl: 18-31; He, Y. and Amasino, R M (2005) Role of chromatin modification in flowering-time control, Trends Plant Sci 10, 30-35; Baeurle, I. and Dean, C. (2006) The timing of developmental transitions in plants, Cell, 125 (4): 655-664). Primarily using *Arabidopsis* mutants many "early flowering" or "late-flowering" genes were identified (Gazzani S., Gendall, A R, Lister, C., and Dean, C. (2003) Analysis of the molecular basis of flowering time variation in *Arabidopsis* accessions, Plant Physiol 132: 1107-1114; Geraldo, N., Baurle, I., Kidou, S., Hu, X., and Dean, C. (2009), FRIGIDA Delays Flowering in *Arabidopsis* via a Mechanism Involving Cotranscriptional Direct Interaction with the Nuclear Cap-Binding Complex, Plant Physiology, Jul. 1, 2009; 150 (3): 1611-1618; Michaels S D, Amasino, R M (2001) Loss of FLOWERING LOCUS C activity eliminates the late-flowering phenotype of FRIGIDA and autonomous pathway mutations but not responsiveness to vernalization, Plant Cell 13: 935-942; Yalovsky, Shaul, et al. "Prenylation of the floral transcription factor APETALA1 modulates its function." The Plant Cell 12.8 (2000): 1257-1266; Gu, Qing, et al. "The FRUITFULL MADS-box gene mediates cell differentiation during *Arabidopsis* fruit development." Development 125.8 (1998): 1509-1517).

In *Beta vulgaris* so far only very few genes have been characterized in detail. Therein it has been shown that for instances the gene BvFLC is not a key control gene for flowering or vernalization in *Beta vulgaris* (Reeves, P A, He Y, Schmitz R J, Amasino R M, Panella, L W, Richards C M (2007), Evolutionary FLOWERING LOCUS conservation of the C-mediated vernalization response: evidence from the sugar beet (*Beta vulgaris*), Genetics 176 (1): 295-307; Chia, T. Y. P., Mueller, A., Young, C., and Mutasa-Goettgens, E. S. (2008), Sugar beet contains a large CONSTANS-LIKE gene family including a CO homolog that is independent of the early-bolting (B) gene locus, J Exp Bot 59 (10): 2735-2748). In 2011 Kraus et al. showed that BvVil1 seems to have a more crucial role in controlling bolting activity after vernalization (WO 2011/032537).

Bolting and flowering of *Beta vulgaris* plants is undesirable, since in the case of *Beta vulgaris* it is not the seeds or fruits, but rather the underground part of the plant, the storage root, that is used, and the energy stored in the root would be consumed during the bolting and flowering of the plant. Moreover, in some plants, which are called "bolters", an unwanted emergence of shoots occurs in the first year of growing, which is very disadvantageous for harvesting and processing.

It is thus the object of the present invention to provide means to make it possible to inhibit bolting and/or flowering of *Beta vulgaris* plants, and even to completely prevent this.

According to the invention the problem is solved by means of an isolated nucleic acid for the inhibition of bolting and flowering of a *Beta vulgaris* plant, wherein the nucleic acid comprises at least one nucleotide sequence which a) exhibits a sequence or partial sequence of SEQ ID NO: 1 or 2, or b) is complementary to a sequence or partial sequence of a), or c) exhibits in the antisense direction a sequence or partial sequence of a) or b), or d) is a homolog to a sequence or partial sequence of a), ore) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of a), or f) encodes a protein or a part of the protein with the amino acid sequence of SEQ ID NO: 5, or g) encodes a protein with an amino acid sequence of *Beta vulgaris* which is a homolog to the sequence of f), or h) hybridizes under stringent conditions with a sequence or partial sequence of a), b) or c) and/or at least one nucleotide sequence which A) exhibits a sequence or partial sequence of SEQ ID NO: 3 or 4, or B) is complementary to a sequence or partial sequence of A), or C) exhibits in the antisense direction a sequence or partial sequence of A) or B), or D) is a homolog to a sequence or partial sequence of A), or E) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of A), or F) encodes a protein or a part of the protein with the amino acid sequence of SEQ ID NO: 6, or G) encodes a protein with an amino acid sequence of *Beta vulgaris* which is a homolog to the sequence of F), or H) hybridizes under stringent conditions with a sequence or partial sequence of A), B) or C).

The inventive nucleic acid can be used, for example by the RNA interference (RNAi) approach or micro-RNA (miRNA) interference approach (Fire, A, Xu, S, Montgomery, M, Kostas, S, Driver, S, Mello, C. (1998). Potent and specific genetic interference by double-stranded RNA in *Caenorhabditis elegans*, Nature 391 (6669): 806-811) to inhibit bolting and flowering of *Beta vulgaris*, and in particular, if possible, to completely prevent bolting and flowering, for example by inhibiting genes that encoded flowering inducers such as FT, Co, or VIN3.

The nucleic acid is characterized especially by the fact that transgenic or non transgenic plants, in particular *Beta vulgaris* plants, with special characteristics can be produced with it: In beneficial manner they can be used for example for the following purposes or with the following benefits:

Production of non-shoot emergent, non-flowering *Beta vulgaris* plants
    Production of a *Beta vulgaris* plant as winter beet
    Production of a *Beta vulgaris* plant as spring beet
    Increasing the biomass of the *Beta vulgaris* plant
    Increasing the sugar yield
    Avoiding *Beta vulgaris* bolters
    Extension of the *Beta vulgaris* harvesting campaign
    Avoidance of losses in *Beta vulgaris* storage material
    Utilization of the higher humidity in the fall
    Covering of soil and use of the stored nitrogen
    Protection for beneficial insects in the field

*Beta vulgaris* is a biennial plant. After completion of the winter, and the vernalization resulting therefrom, *Beta vulgaris* usually bolts and flowers in the second year. By means of the inventive nucleic acid, for example, a sequence shown in one of SEQ ID NOs: 19-23 or another novel sequence or partial sequence inserted using an RNAi or microRNA-approach, genes can be inhibited and the effects of vernalization can be inhibited or completely prevented. Mechanisms and methods for inhibiting or switching off genes are known to the person of ordinary skill in the art, for example, under the term "gene silencing" and include the already mentioned and known to those skilled in the art RNAi or micro (mi) RNA processes, but are not limited thereto. In an RNAi approach, for example, the sequences of SEQ ID NO: 19 to SEQ ID NO: 23 can, by molecular biology techniques known to the person skilled in the art, be introduced into a *Beta vulgaris* cell in the antisense orientation and under control of a suitable promoter be expressed there.

In accordance with the present invention, the bolting and flowering of the plant can be completely eliminated. Seed of *Beta vulgaris* can be sown earlier, which ultimately leads to a longer growing season and thus leads to a higher biomass and a higher sugar yield. In combination with cold tolerance, sugar beets, for example, can be grown as so-called winter beets. In the case of seeding of sugar beets in August, in the following spring they can already be harvested as spring beets. This allows the farmer an additional crop rotation. By using the nucleic acid according to the invention, even in the case of prolonged cold spells on the field after sowing, there is no longer increased formation of bolters. Even the normal sugar beet bolters previously observed without prolonged cold spells can be prevented or at least significantly reduced. Using the present invention it can not only be accomplished that bolting and the subsequent flowering of sugar beet after an initial vernalization, but, i.e. in the second year, is inhibited or prevented, but the sugar beet can also be subjected to other cold periods without vernalization effects observed.

The sugar beet cultivation is usually from April to October/November. Since not all of the harvested sugar beets can be processed at the same time, they must be stored or intermediate stored. During storage, for example in piles, large losses in storage substance (sucrose losses) occur as a result of by cleavage of sucrose into glucose and fructose. By means of the inventive nucleic acid, particularly when used in an RNAi approach, the sowing and harvest dates can be varied so that the total harvest (campaign) can be extended without loss of harvest. It can allow more sugar beets to be processed for a prolonged period with less loss of storage material.

The term "*Beta vulgaris*" or "*Beta vulgaris* plant" is understood to refer to a plant of the genus *Beta vulgaris*, e.g. *Beta vulgaris* ssp. *vulgaris* var *altissima* (sugar beet in the narrow sense), *Beta vulgaris* ssp. *maritima* (sea beet), *Beta vurlgaris* ssp. *vulgaris* var *vulgaris* (Mangold beet), *Beta vulgaris* ssp. *vulgaris* var *conditiva* (red beetroot/beet), *Beta vulgaris* ssp. *crassa vulgaris* var/*alba* (fodder beet).

The term "plant" according to the present invention includes whole plants or parts of such a whole plant. Whole plants preferably are seed plants, or a crop. "Parts of a plant" are e.g. shoot vegetative organs/structures, e.g., leaves, stems and tubers; roots, flowers and floral organs/structures, e.g. bracts, sepals, petals, stamens, carpels, anthers and ovules; seed, including embryo, endosperm, and seed coat; fruit and the mature ovary; plant tissue, e.g. vascular tissue, ground tissue, and the like; and cells, e.g. guard cells, egg cells, pollen, trichomes and the like; and progeny of the same.

An "isolated nucleic acid" is understood to be a nucleic acid extracted from its natural or original environment. The term also includes a synthetic manufactured nucleic acid.

An "inhibition of bolting and flowering" of a *Beta vulgaris* plant refers to a reduction in the proportion of bolting and possibly flower forming *Beta vulgaris* plants in comparison to a non-inventively modified *Beta vulgaris* plant of the same subspecies or variety in a comparable stage of development, particularly in the second year after passing through a corresponding cold period, i.e. after vernalization. In particular, the term encompasses a reduction of proportion of bolters to not more than 80%, preferably not more than 70%, 60%, 50%, 40%, 30%, 20% or 10%, more preferably not more than 5%, 4%, 3%, 2%, 1%, 0.5%, 0.4%, 0.3%, 0.2% or 0.1% of the percentage of bolting compared to control plants not according to the invention. "Control plants" are preferably plants of the same variety, but they are not modified according to the present invention, and exhibit for example a proportion of bolters of at most 0.01%. The term "suppression" or "complete suppression" of bolting and flowering is understood to mean inhibition of at least 99%, preferably at least 99.5%, more preferably at least 99.8%, or at least 99.9%, that is, a reduction of the proportion of bolters to not more than 1%, not more than 0.5%, not more than 0.2% or not more than 0.1%, especially in the second year after vernalization, compared to a non-inventively modified *Beta vulgaris* plant, for example, a bolting percentage of maximal 0.01%. The term of inhibition or the suppression of bolting and flowering comprises mainly the inhibition/suppression of bolting, regardless of whether it comes to a flowering of the plant or not.

The term "transgenic", "transgene" or "heterologous" as used herein means genetically modified. The term includes also the case that a species-specific nucleic acid in a form, arrangement or quantity is introduced into a plant cell where the nucleic acid does not occur naturally in the cell. If the gene, coding sequence or the regulatory element may be one normally found in the cell, it is called 'autologous' or 'endogenous'. A 'heterologous' gene, coding sequence or regulatory element may also be autologous to the cell but is, however, arranged in an order and/or orientation or in a genomic position or environment not normally found or occurring in the cell in which it is introduced.

The term "homology" refers to identities or similarities in the nucleotide sequence of two nucleic acid molecules or the amino acid sequence of two proteins or peptides. The presence of homology between two nucleic acids or proteins can be detected by comparing each position in one sequence with the equivalent position in the other sequence and determining whether identical or similar residues are present here. Two compared sequences are homologous if there is a particular minimum level of identical or similar nucleotides. "Identical" means that when comparing two sequences at equivalent positions there is the same nucleotide or the same amino acid. It may be necessary to take into account gaps in sequence to achieve the best possible alignment comparison of sequences. Similar nucleotides/amino acids are non-identical nucleotides/amino acids with the same or equivalent chemical and physical properties. Exchanging a nucleotide (an amino acid) with a different nucleotide (another amino acid) with the same or equivalent physical and chemical properties is called a "conservative exchange." Examples of chemical and physical properties of an amino acid include, for example, the hydrophobicity or charge. In the context of nucleic acids there is also understood a conservative or a similar nucleotide exchange when replacing in a coding sequence a nucleotide in a codon by another, whereby due to e.g. the degeneration of the genetic code, the same amino acid or a similar amino acid is encoded as in the equivalent codon in the compared sequence. The person skilled in the art knows which nucleotide or amino acid exchange is a conservative exchange. To determine the level of similarity or identity between two nucleic acids, a minimum length of 60 nucleotides or base pairs is assumed, preferably a minimum length of 70, 80, 90, 100, 110, 120, 140, 160, 180, 200, 250, 300, 350 or 400 nucleotides or base pairs, more preferably the full length of the compared nucleic acids, and in the case of proteins/peptides a minimum length of 20 amino acids is assumed, preferably a minimum length of 25, 30, 35, 40, 45, 50, 60, 80, 100, 150, 200, 250 or 300 amino acids, and more preferably the full length of the compared amino acid sequences. The level of similarity ("positives") or identity of two sequences can be determined using, for example, the computer program BLAST (Altschul S. F. et al (1990), Basic Local Alignment Search Tool, J. Mol Biol 215: 403-410; see eg http://www.ncbi.nlm.nih.gov/BLAST/) with standard parameters. The determination of homology depends on the length of the compared sequences. In the context of the present invention a homology between two nucleic acid sequences, whose length is at least 100 nucleotides, is understood if at least 70%, at least 75%, at least 80%, at least 85%, at least 90%, at least 95%, at least 97%, at least 98%, or at least 99% of nucleotides are identical and/or similar ("identities" or "positives" according to BLAST), and preferably are identical. In the case of a sequence length of 50-99 nucleotides a homology between sequences is understood if there is identity or similarity of at least 80%, preferably at least 85%, 86%, 87%, 88% or 89%, with a sequence length of 15-49 nucleotides with an identity or similarity of at least 90%, preferably at least 95%, 96%, 97%, 98% or 99%. In the case of proteins a homology is assumed, if using the computer program BLAST with standard parameters and the BLOSUM62 substitution matrix (Henikoff, S., and Henikoff, J. Amino acid substitution matrices from protein blocks Proc. Natl. Acad. Sci. USA 89: 10915-10919, 1992) an identity ("identities") and/or similarity ("positive"), preferably identity, at least 25%, at least 26%, at least 27%, at least 28%, at least 29% at least 30%, preferably at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, or at least 99% is shown, preferably the entire length of the protein/peptide, which is compared with another protein, e.g. the length of 260 amino acids in the case of SEQ ID NO: 5 or the length of 245 amino acids in the case of SEQ ID NO: 6, is considered in determination. The person skilled in the art is able with his expert knowledge to use readily available BLAST programs (e.g. BLASTn, BLASTp, BLASTx, tBLASTn or tBLASTx) to determine the homology in question. In addition, there are other programs that the expert knows, and which he can use in the case in determining the homology of two or more comparative sequences or partial sequences. Such programs include those that can be found, for example on the website of the European Bioinformatics Institute (EMBL) (see, e.g. www.ebi.ac.uk/Tools/similarity.html).

The term "hybridizing" or "hybridization" means a process in which a single-stranded nucleic acid molecule attaches itself to a complementary nucleic acid strand, i.e. agrees with this base pairing. Standard procedures for hybridization are described, for example, in Sambrook et al. (Molecular Cloning. A Laboratory Manual, Cold Spring Harbor Laboratory Press, 3rd edition 2001). Preferably this will be understood to mean an at least 50%, more preferably at least 55%, 60%, 65%, 70%, 75%, 80% or 85%, more preferably 90%, 91%, 92%, 93%, 94%, 95%, 96%, 97%, 98% or 99% of the bases of the nucleic acid strand form base pairs with the complementary nucleic acid strand. The possibility of such binding depends on the stringency of the hybridization conditions. The term "stringency" refers to hybridization conditions. High stringency is if base pairing is more difficult, low stringency, when a base-pairing is facilitated. The stringency of hybridization conditions depends for example on the salt concentration or ionic strength and temperature. Generally, the stringency can be increased by increasing the temperature and/or decreasing salinity. "Stringent hybridization conditions" are defined as conditions in which hybridization occurs predominantly only between homologous nucleic acid molecules. The term "hybridization conditions" refers not only to the actual binding of the nucleic acids at the prevailing conditions, but also in the subsequent washing steps prevailing conditions. Stringent hybridization conditions are, for example, conditions under which predominantly only those nucleic acid molecules having at least 70%, preferably at least 75%, at least 80%, at least 85%, at least 90% or at least 95% sequence identity hybridize. Less stringent hybridization conditions include: hybridization in 4×SSC at 37° C., followed by repeated washing in 1×SSC at room temperature. Stringent hybridization conditions include: hybridization in 4×SSC at 65° C., followed by repeated washing in 0.1×SSC at 65° C. for a total of about 1 hour.

The term "complementary" refers to the ability of purine and pyrimidine nucleotides to form base pairs with each other via bridging hydrogen bonds. Complementary base pairs are, for example, guanine and cytosine, adenine and thymine and adenine and uracil. A complementary nucleic acid strand is accordingly a nucleic acid strand that can, by pairing with complementary bases of another nucleic acid strand, form a double strand.

As used herein, the term "homozygous" means a genetic condition existing when two alleles reside at a specific locus, but are positioned individually on corresponding pairs of homologous chromosomes in the cell and the two alleles are identical or at least identical for the one or more mutations.

A "fragment" or a "partial sequence" of a nucleic acid is here understood to be a contiguous section of the nucleic acid, i.e. a sequence segment of consecutive nucleotides of the nucleic acid. Fragments can e.g. be used advantageously in a miRNA or RNAi approach, wherein the sequence can be used, for example, in anti-sense ("antisense") direction. "Anti-sense direction" or "antisense orientation" of a nucleic acid sequence, e.g. a DNA sequence, means here, for example, that a transcription of the DNA sequence results in an mRNA whose nucleotide sequence is complementary to a natural (endogenous) mRNA, so that its translation is hindered or prevented by the attachment of the complementary RNA. An "antisense RNA" or "antisense RNA" is understood to mean one of a particular mRNA or other RNAs complementary to specific RNA. "Anti-sense direction" or "antisense orientation" of an mRNA sequence, therefore, means that the mRNA has a sequence that is complementary to an mRNA sequence, so that its translation may be hindered or prevented by attachment. Partial sequences, which may be advantageously used in the context of the present invention, for example, in antisense orientation, are for example nucleic acids having a sequence shown in SEQ ID NO: 10, 11, 12 or 13 which is a segment of the nucleic acid according to SEQ ID NO: 1 or 2, and/or shown in SEQ ID NO: 14, 15, 16 or 17 which is a segment of the nucleic acid according to SEQ ID NO 3 or 4. However, any other nucleic acids with sequences or partial sequences of SEQ ID NOs: 1 or 2 and/or of SEQ ID NO: 3 or 4 can be used, for example, in the anti-sense direction. In addition, two or more partial sequences may be fused and advantageously used in the context of the present invention, for example, in antisense orientation. Examples of fused partial sequences are nucleic acids having a sequence shown in SEQ ID NO: 19, 20, 21 or 22, each of these sequences contains a segment of the nucleic acid according to SEQ ID NO: 1 or 2 as well as a segment of the nucleic acid according to SEQ ID NO: 3 or 4. In another embodiment two or more partial sequences may be fused and advantageously used in the context of the present invention, for example, in antisense orientation, whereby at least two fused partial sequences are derived from the same nucleic acid according to SEQ ID NO: 1, 2, 3 or 4. The fused partial sequences can be linked by a spacer sequence comprising at least 1, at least 2, at least 3, at least 4, at least 5, at least 6, at least 7, at least 8, at least 9, at least 10, at least 12, at least 14, at least 16, at least 18, at least 20, at least 25 or at least 30 nucleotides.

The partial sequence preferably comprises a nucleic acid with at least 25, preferably at least 30, 35, 40, 45, 50, 60, 70, 80, 90, or at least 100 consecutive nucleotides, more preferably at least 150, 184, 200, 212, 250, 300, 350, 400 or 450 consecutive nucleotides. A part of a protein (see, e.g., letter f) or F)) above) preferably comprises at least 5, preferably at least 10, 15, 20, 25, 30, 40 or 50, more preferably at least 60, 61, 70, 80, 90, or at least 100 consecutive amino acids of SEQ ID NO: 5 or 6. The sequence segment of SEQ ID NO: 5 or 6 (see, e.g., letter f) or F)) above) preferably comprises at least 50, 60, 61, 70, 80, 87 or 90, more preferably at least 100, 105, 120, 150, 200 or 250 consecutive amino acids of SEQ ID NO: 5 or 6. The necessary or useful length of the partial sequence of the nucleic acid or protein or the sequence segment can be selected by the person of ordinary skill in the art with the aid of his general technical skills and, where appropriate, by carrying out routine tests of the approach and the intended effect, without this requiring an inventive step.

The nucleic acid is preferably at least 85%, preferably at least 90%, 95%, 96%, 97%, 98% or 99%, more preferably at least 99.5%, 99.6%, 99.7%, 99.8% or 99.9% identical to a sequence or partial sequence of one of SEQ ID NO: 1-4.

The nucleic acid according to the invention may include one of the sequences of SEQ ID NO: 10-17 or 19-22, preferably in the antisense orientation.

In a preferred embodiment the inventive nucleic acid for the inhibition of bolting and flowering of a *Beta vulgaris* plant as described above comprises a further nucleic acid comprising a nucleotide sequence which (i) exhibits a sequence or partial sequence of SEQ ID NO: 7 or 8, or (ii) is complementary to a sequence or partial sequence of (i), or (iii) exhibits in the antisense direction a sequence or partial sequence of (i) or (ii), or (iv) is a homolog to a sequence or partial sequence of (i), or (v) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of (i), or (vi) encodes a protein or a part of the protein with the amino acid sequence of SEQ ID NO: 9, or (vii) encodes a protein with an amino acid sequence of *Beta vulgaris* which is a homolog to the sequence of F), or (viii) hybridizes under stringent conditions with a sequence or partial sequence of (i), (ii) or (iii).

In a further aspect, the present invention concerns the use of one or more of the inventive nucleic acids for the inhibition of bolting and flowering of a *Beta vulgaris* plant. As already indicated above, the nucleic acid can be introduced into a *Beta vulgaris* plant, for example, in antisense orientation or in form of a hairpin construct, thereby causing an inhibition of the genes responsible for bolting and flowering. Methods which are suitable for introducing a nucleic acid in a *Beta vulgaris* cell are known to the skilled person, and include for example the *Agrobacterium*-mediated transformation (Lindsey, K., and P. Gallois. "Transformation of sugarbeet (*Beta vulgaris*) by *Agrobacterium tumefaciens*." *Journal of experimental botany* 41.5 (1990): 529-536). The introduction of a nucleic acid in antisense orientation into a plant is only one of the known processes for the inhibition or suppression of gene activity (gene silencing). The inventive nucleic acids can also be used advantageously in the context of other procedures or mechanisms that can cause an inhibition or suppression of bolting/flowering, e.g. suppression by co-expression, or as template for the generation of guide RNA (gRNA) in a CRISPR/Cas system.

Furthermore, the inventive nucleic acid may also be used as a probe to identify other factors, genes or gene products, which can be used to inhibit or suppress flowering and bolting of *Beta vulgaris* plants, or may also be used as molecular marker to detect or to identify in a mutagenized *Beta vulgaris* plant or a part thereof one or more mutations in an endogenous DNA sequence or a regulatory sequence of the endogenous DNA sequence, wherein the endogenous DNA sequence has a nucleic acid sequence identical to a sequence which (a) exhibits a sequence or partial sequence of SEQ ID NO: 1, or (b) is complementary to a sequence or partial sequence of (a), or (c) exhibits in the antisense direction a sequence or partial sequence of (a) or (b), or (d) is a homolog to a sequence or partial sequence of (a), or (e) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of a), or (f) encodes a protein or a part of the protein with the amino acid sequence of SEQ ID NO: 5, or (g) encodes a protein with an amino acid sequence of *Beta vulgaris* which is a homolog to the sequence of (f), or (h)

hybridizes under stringent conditions with a sequence or partial sequence of a), b) or c) and/or (A) exhibits a sequence or partial sequence of SEQ ID NO: 3, or (B) is complementary to a sequence or partial sequence of (A), or (C) exhibits in the antisense direction a sequence or partial sequence of (A) or (B), or (D) is a homolog to a sequence or partial sequence of (A), or (E) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of (A), or (F) encodes a protein or a part of the protein with the amino acid sequence of SEQ ID NO: 6, or (G) encodes a protein with an amino acid sequence of *Beta vulgaris* which is a homolog to the sequence of (F), or (H) hybridizes under stringent conditions with a sequence or partial sequence of (A), (B) or (C). Preferably, the one or more mutations cause a reduced transcriptional or expressional rate or a reduced transcriptional or expressional level of the endogenous DNA sequence in the mutagenized plant compared to a non-mutagenized wildtype plant, or the mutation causes a reduction of the activity or stability of the protein or polypeptide encoded by the endogenous DNA sequence compared to a non-mutagenized wildtype plant. More preferably, at least one of the one or more mutations is selected from the group consisting of mutations listed in Table 1.

In a particular embodiment of the present invention the use of the one or more nucleic acids as described above includes in addition to the one or more nucleic acids a further nucleic acid comprising a nucleotide sequence which (i) exhibits a sequence or partial sequence of SEQ ID NO: 7 or 8, or (ii) is complementary to a sequence or partial sequence of (i), or (iii) exhibits in the antisense direction a sequence or partial sequence of (i) or (ii), or (iv) is a homolog to a sequence or partial sequence of (i), or (v) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of (i), or (vi) encodes a protein or a part of the protein with the amino acid sequence of SEQ ID NO: 9, or (vii) encodes a protein with an amino acid sequence of *Beta vulgaris* which is a homolog to the sequence of (vi), or (viii) hybridizes under stringent conditions with a sequence or partial sequence of (i), (ii) or (iii). These nucleic acids may be used for the inhibition of bolting and flowering of *Beta vulgaris* plant.

In a further aspect the present invention concerns a protein with an amino acid sequence of SEQ ID NO: 5 or 6, or a protein having an amino acid sequence that contains a sequence segment of SEQ ID NO: 5 or 6, that comprises preferably at least 50, 60, 61, 70, 80 or 90, at least 100, 120, 150, 200 or 250 consecutive amino acids of SEQ ID NO: 5 or 6, or a thereto homologous protein from *Beta vulgaris*. The protein or any part thereof, or the corresponding amino acid sequences may/could for example be used as a probe at the amino acid level to identify other factors, genes or gene products which can be used to inhibit and/or suppress the flowering and bolting of a *Beta vulgaris* plants.

In another aspect the present invention relates to a method for producing a transgenic *Beta vulgaris* plant comprising the steps of (a) transforming a *Beta vulgaris* cell with one or more inventive nucleic acids and (b) regenerating a *Beta vulgaris* plant from the transformed *Beta vulgaris* cell. The transformation of *Beta vulgaris* cell can occur, for example, using known vectors, e.g. a Ti-plasmid, and is known to the skilled person (Lindsey and Galiois. 1990). The inventive nucleic acids may be found advantageous under the control of a suitable promoter in such a vector. In a particular embodiment of the present invention the method for producing a transgenic *Beta vulgaris* plant, where the bolting and flowering is inhibited after vernalization, comprises the following steps of: (I) Transforming a *Beta vulgaris* cell with a first nucleic acid as transgene and a second nucleic acid as transgene, wherein the *Beta vulgaris* cell is transformed with one construct comprising the first and the second nucleic acid or with a construct comprising the first nucleic acid and another construct comprising the second nucleic acid; and (II) regenerating a *Beta vulgaris* plant from the transformed *Beta vulgaris* cell. Thereby, the first nucleic acid as transgene comprises a nucleotide sequence which a) exhibits a sequence or partial sequence of SEQ ID NO: 1 or 2, orb) is complementary to a sequence or partial sequence of a), or c) exhibits in the antisense direction a sequence or partial sequence of a) or b), or d) is a homolog to a sequence or partial sequence of a), ore) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of a), or f) encodes a protein or a part of the protein with the amino acid sequence of SEQ ID NO: 5, or g) encodes a protein with an amino acid sequence of *Beta vulgaris* which is a homolog to the sequence of f), or h) hybridizes under stringent conditions with a sequence or partial sequence of a), b) or c); and the second nucleic acid as transgene comprises a nucleotide sequence which A) exhibits a sequence or partial sequence of SEQ ID NO: 3 or 4, or B) is complementary to a sequence or partial sequence of A), or C) exhibits in the antisense direction a sequence or partial sequence of A) or B), or D) is a homolog to a sequence or partial sequence of A), or E) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of A), or F) encodes a protein or a part of the protein with the amino acid sequence of SEQ ID NO: 6, or G) encodes a protein with an amino acid sequence of *Beta vulgaris* which is a homolog to the sequence of F), or H) hybridizes under stringent conditions with a sequence or partial sequence of A), B) or C). In an alternative particular embodiment of the present invention the method for producing a transgenic *Beta vulgaris* plant, where the bolting and flowering is inhibited after vernalization, comprises the following steps of: (I) Transforming a first *Beta vulgaris* cell with a first nucleic acid as transgene as defined above; (II) transforming a second *Beta vulgaris* cell with a second nucleic acid as transgene as defined above; and (III) regenerating a first *Beta vulgaris* plant from the transformed first *Beta vulgaris* cell and a second *Beta vulgaris* plant from the transformed second *Beta vulgaris* cell; and (IV) crossing the first *Beta vulgaris* plant with the second *Beta vulgaris* plant and selecting a progeny comprising the first nucleic acid and the second nucleic acid as transgenes.

The invention also relates to a vector or a mobile genetic element that includes one or more inventive nucleic acids. Vectors and mobile genetic elements are known in the art and include, for example, plasmids such as the Ti-plasmid. The vector or mobile genetic element can advantageously contain control/regulatory elements, e.g. a promoter, enhancer, intronic sequence, or terminator.

Furthermore, the invention relates to a transgenic *Beta vulgaris* plant including one or more inventive nucleic acids as transgene, preferably under the control of a suitable promoter, and which is inhibited in bolting and flowering, as well as seeds and/or parts of a *Beta vulgaris* plant transformed with one or more inventive nucleic acids.

In a further aspect the present invention relates to a method for producing a *Beta vulgaris* plant, preferably a non-transgenic *Beta vulgaris* plant, where the bolting and flowering is inhibited after vernalization. In one embodiment the method for producing a *Beta vulgaris* plant comprises the following steps: (I) Mutagenizing one or more parts of a *Beta vulgaris* plant and subsequently regenerating *Beta vulgaris* plants from the one or more parts, or mutagenizing one or more *Beta vulgaris* plants, (II) identifying a plant of (I) which exhibits one or more mutations in a first endogenous DNA sequence and/or in a regulatory sequence thereof and exhibits one or more mutations in a second endogenous DNA sequence and/or in a regulatory sequence thereof, and optionally (III) generating a *Beta vulgaris* plant in which the one or more mutations in the first endogenous DNA sequence and the one or more mutations in the second endogenous DNA sequence are homozygous. The first endogenous DNA sequence has a nucleic acid sequence identical to a sequence which (a) exhibits a sequence or partial sequence of SEQ ID NO: 1, or (b) is complementary to a sequence or partial sequence of (a), or (c) exhibits in the antisense direction a sequence or partial sequence of (a) or (b), or (d) is a homolog to a sequence or partial sequence of (a), or (e) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of a), or (f) encodes a protein or a part of the protein with the amino acid sequence of SEQ ID NO: 5, or (g) encodes a protein with an amino acid sequence of *Beta vulgaris* which is a homolog to the sequence of (f), or (h) hybridizes under stringent conditions with a sequence or partial sequence of a), b) or c) and the second endogenous DNA sequence has a nucleic acid sequence identical to a sequence which (A) exhibits a sequence or partial sequence of SEQ ID NO: 3, or (B) is complementary to a sequence or partial sequence of (A), or (C) exhibits in the antisense direction a sequence or partial sequence of (A) or (B), or (D) is a homolog to a sequence or partial sequence of (A), or (E) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of (A), or (F) encodes a protein or a part of the protein with the amino acid sequence of SEQ ID NO: 6, or (G) encodes a protein with an amino acid sequence of *Beta vulgaris* which is a homolog to the sequence of (F), or (H) hybridizes under stringent conditions with a sequence or partial sequence of (A), (B) or (C). In another embodiment the method for producing a *Beta vulgaris* plant comprises the following steps: (I) Mutagenizing one or more parts of a *Beta vulgaris* plant and subsequently regenerating one or more *Beta vulgaris* plants from the one or more parts, or mutagenizing one or more *Beta vulgaris* plants; (II) identifying a first plant of (I) which exhibits one or more mutations in a first endogenous DNA sequence as defined above and/or in a regulatory sequence thereof and a second plant of (I) which exhibits one or more mutations in a second endogenous DNA sequence as defined above and/or in a regulatory sequence thereof; (III) crossing the first plant with the second plant and selecting a progeny comprising the one or more mutations in the first endogenous DNA sequence and/or in a regulatory sequence thereof and the one or more mutations in the second endogenous DNA sequence and/or in a regulatory sequence thereof; and optionally (IV) generating from the progeny of (III) a *Beta vulgaris* plant in which the one or more mutations in the first endogenous DNA sequence and the one or more mutations in the second endogenous DNA sequence are homozygous.

In a preferred embodiment the step of mutagenizing comprises the steps of: i) Subjecting pollen or seeds of a *Beta vulgaris* plant to a sufficient amount of the mutagen ethylmethane sulfonate (EMS) or other mutagenic chemicals or mutagenic radiation to obtain M1 plants, ii) optionally allowing sufficient production of M2 plants, and iii) isolating and analysing genomic DNA of M1 and/or M2 plants.

Preferably, the one or more mutations cause a reduced transcriptional or expressional rate or a reduced transcriptional or expressional level of the endogenous DNA sequence in the mutagenized plant compared to a non-mutagenized wildtype plant, or the mutation causes a reduction of the activity or stability of the protein or polypeptide encoded by the endogenous DNA sequence compared to a non-mutagenized wildtype plant. More preferably, the one or more mutations result in a loss of function, i.e. the expression/transcription of the mutated DNA does not lead to the synthesis of a functional protein (e.g. functional AP1 protein or FUL protein, respectively).

The one or more mutations may cause an alteration of the amino acid sequence of AP1 or FUL, in particular the one or more mutations can be a point mutation resulting in at least one amino acid exchange, the exchange of an amino acid coding codon to a codon carrying the stop signal of translation (stop codon), or the change of the start signal of translation (start codon). The techniques of introducing such mutations via mutagenizing are well-known to the person skilled in the art. In a preferred embodiment, wherein the one or more mutations are effected in the endogenous AP1 gene or FUL gene, the obtained *Beta vulgaris* plant is non-transgenic. Preferably, the mutation is effected via non-transgenic mutagenesis, transposon mutagenesis, in particular chemical mutagenesis, preferably via EMS (ethylmethane sulfonate)-induced TILLING or targeted genome editing (e.g. CRISPR/Cas, TALEN, Zinc Finger nucleases, etc.). Exemplary, Table 1a and 1b show possible point mutations within the genomic DNA and cDNA of AP1 and FUL resulting in a nucleotide exchange from cytosine (c) to thymine (t) and thereby generating a stop codon. Such mutations can reduce the activity or stability of the corresponding protein or polypeptide encoded by the endogenous DNA sequence compared to a non-mutagenized wildtype plant, or can result in a loss of function of the corresponding protein.

Additionally, the one or more mutations may cause an alteration of the amino acid sequence of the AP1 protein or FUL protein by an insertion or deletion of one or more amino acids, e.g. through a shift of the open reading frame. The insertion can be introduced for instances by transposon mutagenesis and deletion can be created for instances by genomic engineering. Insertion and deletion can occur in any nucleotide sequence encoding one of the above described proteins, in a nucleotide sequence of an intron or in a nucleotide sequence of the 5' untranslated region (UTR) or 3' UTR of the AP1 gene or FUL gene. The insertion can have a length of at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 12 nucleotides, at least 14 nucleotides, at least 16 nucleotides, at least 18 nucleotides, at least 20 nucleotides, at least 25 nucleotides, at least 30 nucleotides, at least 40 nucleotides, at least 50 nucleotides, at least 75 nucleotides, at least 100 nucleotides, at least 200 nucleotides, at least 300 nucleotides, or at least 500 nucleotides. If such insertion or deletion occurs for instances in a regulatory element (e.g. promotor), that may reduce the transcriptional or expressional rate or a reduced transcriptional or expressional level of the corresponding endogenous DNA sequence in the Beta vulgaris plant cell.

As used herein, the term "reduced expressional rate" or "reduced expressional level" means a reduction of the expressional rate or of the expressional level of one or more nucleic acid sequences by more than 25% or 30%, preferably by more than 40%, 45%, 50%, 55%, 60%, or 65%, more preferably by more than 70%, 75%, 80%, 85%, 90%, 92%, 94%, 96% or 98% compared to the given reference. It may be that the reduction of the expressional rate or of the expressional level is 100%, e.g. in case of knock-out mutants or loss of function mutants. Preferably the reduced expressional rate or expressional level results in an amended phenotype where the bolting and flowering is inhibited after vernalization. The term "reduced transcriptional rate" or "reduced transcriptional level" means a reduction of the transcriptional rate or of the transcriptional level of one or more nucleic acid sequences by more than 25% or 30%, preferably by more than 40%, 45%, 50%, 55%, 60%, or 65%, more preferably by more than 70%, 75%, 80%, 85%, 90%, 92%, 94%, 96% or 98% compared to the given reference. It may be that the reduction of the transcriptional rate or of the transcriptional level is 100%, e.g. in case of knock-out mutants or loss of function mutants. Preferably the reduced transcriptional rate or transcriptional level results in an amended phenotype where the bolting and flowering is inhibited after vernalization.

TABLE 1a

List of positions in genomic DNA and cDNA of BvAP1 where a point mutation causes a nucleotide exchange from cytosine (c) to thymine (t) generating a stop codon.

| Gene name | Position in genomic DNA (SEQ ID NO: 1) | Position in cDNA (SEQ ID NO: 2) |
|---|---|---|
| BvAP1 | 52 | 52 |
| BvAP1 | 151 | 151 |
| BvAP1 | 6999 | 262 |
| BvAP1 | 7640 | 316 |
| BvAP1 | 8573 | 343 |
| BvAP1 | 8606 | 376 |
| BvAP1 | 8618 | 388 |
| BvAP1 | 8621 | 391 |
| BvAP1 | 8648 | 418 |
| BvAP1 | 11796 | 433 |
| BvAP1 | 11826 | 463 |
| BvAP1 | 21152 | 484 |
| BvAP1 | 21313 | 541 |
| BvAP1 | 21319 | 547 |
| BvAP1 | 21322 | 550 |
| BvAP1 | 21328 | 556 |
| BvAP1 | 21334 | 562 |
| BvAP1 | 21340 | 568 |
| BvAP1 | 21346 | 574 |
| BvAP1 | 21352 | 580 |
| BvAP1 | 21358 | 586 |
| BvAP1 | 21361 | 589 |
| BvAP1 | 21364 | 592 |
| BvAP1 | 21382 | 610 |
| BvAP1 | 21391 | 619 |
| BvAP1 | 21576 | 688 |
| BvAP1 | 21582 | 694 |

TABLE 1b

List of positions in genomic DNA and cDNA of BvFUL where a point mutation causes a nucleotide exchange from cytosine (c) to thymin (t) generating a stop codon.

| Gene name | Position in genomic DNA (SEQ ID NO: 3) | Position in cDNA (SEQ ID NO: 4) |
|---|---|---|
| BvFUL | 19 | 19 |
| BvFUL | 52 | 52 |
| BvFUL | 19373 | 235 |
| BvFUL | 19552 | 316 |
| BvFUL | 19561 | 325 |
| BvFUL | 19689 | 376 |
| BvFUL | 19704 | 391 |
| BvFUL) | 28161 | 433 |
| BvFUL | 28185 | 457 |
| BvFUL | 28191 | 463 |
| BvFUL | 28194 | 466 |
| BvFUL | 28447 | 541 |
| BvFUL | 28450 | 544 |
| BvFUL | 28465 | 559 |
| BvFUL | 28468 | 562 |
| BvFUL | 28507 | 601 |
| BvFUL | 29166 | 664 |
| BvFUL | 29196 | 694 |
| BvFUL | 29217 | 715 |
| BvFUL | 29226 | 724 |

Thus, the present invention relates to a Beta vulgaris plant, preferably a non-transgenic Beta vulgaris plant, where the bolting and flowering is inhibited after vernalization, wherein the plant exhibits one or more mutations in a first endogenous DNA sequence and/or in a regulatory sequence thereof and exhibits one or more mutations in a second endogenous DNA sequence and/or in a regulatory sequence thereof. The first endogenous DNA sequence has a nucleic acid sequence identical to a sequence which (a) exhibits a sequence or partial sequence of SEQ ID NO: 1, or (b) is complementary to a sequence or partial sequence of (a), or (c) exhibits in the antisense direction a sequence or partial sequence of (a) or (b), or (d) is a homolog to a sequence or partial sequence of (a), or (e) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of a), or (f) encodes a protein or a part of the protein with the amino acid sequence of SEQ ID NO: 5, or (g) encodes a protein with an amino acid sequence of Beta vulgaris which is a homolog to the sequence of (f), or (h) hybridizes under stringent conditions with a sequence or partial sequence of a), b) or c) and the second endogenous DNA sequence has a nucleic acid sequence identical to a sequence which (A) exhibits a sequence or partial sequence of SEQ ID NO: 3, or (B) is complementary to a sequence or partial sequence of (A), or (C) exhibits in the antisense direction a sequence or partial sequence of (A) or (B), or (D) is a homolog to a sequence or partial sequence of (A), or (E) at least 80% or 85%, preferably at least 90%, 95%, 96%, 97%, 98% or 99%, or more preferably at least 99.5%, 99.6%, 99.7%, 99.8% or 99.9% identical to a sequence or partial sequence of (A), or (F) encodes a protein or a part of the protein with the amino acid sequence of SEQ ID NO: 6, or (G) encodes a protein with an amino acid sequence of Beta vulgaris which is a homolog to the sequence of (F), or (H) hybridizes under stringent conditions with a sequence or partial sequence of (A), (B) or (C). Preferably, the one or more mutations in the first and/or the second endogenous DNA sequence are homozygous.

Preferably, the one or more mutations cause a reduced transcriptional or expressional rate or a reduced transcriptional or expressional level of the endogenous DNA sequence in the mutagenized plant compared to a non-mutagenized wildtype plant, or the mutation causes a reduction of the activity or stability of the protein or polypeptide encoded by the endogenous DNA sequence compared to a non-mutagenized wildtype plant. More preferably, the one or more mutations result in a loss of function, i.e. the expression/transcription of the mutated DNA does not lead to the synthesis of a functional protein (e.g. functional AP1 protein or FUL protein, respectively).

In a preferred embodiment of the *Beta vulgaris* plant or a part thereof of the present invention is a *Beta vulgaris* plant or a part thereof as described above wherein the one or more mutations cause an alteration of the amino acid sequence of AP1 or FUL, in particular the one or more mutations is a point mutation resulting in at least one amino acid exchange, the exchange of an amino acid coding codon to a codon carrying the stop signal of translation (stop codon), or the change of the start signal of translation (start codon). Preferably the point mutation in the AP1 gene (i.e. first endogenous DNA sequence) is selected from the group consisting of mutations listed in Table 1a or indicated by SEQ ID NO: 33 or SEQ ID NO: 37 and/or the point mutation in the FUL gene (i.e. second endogenous DNA sequence) is selected from the group consisting of mutations listed in Table 1b or indicated by SEQ ID NO: 34 or SEQ ID NO: 38. Corresponding positions in allelic variants of AP1 and FUL are also included. More preferably, the point mutation in the AP1 gene (i.e. first endogenous DNA sequence) is a nucleotide exchange from cytosine (c) to thymine (t) at position 262 of SEQ ID NO: 2 or at position 6999 of SEQ ID NO: 1 or corresponding position in allelic variants of AP1, and/or the point mutation in the FUL gene (i.e. second endogenous DNA sequence) is a nucleotide exchange from cytosine (c) to thymine (t) at position 316 of SEQ ID NO: 4 or at position 19552 of SEQ ID NO: 3 or corresponding position in allelic variants of FUL. Consequently, the mutated AP1 gene (i.e. first endogenous DNA sequence) can have the sequence of SEQ ID NO: 39 leading to a cDNA according to SEQ ID NO: 35, and/or the mutated FUL gene (i.e. second endogenous DNA sequence) can have the sequence of SEQ ID NO: 40 leading to a cDNA according to SEQ ID NO: 36.

In an additional aspect of the invention the above described methods for producing a transgenic or non-transgenic *Beta vulgaris* plant can be combined. That means for instances that only one of the first and second endogenous DNA sequences have been mutated by introducing one or more mutations and the expression of the other, non-mutated DNA sequence is suppressed or silenced using the transformation approach as described above.

A further aspect of the invention is a *Beta vulgaris* plant or a part thereof produced or producible by any of the methods for producing a *Beta vulgaris* plant as described above.

The invention is described below with reference to exemplary embodiments and the accompanying figures purely for illustrative purposes.

BRIEF DESCRIPTION OF THE FIGURES

FIG. 6: Alignment of the amino acid sequences of the protein AP1 from *Beta vulgaris* (SEQ ID NO: 5) and from *Arabidopsis thaliana* (SEQ ID NO: 41) based on the EMBOSS Needle algorithm; BvAP1=*Beta vulgaris* AP1, AtAP1=*Arabidopsis thaliana* AP1

FIG. 7: Alignment of the amino acid sequence of the protein FUL from *Beta vulgaris* (SEQ ID NO: 6) and from *Arabidopsis thaliana* (SEQ ID NO: 42) based on the EMBOSS Needle algorithm; BvFUL=*Beta vulgaris* FUL, AtFUL=*Arabidopsis thaliana* FUL

EXAMPLES

1. Inhibition of Bolting and Flowering by RNAi Constructs Targeted to AP1 and FUL Identification/isolation and characterization/annotation of complete cDNAs of sugar beet for inhibition of bolting and flowering:

By analysis within a specially created proprietary sugar beet EST database, the 780 base pairs (bp) long cDNA (SEQ ID NO: 2) of BvAP1 as well as the 735 bp long cDNA (SEQ ID NO: 4) of BvFUL have been identified. In addition, corresponding genomic DNA sequences could be identified. An alignment of genomic DNA with cDNA shows the structures of the entire DNAs. AP1 consists of 8 exons and 7 introns, FUL of 8 exons and 7 introns.

A comparison of the resulting full-length DNA and the translated protein sequence shows only low sequence similarity with *Arabidopsis* homologs AtAP1 and AtFUL. At protein level the identity over the entire sequence length to AtAP1 is at 65.6% (see also FIG. 6) and to AtFUL is at 57.3% (see also FIG. 7), at cDNA level the identity AtAP1 is 71% and to AtFUL is 72% (see Table 2).

TABLE 2

Sequence comparison of BvAP1 and BvFUL with *Arabidopsis thaliana* (At)-AP1 and -FUL-candidates based on the protein sequence and cDNA. Results given as sequence identity based on the EMBOSS Needle algorithm (www.ebi.ac.uk).

| | AtAP1 protein (SEQ ID NO: 41) | AtFUL protein (SEQ ID NO: 42) | AtAP1 cDNA | AtFUL cDNA |
|---|---|---|---|---|
| BvAP1 protein (SEQ ID NO: 5) | 65.6% | | | |
| BvFUL protein (SEQ ID NO: 6) | | 57.3% | | |
| BvAP1 cDNA (SEQ ID NO: 2) | | | 71% | |
| BvFUL cDNA (SEQ ID NO: 4) | | | | 72% |

Production of RNAi constructs targeted to AP1 and FUL and inhibition of bolting and flowering in sugar beet:

For the production of RNAi constructs the sequences of SEQ ID NO: 19 to 22 were synthesized. Sequence of SEQ ID NO: 19 includes a partial sequence of AP1 according to SEQ ID NO 10 with a length of 184 bp and a partial sequence of FUL according to SEQ ID NO 14 with a length of 212 bp. Sequence of SEQ ID NO: 20 includes a partial sequence of AP1 according to SEQ ID NO 11 with a length of 150 bp and a partial sequence of FUL according to SEQ ID NO 15 with a length of 150 bp. Sequence of SEQ ID NO: 21 includes a partial sequence of AP1 according to SEQ ID NO 12 with a length of 100 bp and a partial sequence of FUL according to SEQ ID NO 16 with a length of 100 bp. Sequence of SEQ ID NO: 22 includes a partial sequence of AP1 according to SEQ ID NO 13 with a length of 50 bp and a partial sequence of FUL according to SEQ ID NO 17 with a length of 50 bp.

For the further processing the sequences have been amplified by PCR using PCR Primers with SalI/SmaI restriction sites like primers according to SEQ ID NO: 25 (forward) and 26 (reverse) for the amplification of SEQ ID NO 19. The PCR was performed using 10 ng of genomic sugar beet DNA, a primer concentration of 0.2 micron at an "annealing" temperature of 55° C. in a Multicycler PTC-200 (MJ Research, Watertown, USA).

Figure 1:
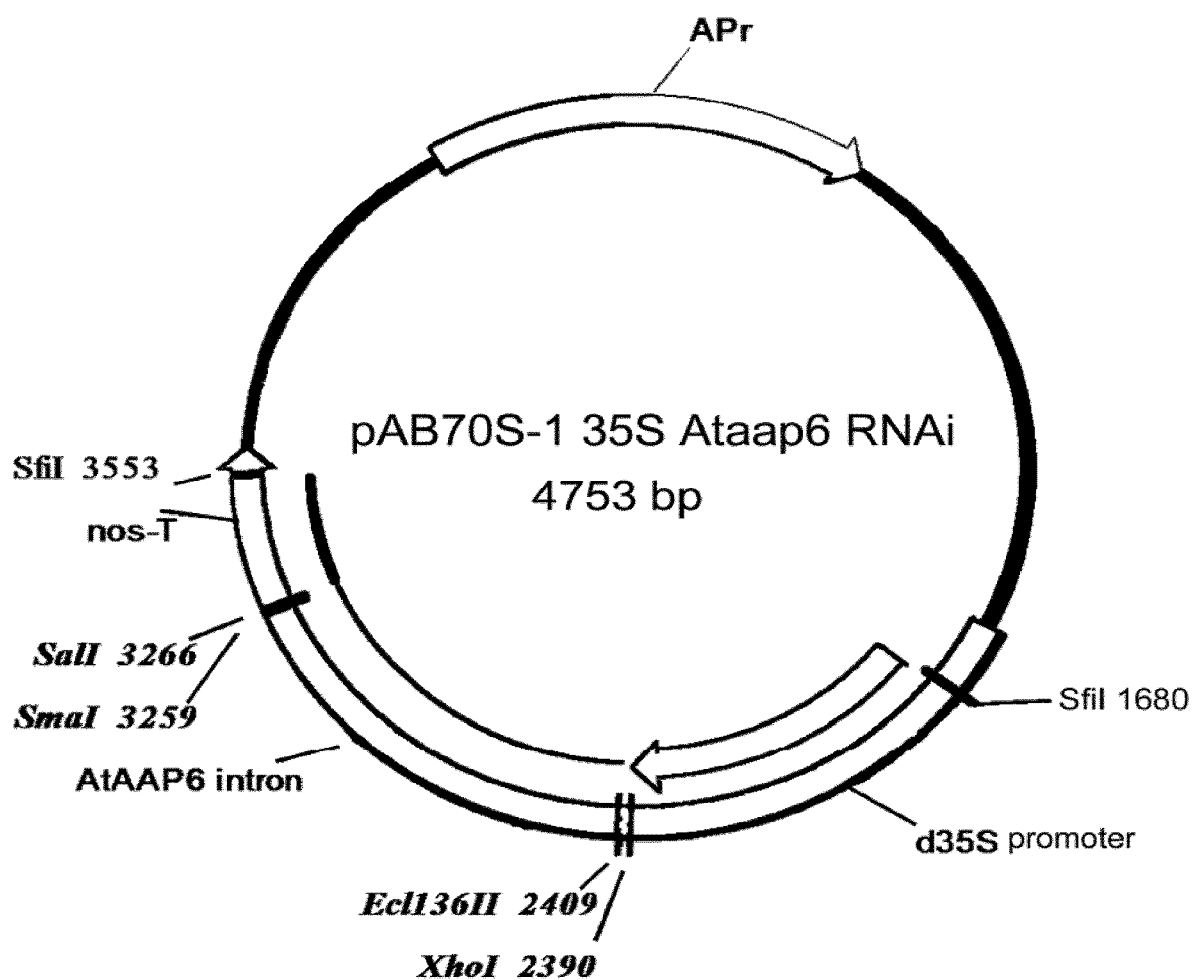
FIG. 1: Schematic structure of cloning vector pAB70S-1 35S Ataap6 RNAi

The PCR products were each integrated into the vector pAB70S-1 35S Ataap6 RNAi (FIG. 1). The vector is designed for the production of "intron-spliced" hairpin structures. The vector contains the d35S promoter for constitutive expression, the ATAAP6 intron from *Arabidopsis thaliana* and one polyA terminator (nos-T). The ATAAP6 intron is flanked by the interfaces or cleavage sites XhoI/Ecl136II on the 5'end or by the restriction cleavage sites SmaI/SalI at the 3'-end. This enables the integration of identical fragments in a "sense" and "antisense", if these fragments have the compatible restriction sites XhoI or SalI, or are stumped on the other end ("blunt end"). For this the original PCR products were reamplified with new PCR primers extended beyond these restriction sites. For further use the PCR fragments were cloned into the TA cloning vector pCR2.1 (TOPO TA Cloning Kit (Invitrogen, Carlsbad, USA)) and transformed in *E. coli*. A blue-white selection enabled the identification of recombinant plasmids (Sambrook et al. 201, in Molecular Cloning. A Laboratory Manual, Cold Spring Harbor Laboratory Press, 3rd edition, New York). In the white colonies the expression of ss-galactosidase is suppressed by an insert, which results in white colonies, because the enzyme substrate added to the medium is no longer cleaved. After a subsequent sequencing with M13-fwd/rev-primers, the analysis and the alignment of the sequence data was performed using the program Vector NTI (Invitrogen, Carlsbad, USA).

Figure 2:
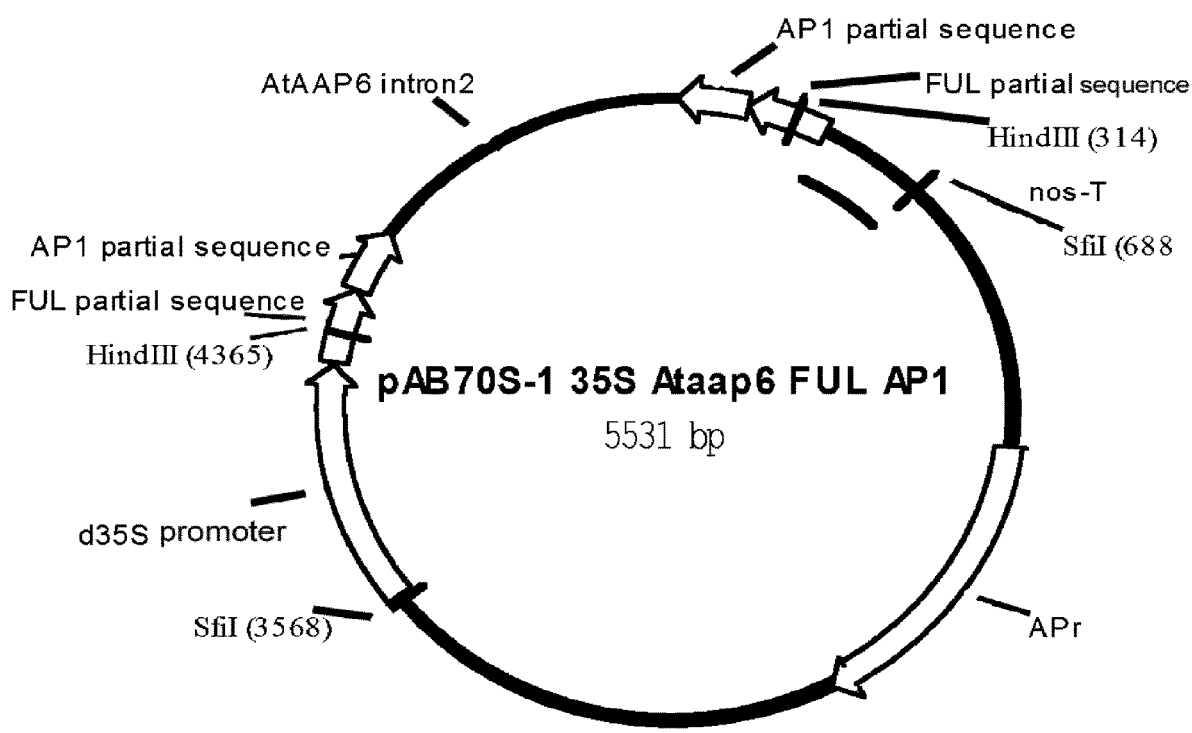
FIG. 2: Schematic structure of cloning vector pAB70S-1 35S Ataap6 FUL AP1 including partial sequences of AP1 and FUL

The fragments Sal-SmaI and XhoI-SmaI-were each cut from the topovector by SalI/SmaI or XhoI/SmaI and then subsequently first ligated "in sense" with the SalI/SmaI or XhoI/Ecl136II cut pRTRNAi vector. Subsequently, the same fragments were religated for a second time in "antisense" in the compatible XhoI/Ecl136II or SalI/SmaI. The cloning resulted in, for example, pAB70S-1 35S Ataap6 FUL AP1 (FIG. 2).

Figure 3:
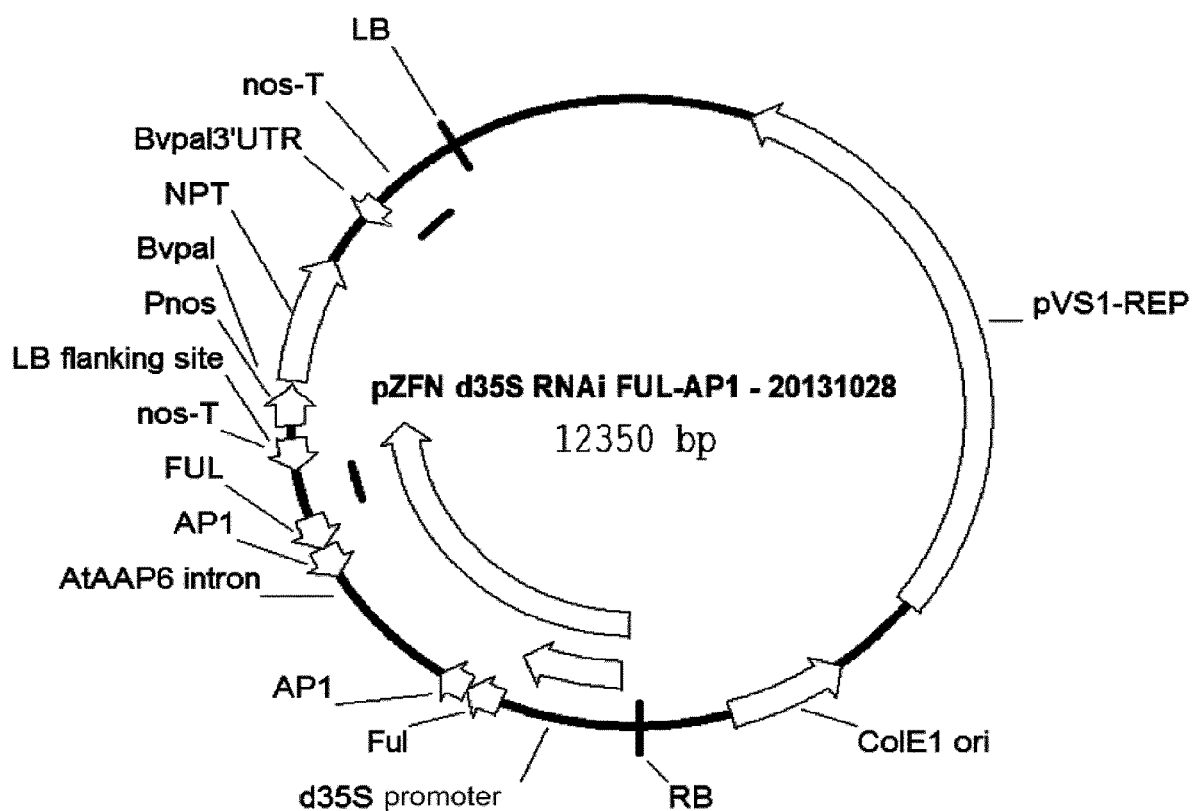
FIG. 3: Schematic structure of binary Ti-plasmid pZFN d35S RNAi FUL-AP1 including partial sequences of AP1 (212 bp) and FUL (184 bp) used in *Agrobacterium*-mediated transformation

Production of transformation constructs and sugar beet transformation:

For plant transformation the binary vector pZFN was used. The expression cassettes were cut using SfiI to transfer it into the binary vector pZFN to create pZFN d35S RNAi FUL-AP1-212-184 (FIG. 3), pZFN d35S RNAi FUL-AP1-150-150, pZFN d35S RNAi FUL-AP1-100-100, and pZFN d35S RNAi FUL-AP1-50-50. Each of the binary vectors was transformed in *Agrobacterium tumefaciens* strain GV3101 pMP90 by a direct DNA transformation method (An, G. (1987), Ti binary vectors for plant transformation and promoter analysis, Methods Enzymol. 153, 292-305). The selection of recombinant *A. tumefaciens* clones was performed using the antibiotic streptomycin (50 mg/l). The transformation of sugar beet and regeneration were carried out according to Lindsey et al. (1990) and Lindsey et al. (1991, "Regeneration and transformation of sugar beet by *Agrobacterium tumefaciens*, Plant Tissue Culture Manual B7: 1-13, Kluwer Academic Publishers).

The transgenicity of the plants was verified by PCR. The use of designed primers led to the amplification of a particular DNA fragment from the nptll gene. The PCR was performed using 10 ng genomic DNA, a primer concentration of 0.2 micron at an annealing temperature of 55° C. in a Multicycler PTC-200 (MJ Research, Watertown, USA).

Verification of the flowering and bolting behavior of the transformants:

For each of the RNAi constructs five transgenic sugar beet lines were regenerated carrying the corresponding binary vector pZFN d35S RNAi FUL-AP1. The sugar beet plants were grown for several weeks in sterile culture media, propagated and then rooted together with non-transgenic isogenic controls. 7-9 plants per line and control were transferred to the greenhouse. The transgenic lines were grown in pots and then tested in different vernalization regimes to determine the bolting and flowering behavior. After an adjustment period, the plants were subjected to vernalization for three, four and six months at 8° C. in a cooling chamber (winter simulation). Subsequently, the transformants, as well as identically treated non-transgenic control plants, were transferred back into the greenhouse (25° C.). Shortly after transfer, already after 10 days, the control plants began to grow shoots. After 4 weeks the control plants began to bloom. In contrast, several transformants lines showed surprisingly no response to the shoot and flower induction by vernalization. Hereunder were lines of each used RNAi construct.

Thus, the resulting transformants behaved like not-vernalized sugar beets. They neither developed shoots nor blooms. None of the plants showed deviations from the normal phenotype. The plants were cultivated further; they continued to develop to normal beets with normal beet bodies.

These lines were again tested in a greenhouse supplied with soil for optimal root growth without temperature control in two winters (2013/2014; 2014/2015). None of the plants did bolt or flower.

Surprisingly, using the inventive approach, the vernalization or its effect, namely the bolting and flowering, were completely blocked in sugar beet.

2. Inhibition of Bolting and Flowering by RNAi Constructs Targeted to AP1, FUL and VIL1

For this approach an RNAi construct comprising partial sequences of AP1 and FUL cDNA was extended by a third partial sequence of 399 bp based on cDNA of the BvVil1 gene from *Beta vulgaris* (WO 2011/032537). VIL1 was chosen due to its involvement in flower formation.

PCR product BvVil1 RNAi was amplified using a forward primer according to SEQ ID NO: 27 and a reverse primer according to SEQ ID NO: 28. BvVil1 cDNA was used as template. The amplification led to a VIL1 cDNA fragment according to SEQ ID NO: 29. Additionally, PCR product BvFUL-AP1 was synthesized and amplified using primers according to SEQ ID NO: 25 and 26. Vector pZFN as described above was used as template. The amplification led to a FUL-AP1 cDNA fragment according to SEQ ID NO: 30.

Figure 4:
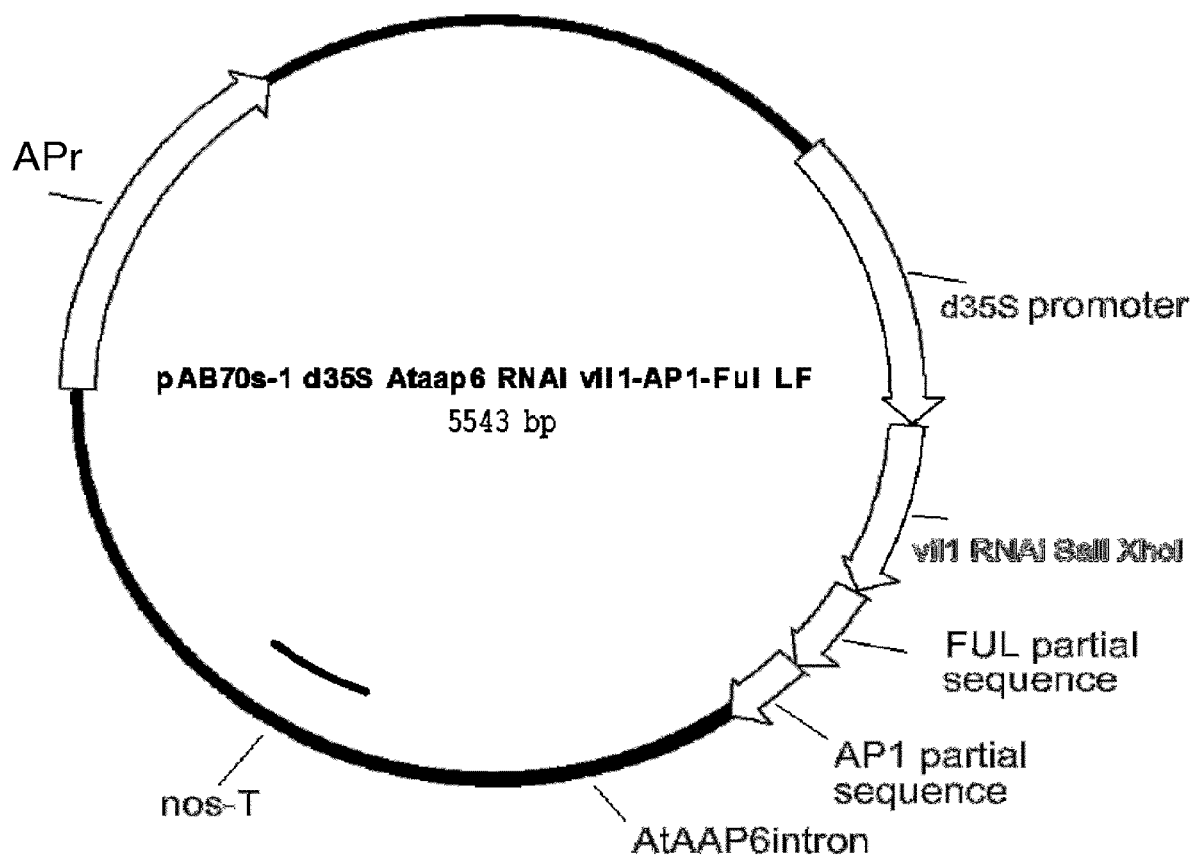
FIG. 4: Schematic representation of cloning vector pAB70s-1 d35S Ataap6 RNAi vil1-AP1-FUL LF including partial sequences of AP1, FUL and VIL1
Figure 5:
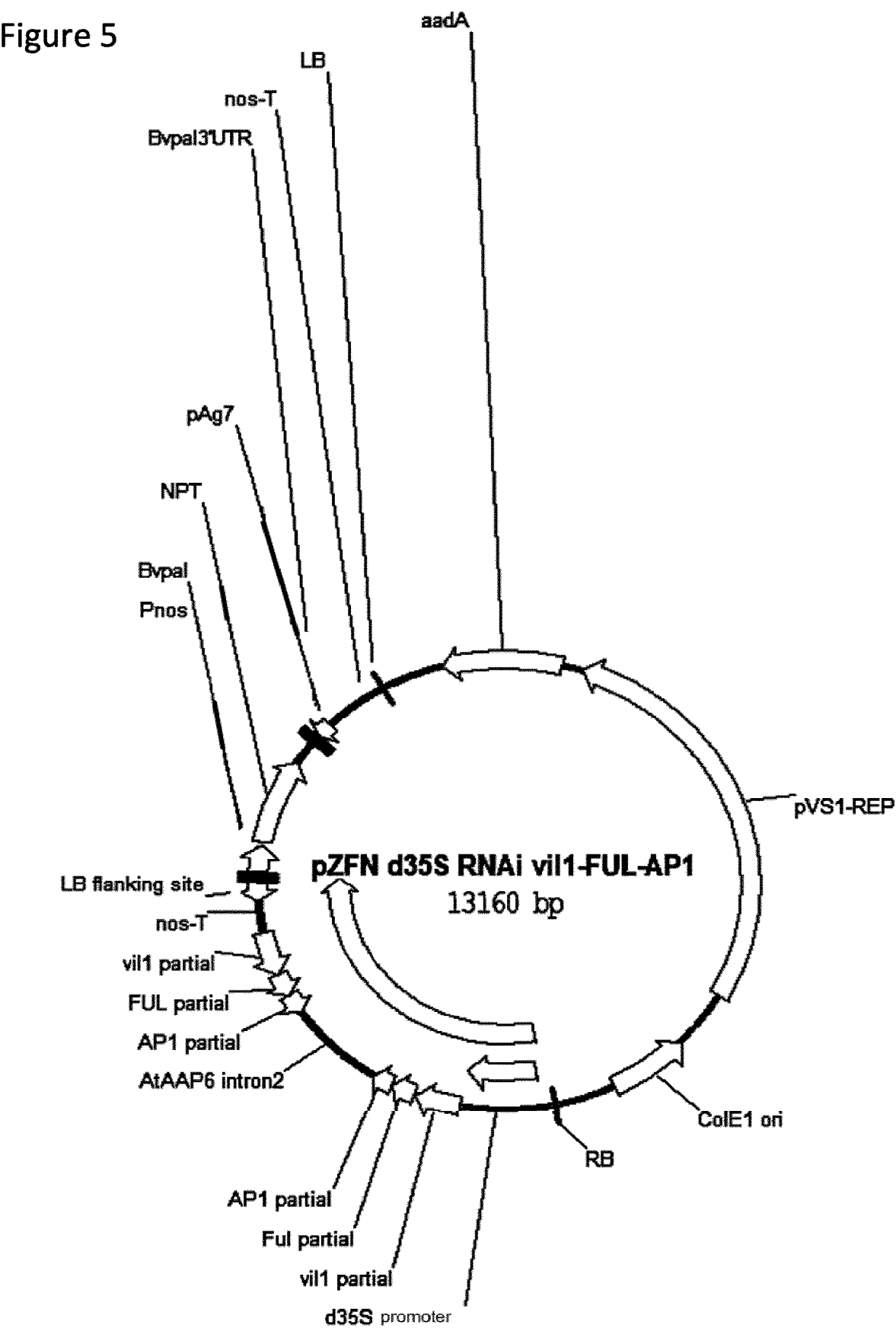
FIG. 5: Schematic representation of the binary Ti-plasmid pZFN d35S RNAi vil1-FUL-AP1 including partial sequences of AP1, FUL and VIL1 used in *Agrobacterium*-mediated transformation

Both amplified DNAs were cloned into vector pAB70S-1 35S Ataap6 RNAi (FIG. 1). PCR product BvVil1 RNAi was cloned using Ecl136II and XhoI. PCR product BvFUL-AP1 was added using XhoI and SmaI. The resulting intermediate pAB70s-1 d35S Ataap6 RNAi vil1-AP1-FUL LF (FIG. 4) was used for another PCR step. The vector pAB70s-1 d35S Ataap6 RNAi vil1-AP1-FUL LF was used as template for forward primer according to SEQ ID NO: 31 and reverse primer according to SEQ ID NO: 32. The PCR product was an RNAi construct which then was cloned into the vector using SalI and SmaI. The resulting vector was cut using SfiI and cloned into vector pZFN resulting in vector pZFN d35S RNAi vil1-FUL-AP1 (FIG. 5).

Vector pZFN d35S RNAi vil1-FUL-AP1 was used to transform *Agrobacterium tumefaciens* Gv3101 pmp90 which subsequently was used to generate transgenic sugar beet lines. Transgenicity was confirmed by PCR. After regeneration nine plants of one line were rooted as described above. After vernalization in the greenhouse none of the plants did bolt or flower.

3. Inhibition of Bolting and Flowering by Knock-Out Mutants of BvAP1 and BvFUL

Mutagenization of sugar beet cells and identification of BvAP1 and BvFUL mutants:

A sugar beet mutant population has been created by treatment with different EMS concentrations for different durations of incubation. From treated cells M1 plants could be regenerated. Through selfing of the M1 plants several thousands of M2 plants were grown.

These M2 plants were screened for knock out mutations in the BvAP1 gene and the BvFUL gene. For that, DNA was been extracted from collected leaf samples and analysed by use of designed primers. Thereby, point mutations in the genes which introduce additional stop codons into the coding sequence of the genes could be identified. One plant showed a point mutation in the AP1 gene which is a nucleotide exchange from cytosine (c) to thymine (t) at position 262 of the cDNA (SEQ ID NO: 2) or at position 6999 of the genomic DNA (SEQ ID NO: 1). A second identified plant contained a point mutation in the FUL gene which is a nucleotide exchange from cytosine (c) to thymine (t) at position 316 of the cDNA (SEQ ID NO: 4) or at position 19552 of the genomic DNA (SEQ ID NO: 3).

Verification of the flowering and bolting behavior of single mutants:

Cells of the identified sugar beet mutants were cultured for several weeks in sterile culture media, propagated and then rooted together with non-mutated controls. 5 plants per mutant and control were transferred to the greenhouse. The mutant lines were grown in pots and then tested in different vernalization regimes to determine the bolting and flowering behavior. After an adjustment period, the plants were subjected to vernalization for three months at 8° C. in a cooling chamber. Subsequently, they were transferred back into the greenhouse (25° C.). Shortly after transfer, already after 11 days, the control plants as well as the mutant lines began to grow shoots. After 4 weeks all plants began to develop flowers.

Verification of the flowering and bolting behavior of double mutants:

F1 progenies of a cross of AP1 mutants with FUL mutants have been analyzed for identification of plants carrying the mutated AP1 gene and the mutated FUL gene. Two F1 plants could be detected which then were selfed to generate a F2 population. Selected plants of the F2 generation have been tested in greenhouse as described above. Shortly after transfer, already after 10 days, the control plants and most of the selected plants began to grow shoots. However, a few plants showed surprisingly no response to the shoot and flower induction by vernalization. These non-bolting plant were all homozygous for both of the identified point mutations in AP1 gene and FUL gene, expect two of the plants which showed a heterozygous genotype for at least one of the mutation.

SEQUENCE LISTING

```
<160> NUMBER OF SEQ ID NOS: 42

<210> SEQ ID NO 1
<211> LENGTH: 21668
<212> TYPE: DNA
<213> ORGANISM: Beta vulgaris
<220> FEATURE:
<221> NAME/KEY: misc_feature
<222> LOCATION: (9833)..(11385)
<223> OTHER INFORMATION: n is a, c, g, or t
<220> FEATURE:
<221> NAME/KEY: misc_feature
<222> LOCATION: (12467)..(12605)
<223> OTHER INFORMATION: n is a, c, g, or t
<220> FEATURE:
<221> NAME/KEY: misc_feature
<222> LOCATION: (13741)..(14088)
<223> OTHER INFORMATION: n is a, c, g, or t
<220> FEATURE:
<221> NAME/KEY: misc_feature
<222> LOCATION: (16396)..(17194)
<223> OTHER INFORMATION: n is a, c, g, or t

<400> SEQUENCE: 1
atggggagag gaagagtgca gctgaagagg atagagaata agatcaacag acaagtaact      60
ttttcaaaga gaagaagtgg acttgtgaag aaagctcatg aaatttctgt tctttgtgat     120
gctgaggttg ctctgatcat ttttttctcac cgaggaaaac tctttgagta ttcttctgat     180
```

```
tcttcgtaag tatatatata tatatattaa tagtaactac ttgttttctg ctttctattt      240
ttaggtctga tgcatattta atttaggtaa tattaattcc ttatatctga tccttaattt      300 tttttctt taccatttca tttttgtttg ttttgaataa agaaaatttt cccttcacg         360 tgtgtcgaat aggtcaaaat ttttacttga aggatgttct ctttgattac taaaatagga     420
tccaacaatc acctgaaata aaggaagaag atggtgcaaa gttttactg tcatacttag      480 tatttgataa atattctatg atgaacttgt ataaattagg aaatagacct aactttcatg     540
cacgaaaaca ttattccttc attcaatttt tttattactt aaggatttac ttttttattg     600
atcatatgaa gtagtagtac ttgtaatcat tcaattttt tgttggttaa ataggactac      660 atttaaaac aacccaattt taaaatttt tgtgtgaatt tcttcccttt ttaaaaataa       720
agtctattat catagcttag agtagctgtg gcaaagctag acgaaataat acagaaatct     780
ggaaaggaaa ttgtactact tacatgaaca cacttattta ttacttgcat gatatctgcg     840
aaaaagttta tagcaaattt ggttaatata tagcgtagta ctttggatat taatattact    900
agtgtacaaa tacttgatcc aatgggtaat gaaacttatg aagatttga ccatacatga     960 tgatgctaaa tattaattgt tattgtccag ctttgttttc cctccatcca ttggcatctt   1020
catctttaca ttgctactcc actcacttgt caattgtttc gtcctttatg ttctttattc   1080
acatgtgcac catacttcaa tactttcccc ttctttatcc tcagttttt tttcttgtca    1140 ttttagggtt aatatccaat gaatctagt ttgctcgttt tagatctaat tttaattcga    1200
tcacaaccat ccatattttt gtttcttagc ttgacatcta ttctatggat ctgggatctt   1260
cggtgtatag atgttctcgg ttttcagatc aagatcctat tcatagaccc atttattgta   1320
aacacttaaa tgtgttctta aaaagttagt ggctcgccaa gtcaactcaa taacataacc   1380
cccacgactt cattacatta cacaatgaaa gattagatgt atgagtttgt gaagcttata   1440
attctatttc aagtaggact aggatgtttt gtgcaatcag cagctagtag tcttttaat    1500 ttaagtcagt cttcattgtg catcatatat ttttagaaat atatgcaagt ttgaaaccat   1560
ttagaacctc atgacccgcc tgactcacta taaaccggca agagcttaat ttttcacagc   1620
tttgtatctt tatgagtagc gctagctagg ggtatgggca tagaaaaaaa gggtttgggt   1680
tagggtctta caagatctta tccgctattt ttatttcata atctttcaaa atacatgttt   1740
aataattcaa aatacatgtt taatactatc tccatttcac aacatatgca ccaattgcct   1800
agctatggtc caacctagtt ggtttgtagc ttgcattgga tggttaggat gtattggagt   1860
tgtttatgtg caatcaaatt ttaattacgt atcaaaaaaa aaaaaaaaaa aacatatgca   1920
ccaatttcca tttggacaca cttattgacc aatttttgac aatattttc tcaccatttt    1980 gtaagaaaaa tcaaaatcaa gtggaatttt gttaagtta tctcagtcaa aagattccat   2040
acatcgacat tttataattt ttaatcatac gcaattagaa atatcaatgt ctaaagaagc   2100
gtgttggaat acgtgaaaaa gcaaatgata catgaaacag atgtagtata tagaaaactt   2160
aattttgtgt cactcggatg tatgtgggcg gagccttcct agaaggcgta cccaccttag   2220
tggctctgaa tctttgacga cccgttcggt tggtggtgat aatagatggt aatagtaatg   2280
taatttagtc taaatttata aataaatatt aatatcatta cccatggtaa tacaagttct   2340
tcacaaaaca tgtttcattt aaaaattatc attactacct tttcaagtgg tattggatga   2400
taataaaatt ttaggcaggg aaatgggtat tgggatgaac attaccatgg gtaatgacat   2460 gcaattttg ttacaagaat acagtataat acattactat tgccaccatg tataaccatt    2520
aatcaaatgg accgtgagga tatgatgttg aagaagaagt cttaacctct acgctattat   2580
```

```
ttactagggt ctgtaaattt tccttttta  attataattc ttgtgaaatc ttcttcactg    2640
atggtactag cttattagga tgggtttctt tagtatattg aaggctcttg ttgacagagt    2700
ataaaaatat ttttggggtc gcaaccatca atttaaactt ttgtttgatt ataaaattat    2760
tttttgaaca tcaacaatct acttaaattt ttggttgagt tagttctttg acatggtatc    2820
acaaccatca tgacataaag gtctcatatt caaatctcat tcacctctca tttccaagta    2880
gaatatttac ctcaggtatg gtatgaggg  aggcttgtgt tgcatgagtc aataacggat    2940
cttgaccaat aatttaacag gggcgagttg ataaattaag ttttaatgta aaattttaaa    3000
tgatggataa aaacactaat acacaccaaa atataaatat acttttatta atggttacaa    3060
agagcttgta gctaatgtaa taaatcaaaa tcccaaaggt gcaatttta  agaaattatt    3120 tccatttatt tatttgacca ttatgaaatc ttcaagaaat tgagtaagtt tttaagaaat    3180
ttaaggtata gttcattaac taaataaact actccagtaa aaaaaaatta ccaaactgct    3240
ttcttaagta aaaaaataaa taaatttata ttttatgatt gttaggaatg agtgtgagga    3300
aataaaaagt actattatag ttaaataaaa atgaaagttc ttcagagaag aagaatagaa    3360
gatagtacaa tcaatgttaa atattttct  aaattagaca aattgatata aaccaaaaat    3420
aaaggggaag aagaaagaaa taagtaaaaa aagaaagaag gaaagaaaa  aaagaaaaaa    3480 gagaagcaag tgaagaaaaa caaagaagtc caaatgtgtg ttgatgcaag gttcgagctt    3540
gcaacattaa gggctcaaac tttcttttac actttggttc actgccaccg tgcccacagc    3600
ttgttatgtg acatgaagtg tagttttgctt aatttatctt atacagttat ggggggaccaa   3660 gcctccaccc gcccccttcta taatctgtca gtggttgcat ccacacttta agtccaatag   3720
actcttgtct gagaggaggt gatagagtat ataaatattt ttggggcctc aaccattagc    3780
tcaatctttt gattaagttg gttctgtgac acttgtacta tatactagtt atatatatac    3840
tgtaaaacta gtaccacgag aacagtcctt aatacaaaca acatgcccct aatagaattt    3900
tcttagtata cacttaatat aggttgacta gcttttttgcc cttcagtatg cacacacctt   3960
ttataatctg tatcgttgtc tggtagatga taataaacct cagtattggc aatatatgaa    4020
atgacataat ggccatgttt ggtgattaga gtttagagtt tagaggttac agttcagagt    4080
ttgtggttag atgattactt ttttgttcag aggatttgac tgctgattta aataattgtt    4140
gtgtaaaggt gtttggtaac acttagctta ttgtttagag ttttgtactt tttagagcat    4200 gtaaatgac  atttatggac atatgtattt ttttaaaaca aattttagta gtaattatat    4260
ggacaaaata gtcatttgtt ttttctctct ccaaaactct catgaaaaag ctcctctacc    4320 cagcttttc  aaaagagagt tttgatcaga gttttcggta caaaactctc tttagtcctc    4380
tctctcacca acaccccaaa ttagagttt  tattggtcaa aactctaaac tctctccaaa    4440
cctctaaact ctctctaaaa ctctctcccc caaacacccc caattctta  gaaaaatttg    4500 ttgctccttt ttattgcact atatttctat ctccaaacat aaagtttctt ttacaaattt    4560
tcatttctac tccataccac ctttatatgg caatataatt tctatgaatt aaaatgttca    4620
caagttttga ggtggatttc aagagcatgg acaatatgat catgagactc tccatacaaa    4680 aattacccctt aaattttata atcatacacc aagcggtcgt taaagtattg gaagtgcttg    4740
agtagtttgt gaaattaac  atataataaa gtgcagatct cccctctagt aagtagtaag    4800
aagtagtaag acgatgtccc tcatttgaga aagagaaaaa cccttatcag tttctcttgt    4860
ttctttgact gaacgcaagt caaatagaag tatgtaacta ggaaatcctt ggagaaatag    4920
```

```
attttctttta aaactataaa agtataccta tatatatggt aacccacaaa aatgtatata    4980
atctgatcaa tatctaaaca aagtattctt atgttttctt tcatcttgct tatttcctcc    5040
cttcccttt cttactttaa tttgtttact ctctttaact tatttctttg cgtatctcat    5100
ttcactttac aaggatatat agttgattat gacagcttaa taaatatatt ttggaactag    5160
gatttattgg ttgtcgttgt tatttaatt tctacactga tcggctagag tttctagaac    5220
atagggcttt attgaaacca ttagttaaca aaattgaatg acaatgattc aatatgatag    5280
aatatgtatg tattagttaa tgtttgatta ttgtttgtat gtatataatc aaagattatt    5340
tagtaatact tctatataca tattctatta gaatcactta gaaagaccca ttgaacaata    5400
ataaggatag gcagacaagc aaacaaaaga aaaataaacc tgttactcct tccatttctt    5460
aatgttctac tcggaattat agatacacac tttgacacaa attagaaaga gagtgtaaaa    5520
agtggatcca tattaatatt tttattttt taaatgagga gagaagtgtg ggtttattat    5580
gtttcaaggg agatagagag cattgaatag tgagagaata tgtgccaaag ataattaaat    5640
cattgtaaat cttttgccaa ataaagaata aagcatgtga gtaaaacttt aaaaaatggg    5700
cgaaaaagga aagttgagta gaactttaag agacggaagg aatatagaag aggacgtgac    5760
agatgggagg aagatcagac atcttagaag gggaatagtt aaatttgaga tagtctttta    5820
attaaggttc tcactaaaga agatataaca gtagggaaa gctaaaggtt attcaaaact    5880
ttccttccca tcttcatcac ttcatgtctt tactttagag ctcttaacac ttagcctatg    5940
aaattctgaa ctctttgtaa gattagtgat agataaaaga atcttatcaa tttaatttat    6000
aaatacaaca ggattcaata aaagatata gagatctata aataaagagc catactgttg    6060
tgaacttta tatctatcaa aacctttgca cattagacgt ggtataacta aatcaggctt    6120
atcgaaattt ttaaaattg ttttcattat agcccctta tatttagaag ttctaagatg    6180
attgcataga tagttgatgc accgttctgg tcgactttt taaacacttc tttttgataa    6240
attttttt tgtattcga atcattattt taggtgtata aagagctgca aatgatctag    6300
atgagattga tctcggtttc atttatatgc taatagtgtg ttagatacac actattaaaa    6360
aagtcatatg acttagagat tattatggaa aagggatagt gcaccgatat taatataatg    6420
gaaaatgaca cacgagttgt ccataataac atgtgaaaag tgaactattt aaaaggtttt    6480
tctgacctag tacatacaag gtgcgtaggt ttagctattt tagttttta gttttatttt    6540
ttaaagtgaa gttagttatt gatctgaaat catataacat gtacgtaccg tagatataaa    6600
aaactaccaa gtatatatca atttgaaata aacattattt taatatggca aaatcacaat    6660
tgttgactag acctaacact gaagaaaact atgtcatgtt tatcaattat gttgcataca    6720
gttaaaaaca aatatgttag agaaatcgtt atttgaaata gaaagttgc gcaaaatagt    6780
gattaacatc aaaatatgtt cagaaagttt ttataaatat gtgatcttgc attgtctgtt    6840
gactgtcgag gttatgata atttccccctt tttccaatgc aaaacttgtt gtgctatttt    6900
ctaatgatat attttttcaa agtatggaga agatcctaga aaggtatgag aggtattctt    6960
acgcagaaag acggctagct tcaaatgatc cagactcaca ggtagtgcat ttatgtaaat    7020
atagatatac tcttcatgcc caagaagcct gaattttta tcccactacg tactgcaaag    7080
ccaagtttaa ttgaataatt gtcctgttta aattatttag ttttcagtac aataatgtaa    7140
tcattagttt gcatgtttaa aaagaaaag cacaagttct gatcaagtga aatataaatt    7200
gtaacgaaag agccaagcta gacaattacc tagctaggag ttatttgtta tcgttttgt    7260
ttttaatttc tagttttttt ttttaaacta gaaaatatag tttcaatctt tgttatcag    7320
```

```
ttttcaaaat gacatattta acataaatat gattgatttt aaattcattt attatatcat    7380
atttcatttc aaaataagtg aaacacttgt ctcaaaaagc tcactctcac ataaatgata    7440
aaagtgtttc acttatttta aaacggaaga attatgactt ttacttttca taaaacgaaa    7500
aactgaaata tgacaataat ctcaaatagc ttggagaaac cagatttcta tatatttccg    7560
tgatgaaatc acttttcatt atacgtaggt aaactggacc tttgacttcg caaaactgaa    7620
ggcgaagctt gaacttctac aaaggaatca taggtatgat ggcaatatgt cataattttt    7680
ctattattat ttttgcttcc aaaaccagac catatgtttg tatatttata tagtgatata    7740
ctccatccgt ttcattttaa tctatacatt tacacttatc aggtatgtca atgcaaaatt    7800
ttgaggatat atatctttag ttttgtattt ataaaaatta taaaaagtac atattaataa    7860
aatacatatt atgatgaatc taacaagatc ccacatgacg atatttccgt ccgcgtatga    7920
ataacaaata atggccaaag tgaaatttgt gaatagtgta aaatatcaaa gtgtaacaat    7980
taaaataaaa cggagggagt agtacttgtt tgtcacatac ttacttatttt ttgttctctc   8040 cacaatgaaa ctgttctttc taataattaa aaaaagtgca tatgttgatg atttctctgt    8100
cactttaagt ggatattgaa tagtgataat ggattacttt gtgtataatt gcatttcaca    8160
tttgggtcta atttttatacc cttttcgcat atcatgcttt gtgaatagta catatgatgt    8220
tcaagaatgt gagaagacat atcatacttt tgatatacct caaacatggg tgtatactgt    8280
atagtgaacg aaagtgttag tgtaattttta tttaggaggt ttagtggttt gtcctatata   8340
taatgctagt agttatacac catagttgtt gatgagcatc aactggcttt cctaacattt    8400
ttttctccat aactttaccc ttaccttaca ttagattact ctaggattac attctaccta    8460
aaatattatt actcccatca ttttaggtaa atattttttac tttgatttttt cgattatttt   8520 caagagttta aaataatgat taaaatttac catgatcagg cactacttag gacaagagct    8580
tgactcactt aacatgaagg aacttcagag tttagagcaa caacttgata ctgctctcaa    8640
aaatgttcga tctaggaagg taagaaattt tacttgtcta ccgtagtttc ataataaatt    8700
agtatttggg ctcgggcttt gccccagatt ggtattgtct tttcaaattt gatatgcatt    8760
tttttccatt tccactaaaa tatattaaga aaattcaaca tttaaaggat acaaatataa    8820
taatgtggat acttaaagta tgattaaaat ttggttgaga tggtaattgt gtcatgtata    8880
atagcaagaa gtcacaagtt caaagctcgt tgcaagctaa atttattttt gttgattgac    8940
atgacttatc aacacactgg acaattctaa tcatctagtg gagtagcata tactagcaat    9000
ttatgcacgt gatgtgtgcc ttacttttttt agaaatataat ttataacttt tttgagcata   9060
aacaaaggta aaatttgaac attagacata tttttttggg ctagctaaat ttgttgttta    9120
aacctatatc acttaaccaa actcctcttt tattatttat tgatttatat tttatttaaa    9180
atttttaaaa ttaaaatgat gagcaataaa agaatgttaa gtagatttat taagtatttc    9240 ttatatttttt atcaacaaag tattttgtgt taattaaatt atttcacttt gttaattgat   9300
tgtattttcc ttttttaattt attacttgat tgtgtattga ttgatcaaac ataattttttt  9360 tgttaatttt tttatgctat atttgaattt attttttcttt catctgttttt tggtagagta  9420 gttgattttac taaagggtaa ttaaataaat ttattggggg acaccatagc tccccccctcc  9480 cttatataat agagatttgt atagatttat tgtcttcctc aattattgat taactagtct    9540
tctatgcacg cgatgcgtgt gttgattgtt tgggtctatt cttaatataa atttcatcaa    9600
aatataatta tagtagtgtg atttacaatt attgctatac aaactactgt aatttataaa    9660
```

| | |
|---|---|
| gttgttagaa attgagataa aaatttagat gtgaaatttt gtggtcaaat tatatttgta | 9720 |
| atttttaaa ctgagtaacc gttttctca tcatgtcaag ttactttgtt aatgcttatt | 9780 |
| taatttatta ttggaatttt tgacccatct ttaaattaga aaaggatata atnnnnnnnn | 9840 |
| nnnnnnnnnn nnnnnnnnnn nnnnnnnnnn nnnnnnnnnn nnnnnnnnnn nnnnnnnnnn | 9900 |
| nnnnnnnnnn nnnnnnnnnn nnnnnnnnnn nnnnnnnnnn nnnnnnnnnn nnnnnnnnnn | 9960 |
| nnnnnnnnnn nnnnnnnnnn nnnnnnnnnn nnnnnnnnnn nnnnnnnnnn nnnnnnnnnn | 10020 |
| nnnnnnnnnn nnnnnnnnnn nnnnnnnnnn nnnnnnnnnn nnnnnnnnnn nnnnnnnnnn | 10080 |
| nnnnnnnnnn nnnnnnnnnn nnnnnnnnnn nnnnnnnnnn nnnnnnnnnn nnnnnnnnnn | 10140 |
| nnnnnnnnnn nnnnnnnnnn nnnnnnnnnn nnnnnnnnnn nnnnnnnnnn nnnnnnnnnn | 10200 |
| nnnnnnnnnn nnnnnnnnnn nnnnnnnnnn nnnnnnnnnn nnnnnnnnnn nnnnnnnnnn | 10260 |
| nnnnnnnnnn nnnnnnnnnn nnnnnnnnnn nnnnnnnnnn nnnnnnnnnn nnnnnnnnnn | 10320 |
| nnnnnnnnnn nnnnnnnnnn nnnnnnnnnn nnnnnnnnnn nnnnnnnnnn nnnnnnnnnn | 10380 |
| nnnnnnnnnn nnnnnnnnnn nnnnnnnnnn nnnnnnnnnn nnnnnnnnnn nnnnnnnnnn | 10440 |
| nnnnnnnnnn nnnnnnnnnn nnnnnnnnnn nnnnnnnnnn nnnnnnnnnn nnnnnnnnnn | 10500 |
| nnnnnnnnnn nnnnnnnnnn nnnnnnnnnn nnnnnnnnnn nnnnnnnnnn nnnnnnnnnn | 10560 |
| nnnnnnnnnn nnnnnnnnnn nnnnnnnnnn nnnnnnnnnn nnnnnnnnnn nnnnnnnnnn | 10620 |
| nnnnnnnnnn nnnnnnnnnn nnnnnnnnnn nnnnnnnnnn nnnnnnnnnn nnnnnnnnnn | 10680 |
| nnnnnnnnnn nnnnnnnnnn nnnnnnnnnn nnnnnnnnnn nnnnnnnnnn nnnnnnnnnn | 10740 |
| nnnnnnnnnn nnnnnnnnnn nnnnnnnnnn nnnnnnnnnn nnnnnnnnnn nnnnnnnnnn | 10800 |
| nnnnnnnnnn nnnnnnnnnn nnnnnnnnnn nnnnnnnnnn nnnnnnnnnn nnnnnnnnnn | 10860 |
| nnnnnnnnnn nnnnnnnnnn nnnnnnnnnn nnnnnnnnnn nnnnnnnnnn nnnnnnnnnn | 10920 |
| nnnnnnnnnn nnnnnnnnnn nnnnnnnnnn nnnnnnnnnn nnnnnnnnnn nnnnnnnnnn | 10980 |
| nnnnnnnnnn nnnnnnnnnn nnnnnnnnnn nnnnnnnnnn nnnnnnnnnn nnnnnnnnnn | 11040 |
| nnnnnnnnnn nnnnnnnnnn nnnnnnnnnn nnnnnnnnnn nnnnnnnnnn nnnnnnnnnn | 11100 |
| nnnnnnnnnn nnnnnnnnnn nnnnnnnnnn nnnnnnnnnn nnnnnnnnnn nnnnnnnnnn | 11160 |
| nnnnnnnnnn nnnnnnnnnn nnnnnnnnnn nnnnnnnnnn nnnnnnnnnn nnnnnnnnnn | 11220 |
| nnnnnnnnnn nnnnnnnnnn nnnnnnnnnn nnnnnnnnnn nnnnnnnnnn nnnnnnnnnn | 11280 |
| nnnnnnnnnn nnnnnnnnnn nnnnnnnnnn nnnnnnnnnn nnnnnnnnnn nnnnnnnnnn | 11340 |
| nnnnnnnnnn nnnnnnnnnn nnnnnnnnnn nnnnnnnnnn nnnnntatat atatatttag | 11400 |
| ctaagaaaaa aaagacattt cattgggga taccataact ccccttagc ttatataata | 11460 |
| gagatactat acttcttttc tgatagtgtc aaatttaatt ataaatcttt aacattggcc | 11520 |
| aattaataat tggacaagaa aaaatgaga caataataaa taaggcgatc ttcacagacg | 11580 |
| tattaacatg atggtaatta aaatgttaa tcatagatct ttgtgttatc ttaataaat | 11640 |
| aaatttacta attagaatgt atcacataaa gtaagtatta atagcagcat aggataattc | 11700 |
| ttataatgga gattttatat ttttttatat aattatatga tttattgttg aaaatattag | 11760 |
| ttgatttaa ctggttgttt attcaatgac agaaccaact gatgcacgag tccatttctg | 11820 |
| aactccagaa gaaggtaata actccatttt ttactctcaa aggtttattg ttttaactt | 11880 |
| atttcttcta accttttata tatgagaagg tattgggtta gacgcgtctg accataaat | 11940 |
| taggtcggat gactttcagt tggtttcaat tttatttcag ttggtttcaa tttttgtcca | 12000 |
| gttggtttca atttttgttc agttggtttc aatttttttt agctggtttc aatttttgtt | 12060 |

```
cagttggttt caatatttt tagttgatct tttttattc agttggatgt cttttaagtt    12120
cagttactta tcttattgtt tcatttacgt gttttattgt aactgaaaac aaaacttaag    12180
taaatgaaat aaaataagtt ctaaataaaa gcaacttagg gcctgttctc cccagcttat    12240
tttcagttca gttcaattca gttcagttca attcaattca tttcagttca gttcagatca    12300
gatcagttca gttcagatca gatcagttct tgacaatact tttactctca catatcacta    12360
ttcatttcag ttcagttcaa ttcaattcag ttcagttcaa ttcagtttag ttcagttcag    12420
ttcagttcaa ttcagttgtt ttatgccgaa gagaacaggc ccttagnnnn nnnnnnnnnn    12480
nnnnnnnnnn nnnnnnnnnn nnnnnnnnnn nnnnnnnnnn nnnnnnnnnn nnnnnnnnnn    12540
nnnnnnnnnn nnnnnnnnnn nnnnnnnnnn nnnnnnnnnn nnnnnnnnnn nnnnnnnnnn    12600
nnnnnattca tttcagttca gttcaattca attcagttca gttcaattca gtttagttca    12660
gttcagttca gttcaattca gttgttttat gccgaagaga acaggcccct agttttcagt    12720 tactatatt atcgtttcag ttagttttct tattctttca tttaacaact aactaaaata    12780
aaaaaaaaaa aactaactga aagcaaaact taattaaatg caaaaaatta agttctaaat    12840
gaaaccacat acgatcgaaa tttcaatcat ttcaaacatt atggtgtttt cgattctttc    12900
aaagaaggca agctgctccc gctattctac cctctttaga tcacaataaa gctcaggcct    12960
cacattcaaa gttcctcaa agatggacgt tccaagtatc acatagacac atagtcctct    13020
tctccaaacg ctctccttcc tatcttgatg tcattagcaa acttcttgat ccagacggcg    13080
ccaacaaccg caccatgatc tccctctaaa gtactgacgg cccgtttggt tgttggtcat    13140
aaatgatggt aatgggaatg aagttgtgtg taaatttgtg aaaaatatca ttgtccattc    13200
ccatggtaat gctaatttat cttaatgtgt ccactttcct tctagaattt tcattctcat    13260
ccaataccac cttgtaaggt ggtaatgagt ggtaatgaaa attgcttccc cttggagaca    13320
aaaatacaag tttaggagtg agattgattg ctcatggaga aaaaaagtct ccccatggag    13380
atattaaggg tgattcccta ataaaattac acttaaaatt tattcccatt accgcaattt    13440
attaacatct accaaacggg ccgtgaaagt cttgaaacac atagtcgagt gagtagcttt    13500
gaggaaccat ctgtaaaaga acctgaggga gccaatgtgt gcgtaagtac caacggcgtg    13560
ttgtcagtgg aaaaggtggt gccgtggtgg cactcagtag tgatggagcc gccgtggtgt    13620
ttgagtgttg ccaaatacaa aggcggaatt tcgtaatctc taatttcttc tgtgaaattt    13680
ttgggatcag cctgtccgac caaacacatt ggatcaaacg gtctgaccca atagtttcaa    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnga tataaataga    14100
gatggaggac aagggtcttg gttttgtcat gttgtcaaag agttgaacaa tggttttttc    14160
gtattgttaa aaaattaaaa aaccagaggc cttcaatctc ttgatagata tagatagaaa    14220
aggaggacaa ggccgttctt ggttttgtta tattgtcaaa gagttgaaca atgatttttt    14280
cgtgttgtca aaaattaaa caatgaaaaa agatggcggg tgcttgatct aatagatcgg    14340
accatggatt gaaggtcttt taacttattt tatatatata ttgaacttat ctgaagatta    14400
```

-continued

```
tttaactctt tgaaattgta ttaacttccg aactttatga acttttttaa ttcttcaaaa    14460
cttatctaca ttttatttga aaaaatattg aagacaaaaa aaccctcagt tggtttaaag    14520
ctgcggtaag atagagtgta aatgttattt tttttttatta aatcaagaaa taaaaagaaa    14580
tattaaataa aaagaattaa aaatggaaat gatgacagaa acttatggct tggaggagca    14640
atacttttaa gatagaccta aaccttaaat aagttaaaat ggaagtaatt tttcagtaga    14700
atcttattcc aatctatact ccgtgtttac tccatgtaat gcacatataa taaaaaaatt    14760
agaaattaca tagtataagg tttgatcctg tgactgtaag tttatatact aacttcttaa    14820
ccactagagc aagtgatatt tagtgttatc attttaaagt ataattttaa caaatgaaat    14880 tttttttctta cccggaacat agctcggacc taataactag ttgaacaatt ataatctgta    14940
acttaaaatg atcctaatta ctgtactttc attacctata ataatagaat cttactatca    15000
ttggttcaga aaaaaaaaat cttattaaat gttaaccatt tatttgtaat tgaaacatac    15060
atgcacataa atgtaacttt tagtttatct taacttaaaa actgagaaaa tgttagttgg    15120
aaacttttgt atatatgttt ggataaacga cgctcaaaag tagggctaa aattttagta     15180 gataatataa gattatactc catctgttct agatagactt ctcatttta attttggcag     15240 tattcataaa taaggaaat cttttcaaaaa aatttccaat ataagaaa aaaataatc       15300 atgtgcggtt ttgtttgatt cgtctcattg tgtacattag gaaaattaaa cttatataat   15360
ttttactact atgtaattaa agatattaac gatacaaaat gtgtattgac aaacttatat   15420
tggagtaata ggaagtctat taagggaccg aagaaatatt acgtaaataa atctaataca   15480
aactaatata aattctactc cagacaataa agattctgtc ttatattgcc aagatatagt   15540
agctatttat tttatcttaa caaacataaa tgtttctaat gcttaaacat ggacatgtat   15600
tattttgtaa aatattatgt attatccaaa gttacatatt taaaggaagt tctattgctt   15660
gctctctttt agcactgccc aaaaaggtta aagtaatttt ttttctctgt ttaaaaaaaa   15720
aatgcattat atacagataa ttttttgctag tcaataaagc tatccttatg acttatgagt   15780
gctacttgac tagggatgtg ttgtactcaa ttggaggtat acatacacca agattataga   15840 gctttttattt tgcctataaa aaatggaagc cggataggat accaaaaaag ctttgactta   15900
aatttgtaat gcataaaaat gatgatacct aacttattag ccatacttat ctaagcgtac   15960
gtcaatttaa atattgtgtt attgattaat aatgatcctt atatatccat attttgacaa   16020
ttaaacggta aattagagag aaaagtttga gaaaataatt atagcttacg taatgctata   16080
atccaaagtg tctccgcaca agcgtgggac aaaatagtac tttcggagaa gttacaatca   16140
acagctaggg agtcttcatt gttcttgaat agaaggatgg aaacaaagtt caccttcttt   16200
tattaaagta ttaaggtttg ttattagctc aatatccaat actttctctg ctttttatta   16260
cttcgtctgt ttcaaattaa atgattttt ttttatttta cactattttt aaatttcact    16320
tttaccatca tttatgattt atatgtgaat gaaaacatag ttacgtgtga tcttgttttt    16380 ttttttttt tttgtnnnnn nnnnnnnnnn nnnnnnnnnn nnnnnnnnnn nnnnnnnnnn    16440
nnnnnnnnnn nnnnnnnnnn nnnnnnnnnn nnnnnnnnnn nnnnnnnnnn nnnnnnnnnn    16500
nnnnnnnnnn nnnnnnnnnn nnnnnnnnnn nnnnnnnnnn nnnnnnnnnn nnnnnnnnnn    16560
nnnnnnnnnn nnnnnnnnnn nnnnnnnnnn nnnnnnnnnn nnnnnnnnnn nnnnnnnnnn    16620
nnnnnnnnnn nnnnnnnnnn nnnnnnnnnn nnnnnnnnnn nnnnnnnnnn nnnnnnnnnn    16680
nnnnnnnnnn nnnnnnnnnn nnnnnnnnnn nnnnnnnnnn nnnnnnnnnn nnnnnnnnnn    16740
nnnnnnnnnn nnnnnnnnnn nnnnnnnnnn nnnnnnnnnn nnnnnnnnnn nnnnnnnnnn    16800
```

```
nnnnnnnnnn nnnnnnnnnn nnnnnnnnnn nnnnnnnnnn nnnnnnnnnn nnnnnnnnnn    16860
nnnnnnnnnn nnnnnnnnnn nnnnnnnnnn nnnnnnnnnn nnnnnnnnnn nnnnnnnnnn    16920
nnnnnnnnnn nnnnnnnnnn nnnnnnnnnn nnnnnnnnnn nnnnnnnnnn nnnnnnnnnn    16980
nnnnnnnnnn nnnnnnnnnn nnnnnnnnnn nnnnnnnnnn nnnnnnnnnn nnnnnnnnnn    17040
nnnnnnnnnn nnnnnnnnnn nnnnnnnnnn nnnnnnnnnn nnnnnnnnnn nnnnnnnnnn    17100
nnnnnnnnnn nnnnnnnnnn nnnnnnnnnn nnnnnnnnnn nnnnnnnnnn nnnnnnnnnn    17160
nnnnnnnnnn nnnnnnnnnn nnnnnnnnnn nnnngtacat caaggaaatt tgcattaatg    17220
aaaaacggga gtacaaccta atggtaatac aaccaaacta aacagaaaga agaaacaaca    17280
gacagtaaga aaacctctat aacgcgtaaa aacaatttaa cataaacact aactagaaaa    17340
agtccaggcc gaataacatt tgtcttgtgc gatggggagg gaagatgaag gagagtgaaa    17400
atctgttgaa agacacaact ctgacgatct tcatagagag attgtcgtac aactgctagt    17460
agatcctgtc cactaggcac gaaatcccaa ggtccttgat gagcctcctg ggattctcct    17520
gattcgttga acaaagaagt cactttcgag agtaacttcg gaccctgctg cgagggtctt    17580
cgaaaatcag tcacattaga ctgaaacccg aaaaacaagg tggaggtctt gacgtgcccc    17640
aaaacaagtt gggggcgtcc cacaagatgc gttttttagg tgtgatgaca catgatgtca    17700
tcacgagaaa ttggggcgag ttagtttgat gaactacgcc ccactgacgg atcctaagat    17760
ccaaagtgac aatctcgaaa ccagaagacc gacaaacaac agatctgaaa catacaaaca    17820
tgaaaataat gaaagcataa actgccaccc gacatataga gctccggcaa acaacaccat    17880
caagaacttg caccaaagac ttccttggca tactaaagac actgattcca actaacacta    17940 gcggggacg gggaagggac actcgactac acctaaacct aaccagggga cggggaaggg    18000
gaacttagac taaaccttcg taaaagggg gggatcgggg aggggaaaac cttgaccaag    18060
gaagctggtt ttaaaaacca cttagccgag ccaaaaaccg tgggtgggaa gaagaaacag    18120
accacaaaca gggggaaccg ggggatggga actcaccgaa caggggaggg ggagaaatcg    18180
cacagactcg gggaacgcct aaggactggg ggacgaccaa cgaacgaaag gttgggggtgg    18240 tgcgaaaaca agggaggggg acgcaccgac gaacaaaaaa accgacgaag aggccgaaaa    18300
agcgaaaggc cgacggagat aagattgaaa ggcgacgaaa aagaaaaag gaacaaaacg    18360 aaagaaaaac gaactcgtcg gagacccgcc ggagacctac gcggcgccgg atctccggcg    18420
agttctaggg ttagagggtt tgttgtgttt gtttaggag aaggcagagg tttttttttt    18480
ttacgtgtga tcttgttaga tttgtcttaa catgtattct ttaatatact tttttttta    18540 taatttttgc aaatgcaaaa ttagagatat atgtcctcta aattttacat tcacatacgt    18600
gataaataag agtgctacaa ctaatttgaa acggataaag tatttgaatt gttttcatt    18660 taaaaaagtt cgctatcatt tataatgtta tatatttgcc aatatgttat ctctttctct    18720
ctcttaccag agtttagatc cagtagagtt agtaaataat tctaccacgt agagttgaac    18780
aaatcatagc cattgatttt caaatcattg gtttatatat tctttcccaa aactcccccc    18840
tattttcccc aaaaatcctc cccctcctta tctctttcca taaaatctga gtcgttgatt    18900
ttaaaatata aggtttggat tcaactccac tatgtagagt tttcatcaaa ctccaccgaa    18960
tccgagcccc tcctaccata gtacttcttg attccccat atttctttcc tcatcttggt    19020
cctcaagcac attttaatat tatgggtatt aaacaataga gaaagtattt acttatagag    19080
aaagtatttt caatgattcc ctaaattttt ttttgaaaga aagaaaaggg atttcattaa    19140
```

```
tatttcgcca aacggcactt acaagtcatt tctgaaaaac ataaaattct aaagaaata    19200 catatcaccc tagaaatgta aacatcgcag atttgactta attttgcctt aataaaaatc   19260
ttcatctgaa gcaatgcaat ctgtgagttc gctctggttc ggcatacgat ctgcagatgc   19320
ggaaattttg ggatgaacgt actccaatag tcttccataa ttttacagaa gttgtgaaac   19380
cctaattctt catgttgaat ctcgaacttc aaccaatgag ataatttct catacctaaa    19440 aacaaaagaa ccatactcac aactcccata ggggagaagg agatttccaa acagaaact     19500 aaaaaccca taaagggtt tgagaaaatc tcataaagag atactaatt attgaacaaa        19560 acaagaaaat gaactaaaaa ctgaaaataa aagggaaaaa ggggcttacc atggatgaaa    19620
acatccatgg cagcccccta attgatgaag aaggggtaag ggaggctagg gttttagaga    19680
gagaaaagga gaggggaggc taggttttaa aaaaaatat aatgattccc taaatttact     19740
tatatatatt taccaagatg acgtgatgtt ttacaaggcc catgattttt acgcgatcat    19800
gaaaaacaca gccaatttga atggagcaaa tatctacgcg tcattttaga tattttgta    19860 tgggaaagtt tttttttgacc aatgtaatta ttaagaagca tcggccaccg ggtagataag   19920
atgtcactat acatccttt ccaaacttaa gtatgcctgt tgaacttttg ttgcgtttgc     19980
agattcattt gaaattatat ttcctcagat cctctacttg taaaagaatg ttccattatt    20040
ttcttagttt acatgatatt tacaatagta tttgtctaca ttttgttcat attacttagt    20100
gatcagtgta tacgtcatat attagtttga actttgaaga catttatttt ctatatactt    20160
cctttgtctg ctaaattact ttggaaagct ttgtttttt tattaatata agacccttg      20220 gagtttggaa atcactatct aatgaaatat ataattcatc attagaacaa aaatacaaat    20280
atcgtactat cacctatcat gttccttttg gatttcgctt cacaaaaata catttaaaa    20340 aaaaataaaa taacaaatgg tagctaacaa cttattactt ttaaaagttt gtgtgcaccc    20400
taataagtac tcaaagtagt atgtaacaga gagagtataa tgctaaaata caaactaaat    20460
aaacaagaaa gtgtttctca acaataattt gctgcaggaa ttaggaaaca aagtaaataa    20520
attgcatgtt tatcatcaat acaatttact ggtagttaat tacaaacttc actcatgata    20580
attgaaagag gccactcaat ttcagctagg agttgtttat ttatttattt ttctttcagt    20640
taaattttga ctacccacaa aatcttcatc tggacctaat ctgcaatttg tggattttgg    20700
atgaaatttc taacctatt aagtagtctt attgtttaaa taacccatgc aattaaatta    20760
ggttatatgg gggtgattca tttaccaggc ccaagatttt atctcattct caattattat    20820
cgcaacaccc atgaacctaa gccaacatga cttatttacc aggccagcta gagaagaaca    20880
aggttgctga ttttcttgtc cgtgattgta gaagaaatgt tagaaatcta aatgttgtta    20940
gggatttacc cctccccct actgagtgta tgaacttatt attgacggat tgttgtaggc     21000
ttccaagcca aaactctgat taagttttct tttatgccat tttaaccaaa aaaaaaaaa    21060 aagctaggaa gctagctcag cgcgctctaa ttatttcaca tgtgacatgt tttacactta    21120
ttcatacttc tatatgcagg agagggcaat gcaggagcac aataacatcc tgtctaagaa    21180
ggtacttgca cttgaccagt ttgtgtaata ttgtaattta atttcttaga ttttggttgc    21240
atgctttgat gacgaatgac gattgacgaa tacatttta tgcagatcaa ggagagagga     21300 aaaatctag agcaagtgca acagatgcag tggcagaacc agcaccagca ccagcaccag     21360
cagcagccgc caccgccgcc acaaaatcat caagttcctc ctgatgcatc aaatttcatg    21420
ctcccacctc caattccttc tttgaacacg gggtagttac ttcttcaact taatttcctc    21480
tattcaatat taagttaaga aacagatcac gtgattagtt cgttaatatt gctaattaat    21540
```

```
aatcatattg ttatatatca tgcattagtg ggtaccaagg acaatttggt ggagaagtaa    21600
ggaggaatga tcttgacctg acgctagaac cgatatactc atgtcacatg ggatgcttta    21660
caacatga                                                             21668

<210> SEQ ID NO 2
<211> LENGTH: 780
<212> TYPE: DNA
<213> ORGANISM: Artificial Sequence
<220> FEATURE:
<223> OTHER INFORMATION: BvAP1 cDNA

<400> SEQUENCE: 2
atgggaaggg gtagggttga gctgaagagg atagagaata agatcaacag acaagtaact      60
ttttcaaaga gaagaagtgg acttgtgaag aaagctcatg aaatttctgt tctttgtgat     120
gctgaggttg ctctgatcat tttttctcac cgaggaaaac tctttgagta ttcttctgat     180
tcttctatgg agaagatcct agaaaggtat gagaggtatt cttacgcaga aagacggcta     240
gcttcaaatg atccagactc acaggtaaac tggacctttg acttcgcaaa actgaaggcg     300
aagcttgaac ttctacaaag gaatcatagg cactacttag acaagagct tgactcgctt     360 aacatgaagg aacttcagag tttagagcaa caacttgata ctgctctaaa aaatgttcga     420
tctaggaaga accaactgat gcacgagtcc atttctgaac tccagaagaa ggagagggca     480
atgcaggagc acaataacat cctgtctaag aagatcaagg agagaggaaa aaatctagag     540
caagtgcaac agatgcagtg gcagaaccag caccagcacc agcaccagca gcagccgcca     600
ccgccgccac aaaatcatca agttcctcct gacgcatcaa atttcatgct cccacctcca     660
attccttctt tgaacacggg tgggtaccaa ggacaatttg gtggagaagt aaggaggaat     720
gatcttgacc tgacgctaga accgatatac tcatgtcaca tgggatgctt acaacatga      780

<210> SEQ ID NO 3
<211> LENGTH: 29237
<212> TYPE: DNA
<213> ORGANISM: Beta vulgaris
<220> FEATURE:
<221> NAME/KEY: misc_feature
<222> LOCATION: (1029)..(1924)
<223> OTHER INFORMATION: n is a, c, g, or t
<220> FEATURE:
<221> NAME/KEY: misc_feature
<222> LOCATION: (20703)..(20722)
<223> OTHER INFORMATION: n is a, c, g, or t

<400> SEQUENCE: 3
atggggagag gtagggttca gctcaaaaga attgaaaaca agatcaaccg tcaagtgacc      60
ttctccaaac gtcggattgg attgttgaag aaagcgcacg agatctccat tctctgcgat     120
gccgatgtag ctctcatcat cttctccact aaaggcaagc tcttcgagta tgcttctgat     180
acctggtatg tctaattttta taacttcttc ttttgtacat caataatttt atcatcgact     240
caactaaaag cttaagcaga tggttagggt tctattatta ttgaattacc tcaaatttgt     300
catcgactca actaaaagta gagtatattt catgtagatc aggtgctttt tttgaatata     360
ttgtcagttt tagaactaca aaatgttgaa cacaagtatt tatacgcacg ctgacatgtg     420 aatttttttaa ttgacaactt tctaaattaa tactctaaat tactaatatg aagaacgtaa     480
tttattattt atcactttca gacaaaggca tgtttgtttt ttctattatt tttcccatga     540
aaattctcac caatatccga ttctgtatgt taatttttagt aatttctaat tttgatgact     600
```

```
taataaattg taaaaaagta taaaataaac aaatatccaa aacatctttg ttttcaagag    660
aaatatctta aaaacttttg tttttttaaga gaaatatctt aaaacacttt ttatcatact   720
actatgatga tgtataaatc tattcaaaaa aaaaaaaaaa tgatgatgta aaataatttt   780
aaagagttaa gtttattaga aattatagat atttatagag ctgagtaata aaataatact   840
ctacagatta tatgtagctg atgtagtgtg tctgctcctg taagatttcc tttttatctc   900
caaaaaaatt gcattgatat tcgagccttg ccgacccccct tttcctcttc aaccatttga   960
taagatccta tgcactgagt aatctagtat tatatgttag atgttatata ttaataagct   1020
aaaattgtnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnnnnnnnnn   1860
nnnnnnnnnn nnnnnnnnnn nnnnnnnnnn nnnnnnnnnn nnnnnnnnnn nnnnnnnnnn   1920
nnnngatgat attatgtatc attattatca gtcatttatt attgatagat aatgttatta   1980
tttccataga tcatatataa tcttaccata tttactccct atgattatat atttctatct   2040
attaacatag taatagtgat atactaacaa cgagtatctt tcaagtaaat aaatcatata   2100
tatagggtta gaaggtaaaa aagacaatat tttatgagac tttatttaca cccttcgtct   2160
cataaactcc tttctatttt ttgtgttcac tcgtttttcta agttttttc tacttctttt   2220 acttttatt ggataaatac ttttttccgtc tgtatgtgat ctacttatat tagtatttat   2280
agatagatta tactcttaaa gtattacatt cacaaaatca tgtgaattat taattaaagt   2340
aaaattatga gtatggtatt ataacttaaa cgaagtagtt gtattgttta aaccaataag   2400
tataataact tataaaactt aaaagttgat tctacactta tcatgcactt gtgttttgat   2460
gggttaaaaa ttagctagta cataagtaac ataacataaa cttatctctg tatagtatgt   2520
tgaattatta ctttatattt gaaaagaaca aagacacaat aagtccaaaa gatccgatct   2580
tttgattatc aactatgtaa gtgtctttcc taaatgatca atcaccttaa ttagtatact   2640
aaacaggaca attatgacat ataacacttt tctatttgta caagttaatt aacccattga   2700
cattcattca gttagcctac attttttcaat aggtagtcat catcattctt ttttttaacca   2760 atttttttac aataaccatt acctaccaac aacattttca aataatgaac tgaatgatgg   2820
attccgtcaa ggaaattgtt cgtggacagt tgtttaccct cccaaatttc ctttaatctc   2880
atgctttctc catcatccaa acaatctaat accaatcgtt ttctctaatt gcataaaccc   2940
taattgttga atcctttaat cttgcctttt cacattgccc aattcctta gtatgatatt   3000
```

```
ttttattcga taatccctga taagtaaatt cactaatcta atttcagatg gattgttgta    3060
gagattgggg aattgaagat ttttgccctt ctttgttctt gttacaatg aaggatgaag      3120 tttcatggaa tattgaagag aaatttgaga aagaaagaa agtgtgggct ttactgacga      3180
caaaaactgt catttggtg gtttttttca ctaaggcatg tttggcacta gcgtttaagg      3240
tagcggttag cgatttgaca agatcaaaac gctacttaag aaaatgatga gtgtttggta    3300
agatagtggt tgttgtagca ggtagcaatt agagtagatt atgagtagcg gttgtggaat    3360
gttactacaa gtaacgtttg agatttagag gtagcagtcc agcaaagaaa cattgtataa    3420
tagcataagg tagaattaat taaccaatgt ttttttattt cttttccctt ttattgttta     3480
ttaataattt tattttatgc caattcaatg tttatttac aatagcaaaa atgtaattta      3540
aatatttatt ttaaacataa taaattttat aagtattta gtaaaattgg taatataaat     3600 tttcgaggg ttgaatattt tcttagatgt atacattcct ttgaatagtt aaaaaatcat     3660
atctcctttt tgtgtaactt ctttgaaaaa taaatcttga atttaactat tgaacgaaca    3720
tatgaaatta ttgtagttca tttcatatta taataatgt taggtattgt cttttacaat     3780
ttcaactact tttggcaaac aattctgatt aaacagctat tttaatcgct gatcgttgac    3840
agcaaccgct aacagctact agaaccgcta cttttgccaa acatgcctaa accaagtaat     3900
atcggggatt cttattata taaaaagtta ataatgtgat tatttgaaaa aaaggttgac    3960
tttatatgtt gtttaaagaa aaaaaaacat ttattaatag aaaatatact atataggtct    4020
ctatataccc agggcgaaat gaatgtgtat cttttcaaat gagtatgcgt acatgttctg   4080
taaatgcata tttcatatga gcataatgtt tttactatta ttatgcacat ttgtgtttta    4140
atttttcaaa tgagtatgta aggaaaacat gtattcttgg catgtcagtg ttagtgattt    4200
ttgttgttat ataaatgttt tcgtgatttg tgaatgtggt acaaacattc atgtgccatg   4260
gcgtttagca aaacttttct agctcacatg atgcttcaag ctaattgcaa tgaactaata    4320
taagggagag gacattttac gaattagttt tacattgata gtagtttgaa gaagatagtt    4380
taggagatag tttgttggaa tagaagctat gtgttagaat tagttatagt catcaatttt   4440
tgaataagac tcattattat ttcaatccctt ctaccttta attactagtc caactctcac   4500
tctttggtat taaattacac cattcctacg gactatctaa caactctaac cacggcccat    4560
acttttctct cttaacataa aataaatatta cgcttactaa ctactaactc ctatgacatc   4620
taccttttca ataaaataac aattgataac tatataacaa cttataatct aaaagtaagt    4680
gtcttgataa gtgtagagta ttgtgggacg aagggagtaa ttcatagcaa atactatcat   4740
agcaatacaa tactaggaga ctaagatgtg agttttgaac ttcaaaaaaa aatatacgcg    4800
acatagttca ccggaagaac tgcagcacaa caaatgcaaa tggggattaa atgaggagtt    4860
cacctacatc acacacaaga gcgattgagg attttcagat ctggaagaag agcgaaaaat    4920
caggcgagag cttcaacttt cggagtttaa tggaagagct aatgatgatt gaattattca    4980
gttggattta tcttttgtaa gatgaggga tgaagttgaa gattgccata ataacccttg     5040
agggcgacac aatggtggtg ggaatggaaa tatggaccac gaccgattta tgagtggaaa   5100
gaattgaagt ctctgataca atgacgtttt ggtatatcat cggtgctttc atggctgtca    5160
gatctaccga aaggaaaagt agtggtgaaa acaaatgtcg ttcaaaccaa ccacctttga    5220 cttttcaatat tgaagtgaca aggaaaactg gcacccttagc tagtgacttg gtggagtctt   5280
tgcgtaaacc ggtggaaaag aagcttatct ttgagttta gtgtggtctt ggtgcttgtt    5340
```

```
taagtggctt gactatttag gaggaaaaaa atcaattgtg aacaattggt gagtaaccta    5400
aaaatcaatt gtgaacaatt ggtgagtaac ctaaaaatca attgtgaaca attggtgagt    5460
aacctttaaa ccagactcaa gagtgggaaa gaggcggtta gacaagtaga tttagaggaa    5520
gaggaggtag aaaatagatt agaatttttt ttgggagttt tcaaatgtag tggtatcggc    5580
tcataacaag gtggtcaaat ggatggagag cttggtcgtt tgagtagtct catggtggtg    5640
attataacta cgttggcgat aaacaagttc gctttaccaa gaagttgatt ggtggaagag    5700
agattttcat aaagaggggc tcgtatagca acagctttgt gtggtctcag tttcattgtc    5760
ggcaaagccg tgggtggtaa atatggtgat tttggagatt gttatgatgg agggagttat    5820
ggtggtttca tgagacatgg atgctatggt ggtgctgtga tcggtggaga agaggagctc    5880
gtgaaaggtc actctgatgg agcggtgta atggtggtct aggttttttc ggcatcggag     5940
gttgcgtatc tcgtgaaggt tcacatttgt acaccggtga atactatggt ggtgaactag    6000
gatgacagtc aaggtgacca tagtagaaaa aaaaaacata aaccatgtag cttagatgat    6060
ttgaaaaaaa atcatgtttt tggagaagaa tcttaaatat tatgacagag gcaaacttgt    6120
cattgaccaa atagatgaca tagcaattgc acgtgtctcg ttaaaatttg aaaccataaa    6180
aaattcaaat tgcacttcat atgcctttct tttggttgaa aacttcatat accctaatgc    6240
gtcaatatgg ttctttttcc aaaaaaaaaa gtaaattatt tcggcgttag taaaagcagg    6300
tccacctcca taatccattt tattaagcca actcctctac cctactttg caacctatca    6360 tttcttattt tctaaaatca tatcaaaaaa acaagtgtga acccaaaact aactatatta    6420
tacctaagtc taatttcttc atccaatgtg ttcaaccca tttttcaacc cttccactca    6480
taaacccatc ttctttcact cctaaaactt tcagctcacg ctcgtatcac ctctttactc    6540
acatatcagc ccaaacgatt tcttattgaa tccactaaat tatgtatatc gatttttca    6600 ccaagtactc cgagttttca aaaaatttac ctggtacccc caagttttca aactacacgg    6660 gatacccta agtttcaaac taatacactc agatacccctt aatgactaac gacattaatc    6720
gccgttagtc attaacctta atttttctaga tttcaaccta attaaccact aaccctaacc    6780
ccaaccctaa ccctaataat aaccctaaac ctaaccctaa ccaccccctcc ccaaccctcc    6840 caccacccct gccccccatc ctccactcct gcgcagccag caggccccc acccatttga     6900 ttttaaggaa gaaacacgta tcagggaagg gggagaactt agctctgaca gcggcaacgg    6960
accaccgacg agtctggact gtaggacggc agcgtcaagg cgcgagccgg ttgggctact    7020
gcagttcaaa gcaaacaggg gaggggaatc gagccgagaa gagagctaag gaaagagggg    7080
tgatgggcgt tgcggagatg gtgcgcatag tggtggtggt gtgggggagc tgtggtgggg    7140
gagaaatcga atgggtgggg gagagagggt gggggctgc ggtggggttg gggctggagg     7200
gggtagggtg ggtgggtgga ggggtggtgg ttgggtggta gtgggacaac tctcaaacat    7260
gattctttct caaacatgat tctttctcat atccttttt ggattccctt aaaaaaatcc      7320
atatccaaat aacgttgacc ggtgagggac aactctttaa cactattctt tctcaaatct    7380
tatgaaatct tcacatttaa ctcgatctcc cttcaatga acctaaagat atatattaat      7440
agagttgcaa attcctaaac tctagaaaat tcaaatacaa cataagagtc ctagattctt    7500
ccacaagatg tattatatct ttcaaagttt cccagataaa attagtaatt aggaaactcc    7560
ttaacaagga tacttaaagt tttatctaaa tcttgcataa attgaaatcc aaccataatt    7620
atgaataaat aatcataaag aatcctaaca taaataacta gaaataagga taataaagaa    7680
gcaacaaaag aatctcataa ccaccatttg aatcccgcat gagaacccaa atagttgttg    7740
```

```
ttccttataa aaacccacca cctttcttcg ggtattatga cggtattgga ctatagtatg    7800
agacgagatc tcttaatcac caatcaacta ttgtaaactt gtgagcctga ataatttatt    7860
tgagatacaa ttctaaggtt gtttatgaac gtgtttggta aaattgttat tgataactcg    7920
ttcgtggaaa ataaatgcaa aagtcaacat gccaaaaaaa gtgctaaaat caactttcgg    7980
ctttgcttga aatgttaagt tttaagctat ccaagagcca ttagtcaaaa tctattgaaa    8040
gcgtactcaa aaaccattta tcaaacaccc ctacaaatcc ctttagaaaa caataggagt    8100
tgtacaatat aagtattgag ttataaagtt gatcaagtga tttaggaggt tgttccaaat    8160
caatctacaa gagtttgtat acttataccc cttcgttttt ttaattgtta cacttaggcc    8220
ttgtttgaca aatagagttt agcggttaga gtttagattt tgctgttaga gttttaactt    8280
tttgttaaat agatttgact gctgatttga caacttcttc ttataaatgt gtttggtaat    8340
tattaacaga ttgctaaaag cttattaccc tttatttatg tgaaatgaca tgtatagaca    8400
ttttaatcca catgggtatt attattatta ttattcgagg catacaagtc attgaatata    8460
tttttaccta atcctctaaa gaaaaagctc ctattaggag cttttcattt tcgagagttt    8520
ttattccaga actctcttca aaactctttt ttaccaaaga ataggagctt tttcatttca    8580 agagtttta ctccagaact ctctttaaaa ctcttttta ccaaacaccc cttttagagt    8640
ttttgactag tcaaaactct aaaagtggtc caaatttctc ttttaactcc aaaactctaa    8700
ttgccaaaca ccccttaca cttttcacgc ataccaatgc aacactttga cgattaacat    8760
ctccagtttt ttatttgtaa aaattataaa gagtgcatat taataagtag ggctgttcaa    8820
agtgcggtct ggaccgcacc aaaccgcaac ccaaaccgtt gtttcgcggt ttggtttggt    8880
ttgcggtttt aaaattgcgg tttgggttat gatttcaagc aaaccgcggt ttgcggtttg    8940
ggttgggttt ttattttgt aaaccaaaac cgcaccgcaa accgcaatgt tacatttttt    9000
ttaaaaaaat aaattaaata catttatgaa ggtgacatac aattataaaa ttgaaaaaag    9060
aagtttgagg taaaaaactt taacacttat gataaatcat tatatatgtt taattatgaa    9120
ttcagcttca tatctatttg gactcttatt aacaattttc ttttaatctt aggaaacaaa    9180
agtaatgtcg cggaggaaat aatggttaaa ccgcaaccca aaccgcacca aaccgttttg    9240
cgcggtttgg gttgggttgg tttgggaaaa agtgcggtgc ggtttgggtt ggaaaatttt    9300
caaaccgtat atttgcggtt tgggttgggt tacatcccaa accgcacaaa cccaaaccgc    9360
gaacacccct attaataaga tacatattaa ttcgaatttg acaagatcca catgactatg    9420 ttttattcg cgtataaacc acaaaagaag gttcaagtaa aatttgtgta tggtgtaaca    9480
tgtcaatcaa agaacggagg taatatttgt caagacactt tagtcacttc taaattccta    9540
taaacaaaga aatatggaag aaaactggtg atgaaaattg aaaaggtggg tataataaga    9600
gagacacaat tctaaaataa gaaaatatta ataataaaat aataagttac gataggcctc    9660
atgtttgaaa acgaaaaaa taaggagata gttcgtgtaa aaaggaggga gtaagggta    9720 atgcatactt tgtattgcaa gcttagtttt aaaaggcata agacgcaaag cgcatcgagg    9780
cacaagacga aggcgcatgc atctcgtagt tgaggcgtgt aatgatttta cttcacaacc    9840
acctgagcaa cccaatacag aacgaccaca agaaaaatag aaagaaagga aatgattttg    9900
attgatcagc agaaaataca gagcattcga gaggctcagt ctctcccaag gactacaaga    9960
tactactaaa tttcacaccc ccttcagtcc ccttacaccc ttatttatac tacttctgct    10020
ctcctatttt aacggctact gacattctct gagctggcct gctattcctc tttttgtgct    10080
```

```
gacatttctg aatattctgt ggtagtggct ccattctcac atttggacag gtttaccct    10140
ccatttcttt cgtgcatacg tcagccacgg tttggggatt gaattcatta cattaccctg   10200
cccccaaaga ctcaccttgt cctcaaggtg aaggaaggg aaacgttctt gcaccaaatc    10260
tgcatcttcc cacgtggctt caaaaggtgc taagtcctt catttcagta gcacttcagt    10320
ctgcgtatgc ctccctctct gtgtctgacg tacgtccaat aattcttcag gttccacaac   10380
tagttccaag tctgctgcta gttgagttgg tacagtggtt gctgcctggg catctccaat   10440
tgctcgtttg agctgggata cgtgaaatat aggatgtatt ttactggtgc ctggtaactg   10500
gagtttatag gcgaccttgc ccaccttttg cagaacaggg aatgggccat agaagcgggc   10560
tgccagcttc tcaaatggtc gcttggccaa ggattgttga cggtatggct ggagctttaa   10620
gtaaaccaga tccccacctt caaaggactc atcgcgcctt cttgtgtcag cataggcttt   10680
catcttttgc tgggagcgta gtagatgaaa gcgtaaatca tcgaggatgg catcccgttc   10740
ttgcaacact tcctctaagt tatctactgg cgtttgccct ctgcctactc gccacaagtg   10800
tgtgggtcac gcccgtacaa caccctgaat ggagtcagct tagtagacat gtggggagag   10860
gtgttgtgtg agtattcagc ccaagggagc cactttgccc aagtcttcgg gtgccccgcc   10920
acgaaacatc tcagatatgt ctcaagtcct ttgttcacaa tctcagtttg tccatcggtt   10980
tgcgggtgat aggcggtgct tctccttagt gttgtccctt ggagtcgaaa caactctttc   11040
caaaaagtac tcagaaaaat tcgatcccta tccgaaacga ttgatgccgg aaacccatga   11100
agttttacaa cctccctgat gaaagcttca gccacttgtg agagcactaa aaggatgacg   11160
aagcccaatg aaatgcgcat atttcgataa acggtccacc actactaaga tcgtgtccac   11220
cccttggac aagggcaatc cttctatgaa atcaagagtg atatcctccc aaacctgagc    11280
tggaatggct aagggctgca gtaggcctgc tggcttttgt tgagagctct tatgctgttg   11340
acaaatgcta catcgctgca cgtacaatgc cacgtgcttc ctcataccta tccaatacca   11400
ctcagccgcc aacctaaggt acgtttttac ttcacctgca tgtcctcctt ctggggaatc   11460
atggtaagct atcatcaact taggaatgat gacggaagtg ttgggaatta ccattcgccc   11520
cttataccgc agcttgccat cctccaccgt gaaccccaca agtggtttat ctccctgcgc   11580
cacttcttcc ctgagccttt taaggaacca atcctcctct acctcttttt ggagctctgc   11640
ccagtccact ccttgggttg tgattatggt ccctagctcc atttcaccta cagttttcct   11700
agaaagcgca tccgcaacct tgttggttgc ccccggtttg tagtgtattt caaagtcaaa   11760
cccaattaat ttgcttaccc atttctgaaa atcagccccc acttcccgtt gttgtgtgat   11820
gaaacgcaaa ctttgttgat ccgtatggat cacaaatctt ctccccaaaa ggtaatgttt   11880
ccatttctgg accgcaaggc atatggcaat taattccttc tcataaacgg acttgtgttg   11940
tgctctcggt ccaaggagct tgctgtagaa tgcaatgggc ctgccctctt gcattaggac   12000
tgcccccacc ccatacccag acgcatccgt ctcaactacg aaaggcttat ggaaatcggg   12060
catagcaaga accggtggct gggtcatagc ttcctttaag tgagagaaag ctgaagtagc   12120
ttttttcggac cagccaaagg agtccttacg caattgctcg gtaaggggct gggcaatttg   12180
cgcgtattgc ctgataaact tgcgataata cccggtcagc cctaaaaatc ctcgaagctc   12240
cctcaaattc ttgggaactt cccactccac catggccctt atcttctcca tgtctactgc   12300
cacccccatgc tgcgaaattt acatgcccca agtaggccac tgtcttcctc cccaagtcac   12360
atttcttctg gttagcgaac agtttgtgca atgctaacag ctgcaacacc aatcccatgt   12420
gtcgtgcgtg gtcctctttg gtcttactgt agaccagaat gtcgtcgaag aagaccagca   12480
```

```
caaacttcct cagatatgga cggaaaacgt tattcatgag tgactgaaaa gttgctgggg   12540
cattggtgag cccaaagggc attacgagaa attcgtaatg tccttcatgg gtgcgaaaag   12600
cagtcttatg ggtatcctcc gggcgaacta aaatttgatg gtatccggcc ttaaggtcga   12660
gtttagagaa gatggtagcg ccatgtaact cgtctagtag ctcatcaatg accggtatcg   12720
gatacttatc cggaaccgtc tccttgttca agcccgata atcgacacaa aacctccaag    12780
aaccatcttt tttcttcacc aataatacgg ggcttgaaaa tggactagtt gagggcttga   12840
tgatgcctgc ctccagcatc tctcggatga gtctctcgat ttcgtctttt tgaaattgag   12900
ggtaacggta tggcctaacc cccaccggat tactgccttc cttcaacgtg attgcatgct   12960
catgccccct ctttggtggc aggcccaccg gagtatcaaa aacttccgca aactgactaa   13020 ttacttctg taaaaattcg ggtacttctt gtgcctcctt caactccgct tctccccttt    13080
tcccatcatc ctcaatctgg ttgagctcca agagaaaacc ccttttttct tttcggattg   13140
cctttatcat ggctctaagt gagattttag atcttgctaa ggaagggtcc cctctcaatg   13200
tcaccactct gccctccact tcaaactgca taacctgagt tttccagttg gtaatcactg   13260
accccaattt ctcgagccac tgcactccta atattaaatc tgagttaccc aggccgagag   13320
gtaaaaaatc ctctgttact tcgatttccc ccagctttaa agtcaccct tgacacaccc     13380 cagtaccatg gacagcttca ccattcccta aagacactcc aaatcccct gcatctgaga    13440 tgaccaactc aagttcctca acagttaaca aggaaataaa attgtgagtg gcacccgggt   13500
caatcatgac caccacctct cttcctttaa ttttctagt gattttcatc gttttaggac     13560
tcatcaaacc aatcacagag ttgagagata cctcagtagg aagttccggt ggtggttcgg   13620
acggtggtgc acgagctgcg tcgctcacct cttcggtttc ttcctcctcg tcatgcatca   13680
gaatcacgct gatctctttt ctccggcaga gtggccggc ggtccactta tcgtcacatt     13740
tatagcacaa cccttttgct ctcttctctt gatattcttt tcggaaagt cgcttgaact     13800 ctacagattt ttttccttgc cccccagcaa ttggatacgt gttcaaggtg ttggaatttc   13860
cccctgggtt ttgggcccac attttgctgg caggtgggtt gaggctggtc gttggattga   13920
aggaagcccc tacactcctt gtcattcccc ctctgttata aatcgagtaa ggcccattct   13980
tagttggccc acttctttta taacccacaa tcctattcct ttcctcaatt cggcctgcta    14040
gttccattgc ttgctctagg tccataggat tgagtaacct gacctccact ttgatatcct    14100
cttccagccc attaatgaac tgacccatga gtatttcttc tggtactcta ctcaacggtg   14160
ccgccttctc aataaaagtg cgtcgatact catccaccgt ggtggtttgc tttgtggcca    14220
accaccgttc ccacaatgaa ccatagtggg ttggtcgaaa ctgacggagg aggtactcct   14280
tcagatctgc ccaccacctt atcggccgcc ttttattctc ccactggtac cacctgaggg   14340 catcccctc tatagacaca accgccgcct ccagggcttc actgctactc aggccataaa    14400
acgaaaaata tcgctcggct ctaaggatcc acccatccgg atcggaccca tggaaaatgg   14460
gcatctctaa ctttcgatat ttccagttcc ccccggaagt cgaacctcct ggccctccac   14520
ctgagccgcc atccccatac gatcggcccc cgagctggaa acctccatat tcgtccccatt 14580 ctcggccccc cagatttatc aggtcaggag ccctccgttc cggcggtcgg gggtgtccag   14640
tgacggtttc gggtgtctcc cgcgagggtt gtggcaaggt tgctcggatt tcaacctgaa   14700
atttcctctg ttcagcacgc aacccttgaa tcgtcccatc ctgtgtctcc cttgaccggt   14760
taatccggtc ctccagccta acggccaaga cctccatctc ctcgcgactc ttcctcgccg   14820
```

```
cctcattctg gccttccaag atttgagcgg tcaacgattc ccccatggca ttaatggcag   14880
attccaccgc cctggacacc atggtggcca ctgacccttc gagggctgcc attctttctt   14940
ctaatgaatc caccctctgc acttcgtttc ttggtgccat ggatcgatgc tctgatacca   15000
agtgtaatga ttttacttac ttcacaacca cctgagcaac ccaatacaga acgaccacaa   15060
gaaaaataga agaaaggaa atgattttga ttgatcagca gaaaatacag agcattcgag   15120
aggctcagtc tctcccaagg actacaagat actactaaat tcacacccc cttcagtccc   15180 cttacaccct tatttatact acttctgctc tcctatttta acggctactg acattctctg   15240
agctggcctg ctattcctct ttttgtgctg acatttctga atattctgtg gtagtggctc   15300
cattctcaca tttggacagg tttacccctc catttctttc gtgcatacgt cagccacggt   15360
ttggggattg aattcattac aaggcgcacc tttggtacca agagacttag acatcaaata   15420
aagaagcatt gtaatactta gaataaacat tgttttata ttctaaaaca catattttct   15480
ctaagcacac ctagtaatctc atagtggatg tcatctagtt taggtggtaa ggttttattg   15540
agttggtact caagacctca gacttagagg tggcaaacgg atcatcgggg tcgggtgaaa   15600
atgagtcggg tcataatcgg gtcacctttg tgtccaggtt acggtcaggt cgagttcgtt   15660
cgggtacgag ttcatattga gtccatgagg tttcatgtca tatcgggtcg ggttagattg   15720
gatttacaat ttcgcaaata aataaaacgc atataatact aaagagagta aattaaataa   15780
ttaacggaca ctagctaaat catatattag tattttatga tgtattttcc ttaaatttat   15840
ttaaaaaata actaatatga caattttcg ggccgggttc gggttgtggt catcattatc   15900
gggtcaattt agtatcgggt aggctcgggt tcatgtcata ttcgggtcta ttttaattcg   15960
agtcgggtta tttcggattt aagctctatt tcgggtcagt attttcgatg aagaacgggt   16020
ttcggatcgg gtcaccggat acggatctat tttgccgagt cagactgctt ttcaaaccta   16080
ataatctcag ttttccacc tattcagatt tgcctatgat ctctatttag ataaatgagt   16140
acaatattgt gtctatccat gaaaatgaat atctcacaat gtaaaaggat atctctaaat   16200
ttcactaatc actctatctg ttttgaataa taatattcta ttttattgca tgtagtaaag   16260
atcgagtatt tagtgagatt tggagaaaag aggaggctag agagaaacta ggatttagag   16320
aggagaaggg ggctctgtaa cacatacaag atagatactc ttttacacta acttttcaag   16380
atactcaaca tataaaatca gcatcatctt ccaaacaaca actttaagcc acccatgaat   16440
cttaattaga taataaaaca taatcgtgaa tcatctatcc tttgtttggg gggatcctaa   16500
agcaattgag gaaaagcttt gatgcaaata tcaattgtgt aaaaaagcaa gtattcgttc   16560
gtgatgttgc tatactaggt tatttttgg atccaaaagt cattcctact agaatcattt   16620
aggaaaattg tcagtatgaa ttttaaattc aggttataac caaagataat tgaaaattgt   16680 caaactttc aaataattcc gaaataaaca tgtttgtaac atggataaac ttttcattgc   16740
ttttcaaata attccaaaat aaacatgtta taacatagat aaccttttca gataattcca   16800
aaataaacat gttgtatcat ggataaactt ttcattgttt ctagtcactt aaaattctaa   16860
aaaaatcttt cctccctact gttactctct ctagcaccaa atctatcaca tgagaaggca   16920
gaggttttca aaataaaccg ttacttaatt tggtacttat ttcttgatcg gtgttcatat   16980
catatgagtt cctactctat atctctctac tcttctaaat ccttgtgtca cttcctgtgt   17040
ttcataaata aaaaggagga agtattagtt ttgaaacgaa aggagtatgg tgcatacatt   17100
gatagaaaaa agaagttatt tgtccttatt tcactcatat aacaacacca aattctgtat   17160
tgttatcaca aaataaaact tggattatct ttgtttcata gcccaaattt agaattagtt   17220
```

```
tgtcagattt ccaatcatct aattacaata ttagagctag acctaggaca aaaggtgggt    17280
ttggctactt ggtaatagct atgtctagtg ctaggatatg tcattgtcgt agaaccatgt    17340
tatggacatc ttaagaaaca aggttaacct aattggttgg agatcctact ttcactttta    17400
taataaagtt tcgattcttg cctatttgta aagtagaatt cctaaatttc ccttcactga    17460
tatttatctt aacataaaaa aatgttataa acattgggat tgtatataag tcaaaataaa    17520
ttgacaatct tggtaacaac taagttaaca ttaattttat aagtaaatga ttaatcccaa    17580
tataatctct tatttagtaa atgagacaaa cttgtacacc ttcgtgttag actcgttaat    17640
gttcgctaac aattcattca gtagtcaaca gcattttaaa tttgaaataa gtgttcttgt    17700 ggttttgag agatcaagca agaaaacatg tctctcccct ttgaccaact aattgggatt     17760
aagaatacta gttttaagat tttaagaatg agttatagtc tttcttagac cgctacaatc    17820
cccttgttga tatgaaccag atatattttg tgttcaaata gtagatcaat gcattgttga    17880
taatcctttg ttaatgtact tgttgatctt attttgtact tttggtagat gcgctatact    17940
ttctttcgat tgctcatttt gaactcttaa ctacatatgt tagtttaagt agatgattta    18000
gaattgctat ttcaatcttc aataagcaat ttaagttgtc aaaccttgtt tcacatcatt    18060
agggtgaaag ttatttggat aaagacctat atctaattca atccaaagca aattagtaat    18120
gcggattgga ctcaaactat gtttagattg gattcgaatt gagtttcttt tcttttctt     18180 aaaaaaattg gattttccga tcgaattgag ggtgattaga tccaaaataa ccgaatagta    18240
gataggattg tgttgtata ttagaattgg gcttaaggat ttccatttta acaaaaaaac      18300
caaatggtcc gactatcaaa aactataatt tgatagtcat gcctatcgaa aactttattt    18360
tcattctcgc acctaattat gggcttgtat aaattagttc tactatcgaa aactaatttt    18420
gatgctcgtg cctaatttaa attttcgaaa aaatgaagtt aagaaaattg gatatttcgg    18480
attggatcca atatatcttg tgaattatta atttggatta gtttggactc aaattcttat    18540
tggattggat tcaaattaaa agattaaaat tcaaattttg ttcgaatcaa attggagtag    18600
gcttaagttt aaatcataca ccgaacttc accactaccc atcatgctta agcttctaat     18660
gtaagagagt gtttgggagt tgagctcgaa caactaaatt tctaaaagaa ccaagttcaa    18720
acaagaaatc taaagctcg attaaacttg agtcaagctc aaacacctat attccttatt     18780
ggagcttgac tgaagattga acacttattc cttattaagc tttacgctaa acattgctc     18840 gactcaactc ttctacatcc ctatagttca aaagaaatag ttgtgggctg tggtgctctt    18900
gtagaccaac gcactagttt aacaaagcta agtgcctgac tgcaattcca tacacattac    18960
gatcaccatg acctagtttc agctcacact ttggaagtct aatttgaact tgttctctac    19020
ctccaattca ttgtgggta ggaggcgata gttaagggat caaaatctta tgatataact     19080
tgcataggct atgccactat ataatgcgtc ttgtgtccca tattagttta atcaaattga    19140
aatgttttac catttatatc ttcaattatg tatggatact aatatttgat ttgacgtttg    19200
atatgatatt aaatgtggac tgttattctt gatgtgcttg agaagctttt ttggggccag    19260
ttagaaacta tattccttt atggtcctaa ctaggttgtt gttggtgtgt tcccaaataa     19320
cagcatggaa aggatactcg agcgctatga aagacactca tatgcagaga gacaactgac    19380
tgctccagat cctggatccc atgtaatcca gctaggcaac tatcttttct aagcatttaa    19440
atcgttgaga tttcaatttt aaatgtgttt taactgataa ttcatgcatt atatgcttag    19500
gtaagtttga ctctggaaca cgcaaaactt aaggctaggc tggacattct tcagaaaaat    19560
```

```
caaaggtaat aagatccaga ccaaatataa tttgtataat aaccaccttg tgaggaaaat   19620
ttaagatcct tgataatttc aggcattaca tgggagaaga acttgatacc ttgagtctca   19680
aggagcttca gaatttagag catcaaattg acagtgctct aaacacatc aggtcaaaga    19740 aggtagtttc acagttgcat tagatcatct tatggatcaa ttggatcact tgtttgtatt   19800
ttagcgttgc tcaacacggt cgtctaatat agtgtgcaaa acgacctaca gggcaacacc   19860
ttttataggg ctcgaaaata cgaaaaatta atgtttgtt ttagtcatat tgttcaaacc    19920
caagctttat cttgtcaaaa atattttata atgattattt tttagaatac attatttaca   19980
tttttgcaat ttatgcataa tacttctaag gtccaacttt ataattgaaa tagaagtcct   20040
taaattttaa agacgacctt gaggaaacct aatttcttct catatataat taaatcaatt   20100
attctacaag ttagtagaac aaatactaca ataacaacaa tattgaagcc ctaatctcag   20160
taggattgga ttgattgtat gaagtcttat tagtggccgt taaatgtttc ttgtaggtca   20220
agatgacatg gctcatatag taaggttact tgactaaaag acgaggattt gtttcgactt   20280
agattttaac aagtttccct catttgttaa cacctaagcg tactaaatca aattctaggt   20340
tttactcact caaatttccg atttaggaag ggcttgagga tagttgtatt atcgtaactg   20400
actaatcaaa ggagcctctc ttagatcagg tttcacttgc caattctaac aacttgtttg   20460
gtaaaaggaa tttggaatga aaagaaagga attgaaaaga acattctac ttttcaatgt    20520 ttcattcaaa ataacatttt taagtgatag gaaatggaaa gaagtgaaac gaaagcctct   20580
ttacaaaatt atcattttc tacccccccc cccccccaaa aaaaaaaaa aaaataagta    20640 gtaagtagta gaagaagaaa taataacta acaagagtag taagttttta cgttttcttt    20700
ctnnnnnnnn nnnnnnnnnn nnattcaaat cagaactgaa tagtcataac cggaagatta   20760
gtttctctct agcgtgacta gggtttgagt aaaaagagaa aacttaaatc aaacatggga   20820
tattaaggtt ttttttcctt tcttcagttc ttttctcttc ccaatccttt cctaaaaatg   20880
aaccaaacag gctgcaaggt tttcacttgc ttaacacaag atttattttt aaaaataatt   20940
acactccaaa cttttaagct taaaaccaat tttaattcaa atcagaactg aatagtcata   21000
actggaagat tagtttctct ctagcgtgac tagggtttga gtgaaaaagt ctagggtttc   21060
atgtcattct tcttgcttcg agtcccttct tgggattgtt gttagccatt atggctaccg   21120
aaatcgttat taaatgtcta aatcttagaa ttactgctga agaaaacaac ttggtgtttc   21180
tcgaagatgt tgatgataac tcgcagcacc atacgctcgc actggcgatt gttggaaagg   21240
ttctttcgtc aagaccatac aatttcgagg cacttaaatg aaccttaaac tagatatggg   21300
tgatatccaa aggagcccta cttcacccta ttgaaaacgg acttttgtg gtacaatttg    21360 cgacaattaa ggaccgatct aaggttctag tcagcagacc atggaccttc gatataaacc   21420
ttgttctctt agatgctatt gaaggggta ctcaatcttg acccattgcc cgttttggac    21480
tcgcttgtat aaccttccta tggactgccg atatgagaag ttcatcaaaa actattgttg   21540
gtgtattggg ggaggtattg gaagttgatt ttgacaggat tgtttgggat aaatctgcaa   21600
gagtaaaggt gaagattgac attacaaaat cgttttgtcg tgtgcagatg atcaagacta   21660
acaggggtga ggctgtgatg atcaatgtta agtatgaaag acttcctaca atttgttatg   21720
tgtggaattc tggccatatt gaaagagatt gtgtgaagac ccaggaagaa gagaaacaag   21780
tggagagaca atagggggtc ttggaggcct ctccgcgtag gggacgatta agatggtga    21840 aagagtcgaa agccttcctt cagtgtgctc gtacactcca ctttaataac aaggaagaag   21900
taaggggtga ggaaccacgg gattatgtgg agccgagggg ttattgtcgg ctatcttagg   21960
```

```
gggtaaaact tggtggtcc aggagatagt ggacggctct aaggatgcca tcgaggaagt    22020
tcgtgctgaa ggtgcaccac tctagccccc ttgtacccct tgggtaatgc catgctacct    22080
tttacttttg ctgttgggag tgctaatcct actccctccc accgaaaagt taaaattaaa    22140
aacaaggcaa gggttcaggg tgttttgaac caagttaatg ttgtgggtgt tggggggttg    22200
gctaataatg ggggttgtga gaaaaggata ttccccaacc cgatggtgtt agaaaaagaa    22260 aagggggttca atgaagaggg tttaagatag caaaacgaga ggattgtatg taacctatca    22320
gtagggaggt aactattgag gtggaggtgg gcgagaccca accccgcccg acattatgaa    22380
tatcctatgt tgcaactgtt ggggattggg caaccccgg gaagttcgga tgcttcgtag    22440
gtggagcaat agtgctacac tgagttcggt ttttatttct aaaactatga ttagtggtcg    22500
tgatgtggaa agggtgcaaa gcgggtaggg ttttgattgg gcaattgggg tggatagcgt    22560
tggaacttca agagtttggt gcatttattg gaaagctggg gaagtggact ttactctagt    22620
ctctctatca agtcatcata tttgtgggaa tgtgaagctt gttgatggga aggtatgatg    22680
cttagtgagt atttatggtt gggcggatac aattcaaaag tataaaacat gggagcttat    22740
gcaatccttt cactcatatc atgggccgat attgtttggt tgggacttca atgagatttt    22800
gacaatcgga gaaattgaag gagggtccga aactcaatga agtaacatgc ataattttct    22860
agaaacttta tgatgacatga agcttaggga ccttggctat tcgggaactt ggtatacata    22920
agagagaggc tttaagccac ggaagagaat gagggagaaa cttgatcatt tgttgcatc    22980 ttcatcatgg tgtgacttct ttccgaaagc tacagttgag cacttgatgc gctacaaatc    23040
ggaccacact cctattttgg ttcgccttgt aggccatcag tgaagacata agaagaaaaa    23100
gacgtagttt tgttttgaga ctgcttgggt gcttgaggaa ggttgtgagg cccaatgggt    23160
gagtcatggg ccgggtttac tcgcgaggta tttatcgagc gctttaaagc cgtggaaggt    23220
gggttcaaag caaggagtga tgggtctctt agtaatctgg gcccgcgtgt gagggagatt    23280
gaggaggcca ttatagatgg gaggcagcga agcagataag gactatgagg ctctatgaga    23340
ctcctctccc acgaaagtta gacgaggtgt tggacaagca ggagacgttt tggttttga    23400 ggtctcgtgt gagttagata aaggatggtg atcgtaatac acaatatttc caccacaaag    23460
cttcccaaca caaacgtcgc aactacatag cggggatgta tgataataaa ggggtgtggc    23520
aagataacga agaggatatt gaagggaata tttcagagta ttaccaaacc tcgttcggtt    23580
cgtgctcccc ctctaggaag aacgtcgcgg ttgtccttga ggttgtgagc ccggtgataa    23640
ctgatgatat gaatatggcg gttatgaaat cttacactaa agatgaggtg tgggaagcac    23700
taaaccacat gaagcctaac ggaatgcatg ccatcctta tagaggttct ggaataccctt    23760 ggagatgata ttcatctgt cattttaggt attattcatg gcacccgacc ccagatgttt    23820
ttaacaagac taatattgtg ctcattccta aagtcaaatc cccaaatctt gtttctgagt    23880
ttcgcccgat tagcctctgt gatgttatct ataaacttgc ctcaaaagta cttgctaaca    23940
gattaaaaca ggtttgcctg acattgttta tgataaccag agtgcatttg tgtccggaag    24000
ctatattacg aacaatgctt tgatttctct tgaattattt gactctatga aaaaatgata    24060
cagagctagg aaaggttttg tgtcgatgaa attggatatg agtaaagcct ataaaagagt    24120
tgagtggtgt ttttcagta gtgtgttgga gaagttggat tttgctgaat catgagtgaa    24180
tgttgttatg agatgtgtgt cttttgtgca gtactctttt gtggtaatg ataatatatg    24240 tggagctctg acaccctcaa gggggctttg acagggagac cctatatccc cgtatttgtt    24300
```

```
tatacttgtt gcagataccg ttttagctct tcttagcaag gcattcaaca atgcgtggct   24360
atacttgata ttctcaacaa atatgaggca gcatcaggct agaaaataaa tattgacaag   24420
tcaggaatct cttttcaataa aagatttgac gtattttatg gccatgaaac aagttgagaa   24480
gcatcagaaa gacttggtat cccaactttg gctaggagtt cgaaaaaagt catatttgct   24540
gacattcaag agcgaatttg gaagaagctg cacggatgga gagaaaaact tctcgcgggc   24600
ttgaaaagaa actctcttaa aagttgtggt tcaagcaatt ctaacctatt tggtgggcgt   24660
ttacagattc ctaaccagta ttatccaggc cattcatttg gccatggtaa agttttggtg   24720
ggggtcgaaa agggcccaca attcgatgca tctgggggga tatgtgctca ccaaaatgtt   24780
taaggagcct tagcttttaaa gacttagggg tgttcaatga acctaaacta aggaggaatg   24840
cgtggcattt gattcctgct ggtgagtccc tttcggtcg agtgttctcg gccaagtact    24900
attcgaagtc aaccttttg gactcatttc taggtccggt aggtagcttc tcttggaaga    24960
gtatttgggg ggccaaggca ttagttaagg gtgttttatg gtgcgtaggc aatggcagac    25020
aaatcaacat atggcgtgac tcgcgggtgt tgaatggtga tagtaggttc atccccggag    25080
agcgcgtttc aggccttgag gatgtttgtg atctaataga ttttgcacaa tggagtgcga    25140
tgtggacctt gtcacgattg cttcaatgaa gatgatgctc aagccatttt agtcatacct    25200
ctaagtaagc gccttctgaa ggacatggtc tcttgggctt tcactaagga tgaattttt     25260 ttgtaaaaac aacctatatg gccggttggt cgaggaattt gaatttgttt cacaaagcat    25320
ggctgcaaat ctggggcctt aacgtgtctc cgaaggtctg ccacttcctt ggcgtttat    25380 gctcggtacc cttcctgttc gagctctttt aaaacgacgc cacataactg atgatgattc   25440
atgtcctttg tctaaaggag cccggaaagc atatcacacg cgttgttcta ttgcccatat   25500
gtagccgaag catgggagag tgcgggcctc acaaattgtt tgcctttgtt tgatgggct    25560 ggtatgcttg atgcgtgggg ggagtgggaa acaatcgatg actagtccct tgtaagactt   25620
agcttcttgg cttatcactt gtggtttagg cgaaataaat gtgttttga aggggtggtg     25680 agagcgaatg agagtgttgt ggaatatgcc actaaagcta ctgttgatca tggtttgtat   25740
agtgcccgca tttatggtgg gtcgaaggct accgcatcca aaagctcgaa ggtatgggtt   25800 cccctccag cttgtcgtac gatctaaagg ttgatgcatc agtggggaat ggtggatggg     25860
tggggctagg agtaatcgcc tgaaactaga aaggggaggt gctcgtggct gcaactagga    25920
gggtcagagc ttgtggcccg tggaaatggc tgaagggaag gctctttgtc ttgctcttag   25980
gcttgcctcg ctcatacaac ttgcaagaag tgatcgtgga gtttgactgt caatcttggt   26040
gaaccatctc tccaagggtg ctatttactt tgcatttta agtcaaagct tgaaccttga     26100
taaaaaaatc ccgttcgaca tgaaaagtgc cttgattttg cgggtttggg agtgccttat   26160
tgattctggg gtttgatttg taacacctt agtaaaaaca tgtaagctaa ctgtaaaacg    26220
aacattaatc aaactaggat atgtaaaatt cctaaatcaa gaagaatttc cacttgtgct   26280
gaatttgtcc accttgcatg acacccaata aaagcccatg tctcctagaa ccccttatgc   26340
cgccttattc atctttctc aagttgagtt ggagtcctct atggtccact cgacttcttt    26400
agcacactct cggtaaaaac ttttaatatt atttttattt agactccacc atcttgacat   26460
ttattccttc ttaaacttgc ttcacacaaa catctaacac tagaattcta tatagaatag   26520
cttgaatctc tcttaggata accttatagt aaatgcaact acgccatacc ttaaaccttt    26580
ctaagaggag ctttatcgta tttacattcg cttcactttg aaacgtcgct aagtgtatgt   26640
tgcactttcc aaaccatgtg ttagctaaga ccaagttata tgactgcata acctaaatag   26700
```

```
tcttcctcga gaaaattcac tagttggatc ggaagagttt gtgtaaatct atggcggcgc   26760
gggactgggc cttcacgatt tcaagtgttt taatgcagct cttctaggta aacaagtttc   26820
ctaatagcgt ggtgactcaa atattgagga cttgttgtta tactaatgct attcctggcg   26880
gcacttaagg ggtgaaatag gtggtacaaa ggagtgcttg atggcgtgtg ggtagtagtt   26940
gaatatatca gtatgatcaa gtccatggat ccctcgtact tattcgtgca agattatttt   27000
tccacgaggc aaagcgagcg agaatcttaa ggtttatgat catattcatc ttgtacgtgc   27060
taagggtaat gtccctttca ataatgagct atttctcctt ttgagcaaga gcgtatctta   27120
agcattcctc gtagttctcg tctcccccaac gatgttttat gttggaatct gaatttggag   27180
aaagacggag acttttcgtt cggtctatcg agccattctt ttgagttgga tggcgagagc   27240
gtgatttcat cgtcaatacg ctctaattta tggagtataa tatggcagga tagtacctttt   27300 caacgtgtta agcttttatc tgcattgtcg acacaaaggg gattgagtaa gcctgtgccg   27360
agtatggaac cattgtgtaa tctttatgcg ttggaggatc aatggagcta cacttcttac   27420
gagactttgt tattggaagg gcttatatgg gatccaacta gggtagtcaa aacattggtc   27480
ggggctgcgc tgcaattttg gggacttggc accggcgttt ttggagtagc tccctcatgt   27540
ggaacatagg cttttgatga cgatatacta ggctagatgg aatataagag agaggtgttt   27600
gtttgaggag gaggtttgtg atccctatca aaccacatgc ataatctcat ggcgtagctt   27660
catgtggaac actgacatat tgcatgtgta gggttaggtg cttgcctagg acaccacatg   27720
ggaagagctc cgttaagctt aatgtggatg gagggtgtgt ggaagggttg ggtgcgtcca   27780
ctggagtggt gattagggg atggatgaaa aagcgttgta gttgcaacat agaaaggtgg   27840
aggactgcga ggaaccgtta aaaaggctat atttatggt gttcatttgg ttgtggaagt   27900 cgattttga aatatggttg ttggaagtga ctatcttcac ctcgttgaag caacttcttc   27960
aaaagtggaa ggcaaaaata gcttccatgt tattgttgat gacattgttc atggtagtgg   28020
tatgttaaat acttcgtctt gtagttttgt tcgtagggat gggaataggg tttctcacga   28080
actcccccat ggaaatatca taatggctca tgctcatagg taaatgaata agctaacaaa   28140
attgttcatc tttgcagaac caactcatgc atgaatcgat ttctcagctt cagcgaaagg   28200
tagacagctc tagagagagc atctagtctc aaaaatacca tgagattctg tagtgtcctg   28260
acatgtttta tatgacagga caaagcgtta aaggagcaca acaacttgct atccaagaag   28320
gtataagttc agcaagattg tttagtaaca ttgttaatct tgctgattgc tttgaaacat   28380
gtcttgctat ggttaacaat gttgactgaa ccaaaatagg tgaaggagag ggagaaggtg   28440
ctggctcagc aggcagaatt ggatcagcaa aatcatgaca ataactcatc tggctttgtg   28500
atgtctcaag ctttgccctc actgaataca gggtcagtcc tcaataaccct ctaatcattt   28560 ttccaagatc caaagtaaac atggttcat aatttaatta agatttttt gaaccatgtc   28620 tccatacaac cttactagga ctaatactac taatttaaga ccccaacgat aaacaacaat   28680
aattagccat atctggctag caccttttgg acaacacacc catgagact cttggccaac   28740 ttctttgatt tccttcagtc tgatagatat gaatatcttc tgaagagctc tttggttcat   28800
aattattgat ttagaaaaga attcagcaag gtgagtcatt tggtaacctt aaggtcatta   28860
tgggggtact aaatcaaagt gaagatatat ttaggtggca tcagaagaga tgatatagat   28920
aggttgtatc ctgtcgatag gttatttgga tatgtatcaa aagtttcttt tataatatat   28980
ctatactgat tggttgatgt atcaaatatc cctacagatt gtgaaaaaat cccctacaga   29040
```

```
ttgtgaaaat atccctagaa cctgtgatga tataagatgt gctccgcatg ctttattgaa   29100
cataatgtat tcaattcttg aaatgcagag gaacaagcag cagtgcagtg aagatgaag    29160 caacacaacc accaaatcta aacagcaact ctgcacaaat accgtcctgg atgcttcaac   29220
acatccaaga gcagtaa                                                  29237

<210> SEQ ID NO 4
<211> LENGTH: 735
<212> TYPE: DNA
<213> ORGANISM: Artificial Sequence
<220> FEATURE:
<223> OTHER INFORMATION: BvFUL cDNA

<400> SEQUENCE: 4
atggggagag gtagggttca gctcaaaaga attgaaaaca agatcaaccg tcaagtgacc     60
ttctccaaac gtcggattgg attgttgaag aaagcgcacg agatctccat tctctgcgat    120
gccgatgtag ctctcatcat cttctccact aaaggcaagc tcttcgagta tgcttctgat    180
acctgcatgg aaaggatact cgagcgctat gaaagacact catatgcaga gagacaactg    240
actgctccag atcctggatc ccatgtaagt ttgactctgg aacacgcaaa acttaaggct    300
aggctggaca ttcttcagaa aaatcaaagg cattacatgg gagaagaact tgataccttg    360
agtctcaagg agcttcagaa tttagagcat caaattgaca gtgctcttaa acacatcagg    420
tcaaagaaga accaactcat gcatgaatcg atttctcagc ttcagcgaaa ggacaaagcg    480
ttaaaggagc acaacaactt gctatccaag aaggtgaagg agagggagaa ggtgctggct    540
cagcaggcag aattggatca gcaaaatcat gacaataact catctggctt tgtgatgtct    600
caagctttgc cctcactgaa tacaggagga acaagcagca gtgcagtgga agatgaagca    660
acacaaccac caaatctaaa cagcaactct gcacaaatac cgtcctggat gcttcaacac    720
atccaagagc agtaa                                                    735

<210> SEQ ID NO 5
<211> LENGTH: 259
<212> TYPE: PRT
<213> ORGANISM: Beta vulgaris

<400> SEQUENCE: 5

Met Gly Arg Gly Arg Val Glu Leu Lys Arg Ile Glu Asn Lys Ile Asn
1               5                   10                  15

Arg Gln Val Thr Phe Ser Lys Arg Arg Ser Gly Leu Val Lys Lys Ala
            20                  25                  30

His Glu Ile Ser Val Leu Cys Asp Ala Glu Val Ala Leu Ile Ile Phe
        35                  40                  45

Ser His Arg Gly Lys Leu Phe Glu Tyr Ser Ser Asp Ser Ser Met Glu
    50                  55                  60

Lys Ile Leu Glu Arg Tyr Glu Arg Tyr Ser Tyr Ala Glu Arg Arg Leu
65                  70                  75                  80

Ala Ser Asn Asp Pro Asp Ser Gln Val Asn Trp Thr Phe Asp Phe Ala
                85                  90                  95

Lys Leu Lys Ala Lys Leu Glu Leu Leu Gln Arg Asn His Arg His Tyr
            100                 105                 110

Leu Gly Gln Glu Leu Asp Ser Leu Asn Met Lys Glu Leu Gln Ser Leu
        115                 120                 125

Glu Gln Gln Leu Asp Thr Ala Leu Lys Asn Val Arg Ser Arg Lys Asn
    130                 135                 140
```

```
Gln Leu Met His Glu Ser Ile Ser Glu Leu Gln Lys Lys Glu Arg Ala
145                 150                 155                 160

Met Gln Glu His Asn Asn Ile Leu Ser Lys Lys Ile Lys Glu Arg Gly
                165                 170                 175

Lys Asn Leu Glu Gln Val Gln Gln Met Gln Trp Gln Asn Gln His Gln
            180                 185                 190

His Gln His Gln Gln Pro Pro Pro Pro Gln Asn His Gln Val
        195                 200                 205

Pro Pro Asp Ala Ser Asn Phe Met Leu Pro Pro Ile Pro Ser Leu
    210                 215                 220

Asn Thr Gly Gly Tyr Gln Gly Gln Phe Gly Gly Glu Val Arg Arg Asn
225                 230                 235                 240

Asp Leu Asp Leu Thr Leu Glu Pro Ile Tyr Ser Cys His Met Gly Cys
                245                 250                 255

Phe Thr Thr

<210> SEQ ID NO 6
<211> LENGTH: 244
<212> TYPE: PRT
<213> ORGANISM: Beta vulgaris

<400> SEQUENCE: 6

Met Gly Arg Gly Arg Val Gln Leu Lys Arg Ile Glu Asn Lys Ile Asn
1               5                   10                  15

Arg Gln Val Thr Phe Ser Lys Arg Arg Ile Gly Leu Leu Lys Lys Ala
                20                  25                  30

His Glu Ile Ser Ile Leu Cys Asp Ala Asp Val Ala Leu Ile Ile Phe
            35                  40                  45

Ser Thr Lys Gly Lys Leu Phe Glu Tyr Ala Ser Asp Thr Cys Met Glu
50                  55                  60

Arg Ile Leu Glu Arg Tyr Glu Arg His Ser Tyr Ala Glu Arg Gln Leu
65                  70                  75                  80

Thr Ala Pro Asp Pro Gly Ser His Val Ser Leu Thr Leu Glu His Ala
                85                  90                  95

Lys Leu Lys Ala Arg Leu Asp Ile Leu Gln Lys Asn Gln Arg His Tyr
            100                 105                 110

Met Gly Glu Glu Leu Asp Thr Leu Ser Leu Lys Glu Leu Gln Asn Leu
        115                 120                 125

Glu His Gln Ile Asp Ser Ala Leu Lys His Ile Arg Ser Lys Lys Asn
130                 135                 140

Gln Leu Met His Glu Ser Ile Ser Gln Leu Gln Arg Lys Asp Lys Ala
145                 150                 155                 160

Leu Lys Glu His Asn Asn Leu Leu Ser Lys Lys Val Lys Glu Arg Glu
                165                 170                 175

Lys Val Leu Ala Gln Gln Ala Glu Leu Asp Gln Gln Asn His Asp Asn
            180                 185                 190

Asn Ser Ser Gly Phe Val Met Ser Gln Ala Leu Pro Ser Leu Asn Thr
        195                 200                 205

Gly Gly Thr Ser Ser Ser Ala Val Glu Asp Glu Ala Thr Gln Pro Pro
    210                 215                 220

Asn Leu Asn Ser Asn Ser Ala Gln Ile Pro Ser Trp Met Leu Gln His
225                 230                 235                 240

Ile Gln Glu Gln
```

<210> SEQ ID NO 7
<211> LENGTH: 2366
<212> TYPE: DNA
<213> ORGANISM: Beta vulgaris

<400> SEQUENCE: 7

| | | | | | |
|---|---|---|---|---|---|
| atgatagaac | cgcagctgaa | agcatgcaac | aaaaatgtga | agaatccgga | gagcaggaag | 60 |
| actgcttcca | cttcgtacaa | ttctgcttct | aggaagcaaa | gcaggaaggg | agaaaatcct | 120 |
| attcgtgtta | ctccgttagg | agagcaatct | tctgattttg | gatgttctag | tacttggata | 180 |
| tgtaaaaatt | ctgcatgtag | agctgttctg | tctatagatg | atgcgttctg | tcggaggtgt | 240 |
| tcatgctgca | tctgtcatca | atttgatgat | aataaagacc | ctagtctttg | gttggtttgt | 300 |
| gaatccgagt | ctgggcaggg | tgattcttgt | ggattatcat | gccatattga | gtgtgcattt | 360 |
| caacaagaaa | agctgggagt | tgtgaacctt | gggcaataca | tgcatttgga | tgggagttac | 420 |
| tgttgttctt | cttgcggcaa | agtctctggg | atacttgggt | cagtacttct | gttttatgta | 480 |
| gtgagatatt | gacctgaagt | catgcttgtt | ttgatggaag | ataataatt | taaaaaaaat | 540 |
| gttacatgcc | caactattac | aaggccagta | gaaaactatg | agatatatta | attttgatat | 600 |
| tactgtggag | gctcagttga | atttatatgc | ttgagttta | ctcactaatg | gcaggtgttg | 660 |
| gaaaaagcaa | ttggctatag | ctaaggatgc | tcgacgtgtc | gatgtgcttt | gctatagaat | 720 |
| attttgagt | tacagactcc | tcgagggcac | agctaagttt | aaggacctcc | acgagattgt | 780 |
| tgcagaagct | aaaacaaagc | tggaggcaga | ggtgggtcct | atgaacggag | actctgtcaa | 840 |
| gatggccaga | ggtattgtta | gcaggcttgc | tattgctgca | gatgtgcaaa | agctctgttc | 900 |
| gcacgcgatt | gataaagcta | atgaatggct | cgccaatgtt | tctagcatta | gttcaaattg | 960 |
| caaaggttag | aatacataca | gcctttattg | ttctccattt | acttggtgag | tattctatta | 1020 |
| taataaatta | ttaatttctt | ttggcataat | ggtggcagtg | gatgcacttc | ctgctgcatg | 1080 |
| caggtttcta | tttgaagaag | ttacttcttg | ttcacttgct | atagtttga | tagatatccc | 1140 |
| cacaccaatg | actgattccg | tcaaaggcta | caagctatgg | tactgcaaaa | gtagacatga | 1200 |
| gacttttgca | agggagccta | catccgtctt | tccaagggag | aaaagaaaaa | tatctgtaaa | 1260 |
| gaatctcaag | ccttgcaccg | agtacacatt | cagaatagtt | tcctacacag | aagttggtga | 1320 |
| tttaggccac | tctgaggcta | agtgtttcac | caagagtttg | gagatcatta | gtaagaaatc | 1380 |
| caccacagtg | ggctgtaaga | aggaagatcc | ttgtgttgag | aggagctcct | cgaatgcaaa | 1440 |
| ggaacaacat | aattcaaatt | tggctgcaat | atcttctgga | ttcaaggtgc | gggaccttgg | 1500 |
| gaaaatcttg | cacctagcat | gggcccaaga | acagggttgc | cttgaaggtt | tctgcagtgc | 1560 |
| tgatgtagaa | caatgctgtg | gagtaactaa | atgtgaatct | ccaaaagatc | accagtcacc | 1620 |
| tccacctgtt | tctcgtgagc | ttgacctaaa | tgtagtttca | gttcctgatt | taaatgaaga | 1680 |
| ccttacccct | cccttagagt | cttcaaggga | tgaagacaac | ggatgcacgc | tagagcgtgc | 1740 |
| tactgggcct | gatgatgatg | ctgcttccca | tggtgttgag | aagaatgggc | ttgggctagc | 1800 |
| caggtcaaat | ggtagtgggc | caagtgatga | gtctcaagct | tgggctctca | tccgaaatgg | 1860 |
| agatgtgcct | gctgttgatt | ccttggcaga | gacccgtcgg | aagaggtctt | caagtgcgaa | 1920 |
| tgaagaaaca | catgactgtg | acagcactct | gataaatgga | tcgccatttc | ggatttcagg | 1980 |
| cgggcctggt | tctctagacg | gtaactttga | gtattgtgtg | aaggtcatcc | ggtggttgga | 2040 |
| gtgtgagggc | tatctaaaac | aggaatttag | attgaaatta | ttgacttggt | ttagcttaag | 2100 |
| atctactgaa | caagagcgtc | gggtagtcag | cactttcatt | caaactctga | tggatgatcc | 2160 |

| | |
|---|---|
| aaagagctta gcaggacagc tagttgattc ctttggagat ctcatatcca gcaagaggcc | 2220 |
| caggactagt ttcactagta agtttatgtc tatagttgtt ctttgattga gaaatttttat | 2280 |
| gtcttctttc aaacatttct attactcttc ttattctgaa gttttggact aattttgtca | 2340 |
| tgctaattac aggcattcct tcctaa | 2366 |

<210> SEQ ID NO 8
<211> LENGTH: 2285
<212> TYPE: DNA
<213> ORGANISM: Artificial Sequence
<220> FEATURE:
<223> OTHER INFORMATION: BvVIL1 cDNA

<400> SEQUENCE: 8

| | |
|---|---|
| atgatagaac cgcagctgaa agcatgcaac aaaaatgtga agaatccgga gagcaggaag | 60 |
| actgcttcca cttcgtacaa ttctgcttct aggaagcaaa gcaggaaggg agaaaatcct | 120 |
| attcgtgtta ctccgttagg agagcaatct tctgattttg gatgttctag tacttggata | 180 |
| tgtaaaaatt ctgcatgtag agctgttctg tctatagatg atgcgttctg tcggaggtgt | 240 |
| tcatgctgca tctgtcatca atttgatgat aataaagacc ctagtctttg gttggtttgt | 300 |
| gaatccgagt ctgggcaggg tgattcttgt ggattatcat gccatattga gtgtgcattt | 360 |
| caacaagaaa agctgggagt gtgaaccctt gggcaataca tgcatttgga tgggagttac | 420 |
| tgttgttctt cttgcggcaa agtctctggg atacttgggt gttggaaaaa gcaattggct | 480 |
| atagctaagg atgctcgacg tgtcgatgtg ctttgctata gaatattttt gagttacaga | 540 |
| ctcctcgagg gcacagctaa gtttaaggac ctccacgaga ttgttgcaga agctaaaaca | 600 |
| aagctggagg cagaggtggg tcctatgaac ggagactctg tcaagatggc cagaggtatt | 660 |
| gttagcaggc ttgctattgc tgcagatgtg caaaagctct gttcgcacgc gattgataaa | 720 |
| gctaatgaat ggctcgccaa tgtttctagc attagttcaa attgcaaagt ggatgcactt | 780 |
| cctgctgcat gcaggtttct atttgaagaa gttacttctt gttcacttgc tatagttttg | 840 |
| atagatatcc ccacaccaat gactgattcc gtcaaaggct acaagctatg gtactgcaaa | 900 |
| agtagacatg agacttttgc aagggagcct acatccgtct ttccaaggga gaaaagaaaa | 960 |
| atatctgtaa agaatctcaa gccttgcacc gagtacacat tcagaatagt ttcctacaca | 1020 |
| gaagttggtg atttaggcca ctctgaggct aagtgtttca ccaagagttt ggagatcatt | 1080 |
| agtaagaaat ccaccacagt gggctgtaag aaggaagatc cttgtgttga gaggagctcc | 1140 |
| tcgaatgcaa aggaacaaca taattcaaat ttggctgcaa tatcttctgg attcaaggtg | 1200 |
| cgggaccttg ggaaaatctt gcacctagca tgggcccaag aacaggggttg ccttgaaggt | 1260 |
| ttctgcagtg ctgatgtaga acaatgctgt ggagtaacta aatgtgaatc tccaaaagat | 1320 |
| caccagtcac ctccacctgt ttctcgtgag cttgacctaa atgtagtttc agttcctgat | 1380 |
| ttaaatgaag accttacccc tcccttagag tcttcaaggg atgaagacaa cggatgcacg | 1440 |
| ctagagcgtg ctactgggcc tgatgatgat gctgcttccc atggtgttga agaatgggg | 1500 |
| cttgggctag ccaggtcaaa tggtagtggg ccaagtgatg agtctcaagc ttgggctctc | 1560 |
| atccgaaatg gagatgtgcc tgctgttgat tccttggcag agacccgtcg gaagaggtct | 1620 |
| tcaagtgcga atgaagaaac acatgactgt gacagcactc tgataaatgg atcgccattt | 1680 |
| cggatttcag gcgggcctgg ttctctagac ggtaactttg agtattgtgt gaaggtcatc | 1740 |
| cggtggtttgg agtgtgaggg ctatctaaaa caggaattta gattgaaatt attgacttgg | 1800 |
| tttagcttaa gatctactga acaagagcgt cgggtagtca gcactttcat tcaaactctg | 1860 |

```
atggatgatc caaagagctt agcaggacag ctagttgatt cctttggaga tctcatatcc    1920
agcaagaggc ccaggactag tttcactagc attccttcct aaataaatct taactaagga    1980
cggcacacat atcttggata caattcagat gtttaggaca caattttttag gaggcagtac    2040 ctgatttttcc tcgagaaagg gattccatca gtggttaact gcacatttta gaaggtattt    2100
gttagagttt ccttgaccac atttgtagaa agattcacat tgagacaatc attgttgcct    2160
tctcgcattg aaggaaggat atatgcttca atgaatattt aaattctagt tcaatttact    2220
aattaattag tttgttttct caaaaaaaaa aaaaaaaaa aaaagtact agtcgacgcg    2280 tggcc                                                                 2285
```

<210> SEQ ID NO 9
<211> LENGTH: 653
<212> TYPE: PRT
<213> ORGANISM: Beta vulgaris

<400> SEQUENCE: 9

```
Met Ile Glu Pro Gln Leu Lys Ala Cys Asn Lys Asn Val Lys Asn Pro
1               5                   10                  15

Glu Ser Arg Lys Thr Ala Ser Thr Ser Tyr Asn Ser Ala Ser Arg Lys
            20                  25                  30

Gln Ser Arg Lys Gly Glu Asn Pro Ile Arg Val Thr Pro Leu Gly Glu
        35                  40                  45

Gln Ser Ser Asp Phe Gly Cys Ser Ser Thr Trp Ile Cys Lys Asn Ser
    50                  55                  60

Ala Cys Arg Ala Val Leu Ser Ile Asp Asp Ala Phe Cys Arg Arg Cys
65                  70                  75                  80

Ser Cys Cys Ile Cys His Gln Phe Asp Asp Asn Lys Asp Pro Ser Leu
                85                  90                  95

Trp Leu Val Cys Glu Ser Glu Ser Gly Gln Gly Asp Ser Cys Gly Leu
            100                 105                 110

Ser Cys His Ile Glu Cys Ala Phe Gln Gln Glu Lys Leu Gly Val Val
        115                 120                 125

Asn Leu Gly Gln Tyr Met His Leu Asp Gly Ser Tyr Cys Cys Ser Ser
    130                 135                 140

Cys Gly Lys Val Ser Gly Ile Leu Gly Cys Trp Lys Lys Gln Leu Ala
145                 150                 155                 160

Ile Ala Lys Asp Ala Arg Arg Val Asp Val Leu Cys Tyr Arg Ile Phe
                165                 170                 175

Leu Ser Tyr Arg Leu Leu Glu Gly Thr Ala Lys Phe Lys Asp Leu His
            180                 185                 190

Glu Ile Val Ala Glu Ala Lys Thr Lys Leu Glu Ala Glu Val Gly Pro
        195                 200                 205

Met Asn Gly Asp Ser Val Lys Met Ala Arg Gly Ile Val Ser Arg Leu
    210                 215                 220

Ala Ile Ala Ala Asp Val Gln Lys Leu Cys Ser His Ala Ile Asp Lys
225                 230                 235                 240

Ala Asn Glu Trp Leu Ala Asn Val Ser Ser Ile Ser Ser Asn Cys Lys
                245                 250                 255

Val Asp Ala Leu Pro Ala Ala Cys Arg Phe Leu Phe Glu Glu Val Thr
            260                 265                 270

Ser Cys Ser Leu Ala Ile Val Leu Ile Asp Ile Pro Thr Pro Met Thr
        275                 280                 285
```

```
Asp Ser Val Lys Gly Tyr Lys Leu Trp Tyr Cys Lys Ser Arg His Glu
    290                 295                 300

Thr Phe Ala Arg Glu Pro Thr Ser Val Phe Pro Arg Glu Lys Arg Lys
305                 310                 315                 320

Ile Ser Val Lys Asn Leu Lys Pro Cys Thr Glu Tyr Thr Phe Arg Ile
                325                 330                 335

Val Ser Tyr Thr Glu Val Gly Asp Leu Gly His Ser Glu Ala Lys Cys
            340                 345                 350

Phe Thr Lys Ser Leu Glu Ile Ile Ser Lys Lys Ser Thr Thr Val Gly
        355                 360                 365

Cys Lys Lys Glu Asp Pro Cys Val Glu Arg Ser Ser Asn Ala Lys
370                 375                 380

Glu Gln His Asn Ser Asn Leu Ala Ala Ile Ser Ser Gly Phe Lys Val
385                 390                 395                 400

Arg Asp Leu Gly Lys Ile Leu His Leu Ala Trp Ala Gln Glu Gln Gly
                405                 410                 415

Cys Leu Glu Gly Phe Cys Ser Ala Asp Val Glu Gln Cys Cys Gly Val
            420                 425                 430

Thr Lys Cys Glu Ser Pro Lys Asp His Gln Ser Pro Pro Pro Val Ser
        435                 440                 445

Arg Glu Leu Asp Leu Asn Val Val Ser Val Pro Asp Leu Asn Glu Asp
450                 455                 460

Leu Thr Pro Pro Leu Glu Ser Ser Arg Asp Glu Asp Asn Gly Cys Thr
465                 470                 475                 480

Leu Glu Arg Ala Thr Gly Pro Asp Asp Ala Ala Ser His Gly Val
                485                 490                 495

Glu Lys Asn Gly Leu Gly Leu Ala Arg Ser Asn Gly Ser Gly Pro Ser
            500                 505                 510

Asp Glu Ser Gln Ala Trp Ala Leu Ile Arg Asn Gly Asp Val Pro Ala
        515                 520                 525

Val Asp Ser Leu Ala Glu Thr Arg Arg Lys Arg Ser Ser Ser Ala Asn
530                 535                 540

Glu Glu Thr His Asp Cys Asp Ser Thr Leu Ile Asn Gly Ser Pro Phe
545                 550                 555                 560

Arg Ile Ser Gly Gly Pro Gly Ser Leu Asp Gly Asn Phe Glu Tyr Cys
                565                 570                 575

Val Lys Val Ile Arg Trp Leu Glu Cys Glu Gly Tyr Leu Lys Gln Glu
            580                 585                 590

Phe Arg Leu Lys Leu Leu Thr Trp Phe Ser Leu Arg Ser Thr Glu Gln
        595                 600                 605

Glu Arg Arg Val Val Ser Thr Phe Ile Gln Thr Leu Met Asp Asp Pro
610                 615                 620

Lys Ser Leu Ala Gly Gln Leu Val Asp Ser Phe Gly Asp Leu Ile Ser
625                 630                 635                 640

Ser Lys Arg Pro Arg Thr Ser Phe Thr Ser Ile Pro Ser
                645                 650
```

<210> SEQ ID NO 10
<211> LENGTH: 184
<212> TYPE: DNA
<213> ORGANISM: Artificial Sequence
<220> FEATURE:
<223> OTHER INFORMATION: BvAP1 cDNA

<400> SEQUENCE: 10

```
ctagagcaag tgcaacagat gcagtggcag aaccagcacc agcaccagca ccagcagcag    60
ccgccaccgc cgccacaaaa tcatcaagtt cctcctgacg catcaaattt catgctccca   120
cctccaattc cttctttgaa cacgggtggg taccaaggac aatttggtgg agaagtaagg   180
agga                                                                184

<210> SEQ ID NO 11
<211> LENGTH: 150
<212> TYPE: DNA
<213> ORGANISM: Artificial Sequence
<220> FEATURE:
<223> OTHER INFORMATION: BvAP1 fragment

<400> SEQUENCE: 11
ctagagcaag tgcaacagat gcagtggcag aaccagcacc agcaccagca ccagcagcag    60
ccgccaccgc cgccacaaaa tcatcaagtt cctcctgacg catcaaattt catgctccca   120
cctccaattc cttctttgaa cacgggtggg                                    150

<210> SEQ ID NO 12
<211> LENGTH: 100
<212> TYPE: DNA
<213> ORGANISM: Artificial Sequence
<220> FEATURE:
<223> OTHER INFORMATION: BvAP1 fragment

<400> SEQUENCE: 12
ctagagcaag tgcaacagat gcagtggcag aaccagcacc agcaccagca ccagcagcag    60
ccgccaccgc cgccacaaaa tcatcaagtt cctcctgacg                         100

<210> SEQ ID NO 13
<211> LENGTH: 50
<212> TYPE: DNA
<213> ORGANISM: Artificial Sequence
<220> FEATURE:
<223> OTHER INFORMATION: BvAP1 fragment

<400> SEQUENCE: 13
ctagagcaag tgcaacagat gcagtggcag aaccagcacc agcaccagca              50

<210> SEQ ID NO 14
<211> LENGTH: 212
<212> TYPE: DNA
<213> ORGANISM: Artificial Sequence
<220> FEATURE:
<223> OTHER INFORMATION: BvFUL fragment

<400> SEQUENCE: 14
agagggagaa ggtgctggct cagcaggcag aattggatca gcaaaatcat gacaataact    60
catctggctt tgtgatgtct caagctttgc cctcactgaa tacaggagga caagcagca   120 gtgcagtgga agatgaagca acacaaccac caaatctaaa cagcaactct gcacaaatac   180
cgtcctggat gcttcaacac atccaagagc ag                                 212

<210> SEQ ID NO 15
<211> LENGTH: 150
<212> TYPE: DNA
<213> ORGANISM: Artificial Sequence
<220> FEATURE:
<223> OTHER INFORMATION: BvFUL fragment

<400> SEQUENCE: 15
tctggctttg tgatgtctca agctttgccc tcactgaata caggaggaac aagcagcagt    60
```

```
gcagtggaag atgaagcaac acaaccacca aatctaaaca gcaactctgc acaaataccg    120
tcctggatgc ttcaacacat ccaagagcag                                     150

<210> SEQ ID NO 16
<211> LENGTH: 100
<212> TYPE: DNA
<213> ORGANISM: Artificial Sequence
<220> FEATURE:
<223> OTHER INFORMATION: BvFUL fragment

<400> SEQUENCE: 16
aagcagcagt gcagtggaag atgaagcaac acaaccacca aatctaaaca gcaactctgc     60
acaaataccg tcctggatgc ttcaacacat ccaagagcag                          100

<210> SEQ ID NO 17
<211> LENGTH: 50
<212> TYPE: DNA
<213> ORGANISM: Artificial Sequence
<220> FEATURE:
<223> OTHER INFORMATION: BvFUL fragment

<400> SEQUENCE: 17
gcaactctgc acaaataccg tcctggatgc ttcaacacat ccaagagcag                50

<210> SEQ ID NO 18
<211> LENGTH: 399
<212> TYPE: DNA
<213> ORGANISM: Artificial Sequence
<220> FEATURE:
<223> OTHER INFORMATION: BvVIL1 fragment

<400> SEQUENCE: 18
cacagctaag tttaaggacc tccacgagat tgttgcagaa gctaaaacaa agctggaggc     60
agaggtgggt cctatgaacg gagactctgt caagatggcc agaggtattg ttagcaggct    120
tgctattgct gcagatgtgc aaaagctctg ttcgcacgcg attgataaag ctaatgaatg    180
gctcgccaat gtttctagca ttagttcaaa ttgcaaagtg gatgcacttc ctgctgcatg    240
caggtttcta tttgaagaag ttacttcttg ttcacttgct atagttttga tagatatccc    300
cacaccaatg actgattccg tcaaaggcta caagctatgg tactgcaaaa gtagacatga    360
gacttttgca agggagccta catccgtctt tccaaggga                           399

<210> SEQ ID NO 19
<211> LENGTH: 396
<212> TYPE: DNA
<213> ORGANISM: Artificial Sequence
<220> FEATURE:
<223> OTHER INFORMATION: construct comprising BvFUL fragment and BvAP1
      fragment

<400> SEQUENCE: 19
agagggagaa ggtgctggct cagcaggcag aattggatca gcaaaatcat gacaataact     60
catctggctt tgtgatgtct caagctttgc cctcactgaa tacaggagga caagcagca    120 gtgcagtgga agatgaagca acacaaccac caaatctaaa cagcaactct gcacaaatac    180
cgtcctggat gcttcaacac atccaagagc agctagagca agtgcaacag atgcagtggc    240
agaaccagca ccagcaccag caccagcagc agccgccacc gccgccacaa aatcatcaag    300
ttcctcctga cgcatcaaat ttcatgctcc cacctccaat tccttctttg aacacgggtg    360
ggtaccaagg acaatttggt ggagaagtaa ggagga                              396
```

```
<210> SEQ ID NO 20
<211> LENGTH: 300
<212> TYPE: DNA
<213> ORGANISM: Artificial Sequence
<220> FEATURE:
<223> OTHER INFORMATION: construct comprising BvFUL fragment and BvAP1
      fragment

<400> SEQUENCE: 20
tctggctttg tgatgtctca agctttgccc tcactgaata caggaggaac aagcagcagt    60
gcagtggaag atgaagcaac acaaccacca aatctaaaca gcaactctgc acaaataccg   120
tcctggatgc ttcaacacat ccaagagcag ctagagcaag tgcaacagat gcagtggcag   180
aaccagcacc agcaccagca ccagcagcag ccgccaccgc cgccacaaaa tcatcaagtt   240
cctcctgacg catcaaattt catgctccca cctccaattc cttctttgaa cacgggtggg   300

<210> SEQ ID NO 21
<211> LENGTH: 200
<212> TYPE: DNA
<213> ORGANISM: Artificial Sequence
<220> FEATURE:
<223> OTHER INFORMATION: construct comprising BvFUL fragment and BvAP1
      fragment

<400> SEQUENCE: 21
aagcagcagt gcagtggaag atgaagcaac acaaccacca aatctaaaca gcaactctgc    60
acaaataccg tcctggatgc ttcaacacat ccaagagcag ctagagcaag tgcaacagat   120
gcagtggcag aaccagcacc agcaccagca ccagcagcag ccgccaccgc cgccacaaaa   180
tcatcaagtt cctcctgacg                                               200

<210> SEQ ID NO 22
<211> LENGTH: 100
<212> TYPE: DNA
<213> ORGANISM: Artificial Sequence
<220> FEATURE:
<223> OTHER INFORMATION: construct comprising BvFUL fragment and BvAP1
      fragment

<400> SEQUENCE: 22
gcaactctgc acaaataccg tcctggatgc ttcaacacat ccaagagcag ctagagcaag    60
tgcaacagat gcagtggcag aaccagcacc agcaccagca                         100

<210> SEQ ID NO 23
<211> LENGTH: 795
<212> TYPE: DNA
<213> ORGANISM: Artificial Sequence
<220> FEATURE:
<223> OTHER INFORMATION: construct comprising BvFUL fragment, BvAP1
      fragment and BvVIL1 fragment

<400> SEQUENCE: 23
agagggagaa ggtgctggct cagcaggcag aattggatca gcaaaatcat gacaataact    60
catctggctt tgtgatgtct caagctttgc cctcactgaa tacaggagga caagcagca   120 gtgcagtgga agatgaagca acacaaccac caaatctaaa cagcaactct gcacaaatac   180
cgtcctggat gcttcaacac atccaagagc agctagagca agtgcaacag atgcagtggc   240
agaaccagca ccagcaccag caccagcagc agccgccacc gccgccacaa aatcatcaag   300
ttcctcctga cgcatcaaat ttcatgctcc cacctccaat tccttctttg aacacgggtg   360
```

```
ggtaccaagg acaatttggt ggagaagtaa ggaggacaca gctaagttta aggacctcca      420
cgagattgtt gcagaagcta aaacaaagct ggaggcagag gtgggtccta tgaacggaga      480
ctctgtcaag atggccagag gtattgttag caggcttgct attgctgcag atgtgcaaaa      540
gctctgttcg cacgcgattg ataaagctaa tgaatggctc gccaatgttt ctagcattag      600
ttcaaattgc aaagtggatg cacttcctgc tgcatgcagg tttctatttg aagaagttac      660
ttcttgttca cttgctatag ttttgataga tatccccaca ccaatgactg attccgtcaa      720
aggctacaag ctatggtact gcaaaagtag acatgagact tttgcaaggg agcctacatc      780
cgtctttcca aggga                                                      795
```

```
<210> SEQ ID NO 24
<211> LENGTH: 845
<212> TYPE: DNA
<213> ORGANISM: Beta vulgaris

<400> SEQUENCE: 24
ctaggtcaga ttcgctatct atcttcttct tctttttttgt tggtcaatca ctctgaagaa      60
cctttatgac aagtagtatt aagtttcatg aacttctagt ttaaactcgc tctaaaaata     120 ctaaagatt acatttcaat atatattcct gtgttatata tacacatgct gttttgtagt      180
aaatattatg tgaagttggt cttaaaattg acatgatgta aatatcacgt cagttttat      240 aaccgattca aattaaacat cagttataac aagcgatgca aatattatgt gaagttgcat     300
cagttgttaa taaatcgatg taaattattt gcatcaacaa gatacgaatc gtttatttaa     360
gtgatgtaaa atttctttac atcaattata agtaatacaa atattcaata taagtgattt     420
aaaatgatat ttttttttgta gtgatcccat gtgaagttat aattcattct ttcagcatca    480
tagtctcttg gagttttctc tttgtcctca ccacacttat tattctcttc ccttttaact    540
atcaaaagat accctcccct taactttaag attttaaatt aagaaatcgt agacacgaaa    600
aatctaagaa ctaacaaata ttttgataaa gacagcttct aaaattcaat atctgaatag    660
tatctcttgg aaaatgtcgt gttgtggtcg gtcacatttc aacactcttg tacaaaagcg    720
tcaacttgac ttcatgtgac agttttttgtt tattagagat gtttagttgt agaattgatg    780
atttatgtat ataacaacga tattctatag atatatattg atgttaaaag ataaacagga    840
ggaac                                                                845
```

```
<210> SEQ ID NO 25
<211> LENGTH: 29
<212> TYPE: DNA
<213> ORGANISM: Artificial Sequence
<220> FEATURE:
<223> OTHER INFORMATION: forward primer WAG-AP1FUL

<400> SEQUENCE: 25
ctcgagagag ggagaaggtg ctggctcag                                        29
```

```
<210> SEQ ID NO 26
<211> LENGTH: 31
<212> TYPE: DNA
<213> ORGANISM: Artificial Sequence
<220> FEATURE:
<223> OTHER INFORMATION: reverse primer WAG-AP1FUL

<400> SEQUENCE: 26
cccgggtcct ccttacttct ccaccaaatt g                                     31
```

```
<210> SEQ ID NO 27
<211> LENGTH: 31
<212> TYPE: DNA
<213> ORGANISM: Artificial Sequence
<220> FEATURE:
<223> OTHER INFORMATION: forward primer vil1RNAi-fwd

<400> SEQUENCE: 27
gtcgaccaca gctaagttta aggacctcca c                              31

<210> SEQ ID NO 28
<211> LENGTH: 29
<212> TYPE: DNA
<213> ORGANISM: Artificial Sequence
<220> FEATURE:
<223> OTHER INFORMATION: reverse primer vil1RNAi-rev

<400> SEQUENCE: 28
ctcgagtccc ttggaaagac ggatgtagg                                 29

<210> SEQ ID NO 29
<211> LENGTH: 411
<212> TYPE: DNA
<213> ORGANISM: Artificial Sequence
<220> FEATURE:
<223> OTHER INFORMATION: VIL1 cDNA fragment for cloning of VIL1-AP1-FUL
      RNAi construct

<400> SEQUENCE: 29
gtcgaccaca gctaagttta aggacctcca cgagattgtt gcagaagcta aaacaaagct     60
ggaggcagag gtgggtccta tgaacggaga ctctgtcaag atggccagag gtattgttag    120
caggcttgct attgctgcag atgtgcaaaa gctctgttcg cacgcgattg ataaagctaa    180
tgaatggctc gccaatgttt ctagcattag ttcaaattgc aaagtggatg cacttcctgc    240
tgcatgcagg tttctatttg aagaagttac ttcttgttca cttgctatag ttttgataga    300
tatccccaca ccaatgactg attccgtcaa aggctacaag ctatggtact gcaaaagtag    360
acatgagact tttgcaaggg agcctacatc cgtctttcca agggactcga g            411

<210> SEQ ID NO 30
<211> LENGTH: 408
<212> TYPE: DNA
<213> ORGANISM: Artificial Sequence
<220> FEATURE:
<223> OTHER INFORMATION: construct comprising BvFUL fragment and BvAP1
      fragment for cloning of VIL1-AP1-FUL RNAi construct

<400> SEQUENCE: 30
ctcgagagag ggagaaggtg ctggctcagc aggcagaatt ggatcagcaa atcatgaca     60 ataactcatc tggctttgtg atgtctcaag ctttgccctc actgaataca ggaggaacaa    120
gcagcagtgc agtggaagat gaagcaacac aaccaccaaa tctaaacagc aactctgcac    180
aaataccgtc ctggatgctt caacacatcc aagagcagct agagcaagtg caacagatgc    240
agtggcagaa ccagcaccag caccagcacc agcagcagcc gccaccgccg ccacaaaatc    300
atcaagttcc tcctgacgca tcaaatttca tgctcccacc tccaattcct tctttgaaca    360
cgggtgggta ccaaggacaa tttggtggag aagtaaggag gacccggg              408

<210> SEQ ID NO 31
<211> LENGTH: 25
<212> TYPE: DNA
<213> ORGANISM: Artificial Sequence
<220> FEATURE:
```

```
<223> OTHER INFORMATION: forward primer for VIL1-AP1-Ful

<400> SEQUENCE: 31
gtcgaccaca gctaagttta aggac                                           25

<210> SEQ ID NO 32
<211> LENGTH: 25
<212> TYPE: DNA
<213> ORGANISM: Artificial Sequence
<220> FEATURE:
<223> OTHER INFORMATION: reverse primer for VIL1-AP1-Ful

<400> SEQUENCE: 32
cccgggtcct ccttacttct ccacc                                           25

<210> SEQ ID NO 33
<211> LENGTH: 780
<212> TYPE: DNA
<213> ORGANISM: Artificial Sequence
<220> FEATURE:
<223> OTHER INFORMATION: BvAP1 cDNA showing sites for mutagenesis
<220> FEATURE:
<221> NAME/KEY: mutation
<222> LOCATION: (1)..(1)
<223> OTHER INFORMATION: any nucleotide except a
<220> FEATURE:
<221> NAME/KEY: mutation
<222> LOCATION: (2)..(2)
<223> OTHER INFORMATION: any nucleotide except t
<220> FEATURE:
<221> NAME/KEY: mutation
<222> LOCATION: (3)..(3)
<223> OTHER INFORMATION: any nucleotide except g
<220> FEATURE:
<221> NAME/KEY: mutation
<222> LOCATION: (52)..(52)
<223> OTHER INFORMATION: c to t
<220> FEATURE:
<221> NAME/KEY: mutation
<222> LOCATION: (151)..(151)
<223> OTHER INFORMATION: c to t
<220> FEATURE:
<221> NAME/KEY: mutation
<222> LOCATION: (262)..(262)
<223> OTHER INFORMATION: c to t
<220> FEATURE:
<221> NAME/KEY: mutation
<222> LOCATION: (316)..(316)
<223> OTHER INFORMATION: c to t
<220> FEATURE:
<221> NAME/KEY: mutation
<222> LOCATION: (343)..(343)
<223> OTHER INFORMATION: c to t
<220> FEATURE:
<221> NAME/KEY: mutation
<222> LOCATION: (376)..(376)
<223> OTHER INFORMATION: c to t
<220> FEATURE:
<221> NAME/KEY: mutation
<222> LOCATION: (388)..(388)
<223> OTHER INFORMATION: c to t
<220> FEATURE:
<221> NAME/KEY: mutation
<222> LOCATION: (391)..(391)
<223> OTHER INFORMATION: c to t
<220> FEATURE:
<221> NAME/KEY: mutation
<222> LOCATION: (418)..(418)
<223> OTHER INFORMATION: c to t
<220> FEATURE:
<221> NAME/KEY: mutation
<222> LOCATION: (433)..(433)
<223> OTHER INFORMATION: c to t
<220> FEATURE:
<221> NAME/KEY: mutation
```

```
<222> LOCATION: (463)..(463)
<223> OTHER INFORMATION: c to t
<220> FEATURE:
<221> NAME/KEY: mutation
<222> LOCATION: (484)..(484)
<223> OTHER INFORMATION: c to t
<220> FEATURE:
<221> NAME/KEY: mutation
<222> LOCATION: (541)..(541)
<223> OTHER INFORMATION: c to t
<220> FEATURE:
<221> NAME/KEY: mutation
<222> LOCATION: (547)..(547)
<223> OTHER INFORMATION: c to t
<220> FEATURE:
<221> NAME/KEY: mutation
<222> LOCATION: (550)..(550)
<223> OTHER INFORMATION: c to t
<220> FEATURE:
<221> NAME/KEY: mutation
<222> LOCATION: (556)..(556)
<223> OTHER INFORMATION: c to t
<220> FEATURE:
<221> NAME/KEY: mutation
<222> LOCATION: (562)..(562)
<223> OTHER INFORMATION: c to t
<220> FEATURE:
<221> NAME/KEY: mutation
<222> LOCATION: (568)..(568)
<223> OTHER INFORMATION: c to t
<220> FEATURE:
<221> NAME/KEY: mutation
<222> LOCATION: (574)..(574)
<223> OTHER INFORMATION: c to t
<220> FEATURE:
<221> NAME/KEY: mutation
<222> LOCATION: (580)..(580)
<223> OTHER INFORMATION: c to t
<220> FEATURE:
<221> NAME/KEY: mutation
<222> LOCATION: (586)..(586)
<223> OTHER INFORMATION: c to t
<220> FEATURE:
<221> NAME/KEY: mutation
<222> LOCATION: (589)..(589)
<223> OTHER INFORMATION: c to t
<220> FEATURE:
<221> NAME/KEY: mutation
<222> LOCATION: (592)..(592)
<223> OTHER INFORMATION: c to t
<220> FEATURE:
<221> NAME/KEY: mutation
<222> LOCATION: (610)..(610)
<223> OTHER INFORMATION: c to t
<220> FEATURE:
<221> NAME/KEY: mutation
<222> LOCATION: (619)..(619)
<223> OTHER INFORMATION: c to t
<220> FEATURE:
<221> NAME/KEY: mutation
<222> LOCATION: (688)..(688)
<223> OTHER INFORMATION: c to t
<220> FEATURE:
<221> NAME/KEY: mutation
<222> LOCATION: (694)..(694)
<223> OTHER INFORMATION: c to t

<400> SEQUENCE: 33
bvhggaaggg gtagggttga gctgaagagg atagagaata agatcaatag acaagtaact      60
ttttcaaaga gaagaagtgg acttgtgaag aaagctcatg aaatttctgt tctttgtgat     120
gctgaggttg ctctgatcat ttttttctcac tgaggaaaac tctttgagta ttcttctgat    180
tcttctatgg agaagatcct agaaaggtat gagaggtatt cttacgcaga agacggcta     240 gcttcaaatg atccagactc ataggtaaac tggacctttg acttcgcaaa actgaaggcg    300
```

```
aagcttgaac ttctataaag gaatcatagg cactacttag gataagagct tgactcgctt    360
aacatgaagg aactttagag tttagagtaa taacttgata ctgctctaaa aaatgtttga    420
tctaggaaga actaactgat gcacgagtcc atttctgaac tctagaagaa ggagagggca    480
atgtaggagc acaataacat cctgtctaag aagatcaagg agagaggaaa aaatctagag    540
taagtgtaat agatgtagtg gtagaactag cactagcact agcactagta gtagccgcca    600
ccgccgccat aaaatcatta agttcctcct gacgcatcaa atttcatgct cccacctcca    660
attccttctt tgaacacggg tgggtactaa ggataatttg gtggagaagt aaggaggaat    720
gatcttgacc tgacgctaga accgatatac tcatgtcaca tgggatgctt tacaacatga    780
```

<210> SEQ ID NO 34
<211> LENGTH: 735
<212> TYPE: DNA
<213> ORGANISM: Artificial Sequence
<220> FEATURE:
<223> OTHER INFORMATION: BvAP1 cDNA showing sites for mutagenesis
<220> FEATURE:
<221> NAME/KEY: mutation
<222> LOCATION: (1)..(1)
<223> OTHER INFORMATION: any nucleotide except a
<220> FEATURE:
<221> NAME/KEY: mutation
<222> LOCATION: (2)..(2)
<223> OTHER INFORMATION: any nucleotide except t
<220> FEATURE:
<221> NAME/KEY: mutation
<222> LOCATION: (3)..(3)
<223> OTHER INFORMATION: any nucleotide except g
<220> FEATURE:
<221> NAME/KEY: mutation
<222> LOCATION: (19)..(19)
<223> OTHER INFORMATION: c to t
<220> FEATURE:
<221> NAME/KEY: mutation
<222> LOCATION: (52)..(52)
<223> OTHER INFORMATION: c to t
<220> FEATURE:
<221> NAME/KEY: mutation
<222> LOCATION: (235)..(235)
<223> OTHER INFORMATION: c to t
<220> FEATURE:
<221> NAME/KEY: mutation
<222> LOCATION: (316)..(316)
<223> OTHER INFORMATION: c to t
<220> FEATURE:
<221> NAME/KEY: mutation
<222> LOCATION: (325)..(325)
<223> OTHER INFORMATION: c to t
<220> FEATURE:
<221> NAME/KEY: mutation
<222> LOCATION: (376)..(376)
<223> OTHER INFORMATION: c to t
<220> FEATURE:
<221> NAME/KEY: mutation
<222> LOCATION: (391)..(391)
<223> OTHER INFORMATION: c to t
<220> FEATURE:
<221> NAME/KEY: mutation
<222> LOCATION: (433)..(433)
<223> OTHER INFORMATION: c to t
<220> FEATURE:
<221> NAME/KEY: mutation
<222> LOCATION: (457)..(457)
<223> OTHER INFORMATION: c to t
<220> FEATURE:
<221> NAME/KEY: mutation
<222> LOCATION: (463)..(463)
<223> OTHER INFORMATION: c to t
<220> FEATURE:
<221> NAME/KEY: mutation
<222> LOCATION: (466)..(466)
<223> OTHER INFORMATION: c to t
<220> FEATURE:
<221> NAME/KEY: mutation
<222> LOCATION: (541)..(541)
<223> OTHER INFORMATION: c to t
<220> FEATURE:
<221> NAME/KEY: mutation
<222> LOCATION: (544)..(544)
<223> OTHER INFORMATION: c to t
<220> FEATURE:
<221> NAME/KEY: mutation
<222> LOCATION: (559)..(559)
<223> OTHER INFORMATION: c to t
<220> FEATURE:
<221> NAME/KEY: mutation
<222> LOCATION: (562)..(562)
<223> OTHER INFORMATION: c to t
<220> FEATURE:
<221> NAME/KEY: mutation
<222> LOCATION: (601)..(601)
<223> OTHER INFORMATION: c to t
<220> FEATURE:
<221> NAME/KEY: mutation
<222> LOCATION: (664)..(664)
<223> OTHER INFORMATION: c to t
<220> FEATURE:
<221> NAME/KEY: mutation
<222> LOCATION: (694)..(694)
<223> OTHER INFORMATION: c to t
<220> FEATURE:
<221> NAME/KEY: mutation
<222> LOCATION: (715)..(715)
<223> OTHER INFORMATION: c to t
<220> FEATURE:
<221> NAME/KEY: mutation
<222> LOCATION: (724)..(724)
<223> OTHER INFORMATION: c to t

<400> SEQUENCE: 34

| | | | | | |
|---|---|---|---|---|---|
| bvhgggagag | gtagggttta | gctcaaaaga | attgaaaaca | agatcaaccg | ttaagtgacc | 60 |
| ttctccaaac | gtcggattgg | attgttgaag | aaagcgcacg | agatctccat | tctctgcgat | 120 |
| gccgatgtag | ctctcatcat | cttctccact | aaaggcaagc | tcttcgagta | tgcttctgat | 180 |
| acctgcatgg | aaaggatact | cgagcgctat | gaaagacact | catatgcaga | gagataactg | 240 |
| actgctccag | atcctggatc | ccatgtaagt | ttgactctgg | aacacgcaaa | acttaaggct | 300 |
| aggctggaca | ttctttagaa | aaattaaagg | cattacatgg | gagaagaact | tgataccttg | 360 |
| agtctcaagg | agctttagaa | tttagagcat | taaattgaca | gtgctcttaa | acacatcagg | 420 |
| tcaaagaaga | actaactcat | gcatgaatcg | atttcttagc | tttagtgaaa | ggacaaagcg | 480 |
| ttaaaggagc | acaacaactt | gctatccaag | aaggtgaagg | agagggagaa | ggtgctggct | 540 |
| tagtaggcag | aattggatta | gtaaaatcat | gacaataact | catctggctt | tgtgatgtct | 600 |
| taagctttgc | cctcactgaa | tacaggagga | acaagcagca | gtgcagtgga | agatgaagca | 660 |
| acataaccac | caaatctaaa | cagcaactct | gcataaatac | cgtcctggat | gctttaacac | 720 |
| atctaagagc | agtaa | | | | | 735 |

<210> SEQ ID NO 35
<211> LENGTH: 780
<212> TYPE: DNA
<213> ORGANISM: Artificial Sequence
<220> FEATURE:
<223> OTHER INFORMATION: BvAP1 cDNA mutation position 262
<220> FEATURE:
<221> NAME/KEY: mutation
<222> LOCATION: (262)..(262)
<223> OTHER INFORMATION: c to t

<400> SEQUENCE: 35

```
atgggaaggg gtagggttga gctgaagagg atagagaata agatcaacag acaagtaact    60
ttttcaaaga gaagaagtgg acttgtgaag aaagctcatg aaatttctgt tctttgtgat   120
gctgaggttg ctctgatcat tttttctcac cgaggaaaac tctttgagta ttcttctgat   180
tcttctatgg agaagatcct agaaaggtat gagaggtatt cttacgcaga aagacggcta   240
gcttcaaatg atccagactc ataggtaaac tggacctttg acttcgcaaa actgaaggcg   300
aagcttgaac ttctacaaag gaatcatagg cactacttag acaagagct tgactcgctt    360 aacatgaagg aacttcagag tttagagcaa caacttgata ctgctctaaa aaatgttcga   420
tctaggaaga accaactgat gcacgagtcc atttctgaac tccagaagaa ggagagggca   480
atgcaggagc acaataacat cctgtctaag aagatcaagg agagaggaaa aaatctagag   540
caagtgcaac agatgcagtg gcagaaccag caccagcacc agcaccagca gcagccgcca   600
ccgccgccac aaaatcatca agttcctcct gacgcatcaa atttcatgct cccacctcca   660
attccttctt tgaacacggg tgggtaccaa ggacaatttg gtggagaagt aaggaggaat   720
gatcttgacc tgacgctaga accgatatac tcatgtcaca tgggatgctt tacaacatga   780
```

<210> SEQ ID NO 36
<211> LENGTH: 735
<212> TYPE: DNA
<213> ORGANISM: Artificial Sequence
<220> FEATURE:
<223> OTHER INFORMATION: BvFUL cDNA mutation position 316
<220> FEATURE:
<221> NAME/KEY: mutation
<222> LOCATION: (316)..(316)
<223> OTHER INFORMATION: c to t

<400> SEQUENCE: 36

```
atggggagag gtagggttca gctcaaaaga attgaaaaca agatcaaccg tcaagtgacc    60
ttctccaaac gtcggattgg attgttgaag aaagcgcacg agatctccat tctctgcgat   120
gccgatgtag ctctcatcat cttctccact aaaggcaagc tcttcgagta tgcttctgat   180
acctgcatgg aaaggatact cgagcgctat gaaagacact catatgcaga gagacaactg   240
actgctccag atcctggatc ccatgtaagt ttgactctgg aacacgcaaa acttaaggct   300
aggctggaca ttcttttagaa aaatcaaagg cattacatgg agaagaact tgatacctt    360 agtctcaagg agcttcagaa tttagagcat caaattgaca gtgctcttaa acacatcagg   420
tcaaagaaga accaactcat gcatgaatcg atttctcagc ttcagcgaaa ggacaaagcg   480
ttaaaggagc acaacaactt gctatccaag aaggtgaagg agagggagaa ggtgctggct   540
cagcaggcag aattggatca gcaaaatcat gacaataact catctggctt tgtgatgtct   600
caagctttgc cctcactgaa tacaggagga acaagcagca gtgcagtgga agatgaagca   660
acacaaccac caaatctaaa cagcaactct gcacaaatac cgtcctggat gcttcaacac   720
atccaagagc agtaa                                                    735
```

<210> SEQ ID NO 37
<211> LENGTH: 21668
<212> TYPE: DNA
<213> ORGANISM: Artificial Sequence
<220> FEATURE:
<223> OTHER INFORMATION: BvAP1 genomic DNA showing sites for mutagenesis
<220> FEATURE:
<221> NAME/KEY: mutation
<222> LOCATION: (1)..(1)
<223> OTHER INFORMATION: any nucleotide exept a
<220> FEATURE:
<221> NAME/KEY: mutation

```
<222> LOCATION: (2)..(2)
<223> OTHER INFORMATION: any nucleotide exept t
<220> FEATURE:
<221> NAME/KEY: mutation
<222> LOCATION: (3)..(3)
<223> OTHER INFORMATION: any nucleotide exept g
<220> FEATURE:
<221> NAME/KEY: mutation
<222> LOCATION: (52)..(52)
<223> OTHER INFORMATION: c to t
<220> FEATURE:
<221> NAME/KEY: mutation
<222> LOCATION: (151)..(151)
<223> OTHER INFORMATION: c to t
<220> FEATURE:
<221> NAME/KEY: mutation
<222> LOCATION: (6999)..(6999)
<223> OTHER INFORMATION: c to t
<220> FEATURE:
<221> NAME/KEY: mutation
<222> LOCATION: (7640)..(7640)
<223> OTHER INFORMATION: c to t
<220> FEATURE:
<221> NAME/KEY: mutation
<222> LOCATION: (8573)..(8573)
<223> OTHER INFORMATION: c to t
<220> FEATURE:
<221> NAME/KEY: mutation
<222> LOCATION: (8606)..(8606)
<223> OTHER INFORMATION: c to t
<220> FEATURE:
<221> NAME/KEY: mutation
<222> LOCATION: (8618)..(8618)
<223> OTHER INFORMATION: c to t
<220> FEATURE:
<221> NAME/KEY: mutation
<222> LOCATION: (8621)..(8621)
<223> OTHER INFORMATION: c to t
<220> FEATURE:
<221> NAME/KEY: mutation
<222> LOCATION: (8648)..(8648)
<223> OTHER INFORMATION: c to t
<220> FEATURE:
<221> NAME/KEY: misc_feature
<222> LOCATION: (9833)..(11385)
<223> OTHER INFORMATION: n is a, c, g, or t
<220> FEATURE:
<221> NAME/KEY: mutation
<222> LOCATION: (11796)..(11796)
<223> OTHER INFORMATION: c to t
<220> FEATURE:
<221> NAME/KEY: mutation
<222> LOCATION: (11826)..(11826)
<223> OTHER INFORMATION: c to t
<220> FEATURE:
<221> NAME/KEY: misc_feature
<222> LOCATION: (12467)..(12605)
<223> OTHER INFORMATION: n is a, c, g, or t
<220> FEATURE:
<221> NAME/KEY: misc_feature
<222> LOCATION: (13741)..(14088)
<223> OTHER INFORMATION: n is a, c, g, or t
<220> FEATURE:
<221> NAME/KEY: misc_feature
<222> LOCATION: (16396)..(17194)
<223> OTHER INFORMATION: n is a, c, g, or t
<220> FEATURE:
<221> NAME/KEY: mutation
<222> LOCATION: (21152)..(21152)
<223> OTHER INFORMATION: c to t
<220> FEATURE:
<221> NAME/KEY: mutation
<222> LOCATION: (21313)..(21313)
<223> OTHER INFORMATION: c to t
<220> FEATURE:
<221> NAME/KEY: mutation
<222> LOCATION: (21319)..(21319)
<223> OTHER INFORMATION: c to t
<220> FEATURE:
```

```
<221> NAME/KEY: mutation
<222> LOCATION: (21322)..(21322)
<223> OTHER INFORMATION: c to t
<220> FEATURE:
<221> NAME/KEY: mutation
<222> LOCATION: (21328)..(21328)
<223> OTHER INFORMATION: c to t
<220> FEATURE:
<221> NAME/KEY: mutation
<222> LOCATION: (21334)..(21334)
<223> OTHER INFORMATION: c to t
<220> FEATURE:
<221> NAME/KEY: mutation
<222> LOCATION: (21340)..(21340)
<223> OTHER INFORMATION: c to t
<220> FEATURE:
<221> NAME/KEY: mutation
<222> LOCATION: (21346)..(21346)
<223> OTHER INFORMATION: c to t
<220> FEATURE:
<221> NAME/KEY: mutation
<222> LOCATION: (21352)..(21352)
<223> OTHER INFORMATION: c to t
<220> FEATURE:
<221> NAME/KEY: mutation
<222> LOCATION: (21358)..(21358)
<223> OTHER INFORMATION: c to t
<220> FEATURE:
<221> NAME/KEY: mutation
<222> LOCATION: (21361)..(21361)
<223> OTHER INFORMATION: c to t
<220> FEATURE:
<221> NAME/KEY: mutation
<222> LOCATION: (21364)..(21364)
<223> OTHER INFORMATION: c to t
<220> FEATURE:
<221> NAME/KEY: mutation
<222> LOCATION: (21382)..(21382)
<223> OTHER INFORMATION: c to t
<220> FEATURE:
<221> NAME/KEY: mutation
<222> LOCATION: (21391)..(21391)
<223> OTHER INFORMATION: c to t
<220> FEATURE:
<221> NAME/KEY: mutation
<222> LOCATION: (21576)..(21576)
<223> OTHER INFORMATION: c to t
<220> FEATURE:
<221> NAME/KEY: mutation
<222> LOCATION: (21582)..(21582)
<223> OTHER INFORMATION: c to t

<400> SEQUENCE: 37
bvhgggagag gaagagtgca gctgaagagg atagagaata agatcaacag ataagtaact      60
ttttcaaaga gaagagtgg acttgtgaag aaagctcatg aaatttctgt tctttgtgat     120
gctgaggttg ctctgatcat ttttttctcac tgaggaaaac tctttgagta ttcttctgat   180
tcttcgtaag tatatatata tatatattaa tagtaactac ttgttttctg ctttctattt    240
ttaggtctga tgcatatttta atttaggtaa tattaattcc ttatatctga tccttaattt   300 tttttttcttt taccatttca ttttttgtttg ttttgaataa aagaaaattt ccccttcacg  360
tgtgtcgaat aggtcaaaat ttttacttga aggatgttct ctttgattac taaaatagga   420
tccaacaatc acctgaaata aaggaagaag atggtgcaaa gttttactg tcatacttag    480 tatttgataa atattctatg atgaacttgt ataaattagg aaatagacct aactttcatg   540
cacgaaaaca ttattccttc attcaatttt tttattactt aaggatttac tttttttattg  600 atcatatgaa gtagtagtac ttgtaatcat tcaattttt tgttggttaa ataggactac    660
atttaaaaac aacccaattt taaaattttt tgtgtgaatt tcttcccttt ttaaaaataa   720
agtctattat catagcttag agtagctgtg gcaaagctag acgaaataat acagaaatct   780
```

```
ggaaaggaaa ttgtactact tacatgaaca cacttattta ttacttgcat gatatctgcg      840
aaaaagttta tagcaaattt ggttaatata tagcgtagta ctttggatat taatattact      900
agtgtacaaa tacttgatcc aatgggtaat gaaacttatg gaagatttga ccatacatga      960
tgatgctaaa tattaattgt tattgtccag ctttgttttc cctccatcca ttggcatctt     1020
catctttaca ttgctactcc actcacttgt caattgtttc gtcctttatg ttctttattc     1080
acatgtgcac catacttcaa tactttcccc ttctttatcc tcagttttt tttcttgtca      1140 ttttagggtt aatatccaat gaaatctagt ttgctcgttt tagatctaat tttaattcga     1200
tcacaaccat ccatattttt gtttcttagc ttgacatcta ttctatggat ctgggatctt     1260
cggtgtatag atgttctcgg ttttcagatc aagatcctat tcatagaccc atttattgta     1320
aacacttaaa tgtgttctta aaagttagt ggctcgccaa gtcaactcaa taacataacc      1380
cccacgactt cattacatta cacaatgaaa gattagatgt atgagtttgt gaagcttata     1440
attctatttc aagtaggact aggatgtttt gtgcaatcag cagctagtag tctttttaat     1500
ttaagtcagt cttcattgtg catcatatat ttttagaaat atatgcaagt ttgaaaccat     1560
ttagaacctc atgacccgcc tgactcacta taaaccggca agagcttaat ttttcacagc     1620
tttgtatctt tatgagtagc gctagctagg ggtatgggca tagaaaaaaa gggtttgggt     1680
tagggtctta caagatctta tccgctattt ttatttcata atctttcaaa atacatgttt     1740
aataattcaa aatacatgtt taatactatc tccatttcac aacatatgca ccaattgcct     1800
agctatggtc caacctagtt ggtttgtagc ttgcattgga tggttaggat gtattggagt     1860
tgtttatgtg caatcaaatt ttaattacgt atcaaaaaaa aaaaaaaaa aacatatgca      1920 ccaatttcca tttggacaca cttattgacc aattttgac aatatttttc tcaccatttt      1980
gtaagaaaaa tcaaaatcaa gtggaatttt gttaagttta tctcagtcaa aagattccat     2040
acatcgacat tttataattt ttaatcatac gcaattagaa atatcaatgt ctaaagaagc     2100
gtgttggaat acgtgaaaaa gcaaatgata catgaaacag atgtagtata tagaaaactt     2160
aattttgtgt cactcggatg tatgtgggcg gagccttcct agaaggcgta cccaccttag     2220
tggctctgaa tctttgacga cccgttcggt tggtggtgat aatagatggt aatagtaatg     2280
taatttagtc taaatttata aataaatatt aatatcatta cccatggtaa tacaagttct     2340
tcacaaaaca tgtttcattt aaaaattatc attactacct tttcaagtgg tattggatga     2400
taataaaatt ttaggcaggg aaatgggtat tgggatgaac attaccatgg gtaatgacat     2460
gcaatttttg ttacaagaat acagtataat acattactat tgccaccatg tataaccatt     2520
aatcaaatgg accgtgagga tatgatgttg aagaagaagt cttaacctct acgctattat     2580
ttactagggt ctgtaaattt tccttttta attataattc ttgtgaaatc ttcttcactg     2640
atggtactag cttattagga tgggtttctt tagtatattg aaggctcttg ttgacagagt     2700
ataaaaatat ttttggggtc gcaaccatca atttaaactt ttgtttgatt ataaaattat     2760
tttttgaaca tcaacaatct acttaaattt ttggttgagt tagttctttg acatggtatc     2820
acaaccatca tgcataaag gtctcatatt caaatctcat tcacctctca tttccaagta      2880
gaatatttac ctcaggtatg ggtatgaggg aggcttgtgt tgcatgagtc aataacggat     2940
cttgaccaat aatttaacag gggcgagttg ataaattaag ttttaatgta aaatttaaa     3000 tgatggataa aaacactaat acacaccaaa atataaatat actttattta atggttacaa     3060
agagcttgta gctaatgtaa taaatcaaaa tcccaaaggt gcaattttta agaaattatt     3120
```

```
tccatttatt tatttgacca ttatgaaatc ttcaagaaat tgagtaagtt tttaagaaat    3180
ttaaggtata gttcattaac taaataaact actccagtaa aaaaaaatta ccaaactgct    3240
ttcttaagta aaaaaataaa taaatttata ttttatgatt gttaggaatg agtgtgagga    3300
aataaaaagt actattatag ttaaataaaa atgaaagttc ttcagagaag aagaatagaa    3360
gatagtacaa tcaatgttaa atatttttct aaattagaca aattgatata aaccaaaaat    3420
aaaggggaag aagaaagaaa taagtaaaaa aagaaagaag gaaaagaaaa aaagaaaaaa    3480
gagaagcaag tgaagaaaaa caaagaagtc caaatgtgtg ttgatgcaag gttcgagctt    3540
gcaacattaa gggctcaaac tttcttttac actttggttc actgccaccg tgcccacagc    3600
ttgttatgtg acatgaagtg tagtttgctt aatttatctt atacagttat gggggaccaa    3660
gcctccaccc gccccttcta taatctgtca gtggttgcat ccacacttta agtccaatag    3720
actcttgtct gagaggaggt gatagagtat ataaatattt ttggggcctc aaccattagc    3780
tcaatctttt gattaagttg gttctgtgac acttgtacta tatactagtt atatatatac    3840
tgtaaaacta gtaccacgag aacagtcctt aatacaaaca acatgccctt aatagaattt    3900
tcttagtata cacttaatat aggttgacta gcttttttgcc cttcagtatg cacacacctt    3960
ttataatctg tatcgttgtc tggtagatga taataaacct cagtattggc aatatatgaa    4020
atgacataat ggccatgttt ggtgattaga gtttagagtt tagaggttac agttcagagt    4080
ttgtggttag atgattactt ttttgttcag aggatttgac tgctgattta aataattgtt    4140
gtgtaaaggt gtttggtaac acttagctta ttgtttagag ttttgtactt tttagagcat    4200
gtaaaatgac atttatggac atatgtattt ttttaaaaca aatttttagta gtaattatat    4260 ggacaaaata gtcatttgtt ttttctctct ccaaaactct catgaaaaag ctcctctacc    4320 cagcttttc aaaagagagt tttgatcaga gttttcggta caaaactctc tttagtcctc    4380
tctctcacca aacacccaaa ttagagttttt tattggtcaa aactctaaac tctctccaaa    4440
cctctaaact ctctctaaaa ctctctcccc caaacacccc caatttctta gaaaatttg    4500 ttgctccttt ttattgcact atatttctat ctccaaacat aaagtttctt ttacaaattt    4560
tcatttctac tccataccac ctttatatgg caatataatt tctatgaatt aaaatgttca    4620
caagttttga ggtggatttc aagagcatgg acaatatgat catgagactc tccatacaaa    4680 aattacccttt aaattttata atcatacacc aagcggtcgt taaagtattg gaagtgcttg    4740
agtagtttgt gaaaattaac atataataaa gtgcagatct cccctctagt aagtagtaag    4800
aagtagtaag acgatgtccc tcatttgaga aagagaaaaa ccccttatcag tttctcttgt    4860 ttctttgact gaacgcaagt caaatagaag tatgtaacta ggaaatcctt ggagaaatag    4920 atttttcttta aaactataaa agtataccta tatatatggt aacccacaaa aatgtatata    4980
atctgatcaa tatctaaaca aagtattctt atgttttctt tcatcttgct tatttcctcc    5040
ctttcctttt cttactttaa tttgtttact ctctttaact tatttctttg cgtatctcat    5100
ttcactttac aaggatatat agttgattat gacagcttaa taaatatatt ttggaactag    5160 gattattgg ttgtcgttgt tattttaatt tctacactga tcggctagag tttctagaac    5220 ataggcttt attgaaacca ttagttaaca aaattgaatg acaatgattc aatatgatag    5280
aatatgtatg tattagttaa tgtttgatta ttgtttgtat gtatataatc aaagattatt    5340
tagtaatact tctatataca tattctatta gaatcactta gaaagaccca ttgaacaata    5400
ataaggatag gcagacaagc aaacaaaaga aaaataaacc tgttactcct tccatttctt    5460
aatgttctac tcggaattat agatacacac tttgacacaa attagaaaga gagtgtaaaa    5520
```

```
agtggatcca tattaatatt tttattttt taaatgagga gagaagtgtg ggtttattat    5580
gtttcaaggg agatagagag cattgaatag tgagagaata tgtgccaaag ataattaaat    5640
cattgtaaat cttttgccaa ataaagaata aagcatgtga gtaaaacttt aaaaaatggg    5700
cgaaaaagga aagttgagta gaactttaag agacggaagg aatatagaag aggacgtgac    5760
agatgggagg aagatcagac atcttagaag gggaatagtt aaatttgaga tagtctttta    5820
attaaggttc tcactaaaga agatataaca gtaggggaaa gctaaaggtt attcaaaact    5880
ttccttccca tcttcatcac ttcatgtctt tactttagag ctcttaacac ttagcctatg    5940
aaattctgaa ctctttgtaa gattagtgat agataaaaga atcttatcaa tttaatttat    6000
aaatacaaca ggattcaata aaagatata gagatctata aataaagagc catactgttg    6060
tgaactttta tatctatcaa aacctttgca cattagacgt ggtataacta aatcaggctt    6120
atcgaaattt tttaaaattg ttttcattat agccccttta tatttagaag ttctaagatg    6180
attgcataga tagttgatgc accgttctgg tcgactttt taaacacttc tttttgataa    6240 atttttttt ttgtattcga atcattattt taggtgtata aagagctgca aatgatctag    6300
atgagattga tctcggtttc atttatatgc taatagtgtg ttagatacac actattaaaa    6360
aagtcatatg acttagagat tattatggaa aagggatagt gcaccgatat taatataatg    6420
gaaaatgaca cacgagttgt ccataataac atgtgaaaag tgaactattt aaaggtttt    6480 tctgacctag tacatacaag gtgcgtaggt ttagctattt tagtttttta gttttatttt    6540
ttaaagtgaa gttagttatt gatctgaaat catataacat gtacgtaccg tagatataaa    6600
aaactaccaa gtatatatca atttgaaata aacattattt taatatggca aaatcacaat    6660
tgttgactag acctaacact gaagaaaact atgtcatgtt tatcaattat gttgcataca    6720
gttaaaaaca aatatgttag agaaatcgtt atttgaaata gaaaagttgc gcaaaatagt    6780
gattaacatc aaaatatgtt cagaaagttt ttataaatat gtgatcttgc attgtctgtt    6840
gactgtcgag gtttatgata atttcccctt tttccaatgc aaaacttgtt gtgctatttt    6900
ctaatgatat attttttcaa agtatggaga agatcctaga aaggtatgag aggtattctt    6960
acgcagaaag acggctagct tcaaatgatc cagactcata ggtagtgcat ttatgtaaat    7020
atagatatac tcttcatgcc caagaagcct gaattttta tcccactacg tactgcaaag    7080
ccaagtttaa ttgaataatt gtcctgttta aattatttag ttttcagtac aataatgtaa    7140
tcattagttt gcatgtttaa aaaagaaaag cacaagttct gatcaagtga aatataaatt    7200
gtaacgaaag agccaagcta gacaattacc tagctaggag ttatttgtta tcgttttgt    7260 ttttaatttc tagttttttt ttttaaacta gaaaatatag tttcaatctt ttgttatcag    7320
ttttcaaaat gacatattta acataaatat gattgatttt aaattcattt attatatcat    7380
atttcatttc aaaataagtg aaacacttgt ctcaaaaagc tcactctcac ataaatgata    7440
aaagtgtttc acttatttta aaacggaaga attatgactt ttacttttca taaaacgaaa    7500
aactgaaata tgacaataat ctcaaatagc ttggagaaac cagatttcta tatatttccg    7560
tgatgaaatc acttttcatt atacgtaggt aaactggacc tttgacttcg caaaactgaa    7620
ggcgaagctt gaacttctat aaaggaatca taggtatgat ggcaatatgt cataattttt    7680
ctattattat ttttgcttcc aaaaccagac catatgtttg tatatttata tagtgatata    7740
ctccatccgt ttcattttaa tctatacatt tacacttatc aggtatgtca atgcaaaatt    7800
ttgaggatat atatctttag ttttgtattt ataaaaatta taaaaagtac atattaataa    7860
```

```
aatacatatt atgatgaatc taacaagatc ccacatgacg atatttccgt ccgcgtatga    7920
ataacaaata atggccaaag tgaaatttgt gaatagtgta aaatatcaaa gtgtaacaat    7980
taaaataaaa cggagggagt agtacttgtt tgtcacatac ttacttattt ttgttctctc    8040
cacaatgaaa ctgttctttc taataattaa aaaaagtgca tatgttgatg atttctctgt    8100
cactttaagt ggatattgaa tagtgataat ggattacttt gtgtataatt gcatttcaca    8160
tttgggtcta attttatacc cttttcgcat atcatgcttt gtgaatagta catatgatgt    8220
tcaagaatgt gagaagacat atcatacttt tgatatacct caaacatggg tgtatactgt    8280
atagtgaacg aaagtgttag tgtaatttta tttaggaggt ttagtggttt gtcctatata    8340
taatgctagt agttatacac catagttgtt gatgagcatc aactggcttt cctaacattt    8400
ttttctccat aactttaccc ttaccttaca ttagattact ctaggattac attctaccta    8460
aaatattatt actcccatca ttttaggtaa atatttttac tttgattttt cgattatttt    8520
caagagttta aaataatgat taaaatttac catgatcagg cactacttag gataagagct    8580
tgactcactt aacatgaagg aactttagag tttagagtaa taacttgata ctgctctcaa    8640
aaatgtttga tctaggaagg taagaaattt tacttgtcta ccgtagtttc ataataaatt    8700
agtatttggg ctcgggcttt gccccagatt ggtattgtct tttcaaattt gatatgcatt    8760
tttttccatt tccactaaaa tatattaaga aaattcaaca tttaaaggat acaaatataa    8820
taatgtggat acttaaagta tgattaaaat ttggttgaga tggtaattgt gtcatgtata    8880
atagcaagaa gtcacaagtt caaagctcgt tgcaagctaa atttattttt gttgattgac    8940
atgacttatc aacacactgg acaattctaa tcatcagtg gagtagcata tactagcaat    9000
ttatgcacgt gatgtgtgcc ttacttttt agaatataat ttataacttt tttgagcata    9060
aacaaaggta aaatttgaac attagacata ttttttggg ctagctaaat ttgttgttta    9120
aacctatatc acttaaccaa actcctcttt tattatttat tgatttatat tttatttaaa    9180
attttttaaa ttaaaatgat gagcaataaa agaatgttaa gtagatttat taagtatttc    9240
ttatatttt atcaacaaag tattttgtgt taattaaatt atttcacttt gttaattgat    9300
tgtatttttcc ttttttaattt attacttgat tgtgtattga ttgatcaaac ataatttttt    9360
tgttaattt tttatgctat atttgaattt attttttcttt catctgtttt tggtagagta    9420
gttgatttac taaagggtaa ttaaataaat ttattggggg acaccatagc tccccctcc    9480
cttatataat agagatttgt atagatttat tgtcttcctc aattattgat taactagtct    9540
tctatgcacg cgatgcgtgt gttgattgtt tgggtctatt cttaatataa atttcatcaa    9600
aatataatta tagtagtgtg atttacaatt attgctatac aaactactgt aatttataaa    9660
gttgttagaa attgagataa aaatttagat gtgaaatttt gtggtcaaat tatatttgta    9720
atttttttaaa ctgagtaacc gttttttctca tcatgtcaag ttactttgtt aatgcttatt    9780
taatttatta ttggaatttt tgacccatct ttaaattaga aaaggatata atnnnnnnnn    9840
nnnnnnnnnn nnnnnnnnnn nnnnnnnnnn nnnnnnnnnn nnnnnnnnnn nnnnnnnnnn    9900
nnnnnnnnnn nnnnnnnnnn nnnnnnnnnn nnnnnnnnnn nnnnnnnnnn nnnnnnnnnn    9960
nnnnnnnnnn nnnnnnnnnn nnnnnnnnnn nnnnnnnnnn nnnnnnnnnn nnnnnnnnnn   10020
nnnnnnnnnn nnnnnnnnnn nnnnnnnnnn nnnnnnnnnn nnnnnnnnnn nnnnnnnnnn   10080
nnnnnnnnnn nnnnnnnnnn nnnnnnnnnn nnnnnnnnnn nnnnnnnnnn nnnnnnnnnn   10140
nnnnnnnnnn nnnnnnnnnn nnnnnnnnnn nnnnnnnnnn nnnnnnnnnn nnnnnnnnnn   10200
nnnnnnnnnn nnnnnnnnnn nnnnnnnnnn nnnnnnnnnn nnnnnnnnnn nnnnnnnnnn   10260
```

| | |
|---|---|
| nnnnnnnnnn nnnnnnnnnn nnnnnnnnnn nnnnnnnnnn nnnnnnnnnn nnnnnnnnnn | 10320 |
| nnnnnnnnnn nnnnnnnnnn nnnnnnnnnn nnnnnnnnnn nnnnnnnnnn nnnnnnnnnn | 10380 |
| nnnnnnnnnn nnnnnnnnnn nnnnnnnnnn nnnnnnnnnn nnnnnnnnnn nnnnnnnnnn | 10440 |
| nnnnnnnnnn nnnnnnnnnn nnnnnnnnnn nnnnnnnnnn nnnnnnnnnn nnnnnnnnnn | 10500 |
| nnnnnnnnnn nnnnnnnnnn nnnnnnnnnn nnnnnnnnnn nnnnnnnnnn nnnnnnnnnn | 10560 |
| nnnnnnnnnn nnnnnnnnnn nnnnnnnnnn nnnnnnnnnn nnnnnnnnnn nnnnnnnnnn | 10620 |
| nnnnnnnnnn nnnnnnnnnn nnnnnnnnnn nnnnnnnnnn nnnnnnnnnn nnnnnnnnnn | 10680 |
| nnnnnnnnnn nnnnnnnnnn nnnnnnnnnn nnnnnnnnnn nnnnnnnnnn nnnnnnnnnn | 10740 |
| nnnnnnnnnn nnnnnnnnnn nnnnnnnnnn nnnnnnnnnn nnnnnnnnnn nnnnnnnnnn | 10800 |
| nnnnnnnnnn nnnnnnnnnn nnnnnnnnnn nnnnnnnnnn nnnnnnnnnn nnnnnnnnnn | 10860 |
| nnnnnnnnnn nnnnnnnnnn nnnnnnnnnn nnnnnnnnnn nnnnnnnnnn nnnnnnnnnn | 10920 |
| nnnnnnnnnn nnnnnnnnnn nnnnnnnnnn nnnnnnnnnn nnnnnnnnnn nnnnnnnnnn | 10980 |
| nnnnnnnnnn nnnnnnnnnn nnnnnnnnnn nnnnnnnnnn nnnnnnnnnn nnnnnnnnnn | 11040 |
| nnnnnnnnnn nnnnnnnnnn nnnnnnnnnn nnnnnnnnnn nnnnnnnnnn nnnnnnnnnn | 11100 |
| nnnnnnnnnn nnnnnnnnnn nnnnnnnnnn nnnnnnnnnn nnnnnnnnnn nnnnnnnnnn | 11160 |
| nnnnnnnnnn nnnnnnnnnn nnnnnnnnnn nnnnnnnnnn nnnnnnnnnn nnnnnnnnnn | 11220 |
| nnnnnnnnnn nnnnnnnnnn nnnnnnnnnn nnnnnnnnnn nnnnnnnnnn nnnnnnnnnn | 11280 |
| nnnnnnnnnn nnnnnnnnnn nnnnnnnnnn nnnnnnnnnn nnnnnnnnnn nnnnnnnnnn | 11340 |
| nnnnnnnnnn nnnnnnnnnn nnnnnnnnnn nnnnnnnnnn nnnnntatat atatatttag | 11400 |
| ctaagaaaaa aaagacattt cattgggggga taccataact cccccttagc ttatataata | 11460 |
| gagatactat acttctttc tgatagtgtc aaatttaatt ataaatcttt aacattggcc | 11520 |
| aattaataat tggacaagaa aaaaatgaga caataataaa taaggcgatc ttcacagacg | 11580 |
| tattaacatg atggtaatta aaaatgttaa tcatagatct ttgtgttatc ttaataatat | 11640 |
| aaatttacta attagaatgt atcacataaa gtaagtatta atagcagcat aggataattc | 11700 |
| ttataatgga gattttatat ttttttatat aattatatga tttattgttg aaaatattag | 11760 |
| ttgattttaa ctggttgttt attcaatgac agaactaact gatgcacgag tccatttctg | 11820 |
| aactctagaa gaaggtaata actccatttt ttactctcaa aggtttattg tttttaactt | 11880 |
| atttcttcta acctttata tatgagaagg tattgggtta gacgcgtctg accataaat | 11940 |
| taggtcggat gactttcagt tggtttcaat ttatttcag ttggtttcaa tttttgtcca | 12000 |
| gttggtttca attttgttc agttggtttc aattttttt agctggtttc aattttgtt | 12060 |
| cagttggttt caatatttt tagttgatct ttttatttc agttggatgt cttttaagtt | 12120 |
| cagttactta tcttattgtt tcatttacgt gttttattgt aactgaaaac aaaacttaag | 12180 |
| taaatgaaat aaaataagtt ctaaataaaa gcaacttagg gcctgttctc cccagcttat | 12240 |
| tttcagttca gttcaattca gttcagttca attcaattca tttcagttca gttcagatca | 12300 |
| gatcagttca gttcagatca gatcagttct tgacaatact tttactctca catatcacta | 12360 |
| ttcatttcag ttcagttcaa ttcaattcag ttcagttcaa ttcagtttag ttcagttcag | 12420 |
| ttcagttcaa ttcagttgtt ttatgccgaa gagaacaggc ccttagnnnn nnnnnnnnnn | 12480 |
| nnnnnnnnnn nnnnnnnnnn nnnnnnnnnn nnnnnnnnnn nnnnnnnnnn nnnnnnnnnn | 12540 |
| nnnnnnnnnn nnnnnnnnnn nnnnnnnnnn nnnnnnnnnn nnnnnnnnnn nnnnnnnnnn | 12600 |

```
nnnnnattca tttcagttca gttcaattca attcagttca gttcaattca gtttagttca    12660
gttcagttca gttcaattca gttgttttat gccgaagaga acaggcccct agttttcagt    12720
tacttatatt atcgtttcag ttagttttct tattctttca tttaacaact aactaaaata    12780
aaaaaaaaaa aactaactga aagcaaaact taattaaatg caaaaaatta agttctaaat    12840
gaaaccacat acgatcgaaa tttcaatcat ttcaaacatt atggtgtttt cgattctttc    12900
aaagaaggca agctgctccc gctattctac cctctttaga tcacaataaa gctcaggcct    12960
cacattcaaa gtttcctcaa agatggacgt tccaagtatc acatagacac atagtcctct    13020
tctccaaacg ctctccttcc tatcttgatg tcattagcaa acttcttgat ccagacggcg    13080
ccaacaaccg caccatgatc tccctctaaa gtactgacgg cccgtttggt tgttggtcat    13140
aaatgatggt aatgggaatg aagttgtgtg taaatttgtg aaaaatatca ttgtccattc    13200
ccatggtaat gctaatttat cttaatgtgt ccactttcct tctagaattt tcattctcat    13260
ccaataccac cttgtaaggt ggtaatgagt ggtaatgaaa attgcttccc cttggagaca    13320
aaaatacaag tttaggagtg agattgattg ctcatggaga aaaaaagtct ccccatggag    13380
atattaaggg tgattcccta ataaaattac acttaaaatt tattcccatt accgcaattt    13440
attaacatct accaaacggg ccgtgaaagt cttgaaacac atagtcgagt gagtagcttt    13500
gaggaaccat ctgtaaaaga acctgaggga gccaatgtgt gcgtaagtac caacggcgtg    13560
ttgtcagtgg aaaaggtggt gccgtggtgg cactcagtag tgatggagcc gccgtggtgt    13620
ttgagtgttg ccaaatacaa aggcggaatt tcgtaatctc taatttcttc tgtgaaattt    13680
ttgggatcag cctgtccgac caaacacatt ggatcaaacg gtctgaccca atagtttcaa    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnga tataaataga    14100
gatggaggac aagggtcttg gttttgtcat gttgtcaaag agttgaacaa tggttttttc    14160
gtattgttaa aaaattaaaa aaccagaggc cttcaatctc ttgatagata tagatagaaa    14220
aggaggacaa ggccgttctt ggttttgtta tattgtcaaa gagttgaaca atgatttttt    14280
cgtgttgtca aaaattaaaa caatgaaaaa agatggcggg tgcttgatct aatagatcgg    14340
accatggatt gaaggtcttt taacttattt tatatatata ttgaacttat ctgaagatta    14400
tttaactctt tgaaattgta ttaacttccg aactttatga actttttttaa ttcttcaaaa    14460
cttatctaca ttttatttga aaaatattg aagacaaaaa aaccctcagt tggtttaaag    14520
ctgcggtaag atagagtgta aatgttattt ttttttatta aatcaagaaa taaaagaaa    14580
tattaaataa aaagaattaa aaatggaaat gatgacagaa acttatggct tggaggagca    14640
atacttttaa gatagaccta aaccttaaat aagttaaaat ggaagtaatt tttcagtaga    14700
atcttattcc aatctatact ccgtgtttac tccatgtaat gcatatataa taaaaaaatt    14760
agaaattaca tagtataagg tttgatcctg tgactgtaag tttatatact aacttcttaa    14820
ccactagagc aagtgatatt tagtgttatc atttttaaagt ataatttaa caaatgaaat    14880
ttttttctta cccggaacat agctcggacc taataactag ttgaacaatt ataatctgta    14940
acttaaaatg atcctaatta ctgtactttc attacctata ataatagaat cttactatca    15000
```

```
ttggttcaga aaaaaaaaat cttattaaat gttaaccatt tatttgtaat tgaaacatac    15060
atgcacataa atgtaactتt tagtttatct taacttaaaa actgagaaaa tgttagttgg    15120
aaacttttgt atatatgttt ggataaacga cgctcaaaag tagggctaa aattttagta     15180 gataatataa gattatactc catctgttct agatagactt ctcattttta attttggcag    15240
tattcataaa taaaggaaat ctttcaaaaa aatttccaat atataagaaa aaaaataatc    15300
atgtgcggtt ttgtttgatt cgtctcattg tgtacattag gaaaattaaa cttatataat    15360
ttttactact atgtaattaa agatattaac gatacaaaat gtgtattgac aaacttatat    15420
tggagtaata ggaagtctat taagggaccg aagaaatatt acgtaaataa atctaataca    15480
aactaatata aattctactc cagacaataa agattctgtc ttatattgcc aagatatagt    15540
agctatttat tttatcttaa caaacataaa tgtttctaat gcttaaacat ggacatgtat    15600
tattttgtaa aatattatgt attatccaaa gttacatatt taaaggaagt tctattgctt    15660
gctctctttt agcactgccc aaaaaggtta aagtaatttt ttttctctgt ttaaaaaaaa    15720
aatgcattat atacagataa ttttttgctag tcaataaagc tatccttatg acttatgagt    15780
gctacttgac tagggatgtg ttgtactcaa ttggaggtat acatacacca agattataga    15840
gcttttattt tgcctataaa aaatggaagc cggataggat accaaaaaag ctttgactta    15900
aatttgtaat gcataaaaat gatgatacct aacttattag ccatacttat ctaagcgtac    15960
gtcaatttaa atattgtgtt attgattaat aatgatcctt atatatccat attttgacaa    16020
ttaaacggta aattagagag aaaagtttga gaaaataatt atagcttacg taatgctata    16080
atccaaagtg tctccgcaca agcgtgggac aaaatagtac tttcggagaa gttacaatca    16140
acagctaggg agtcttcatt gttcttgaat agaaggatgg aaacaaagtt caccttcttt    16200
tattaaagta ttaaggtttg ttattagctc aatatccaat actttctctg cттttttatta   16260 cttcgtctgt ttcaaattaa atgatttttt ttttatttta cactattttt aaatttcact    16320
tttaccatca tttatgattt atatgtgaat gaaaacatag ttacgtgtga tcttgttttt    16380
tttttttttt tttgtnnnnn nnnnnnnnnn nnnnnnnnnn nnnnnnnnnn nnnnnnnnnn    16440
nnnnnnnnnn nnnnnnnnnn nnnnnnnnnn nnnnnnnnnn nnnnnnnnnn nnnnnnnnnn    16500
nnnnnnnnnn nnnnnnnnnn nnnnnnnnnn nnnnnnnnnn nnnnnnnnnn nnnnnnnnnn    16560
nnnnnnnnnn nnnnnnnnnn nnnnnnnnnn nnnnnnnnnn nnnnnnnnnn nnnnnnnnnn    16620
nnnnnnnnnn nnnnnnnnnn nnnnnnnnnn nnnnnnnnnn nnnnnnnnnn nnnnnnnnnn    16680
nnnnnnnnnn nnnnnnnnnn nnnnnnnnnn nnnnnnnnnn nnnnnnnnnn nnnnnnnnnn    16740
nnnnnnnnnn nnnnnnnnnn nnnnnnnnnn nnnnnnnnnn nnnnnnnnnn nnnnnnnnnn    16800
nnnnnnnnnn nnnnnnnnnn nnnnnnnnnn nnnnnnnnnn nnnnnnnnnn nnnnnnnnnn    16860
nnnnnnnnnn nnnnnnnnnn nnnnnnnnnn nnnnnnnnnn nnnnnnnnnn nnnnnnnnnn    16920
nnnnnnnnnn nnnnnnnnnn nnnnnnnnnn nnnnnnnnnn nnnnnnnnnn nnnnnnnnnn    16980
nnnnnnnnnn nnnnnnnnnn nnnnnnnnnn nnnnnnnnnn nnnnnnnnnn nnnnnnnnnn    17040
nnnnnnnnnn nnnnnnnnnn nnnnnnnnnn nnnnnnnnnn nnnnnnnnnn nnnnnnnnnn    17100
nnnnnnnnnn nnnnnnnnnn nnnnnnnnnn nnnnnnnnnn nnnnnnnnnn nnnnnnnnnn    17160
nnnnnnnnnn nnnnnnnnnn nnnnnnnnnn nnnngtacat caaggaaatt tgcattaatg    17220
aaaaacggga gtacaaccta atggtaatac aaccaaacta aacagaaaga agaaacaaca    17280
gacagtaaga aaacctctat aacgcgtaaa aacaatttaa cataaacact aactagaaaa    17340
```

```
agtccaggcc gaataacatt tgtcttgtgc gatggggagg gaagatgaag gagagtgaaa    17400
atctgttgaa agacacaact ctgacgatct tcatagagag attgtcgtac aactgctagt    17460
agatcctgtc cactaggcac gaaatcccaa ggtccttgat gagcctcctg ggattctcct    17520
gattcgttga acaaagaagt cactttcgag agtaacttcg gaccctgctg cgagggtctt    17580
cgaaaatcag tcacattaga ctgaaacccg aaaaacaagg tggaggtctt gacgtgcccc    17640
aaaacaagtt gggggcgtcc cacaagatgc gttttttagg tgtgatgaca catgatgtca    17700
tcacgagaaa ttggggcgag ttagtttgat gaactacgcc ccactgacgg atcctaagat    17760
ccaaagtgac aatctcgaaa ccagaagacc gacaaacaac agatctgaaa catacaaaca    17820
tgaaaataat gaaagcataa actgccaccc gacatataga gctccggcaa acaacaccat    17880
caagaacttg caccaaagac ttccttggca tactaaagac actgattcca actaacacta    17940
gcgggggacg gggaagggac actcgactac acctaaacct aaccagggga cggggaaggg    18000
gaacttagac taaaccttcg taaaaagggg gggatcgggg aggggaaaac cttgaccaag    18060
gaagctggtt ttaaaaacca cttagccgag ccaaaaaccg tgggtgggaa gaagaaacag    18120
accacaaaca gggggaaccg ggggatggga actcaccgaa caggggaggg ggagaaatcg    18180
cacagactcg gggaacgcct aaggactggg ggacgaccaa cgaacgaaag gttggggtgg    18240
tgcgaaaaca agggaggggg acgcaccgac gaacaaaaaa accgacgaag aggccgaaaa    18300
agcgaaaggc cgacggagat aagattgaaa ggcgacgaaa aaagaaaaag gaacaaaacg    18360
aaagaaaaac gaactcgtcg gagacccgcc ggagacctac gcggcgccgg atctccggcg    18420
agttctaggg ttagagggtt tgttgtgttt gtttagggag aaggcagagg ttttttttt    18480 ttacgtgtga tcttgttaga tttgtcttaa catgtattct ttaatatact tttttttta    18540 taattttgc aaatgcaaaa ttagagatat atgtcctcta aattttacat tcacatacgt    18600
gataaataag agtgctacaa ctaatttgaa acggataaag tatttgaatt gttttcatt    18660 taaaaaagtt cgctatcatt tataatgtta tatatttgcc aatatgttat ctcttttctct    18720 ctcttaccag agtttagatc cagtagagtt agtaaataat tctaccacgt agagttgaac    18780
aaatcatagc cattgatttt caaatcattg gtttatatat tctttcccaa aactcccccc    18840
tattttcccc aaaaatcctc cccctcctta tctctttcca taaaatctga gtcgttgatt    18900
ttaaaatata aggtttggat tcaactccac tatgtagagt tttcatcaaa ctccaccgaa    18960
tccgagcccc tcctaccata gtacttcttg atttccccat atttcttcc tcatcttggt    19020 cctcaagcac attttaatat tatgggtatt aaacaataga gaaagtattt acttatagag    19080
aaagtatttt caatgattcc ctaaattttt ttttgaaaga aagaaagggg atttcattaa    19140
tatttcgcca aacggcactt acaagtcatt tctgaaaaac ataaaattct aaaagaaata    19200
catatcaccc tagaaatgta aacatcgcag atttgactta attttgcctt aataaaaatc    19260
ttcatctgaa gcaatgcaat ctgtgagttc gctctggttc ggcatacgat ctgcagatgc    19320
ggaaattttg ggatgaacgt actccaatag tcttccataa ttttacagaa gttgtgaaac    19380
cctaattctt catgttgaat ctcgaacttc aaccaatgag aataatttct catacctaaa    19440
aacaaaagaa ccatactcac aactcccata ggggagaagg agatttccaa aacagaaact    19500
aaaaacccca taaagggtt tgagaaaatc tcataaagag atactaattt attgaacaaa    19560
acaagaaaat gaactaaaaa ctgaaaataa aagggaaaaa ggggcttacc atggatgaaa    19620
acatccatgg cagcccccta attgatgaag aaggggtaag ggaggctagg gttttagaga    19680
gagaaaagga gaggggaggc taggttttaa aaaaaaatat aatgattccc taaatttact    19740
```

```
tatatatatt taccaagatg acgtgatgtt ttacaaggcc catgatttttt acgcgatcat    19800
gaaaaacaca gccaatttga atggagcaaa tatctacgcg tcattttaga tattttttgta   19860
tgggaaagtt ttttttgacc aatgtaatta ttaagaagca tcggccaccg ggtagataag    19920
atgtcactat acatcctttt ccaaacttaa gtatgcctgt tgaactttttg ttgcgtttgc   19980
agattcattt gaattatat ttcctcagat cctctacttg taaaagaatg ttccattatt     20040
ttcttagttt acatgatatt tacaatagta tttgtctaca ttttgttcat attacttagt   20100
gatcagtgta tacgtcatat attagtttga actttgaaga catttatttt ctatatactt   20160
cctttgtctg ctaaattact ttggaaagct ttgtttttt tattaatata agaccctttg     20220
gagtttggaa atcactatct aatgaaatat ataattcatc attagaacaa aaatacaaat    20280
atcgtactat cacctatcat gttccttttg gatttcgctt cacaaaaata cattttaaaa    20340
aaaaataaaa taacaaatgg tagctaacaa cttattactt ttaaaagttt gtgtgcaccc    20400
taataagtac tcaaagtagt atgtaacaga gagagtataa tgctaaaata caaactaaat    20460
aaacaagaaa gtgtttctca acaataatttt gctgcaggaa ttaggaaaca aagtaaataa   20520
attgcatgtt tatcatcaat acaatttact ggtagttaat tacaaacttc actcatgata   20580
attgaaagag gccactcaat ttcagctagg agttgtttat ttatttattt ttcttttcagt  20640
taaattttga ctacccacaa aatcttcatc tggacctaat ctgcaatttg tggattttgg   20700
atgaaatttc taacctattt aagtagtctt attgtttaaa taacccatgc aattaaatta   20760
ggttatatgg gggtgattca tttaccaggc ccaagatttt atctcattct caattattat   20820
cgcaacaccc atgaacctaa gccaacatga cttatttacc aggccagcta gagaagaaca   20880
aggttgctga ttttcttgtc cgtgattgta gaagaaatgt tagaaatcta aatgttgtta   20940
gggatttacc cctcccccct actgagtgta tgaacttatt attgacggat tgttgtaggc   21000
ttccaagcca aaactctgat taagtttttct tttatgccat tttaaccaaa aaaaaaaaa    21060
aagctaggaa gctagctcag cgcgctctaa ttatttcaca tgtgacatgt tttacactta   21120
ttcatacttc tatatgcagg agagggcaat gtaggagcac aataacatcc tgtctaagaa    21180
ggtacttgca cttgaccagt ttgtgtaata ttgtaattta atttcttaga ttttggttgc    21240
atgctttgat gacgaatgac gattgacgaa tacatttta tgcagatcaa ggagagagga    21300
aaaaatctag agtaagtgta atagatgtag tggtagaact agcactagca ctagcactag    21360
tagtagccgc caccgccgcc ataaaatcat taagttcctc ctgatgcatc aaatttcatg    21420
ctcccacctc caattccttc tttgaacacg gggtagttac ttcttcaact taatttcctc    21480
tattcaatat taagttaaga aacagatcac gtgattagtt cgttaatatt gctaattaat    21540
aatcatattg ttatatatca tgcattagtg ggtactaagg ataatttggt ggagaagtaa    21600
ggaggaatga tcttgacctg acgctagaac cgatatactc atgtcacatg ggatgcttta    21660
caacatga                                                             21668
```

<210> SEQ ID NO 38
<211> LENGTH: 29237
<212> TYPE: DNA
<213> ORGANISM: Artificial Sequence
<220> FEATURE:
<223> OTHER INFORMATION: BvFUL genomic DNA showing sites for mutagenesis
<220> FEATURE:
<221> NAME/KEY: mutation
<222> LOCATION: (1)..(1)
<223> OTHER INFORMATION: any nucleotide except a
<220> FEATURE:

```
<221> NAME/KEY: mutation
<222> LOCATION: (2)..(2)
<223> OTHER INFORMATION: any nucleotide except t
<220> FEATURE:
<221> NAME/KEY: mutation
<222> LOCATION: (3)..(3)
<223> OTHER INFORMATION: any nucleotide except g
<220> FEATURE:
<221> NAME/KEY: mutation
<222> LOCATION: (19)..(19)
<223> OTHER INFORMATION: c to t
<220> FEATURE:
<221> NAME/KEY: mutation
<222> LOCATION: (52)..(52)
<223> OTHER INFORMATION: c to t
<220> FEATURE:
<221> NAME/KEY: misc_feature
<222> LOCATION: (1029)..(1924)
<223> OTHER INFORMATION: n is a, c, g, or t
<220> FEATURE:
<221> NAME/KEY: mutation
<222> LOCATION: (19373)..(19373)
<223> OTHER INFORMATION: c to t
<220> FEATURE:
<221> NAME/KEY: mutation
<222> LOCATION: (19552)..(19552)
<223> OTHER INFORMATION: c to t
<220> FEATURE:
<221> NAME/KEY: mutation
<222> LOCATION: (19561)..(19561)
<223> OTHER INFORMATION: c to t
<220> FEATURE:
<221> NAME/KEY: mutation
<222> LOCATION: (19689)..(19689)
<223> OTHER INFORMATION: c to t
<220> FEATURE:
<221> NAME/KEY: mutation
<222> LOCATION: (19704)..(19704)
<223> OTHER INFORMATION: c to t
<220> FEATURE:
<221> NAME/KEY: misc_feature
<222> LOCATION: (20703)..(20722)
<223> OTHER INFORMATION: n is a, c, g, or t
<220> FEATURE:
<221> NAME/KEY: mutation
<222> LOCATION: (28161)..(28161)
<223> OTHER INFORMATION: c to t
<220> FEATURE:
<221> NAME/KEY: mutation
<222> LOCATION: (28185)..(28185)
<223> OTHER INFORMATION: c to t
<220> FEATURE:
<221> NAME/KEY: mutation
<222> LOCATION: (28191)..(28191)
<223> OTHER INFORMATION: c to t
<220> FEATURE:
<221> NAME/KEY: mutation
<222> LOCATION: (28194)..(28194)
<223> OTHER INFORMATION: c to t
<220> FEATURE:
<221> NAME/KEY: mutation
<222> LOCATION: (28447)..(28447)
<223> OTHER INFORMATION: c to t
<220> FEATURE:
<221> NAME/KEY: mutation
<222> LOCATION: (28450)..(28450)
<223> OTHER INFORMATION: c to t
<220> FEATURE:
<221> NAME/KEY: mutation
<222> LOCATION: (28465)..(28465)
<223> OTHER INFORMATION: c to t
<220> FEATURE:
<221> NAME/KEY: mutation
<222> LOCATION: (28468)..(28468)
<223> OTHER INFORMATION: c to t
<220> FEATURE:
<221> NAME/KEY: mutation
<222> LOCATION: (28507)..(28507)
<223> OTHER INFORMATION: c to t
```

<220> FEATURE:
<221> NAME/KEY: mutation
<222> LOCATION: (29166)..(29166)
<223> OTHER INFORMATION: c to t
<220> FEATURE:
<221> NAME/KEY: mutation
<222> LOCATION: (29196)..(29196)
<223> OTHER INFORMATION: c to t
<220> FEATURE:
<221> NAME/KEY: mutation
<222> LOCATION: (29217)..(29217)
<223> OTHER INFORMATION: c to t
<220> FEATURE:
<221> NAME/KEY: mutation
<222> LOCATION: (29226)..(29226)
<223> OTHER INFORMATION: c to t

<400> SEQUENCE: 38

```
bvhgggagag gtagggttta gctcaaaaga attgaaaaca agatcaaccg ttaagtgacc      60
ttctccaaac gtcggattgg attgttgaag aaagcgcacg agatctccat tctctgcgat     120
gccgatgtag ctctcatcat cttctccact aaaggcaagc tcttcgagta tgcttctgat     180
acctggtatg tctaatttta taacttcttc ttttgtacat caataatttt atcatcgact     240
caactaaaag cttaagcaga tggttagggt tctattatta ttgaattacc tcaaatttgt     300
catcgactca actaaaagta gagtatattt catgtagatc aggtgctttt tttgaatata     360
ttgtcagttt tagaactaca aaatgttgaa cacaagtatt tatacgcacg ctgacatgtg     420
aattttttaa ttgacaactt tctaaattaa tactctaaat tactaatatg aagaacgtaa     480
tttattattt atcactttca gacaaaggca tgtttgtttt ttctattatt tttcccatga     540
aaattctcac caatatccga ttctgtatgt taattttagt aatttctaat tttgatgact     600
taataaattg taaaaagta taaaataaac aaatatccaa acatctttg ttttcaagag      660
aaatatctta aaaactttg ttttttaaga gaaatatctt aaaacactttt ttatcatact     720
actatgatga tgtataaatc tattcaaaaa aaaaaaaaaa tgatgatgta taaataattt     780
aaagagttaa gtttattaga aattatagat atttatagag ctgagtaata aaataatact     840
ctacagatta tatgtagctg atgtagtgtg tctgctcctg taagatttcc tttttatctc     900
caaaaaaatt gcattgatat tcgagccttg ccgacccct tttcctcttc aaccatttga     960
taagatccta tgcactgagt aatctagtat tatatgttag atgttatata ttaataagct    1020
aaaattgtnn nnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
```

```
nnnnnnnnnn nnnnnnnnnn nnnnnnnnnn nnnnnnnnnn nnnnnnnnnn nnnnnnnnnn      1860
nnnnnnnnnn nnnnnnnnnn nnnnnnnnnn nnnnnnnnnn nnnnnnnnnn nnnnnnnnnn      1920
nnnngatgat attatgtatc attattatca gtcatttatt attgatagat aatgttatta      1980
tttccataga tcatatataa tcttaccata tttactccct atgattatat atttctatct      2040
attaacatag taatagtgat atactaacaa cgagtatctt tcaagtaaat aaatcatata      2100
tatagggtta gaaggtaaaa aagacaatat tttatgagac tttatttaca cccttcgtct      2160
cataaactcc tttctatttt ttgtgttcac tcgttttcta aagttttttc tacttctttt      2220 acttttatt ggataaatac ttttccgtc tgtatgtgat ctacttatat tagtatttat        2280
agatagatta tactcttaaa gtattacatt cacaaaatca tgtgaattat taattaaagt      2340
aaaattatga gtatggtatt ataacttaaa cgaagtagtt gtattgttta aaccaataag      2400
tataataact tataaaactt aaaagttgat tctacactta tcatgcactt gtgttttgat      2460
gggttaaaaa ttagctagta cataagtaac ataacataaa cttatctctg tatagtatgt      2520
tgaattatta ctttatattt gaaaagaaca aagacacaat aagtccaaaa gatccgatct      2580
tttgattatc aactatgtaa gtgtcttttc taaatgatca atcaccttaa ttagtatact      2640
aaacaggaca attatgacat ataacacttt tctatttgta caagttaatt aacccattga      2700
cattcattca gttagcctac atttttcaat aggtagtcat catcattctt tttttaacca      2760 attttttttac aataaccatt acctaccaac aacattttca ataatgaac tgaatgatgg      2820 attccgtcaa ggaaattgtt cgtggacagt tgtttacct cccaaatttc ctttaatctc       2880
atgctttctc catcatccaa acaatctaat accaatcgtt ttctctaatt gcataaaccc      2940
taattgttga atcctttaat cttgcctttt cacattgccc aattcccttta gtatgatatt     3000 ttttattcga taatccctga taagtaaatt cactaatcta atttcagatg gattgttgta      3060
gagattgggg aattgaagat ttttttgcctt ctttgttctt gtttacaatg aaggatgaag     3120
tttcatggaa tattgaagag aaatttgaga aagaaagaa agtgtgggct ttactgacga       3180
caaaaactgt catttggtg gttttttttca ctaaggcatg tttggcacta gcgtttaagg      3240
tagcggttag cgatttgaca agatcaaaac gctacttaag aaaatgatga gtgtttggta      3300
agatagtggt tgttgtagca ggtagcaatt agagtagatt atgagtagcg gttgtggaat      3360
gttactacaa gtaacgtttg agatttagag gtagcagtcc agcaaagaaa cattgtataa      3420
tagcataagg tagaattaat taaccaatgt ttttttatt cttttttcctt ttattgttta      3480 ttaataattt tatttatgc caattcaatg tttattttac aatagcaaaa atgtaattta      3540
aatatttatt ttaaacataa taaattttat aagtatttta gtaaaattgg taatataaat     3600
ttttcgaggg ttgaatattt tcttagatgt atacatttct ttgaatagtt aaaaaatcat      3660
atctcctttt tgtgtaactt ctttgaaaaa taaatcttga atttaactat tgaacgaaca     3720
tatgaaatta ttgtagttca tttcatatta aataaatgt taggtattgt cttttacaat       3780
ttcaactact tttggcaaac aattctgatt aaacagctat tttaatcgct gatcgttgac      3840
agcaaccgct aacagctact agaaccgcta cttttgccaa acatgcctaa accaagtaat      3900 atcgggatt cttattata taaaaagtta ataatgtgat tatttgaaaa aaaggttgac        3960
tttatatgtt gtttaaagaa aaaaaaacat ttattaatag aaaatatact atataggtct     4020
ctatataccc agggcgaaat gaatgtgtat cttttcaaat gagtatgcgt acatgttctg      4080
taaatgcata tttcatatga gcataatgtt tttactatta ttatgcacat ttgtgttttta    4140 attttttcaaa tgagtatgta aggaaaacat gtattcttgg catgtcagtg ttagtgattt    4200
```

-continued

```
ttgttgttat ataaatgttt tcgtgatttg tgaatgtggt acaaacattc atgtgccatg     4260
gcgtttagca aaacttttct agctcacatg atgcttcaag ctaattgcaa tgaactaata     4320
taagggagag acattttac gaattagttt tacattgata gtagtttgaa gaagatagtt      4380
taggagatag tttgttggaa tagaagctat gtgttagaat tagttatagt catcaatttt     4440
tgaataagac tcattattat ttcaatcctt ctacctttta attactagtc caactctcac     4500
tctttggtat taaattacac cattcctacg gactatctaa caactctaac cacggcccat     4560 acttttctt cttaacataa aataatatta cgcttactaa ctactaactc ctatgacatc      4620
taccttttca ataaaataac aattgataac tatataacaa cttataatct aaaagtaagt     4680
gtcttgataa gtgtagagta ttgtgggacg aagggagtaa ttcatagcaa atactatcat     4740
agcaatacaa tactaggaga ctaagatgtg agttttgaac ttcaaaaaaa aatatacgcg     4800
acatagttca ccggaagaac tgcagcacaa caaatgcaaa tggggattaa atgaggagtt     4860
cacctacatc acacacaaga gcgattgagg attttcagat ctggaagaag agcgaaaaat     4920
caggcgagag cttcaacttt cggagtttaa tggaagagct aatgatgatt gaattattca     4980
gttggattta tcttttgtaa gatgagggga tgaagttgaa gattgccata ataacccttg     5040
agggcgacac aatggtggtg ggaatggaaa tatggaccac gaccgattta tgagtggaaa     5100
gaattgaagt ctctgataca atgacgtttt ggtatatcat cggtgctttc atggctgtca     5160
gatctaccga aaggaaaagt agtggtgaaa acaaatgtcg ttcaaaccaa ccacctttga     5220 cttcaatat tgaagtgaca aggaaaactg gcaccttagc tagtgacttg gtggagtctt      5280
tgcgtaaacc ggtggaaaag aagcttatct ttgagtttta gtgtggtctt ggtgcttgtt     5340
taagtggctt gactatttag gaggaaaaaa atcaattgtg aacaattggt gagtaaccta     5400
aaaatcaatt gtgaacaatt ggtgagtaac ctaaaaatca attgtgaaca attggtgagt     5460
aacctttaaa ccagactcaa gagtgggaaa gaggcggtta gacaagtaga tttagaggaa     5520
gaggaggtag aaaatagatt agaattttt ttgggagttt tcaaatgtag tggtatcggc       5580
tcataacaag gtggtcaaat ggatggagag cttggtcgtt tgagtagtct catggtggtg     5640
attataacta cgttggcgat aaacaagttc gctttaccaa gaagttgatt ggtggaagag     5700
agattttcat aaagagggc tcgtatagca acagctttgt gtggtctcag tttcattgtc      5760
ggcaaagccg tgggtggtaa atatggtgat tttggagatt gttatgatgg agggagttat     5820
ggtggtttca tgagacatgg atgctatggt ggtgctgtga tcggtggaga agaggagctc     5880
gtgaaaggtc actctgatgg agcgggtgta atggtggtct aggttttttc ggcatcggag     5940
gttgcgtatc tcgtgaaggt tcacatttgt acaccggtga atactatggt ggtgaactag     6000
gatgacagtc aaggtgacca tagtagaaaa aaaaaacata aaccatgtag cttagatgat     6060
ttgaaaaaaa atcatgtttt tggagaagaa tcttaaatat tatgacagag gcaaacttgt     6120
cattgaccaa atagatgaca tagcaattgc acgtgtctcg ttaaaatttg aaaccataaa     6180
aaattcaaat tgcacttcat atgccttttct tttggttgaa aacttcatat accctaatgc    6240
gtcaatatgg ttcttttttcc aaaaaaaaaa gtaaattatt tcggcgttag taaaagcagg    6300
tccacctcca taatccattt tattaagcca actcctctac cctactttg caacctatca      6360 tttcttattt tctaaaatca tatcaaaaaa acaagtgtga acccaaaact aactatatta     6420
tacctaagtc taatttcttc atccaatgtg ttcaaccccca ttttttcaacc cttccactca   6480 taaacccatc ttctttcact cctaaaactt tcagctcacg ctcgtatcac ctctttactc    6540
```

```
acatatcagc ccaaacgatt tcttattgaa tccactaaat tatgtatatc gattttttca    6600
ccaagtactc cgagttttca aaaaatttac ctggtacccc caagttttca aactacacgg    6660
gatacccta  agtttcaaac taatacactc agatacccct aatgactaac gacattaatc    6720
gccgttagtc attaaccta  attttctaga tttcaaccta attaaccact aaccctaacc    6780
ccaaccctaa ccctaataat aaccctaaac ctaaccctaa ccaccccctcc ccaaccctcc   6840
caccacccct gccccccatc ctccactcct gcgcagccag caggccccc  acccatttga    6900
ttttaaggaa gaaacacgta tcagggaagg gggagaactt agctctgaca gcggcaacgg    6960
accaccgacg agtctggact gtaggacggc agcgtcaagg cgcgagccgg ttgggctact    7020
gcagttcaaa gcaaacaggg gagggaatc  gagccgagaa gagagctaag gaaagagggg    7080
tgatgggcgt tgcggagatg gtgcgcatag tggtggtggt gtgggggagc tgtggtgggg    7140
gagaaatcga atgggtgggg gagagagggt gggggctgc  ggtggggttg gggctggagg    7200
gggtaggtg  ggtgggtgga ggggtggtgg ttgggtggta gtgggacaac tctcaaacat    7260
gattcttct  caaacatgat tctttctcat atccttttt  ggatttcctt aaaaaaatcc    7320
atatccaaat aacgttgacc ggtgagggac aactctttaa cactattctt tctcaaatct    7380
tatgaaatct tcacatttaa ctcgatctcc ctttcaatga acctaaagat atatattaat    7440
agagttgcaa attcctaaac tctagaaaat tcaaatacaa cataagagtc ctagattctt    7500
ccacaagatg tattatatct ttcaaagttt cccagataaa attagtaatt aggaaactcc    7560
ttaacaagga tacttaaagt tttatctaaa tcttgcataa attgaaatcc aaccataatt    7620
atgaataaat aatcataaag aatcctaaca taaataacta gaaataaga  taataaagaa    7680
gcaacaaaag aatctcataa ccaccatttg aatcccgcat gagaacccaa atagttgttg    7740
ttccttataa aaacccacca cctttcttcg ggtattatga cggtattgga ctatagtatg    7800
agacgagatc tcttaatcac caatcaacta ttgtaaactt gtgagcctga ataatttatt    7860
tgagatacaa ttctaaggtt gtttatgaac gtgtttggta aaattgttat tgataactcg    7920
ttcgtggaaa ataaatgcaa aagtcaacat gccaaaaaaa gtgctaaaat caactttcgg    7980
ctttgcttga aatgttaagt tttaagctat ccaagagcca ttagtcaaaa tctattgaaa    8040
gcgtactcaa aaaccattta tcaaacaccc ctacaaatcc ctttagaaaa caataggagt    8100
tgtacaatat aagtattgag ttataaagtt gatcaagtga tttaggaggt tgttccaaat    8160
caatctacaa gagtttgtat acttataccc cttcgttttt ttaattgtta cacttaggcc    8220
ttgtttgaca aatagagttt agcggttaga gtttagattt tgctgttaga gttttaactt    8280
tttgttaaat agatttgact gctgatttga caacttcttc ttataaatgt gtttggtaat    8340
tattaacaga ttgctaaaag cttattaccc tttatttatg tgaaatgaca tgtatagaca    8400
ttttaatcca catgggtatt attattatta ttattcgagg catacaagtc attgaatata    8460
tttttaccta atcctctaaa gaaaaagctc ctattaggag cttttccatt tcgagagttt    8520
ttattccaga actctcttca aaactctttt ttaccaaaga ataggagctt tttcatttca    8580
agagttttta ctccagaact ctctttaaaa ctctttttta ccaaacaccc cttttagagt    8640
ttttgactag tcaaaactct aaaagtggtc caaattctc  ttttaactcc aaaactctaa    8700
ttgccaaaca ccccttaca  cttttcacgc ataccaatgc aacactttga cgattaacat    8760
ctccagtttt ttatttgtaa aaattataaa gagtgcatat taataagtag ggctgttcaa    8820
agtgcgtct  ggaccgcacc aaaccgcaac ccaaaccgtt gtttcgcggt ttggtttggt    8880
ttgcggtttt aaaattgcgg tttgggttat gatttcaagc aaaccgcggt ttgcggtttg    8940
```

```
ggttgggttt ttattttttgt aaaccaaaac cgcaccgcaa accgcaatgt tacattttt     9000 ttaaaaaaat aaattaaata catttatgaa ggtgacatac aattataaaa ttgaaaaaag     9060
aagtttgagg taaaaaactt taacacttat gataaatcat tatatatgtt taattatgaa    9120
ttcagcttca tatctatttg gactcttatt aacaattttc ttttaatctt aggaaacaaa    9180
agtaatgtcg cggaggaaat aatggttaaa ccgcaaccca aaccgcacca aaccgttttg    9240
cgcggtttgg gttgggttgg tttgggaaaa agtgcggtgc ggtttgggtt ggaaaatttt    9300
caaaccgtat atttgcggtt tgggttgggt tacatcccaa accgcacaaa cccaaaccgc    9360
gaacacccct attaataaga tacatattaa ttcgaatttg acaagatcca catgactatg    9420
tttttattcg cgtataaacc acaaaagaag gttcaagtaa aatttgtgta tggtgtaaca    9480
tgtcaatcaa agaacggagg taatatttgt caagacactt tagtcacttc taaattccta    9540
taaacaaaga aatatggaag aaaactggtg atgaaaattg aaaaggtggg tataataaga    9600
gagacacaat tctaaaataa gaaaatatta ataataaaat aataagttac gataggcctc    9660
atgtttgaaa acggaaaaaa taaggagata gttcgtgtaa aaaggaggga gtaaagggta    9720
atgcatactt tgtattgcaa gcttagtttt aaaaggcata agacgcaaag cgcatcgagg    9780
cacaagacga aggcgcatgc atctcgtagt tgaggcgtgt aatgattta cttcacaacc     9840 acctgagcaa cccaatacag aacgaccaca agaaaaatag aaagaaagga aatgattttg    9900
attgatcagc agaaaataca gagcattcga gaggctcagt ctctcccaag gactacaaga    9960
tactactaaa tttcacaccc ccttcagtcc ccttacaccc ttatttatac tacttctgct   10020
ctcctatttt aacggctact gacattctct gagctggcct gctattcctc tttttgtgct   10080
gacatttctg aatattctgt ggtagtggct ccattctcac atttggacag gtttacccct   10140
ccatttcttt cgtgcatacg tcagccacgg tttggggatt gaattcatta cattaccctg   10200
cccccaaaga ctcaccttgt cctcaaggtg aaggaaggg aaacgttctt gcaccaaatc    10260
tgcatcttcc cacgtggctt caaaaggtgc taagtccttc catttcagta gcacttcagt   10320
ctgcgtatgc ctccctctct gtgtctgacg tacgtccaat aattcttcag gttccacaac   10380
tagttccaag tctgctgcta gttgagttgg tacagtggt gctgcctggg catctccaat    10440
tgctcgtttg agctgggata cgtgaaatat aggatgtatt ttactggtgc ctggtaactg   10500
gagtttatag gcgaccttgc ccaccttttg cagaacaggg aatgggccat agaagcgggc   10560
tgccagcttc tcaaatggtc gcttggccaa ggattgttga cggtatggct ggagctttaa   10620
gtaaaccaga tcccccactt caaaggactc atcgcgcctt cttgtgtcag cataggcttt   10680
catcttttgc tgggagcgta gtagatgaaa gcgtaaatca tcgaggatgg catcccgttc   10740
ttgcaacact tcctctaagt tatctactgg cgtttgccct ctgcctactc gccacaagtg   10800
tgtgggtcac gcccgtacaa caccctgaat ggagtcagct tagtagacat gtggggagag   10860
gtgttgtgtg agtattcagc ccaagggagc cactttgccc aagtcttcgg gtgccccgcc   10920
acgaaacatc tcagatatgt ctcaagtcct tgttcacaa tctcagtttg tccatcggtt    10980
tgcgggtgat aggcggtgct ctccttagt gttgtccctt ggagtcgaaa caactctttc    11040 caaaagtac tcagaaaaat tcgatcccta tccgaacga ttgatgccgg aaacccatga     11100
agttttacaa cctccctgat gaaagcttca gccacttgtg agagcactaa aaggatgacg   11160
aagcccaatg aaatgcgcat atttcgataa acggtccacc actactaaga tcgtgtccac   11220 cccccttggac aagggcaatc cttctatgaa atcaagagtg atatcctccc aaacctgagc  11280
```

```
tggaatggct aagggctgca gtaggcctgc tggcttttgt tgagagctct tatgctgttg   11340
acaaatgcta catcgctgca cgtacaatgc cacgtgcttc ctcataccta tccaatacca   11400
ctcagccgcc aacctaaggt acgttttac ttcacctgca tgtcctcctt ctggggaatc    11460
atggtaagct atcatcaact taggaatgat gacggaagtg ttgggaatta ccattcgccc   11520
cttataccgc agcttgccat cctccaccgt gaaccccaca agtggtttat ctccctgcgc   11580
cacttcttcc ctgagccttt taaggaacca atcctcctct acctcttttt ggagctctgc   11640
ccagtccact ccttgggttg tgattatggt ccctagctcc atttcaccta cagttttct    11700 agaaagcgca tccgcaacct tgttggttgc ccccggtttg tagtgtattt caaagtcaaa   11760
cccaattaat ttgcttaccc atttctgaaa atcagccccc acttcccgtt gttgtgtgat   11820
gaaacgcaaa ctttgttgat ccgtatggat cacaaatctt ctccccaaaa ggtaatgttt   11880
ccatttctgg accgcaaggc atatggcaat taattccttc tcataaacgg acttgtgttg   11940
tgctctcggt ccaaggagct tgctgtagaa tgcaatgggc ctgccctctt gcattaggac   12000
tgcccccacc ccatacccag acgcatccgt ctcaactacg aaaggcttat ggaaatcggg   12060
catagcaaga accggtggct gggtcatagc ttcctttaag tgagagaaag ctgaagtagc   12120
tttttcggac cagccaaagg agtccttacg caattgctcg gtaaggggct gggcaatttg   12180
cgcgtattgc ctgataaact tgcgataata cccggtcagc cctaaaaatc ctcgaagctc   12240
cctcaaattc ttgggaactt cccactccac catggcccctt atcttctcca tgtctactgc   12300
caccccatgc tgcgaaattt acatgcccca gtaggccac tgtcttcctc cccaagtcac    12360
atttcttctg gttagcgaac agtttgtgca atgctaacag ctgcaacacc aatcccatgt   12420
gtcgtgcgtg gtcctctttg gtcttactgt agaccagaat gtcgtcgaag aagaccagca   12480
caaacttcct cagatatgga cggaaaacgt tattcatgag tgactgaaaa gttgctgggg   12540
cattggtgag cccaaagggc attacgagaa attcgtaatg tccttcatgg gtgcgaaaag   12600
cagtcttatg ggtatcctcc gggcgaacta aaatttgatg gtatccggcc ttaaggtcga   12660
gtttagagaa gatggtagcg ccatgtaact cgtctagtag ctcatcaatg accggtatcg   12720
gatacttatc cggaaccgtc tccttgttca agcccgata atcgacacaa aacctccaag    12780
aaccatcttt tttcttcacc aataatacgg ggcttgaaaa tggactagtt gagggcttga   12840
tgatgcctgc ctccagcatc tctcggatga gtctctcgat ttcgtctttt tgaaattgag   12900
ggtaacggta tggcctaacc cccaccggat tactgccttc cttcaacgtg attgcatgct   12960
catgccccct ctttggtggc aggcccaccg gagtatcaaa aacttccgca aactgactaa   13020
ttaccttctg taaaaattcg ggtacttctt gtgcctcctt caactccgct tctcccttt    13080 tcccatcatc ctcaatctgg ttgagctcca agagaaaacc cccttttct tttcggattg    13140 cctttatcat ggctctaagt gagattttag atcttgctaa ggaagggtcc cctctcaatg   13200
tcaccactct gccctccact tcaaactgca taacctgagt tttccagttg gtaatcactg   13260
accccaattt ctcgagccac tgcactccta atattaaatc tgagttaccc aggccgagag   13320
gtaaaaaatc ctctgttact tcgatttccc ccagctttaa agtcacccct tgacacaccc   13380
cagtaccatg gacagcttca ccattcccta aagcactcc aaatcccccct gcatctgaga    13440 tgaccaactc aagttcctca acagttaaca aggaaataaa attgtgagtg gcacccgggt   13500
caatcatgac caccacctct cttccttaa ttttctagt gattttcatc gttttaggac     13560
tcatcaaacc aatcacagag ttgagagata cctcagtagg aagttccggt ggtggttcgg   13620
acggtggtgc acgagctgcg tcgctcacct cttcggtttc ttcctcctcg tcatgcatca   13680
```

```
gaatcacgct gatctctttt ctccggcaga tgtggccggc ggtccactta tcgtcacatt    13740
tatagcacaa ccctttgct ctcttctctt gatattcttt ctcggaaagt cgcttgaact    13800
ctacagattt ttttccttgc cccccagcaa ttggatacgt gttcaaggtg ttggaatttc    13860
cccctgggtt ttgggcccac attttgctgg caggtgggtt gaggctggtc gttggattga    13920
aggaagcccc tacactcctt gtcattcccc ctctgttata aatcgagtaa ggcccattct    13980
tagttggccc acttctttta taacccacaa tcctattcct ttcctcaatt cggcctgcta    14040
gttccattgc ttgctctagg tccataggat tgagtaacct gacctccact ttgatatcct    14100
cttccagccc attaatgaac tgacccatga gtatttcttc tggtactcta ctcaacggtg    14160
ccgccttctc aataaaagtg cgtcgatact catccaccgt ggtggtttgc tttgtggcca    14220
accaccgttc ccacaatgaa ccatagtggg ttggtcgaaa ctgacggagg aggtactcct    14280
tcagatctgc ccaccacctt atcggccgcc ttttattctc ccactggtac cacctgaggg    14340 catcccctc tatagacaca accgccgcct ccagggcttc actgctactc aggccataaa    14400
acgaaaaata tcgctcggct ctaaggatcc acccatccgg atcggaccca tggaaaatgg    14460
gcatctctaa cttcgatat ttccagttcc ccccggaagt cgaacctcct ggccctccac    14520
ctgagccgcc atccccatac gatcggcccc cgagctggaa acctccatat tcgtcccctt    14580
ctcggccccc cagatttatc aggtcaggag ccctccgttc cggcggtcgg gggtgtccag    14640
tgacggtttc gggtgtctcc cgcgagggtt gtggcaaggt tgctcggatt tcaacctgaa    14700
atttcctctg ttcagcacgc aacccttgaa tcgtcccatc ctgtgtctcc cttgaccggt    14760
taatccggtc ctccagccta acggccaaga cctccatctc ctcgcgactc ttcctcgccg    14820
cctcattctg gccttccaag atttgagcgg tcaacgattc ccccatggca ttaatggcag    14880
attccaccgc cctggacacc atggtggcca ctgacccttc gagggctgcc attctttctt    14940
ctaatgaatc caccctctgc acttcgtttc ttggtgccat ggatcgatgc tctgatacca    15000
agtgtaatga ttttacttac ttcacaacca cctgagcaac ccaatacaga acgaccacaa    15060
gaaaaataga aagaaaggaa atgattttga ttgatcagca gaaaatacag agcattcgag    15120
aggctcagtc tctcccaagg actacaagat actactaaat ttcacacccc cttcagtccc    15180
cttacaccct tatttatact acttctgctc tcctatttta acggctactg acattctctg    15240
agctggcctg ctattcctct ttttgtgctg acatttctga atattctgtg gtagtggctc    15300
cattctcaca tttggacagg tttacccctc catttctttc gtgcatacgt cagccacggt    15360
ttggggattg aattcattac aaggcgcacc tttggtacca agagacttag acatcaaata    15420
aagaagcatt gtaatactta gaataaacat tgttttata ttctaaaaca catattttct    15480
ctaagacacc tagtaatctc atagtggatg tcatctagtt taggtggtaa ggttttattg    15540
agttggtact caagacctca gacttagagg tggcaaacgg atcatacggg tcgggtgaaa    15600
atgagtcggg tcataatcgg gtcacctttg tgtccaggtt acgtcaggt cgagttcgtt    15660 cgggtacgag ttcatattga gtccatgagg tttcatgtca tatcgggtcg ggttagattg    15720
gatttacaat ttcgcaaata aataaaacgc atataatact aaagagagta aattaaataa    15780
ttaacggaca ctagctaaat catatattag tattttatga tgtattttcc ttaaatttat    15840
ttaaaaaata actaatatga caattttcg ggccgggttc gggttgtggt catcattatc    15900
gggtcaattt agtatcgggt aggctcgggt tcatgtcata ttcgggtcta ttttaattcg    15960
agtcgggtta tttcggattt aagctctatt tcgggtcagt attttcgatg aagaacgggt    16020
```

```
ttcggatcgg gtcaccggat acggatctat tttgccgagt cagactgctt ttcaaaccta   16080
ataatctcag ttttttccacc tattcagatt tgcctatgat ctctatttag ataaatgagt   16140
acaatattgt gtctatccat gaaaatgaat atctcacaat gtaaaaggat atctctaaat   16200
ttcactaatc actctatctg ttttgaataa taatattcta ttttattgca tgtagtaaag   16260
atcgagtatt tagtgagatt tggagaaaag aggaggctag agagaaacta ggatttagag   16320
aggagaaggg ggctctgtaa cacatacaag atagatactc ttttacacta acttttcaag   16380
atactcaaca tataaaatca gcatcatctt ccaaacaaca actttaagcc acccatgaat   16440
cttaattaga taataaaaca taatcgtgaa tcatctatcc tttgtttggg gggatcctaa   16500
agcaattgag gaaaagcttt gatgcaaata tcaattgtgt aaaaaagcaa gtattcgttc   16560
gtgatgttgc tatactaggt tattttttgg atccaaaagt cattcctact agaatcattt   16620
aggaaaattg tcagtatgaa ttttaaattc aggttataac caaagataat tgaaaattgt   16680
caaacttttc aaataattcc gaaataaaca tgtttgtaac atggataaac ttttcattgc   16740
ttttcaaata attccaaaat aaacatgtta taacatagat aaccttttca gataattcca   16800
aaataaacat gttgtatcat ggataaactt tcattgtttt ctagtcactt aaaattctaa   16860
aaaaatcttt cctccctact gttactctct ctagcaccaa atctatcaca tgagaaggca   16920
gaggttttca aaataaaccg ttacttaatt tggtacttat ttcttgatcg gtgttcatat   16980
catatgagtt cctactctat atctctctac tcttctaaat ccttgtgtca cttcctgtgt   17040
ttcataaata aaaaggagga agtattagtt ttgaaacgaa aggagtatgg tgcatacatt   17100
gatagaaaaa agaagttatt tgtccttatt tcactcatat aacaacacca aattctgtat   17160
tgttatcaca aaataaaact tggattatct ttgtttcata gcccaaattt agaattagtt   17220
tgtcagattt ccaatcatct aattacaata ttagagctag acctaggaca aaaggtgggg   17280
ttggctactt ggtaatagct atgtctagtg ctaggatatg tcattgtcgt agaaccatgt   17340
tatggacatc ttaagaaaca aggttaacct aattggttgg agatcctact ttcacttta    17400
taataaagtt tcgattcttg cctatttgta aagtagaatt cctaaatttc ccttcactga   17460
tatttatctt aacataaaaa aatgttataa acattgggat tgtatataag tcaaaataaa   17520
ttgacaatct tggtaacaac taagttaaca ttaatttat aagtaaatga ttaatcccaa    17580
tataatctct tatttagtaa atgagacaaa cttgtacacc ttcgtgttag actcgttaat   17640
gttcgctaac aattcattca gtagtcaaca gcattttaaa tttgaaataa gtgttcttgt   17700
ggtttttgag agatcaagca agaaaacatg tctctcccct ttgaccaact aattgggatt   17760
aagaatacta gttttaagat tttaagaatg agttatagtc tttcttagac cgctacaatc   17820
cccttgttga tatgaaccag atatattttg tgttcaaata gtagatcaat gcattgttga   17880
taatcctttg ttaatgtact tgttgatctt attttgtact tttggtagat gcgctatact   17940
ttctttcgat tgctcatttt gaactcttaa ctacatatgt tagtttaagt agatgattta   18000
gaattgctat ttcaatcttc aataagcaat ttaagttgtc aaaccttgtt tcacatcatt   18060
agggtgaaag ttatttggat aaagacctat atctaattca atccaaagca aattagtaat   18120
gcggattgga ctcaaactat gtttagattg gattcgaatt gagtttcttt tcttttttctt   18180
aaaaaaattg gattttccga tcgaattgag ggtgattaga tccaaaataa ccgaatagta   18240
gataggattt gtgttgtata ttagaattgg gcttaaggat ttccatttta acaaaaaaac   18300
caaatggtcc gactatcaaa aactataatt tgatagtcat gcctatcgaa aactttattt   18360
tcattctcgc acctaattat gggcttgtat aaattagttc tactatcgaa aactaatttt   18420
```

```
gatgctcgtg cctaatttaa attttcgaaa aaatgaagtt aagaaaattg gatatttcgg   18480
attggatcca atatatcttg tgaattatta atttggatta gtttggactc aaattcttat   18540
tggattggat tcaaattaaa agattaaaat tcaaattttg ttcgaatcaa attggagtag   18600
gcttaagttt aaatcataca ccgaactttc accactaccc atcatgctta agcttctaat   18660
gtaagagagt gtttgggagt tgagctcgaa caactaaatt tctaaaagaa ccaagttcaa   18720
acaagaaatc taaaagctcg attaaacttg agtcaagctc aaacacctat attccttatt   18780
ggagcttgac tgaagattga acacttattc cttattaagc tttacgctaa aacattgctc   18840
gactcaactc ttctacatcc ctatagttca aagaaatag ttgtgggctg tggtgctctt    18900
gtagaccaac gcactagttt aacaaagcta agtgcctgac tgcaattcca tacacattac   18960
gatcaccatg acctagtttc agctcacact ttggaagtct aatttgaact tgttctctac   19020
ctccaattca ttgtggggta ggaggcgata gttaagggat caaaatctta tgatataact   19080
tgcataggct atgccactat ataatgcgtc ttgtgtccca tattagttta atcaaattga   19140
aatgttttac catttatatc ttcaattatg tatggatact aatatttgat ttgacgtttg   19200
atatgatatt aaatgtggac tgttattctt gatgtgcttg agaagctttt ttggggccag   19260
ttagaaacta tattccttt atggtcctaa ctaggttgtt gttggtgtgt tcccaaataa    19320
cagcatggaa aggatactcg agcgctatga aagacactca tatgcagaga gataactgac   19380
tgctccagat cctggatccc atgtaatcca gctaggcaac tatcttttct aagcatttaa   19440
atcgttgaga tttcaatttt aaatgtgttt taactgataa ttcatgcatt atatgcttag   19500
gtaagtttga ctctggaaca cgcaaaactt aaggctaggc tggacattct ttagaaaaat   19560
taaaggtaat aagatccaga ccaaatataa tttgtataat aaccaccta tgaggaaaat    19620
ttaagatcct tgataatttc aggcattaca tgggagaaga acttgatacc ttgagtctca   19680
aggagcttta gaatttagag cattaaattg acagtgctct taaacacatc aggtcaaaga   19740
aggtagtttc acagttgcat tagatcatct tatggatcaa ttggatcact tgtttgtatt   19800
ttagcgttgc tcaacacggt cgtctaatat agtgtgcaaa acgacctaca gggcaacacc   19860
ttttataggg ctcgaaaata cgaaaaatta aatgtttgtt ttagtcatat tgttcaaacc   19920
caagctttat cttgtcaaaa atattttata atgattattt tttagaatac attatttaca   19980
tttttgcaat ttatgcataa tacttctaag gtccaacttt ataattgaaa tagaagtcct   20040
taaattttaa agacgacctt gaggaaacct aatttcttct catatataat taaatcaatt   20100
attctacaag ttagtagaac aaatactaca ataacaacaa tattgaagcc ctaatctcag   20160
taggattgga ttgattgtat gaagtcttat tagtggccgt taaatgtttc ttgtaggtca   20220
agatgacatg gctcatatag taaggttact tgactaaaag acgaggattt gtttcgactt   20280
agattttaac aagtttccct catttgttaa cacctaagcg tactaaatca aattctaggt   20340
tttactcact caaatttccg atttaggaag ggcttgagga tagttgtatt atcgtaactg   20400
actaatcaaa ggagcctctc ttagatcagg tttcacttgc caattctaac aacttgtttg   20460
gtaaaaggaa tttggaatga aaagaaagga attgaaaaga aacattctac tttcaatgt    20520
ttcattcaaa ataacatttt aagtgatag gaaatggaaa gaagtgaaac gaaagcctct    20580
ttacaaaatt atcatttttc tacccccccc cccccccaaa aaaaaaaaa aaaataagta    20640
gtaagtagta gaagaagaaa taataacta acaagagtag taagttttta cgttttcttt    20700
ctnnnnnnnn nnnnnnnnnn nnattcaaat cagaactgaa tagtcataac cggaagatta   20760
```

```
gtttctctct agcgtgacta gggtttgagt aaaaagagaa aacttaaatc aaacatggga    20820
tattaaggtt ttttttcctt tcttcagttc ttttctcttc ccaatccttt cctaaaaatg    20880
aaccaaacag gctgcaaggt tttcacttgc ttaacacaag atttattttt aaaaataatt    20940
acactccaaa cttttaagct taaaaccaat tttaattcaa atcagaactg aatagtcata    21000
actggaagat tagtttctct ctagcgtgac tagggtttga gtgaaaaagt ctagggtttc    21060
atgtcattct tcttgcttcg agtcccttct tgggattgtt gttagccatt atggctaccg    21120
aaatcgttat taaatgtcta atcttagaa ttactgctga agaaaacaac ttggtgtttc    21180
tcgaagatgt tgatgataac tcgcagcacc atacgctcgc actggcgatt gttggaaagg    21240
ttctttcgtc aagaccatac aatttcgagg cacttaaatg aaccttaaac tagatatggg    21300
tgatatccaa aggagcccta cttcacccta ttgaaaacgg acttttttgtg gtacaatttg    21360
cgacaattaa ggaccgatct aaggttctag tcagcagacc atggaccttc gatataaacc    21420
ttgttctctt agatgctatt gaaggggta ctcaatcttg acccattgcc cgttttggac    21480
tcgcttgtat aaccttccta tggactgccg atatgagaag ttcatcaaaa actattgttg    21540
gtgtattggg ggaggtattg gaagttgatt ttgacaggat tgtttgggat aaatctgcaa    21600
gagtaaaggt gaagattgac attacaaaat cgttttgtcg tgtgcagatg atcaagacta    21660
acagggggtga ggctgtgatg atcaatgtta agtatgaaag acttcctaca atttgttatg    21720
tgtggaattc tggccatatt gaaagagatt gtgtgaagac ccaggaagaa gagaaacaag    21780
tggagagaca atagggggtc ttggaggcct ctccgcgtag gggacgatta agatggtga    21840
aagagtcgaa agccttcctt cagtgtgctc gtacactcca ctttaataac aaggaagaag    21900
taagggggtga ggaaccacgg gattatgtgg agccgagggg ttattgtcgg ctatcttagg    21960
gggtaaaact ttggtggtcc aggagatagt ggacggctct aaggatgcca tcgaggaagt    22020
tcgtgctgaa ggtgcaccac tctagccccc ttgtacccct tgggtaatgc catgctacct    22080
tttacttttg ctgttgggag tgctaatcct actccctccc accgaaaagt taaaattaaa    22140
aacaaggcaa gggttcaggg tgttttgaac caagttaatg ttgtgggtgt tgggggggttg    22200
gctaataatg gggggttgtga gaaaaggata ttccccaacc cgatggtgtt agaaaaagaa    22260
aagggggttca atgaagaggg tttaagatag caaaacgaga ggattgtatg taacctatca    22320
gtagggaggt aactattgag gtggaggtgg gcgagaccca accccgcccg acattatgaa    22380
tatcctatgt tgcaactgtt gggggattggg caaccccccgg gaagttcgga tgcttcgtag    22440
gtggagcaat agtgctacac tgagttcggt ttttattttct aaaactatga ttagtggtcg    22500
tgatgtggaa agggtgcaaa gcgggtaggg ttttgattgg gcaattgggg tggatagcgt    22560
tggaacttca agagtttggt gcatttattg gaaagctggg gaagtggact ttactctagt    22620
ctctctatca agtcatcata tttgtgggaa tgtgaagctt gttgatggga aggtatgatg    22680
cttagtgagt atttatggtt gggcggatac aattcaaaag tataaaacat gggagcttat    22740
gcaatccttt cactcatatc atgggccgat attgtttggt tgggacttca atgagatttt    22800
gacaatcgga gaaattgaag gagggtccga aactcaatga agtaacatgc ataattttct    22860
agaaacttta gatgacatga agcttaggga ccttggctat tcgggaactt ggtatacata    22920
agagagaggc tttaagccac ggaagagaat gagggagaaa cttgatcatt ttgttgcatc    22980
ttcatcatgg tgtgacttct ttccgaaagc tacagttgag cacttgatgc gctacaaatc    23040
ggaccacact cctattttgg ttcgccttgt aggccatcag tgaagacata agaagaaaaa    23100
gacgtagttt tgttttgaga ctgcttgggt gcttgaggaa ggttgtgagg cccaatgggt    23160
```

```
gagtcatggg ccgggtttac tcgcgaggta tttatcgagc gctttaaagc cgtggaaggt    23220
gggttcaaag caaggagtga tgggtctctt agtaatctgg gcccgcgtgt gagggagatt    23280
gaggaggcca ttatagatgg gaggcagcga agcagataag gactatgagg ctctatgaga    23340
ctcctctccc acgaaagtta gacgaggtgt tggacaagca ggagacgttt tggttttga    23400 ggtctcgtgt gagttagata aaggatggtg atcgtaatac acaatatttc caccacaaag    23460
cttcccaaca caaacgtcgc aactacatag cggggatgta tgataataaa ggggtgtggc    23520
aagataacga agaggatatt gaagggaata tttcagagta ttaccaaacc tcgttcggtt    23580
cgtgctcccc ctctaggaag aacgtcgcgg ttgtccttga ggttgtgagc ccggtgataa    23640
ctgatgatat gaatatggcg gttatgaaat cttacactaa agatgaggtg tgggaagcac    23700
taaaccacat gaagcctaac ggaatgcatg ccatccttta tagaggttct ggaatacctt    23760
ggagatgata ttacatctgt cattttaggt attattcatg gcacccgacc ccagatgttt    23820
ttaacaagac taatattgtg ctcattccta aagtcaaatc cccaaatctt gtttctgagt    23880
ttcgcccgat tagcctctgt gatgttatct ataaacttgc ctcaaaagta cttgctaaca    23940
gattaaaaca ggtttgcctg acattgttta tgataaccag agtgcatttg tgtccggaag    24000
ctatattacg aacaatgctt tgatttctct tgaattattt gactctatga aaaatgata    24060 cagagctagg aaaggttttg tgtcgatgaa attggatatg agtaaagcct ataaaagagt    24120
tgagtggtgt ttttcagta gtgtgttgga gaagttggat tttgctgaat catgagtgaa    24180
tgttgttatg agatgtgtgt cttttgtgca gtactctttt gtggttaatg ataatatatg    24240
tggagctctg acaccctcaa ggggctttg acagggagac cctatatccc cgtatttgtt    24300
tatacttgtt gcagataccg ttttagctct tcttagcaag gcattcaaca atgcgtggct    24360
atacttgata ttctcaacaa atatgaggca gcatcaggct agaaaataaa tattgacaag    24420

tcaggaatct ctttcaataa agattt gac gtattttatg ccatgaaac aagttgagaa    24480 gcatcagaaa gactt ggtat cccaactttg gctaggagtt cgaaaaagt catatttgct    24540 gacattcaag agcgaatttg gaagaagctg cacggatgga gagaaaaact tctcgcgggc    24600

ttgaaaagaa actctcttaa aagttgtggt tcaagcaatt ctaacctatt tggtgggcgt    24660

ttacagattc ctaaccagta ttatccaggc cattcatttg ccatggtaa agttttggtg    24720 ggggtcgaaa agggcccaca attcgatgca tctgggggga tatgtgctca ccaaaatgtt    24780

taaggagcct тagcттттaaa gacttagggg tgttcaatga acctaaacta aggaggaatg    24840
cgtggcattt gattcctgct ggtgagtccc tttcgggtcg agtgttctcg ccaagtact    24900 attcgaagtc aaccттттг gactcatttc taggtccggt aggtagcttc tcttggaaga    24960
gtatttgggg ggccaaggca ttagttaagg gtgtttatg gtgcgtaggc aatggcagac    25020
aaatcaacat atggcgtgac tcgcgggtgt tgaatggtga tagtaggttc atccccggag    25080
agcgcgtttc aggccttgag gatgtttgtg atctaataga ttttgcacaa tggagtgcga    25140

tgtggacctt gtcacgattg cttcaatgaa gatgatgctc aagccatttt agtcatacct    25200
ctaagtaagc gccttctgaa ggacatggtc tcttgggctt tcactaagga tgaatttttt    25260

ttgtaaaaac aacctatatg gccggttggt cgaggaattt gaaттгттт cacaaagcat    25320 ggctgcaaat ctgggccttt aacgtgtctc cgaaggtctg ccacttcctt tggcgtttat    25380
gctcggtacc cttcctgttc gagctctttt aaaacgacgc cacataactg atgatgattc    25440
atgtcctttg tctaaaggag cccggaaagc atatcacacg cgttgttcta ttgcccatat    25500
```

-continued

```
gtagccgaag catgggagag tgcgggcctc acaaattgtt tgcctttgtt tgatggggct   25560
ggtatgcttg atgcgtgggg ggagtgggaa acaatcgatg actagtccct tgtaagactt   25620
agcttcttgg cttatcactt gtggtttagg cgaaataaat gtgtttttga aggggtggtg   25680
agagcgaatg agagtgttgt ggaatatgcc actaaagcta ctgttgatca tggtttgtat   25740
agtgcccgca tttatggtgg gtcgaaggct accgcatcca aaagctcgaa ggtatgggtt   25800 cccccctccag cttgtcgtac gatctaaagg ttgatgcatc agtggggaat ggtggatggg   25860
tggggctagg agtaatcgcc tgaaactaga aaggggaggt gctcgtggct gcaactagga   25920
gggtcagagc ttgtggcccg tggaaatggc tgaagggaag gctctttgtc ttgctcttag   25980
gcttgcctcg ctcatacaac ttgcaagaag tgatcgtgga gtttgactgt caatcttggt   26040
gaaccatctc tccaagggtg ctatttactt tgcatttta agtcaaagct tgaaccttga   26100
taaaaaaatc ccgttcgaca tgaaaagtgc cttgattttg cgggtttggg agtgccttat   26160
tgattctggg gtttgatttg taacaccttt agtaaaaaca tgtaagctaa ctgtaaaacg   26220
aacattaatc aaactaggat atgtaaaatt cctaaatcaa gaagaatttc cacttgtgct   26280
gaatttgtcc accttgcatg acacccaata aaagcccatg tctcctagaa ccccttatgc   26340
cgccttattc atcttttctc aagttgagtt ggagtcctct atggtccact cgacttcttt   26400
agcacactct cggtaaaaac ttttaatatt attttatttt agactccacc atcttgacat   26460
ttattccttc ttaaacttgc ttcacacaaa catctaacac tagaattcta tatagaatag   26520
cttgaatctc tcttaggata accttatagt aaatgcaact acgcctatcc ttaaacccttt   26580 ctaagaggag ctttatcgta tttacattcg cttcactttg aaacgtcgct aagtgtatgt   26640
tgcactttcc aaaccatgtg ttagctaaga ccaagttata tgactgcata acctaaatag   26700
tcttcctcga gaaaattcac tagttggatc ggaagagttt gtgtaaatct atggcggcgc   26760
gggactgggc cttcacgatt tcaagtgttt taatgcagct cttctaggta aacaagtttc   26820
ctaatagcgt ggtgactcaa atattgagga cttgttgtta tactaatgct attcctggcg   26880
gcacttaagg ggtgaaatag gtggtacaaa ggagtgcttg atggcgtgtg ggtagtagtt   26940
gaatatatca gtatgatcaa gtccatggat ccctcgtact tattcgtgca agattatttt   27000
tccacgaggc aaagcgagcg agaatcttaa ggtttatgat catattcatc ttgtacgtgc   27060
taagggtaat gtcccttttca ataatgagct atttctcctt ttgagcaaga gcgtatctta   27120
agcattcctc gtagttctcg tctccccaac gatgttttat gttggaatct gaatttggag   27180
aaagacggag acttttcgtt cggtctatcg agccattctt ttgagttgga tggcgagagc   27240
gtgatttcat cgtcaatacg ctctaattta tggagtataa tatggcagga tagtaccttt   27300
caacgtgtta agcttttatc tgcattgtcg acacaaaggg gattgagtaa gcctgtgccg   27360
agtatggaac cattgtgtaa tctttatgcg ttggaggatc aatggagcta cacttcttac   27420
gagactttgt tattggaagg gcttatatgg gatccaacta gggtagtcaa acattggtc    27480 ggggctgcgc tgcaattttg gggacttggc accggcgttt ttggagtagc tccctcatgt   27540
ggaacatagg cttttgatga cgatatacta ggctagatgg aatataagag agaggtgttt   27600
gtttgaggag gaggtttgtg atccctatca aaccacatgc ataatctcat ggcgtagctt   27660
catgtggaac actgacatat tgcatgtgta gggttaggtg cttgcctagg acaccacatg   27720
ggaagagctc cgttaagctt aatgtggatg gagggtgtgt ggaagggttg ggtgcgtcca   27780
ctggagtggt gattaggggg atggatgaaa aagcgttgta gttgcaacat agaaaggtgg   27840
aggactgcga ggaaccgtta aaaaggctat atttttatggt gttcatttgg ttgtgtggaagt   27900
```

```
cgattttttga aatatggttg ttggaagtga ctatcttcac ctcgttgaag caacttcttc    27960
aaaagtggaa ggcaaaaata gcttccatgt tattgttgat gacattgttc atggtagtgg    28020
tatgttaaat acttcgtctt gtagttttgt tcgtagggat gggaataggg ttctcacga    28080 actcccccat ggaaatatca taatggctca tgctcatagg taaatgaata agctaacaaa    28140
attgttcatc tttgcagaac taactcatgc atgaatcgat ttcttagctt tagtgaaagg    28200
tagacagctc tagagagagc atctagtctc aaaaatacca tgagattctg tagtgtcctg    28260
acatgtttta tatgacagga caaagcgtta aaggagcaca acaacttgct atccaagaag    28320
gtataagttc agcaagattg tttagtaaca ttgttaatct tgctgattgc tttgaaacat    28380
gtcttgctat ggttaacaat gttgactgaa ccaaaatagg tgaaggagag ggagaaggtg    28440
ctggcttagt aggcagaatt ggattagtaa aatcatgaca ataactcatc tggctttgtg    28500
atgtcttaag ctttgccctc actgaataca gggtcagtcc tcaataacct ctaatcattt    28560
ttccaagatc caaagtaaac atggtttcat aatttaatta agatttttt gaaccatgtc    28620 tccatacaac cttactagga ctaatactac taatttaaga ccccaacgat aaacaacaat    28680
aattagccat atctggctag caccttttgg acaacacacc acatgagact cttggccaac    28740
ttctttgatt tccttcagtc tgatagatat gaatatcttc tgaagagctc tttggttcat    28800
aattattgat ttagaaaaga attcagcaag gtgagtcatt tggtaacctt aaggtcatta    28860
tgggggtact aaatcaaagt gaagatatat ttaggtggca tcagaagaga tgatatagat    28920
aggttgtatc ctgtcgatag gttatttgga tatgtatcaa aagtttcttt tataatatat    28980
ctatactgat tggttgatgt atcaaatatc cctacagatt gtgaaaaaat cccctacaga    29040
ttgtgaaaat atccctagaa cctgtgatga tataagatgt gctccgcatg ctttattgaa    29100
cataatgtat tcaattcttg aaatgcagag gaacaagcag cagtgcagtg aagatgaag    29160 caacataacc accaaatcta aacagcaact ctgcataaat accgtcctgg atgctttaac    29220
acatctaaga gcagtaa                                                   29237
```

<210> SEQ ID NO 39
<211> LENGTH: 21668
<212> TYPE: DNA
<213> ORGANISM: Artificial Sequence
<220> FEATURE:
<223> OTHER INFORMATION: BvAP1 genomic DNA showing mutagenesis site at position 6999
<220> FEATURE:
<221> NAME/KEY: mutation
<222> LOCATION: (6999)..(6999)
<223> OTHER INFORMATION: c to t
<220> FEATURE:
<221> NAME/KEY: misc_feature
<222> LOCATION: (9833)..(11385)
<223> OTHER INFORMATION: n is a, c, g, or t
<220> FEATURE:
<221> NAME/KEY: misc_feature
<222> LOCATION: (12467)..(12605)
<223> OTHER INFORMATION: n is a, c, g, or t
<220> FEATURE:
<221> NAME/KEY: misc_feature
<222> LOCATION: (13741)..(14088)
<223> OTHER INFORMATION: n is a, c, g, or t
<220> FEATURE:
<221> NAME/KEY: misc_feature
<222> LOCATION: (16396)..(17194)
<223> OTHER INFORMATION: n is a, c, g, or t

<400> SEQUENCE: 39

```
atggggagag gaagagtgca gctgaagagg atagagaata agatcaacag acaagtaact    60
```

```
ttttcaaaga gaagaagtgg acttgtgaag aaagctcatg aaatttctgt tctttgtgat      120
gctgaggttg ctctgatcat ttttttctcac cgaggaaaac tctttgagta ttcttctgat     180
tcttcgtaag tatatatata tatatattaa tagtaactac ttgttttctg ctttctattt      240
ttaggtctga tgcatattta atttaggtaa tattaattcc ttatatctga tccttaattt      300
ttttttcttt taccatttca tttttgtttg ttttgaataa aagaaaattt cccttcacg      360 tgtgtcgaat aggtcaaaat ttttacttga aggatgttct ctttgattac taaaatagga      420
tccaacaatc acctgaaata aaggaagaag atggtgcaaa gttttactg tcatacttag      480 tatttgataa atattctatg atgaacttgt ataaattagg aaatagacct aactttcatg      540
cacgaaaaca ttattccttc attcaatttt tttattactt aaggatttac ttttttattg      600
atcatatgaa gtagtagtac ttgtaatcat tcaatttttt tgttggttaa ataggactac      660
attttaaaac aacccaattt taaaatttt tgtgtgaatt tcttccctt ttaaaaataa      720 agtctattat catagcttag agtagctgtg gcaaagctag acgaaataat acagaaatct      780
ggaaaggaaa ttgtactact tacatgaaca cacttattta ttacttgcat gatatctgcg      840
aaaaagttta tagcaaattt ggttaatata tagcgtagta ctttggatat taatattact      900
agtgtacaaa tacttgatcc aatgggtaat gaaacttatg gaagatttga ccatacatga      960
tgatgctaaa tattaattgt tatttgtccag ctttgttttc cctccatcca ttggcatctt     1020
catctttaca ttgctactcc actcacttgt caattgtttc gtcctttatg ttctttattc     1080
acatgtgcac catacttcaa tactttcccc ttctttatcc tcagtttttt tttcttgtca     1140
ttttagggtt aatatccaat gaaatctagt ttgctcgttt tagatctaat tttaattcga      1200
tcacaaccat ccatattttt gtttcttagc ttgacatcta ttctatggat ctgggatctt     1260
cggtgtatag atgttctcgg ttttcagatc aagatcctat tcatagaccc atttattgta      1320
aacacttaaa tgtgttctta aaagttagt ggctcgccaa gtcaactcaa taacataacc     1380
cccacgactt cattacatta cacaatgaaa gattagatgt atgagtttgt gaagcttata      1440
attctatttc aagtaggact aggatgtttt gtgcaatcag cagctagtag tcttttaat     1500 ttaagtcagt cttcattgtg catcatatat ttttagaaat atatgcaagt ttgaaaccat      1560
ttagaacctc atgacccgcc tgactcacta taaaccggca agagcttaat ttttcacagc     1620
tttgtatctt tatgagtagc gctagctagg ggtatgggca tagaaaaaaa gggtttgggt      1680
tagggtctta caagatctta tccgctattt ttatttcata atctttcaaa atacatgttt      1740
aataattcaa aatacatgtt taatactatc tccatttcac aacatatgca ccaattgcct      1800
agctatggtc caacctagtt ggtttgtagc ttgcattgga tggttaggat gtattggagt      1860
tgtttatgtg caatcaaatt ttaattacgt atcaaaaaaa aaaaaaaaaa aacatatgca      1920
ccaatttcca tttggacaca cttattgacc aattttttgac aatatttttc tcaccatttt     1980
gtaagaaaaa tcaaaatcaa gtggaattt gttaagttta tctcagtcaa aagattccat      2040
acatcgacat tttataattt ttaatcatac gcaattagaa atatcaatgt ctaaagaagc     2100
gtgttggaat acgtgaaaaa gcaaatgata catgaaacag atgtagtata tagaaaactt      2160
aattttgtgt cactcggatg tatgtgggcg gagccttcct agaaggcgta cccaccttag     2220
tggctctgaa tctttgacga cccgttcggt tggtggtgat aatagatggt aatagtaatg      2280
taatttagtc taaatttata aataaatatt aatatcatta cccatggtaa tacaagttct      2340
tcacaaaaca tgtttcattt aaaaattatc attactacct tttcaagtgg tattggatga      2400
```

```
taataaaatt ttaggcaggg aaatgggtat tgggatgaac attaccatgg gtaatgacat    2460 gcaattttg ttacaagaat acagtataat acattactat tgccaccatg tataaccatt    2520
aatcaaatgg accgtgagga tatgatgttg aagaagaagt cttaacctct acgctattat    2580
ttactagggt ctgtaaattt tccttttta attataattc ttgtgaaatc ttcttcactg    2640
atggtactag cttattagga tgggtttctt tagtatattg aaggctcttg ttgacagagt    2700
ataaaaatat ttttggggtc gcaaccatca atttaaactt ttgtttgatt ataaaattat    2760 ttttgaaca tcaacaatct acttaaattt ttggttgagt tagttctttg acatggtatc    2820
acaaccatca tgacataaag gtctcatatt caaatctcat tcacctctca tttccaagta    2880
gaatatttac ctcaggtatg ggtatgaggg aggcttgtgt tgcatgagtc aataacggat    2940
cttgaccaat aatttaacag gggcgagttg ataaattaag ttttaatgta aaattttaaa    3000
tgatggataa aaacactaat acacaccaaa atataaatat acttttatta atggttacaa    3060
agagcttgta gctaatgtaa taaatcaaaa tcccaaaggt gcaatttta agaaattatt    3120 tccatttatt tatttgacca ttatgaaatc ttcaagaaat tgagtaagtt tttaagaaat    3180
ttaaggtata gttcattaac taaataaact actccagtaa aaaaaaatta ccaaactgct    3240
ttcttaagta aaaaaataaa taaatttata ttttatgatt gttaggaatg agtgtgagga    3300
aataaaaagt actattatag ttaaataaaa atgaaagttc ttcagagaag aagaatagaa    3360
gatagtacaa tcaatgttaa atattttct aaattagaca aattgatata aaccaaaaat    3420
aaaggggaag aagaaagaaa taagtaaaaa aagaaagaag gaaagaaaa aagaaaaaa    3480 gagaagcaag tgaagaaaaa caaagaagtc caaatgtgtg ttgatgcaag gttcgagctt    3540
gcaacattaa gggctcaaac tttctttac actttggttc actgccaccg tgcccacagc    3600
ttgttatgtg acatgaagtg tagtttgctt aatttatctt atacagttat gggggaccaa    3660
gcctccaccc gccccttcta taatctgtca gtggttgcat ccacacttta agtccaatag    3720
actcttgtct gagaggaggt gatagagtat ataaatattt ttggggcctc aaccattagc    3780
tcaatctttt gattaagttg gttctgtgac acttgtacta tatactagtt atatatac    3840 tgtaaaacta gtaccacgag aacagtcctt aatacaaaca acatgccctt aatagaattt    3900
tcttagtata cacttaatat aggttgacta gcttttttgcc cttcagtatg cacacacctt    3960
ttataatctg tatcgttgtc tggtagatga taataaacct cagtattggc aatatatgaa    4020
atgacataat ggccatgttt ggtgattaga gtttagagtt tagaggttac agttcagagt    4080
ttgtggttag atgattactt ttttgttcag aggatttgac tgctgattta ataattgtt    4140 gtgtaaaggt gtttggtaac acttagctta ttgtttagag ttttgtactt tttagagcat    4200
gtaaaatgac atttatggac atatgtattt ttttaaaaca aattttagta gtaattatat    4260
ggacaaaata gtcatttgtt ttttctctct ccaaaactct catgaaaaag ctcctctacc    4320 cagcttttc aaaagagagt tttgatcaga gttttcggta caaaactctc tttagtcctc    4380
tctctcacca aacacccaaa ttagagtttt tattggtcaa aactctaaac tctctccaaa    4440
cctctaaact ctctctaaaa ctctctcccc caaacacccc caatttctta gaaaaatttg    4500
ttgctccttt ttattgcact atatttctat ctccaaacat aaagtttctt ttacaaattt    4560
tcatttctac tccataccac ctttatatgg caatataatt tctatgaatt aaaatgttca    4620
caagttttga ggtggatttc aagagcatgg acaatatgat catgagactc tccatacaaa    4680 aattacccctt aaattttata atcatacacc aagcggtcgt taaagtattg gaagtgcttg    4740
agtagtttgt gaaaattaac atataataaa gtgcagatct cccctctagt aagtagtaag    4800
```

```
aagtagtaag acgatgtccc tcatttgaga aagagaaaaa cccttatcag tttctcttgt    4860
ttctttgact gaacgcaagt caaatagaag tatgtaacta ggaaatcctt ggagaaatag    4920
attttcttta aaactataaa agtataccta tatatatggt aacccacaaa aatgtatata    4980
atctgatcaa tatctaaaca aagtattctt atgttttctt tcatcttgct tatttcctcc    5040 ctttccttt cttactttaa tttgtttact ctctttaact tatttctttg cgtatctcat     5100
ttcactttac aaggatatat agttgattat gacagcttaa taaatatatt ttggaactag    5160
gatttattgg ttgtcgttgt tattttaatt tctacactga tcggctagag tttctagaac    5220
ataggctttt attgaaacca ttagttaaca aaattgaatg acaatgattc aatatgatag    5280
aatatgtatg tattagttaa tgtttgatta ttgtttgtat gtatataatc aaagattatt    5340
tagtaatact tctatataca tattctatta gaatcactta gaaagaccca ttgaacaata    5400
ataaggatag gcagacaagc aaacaaaaga aaaataaacc tgttactcct tccatttctt    5460
aatgttctac tcggaattat agatacacac tttgacacaa attagaaaga gagtgtaaaa    5520
agtggatcca tattaatatt tttatttttt taaatgagga gagaagtgtg ggtttattat    5580
gtttcaaggg agatagagag cattgaatag tgagagaata tgtgccaaag ataattaaat    5640
cattgtaaat cttttgccaa ataaagaata aagcatgtga gtaaaactttt aaaaaatggg    5700 cgaaaaagga aagttgagta gaactttaag agacggaagg aatatagaag aggacgtgac    5760
agatgggagg aagatcagac atcttagaag gggaatagtt aaatttgaga tagtctttta    5820
attaaggttc tcactaaaga agatataaca gtaggggaaa gctaaaggtt attcaaaact    5880
ttccttccca tcttcatcac ttcatgtctt tactttagag ctcttaacac ttagcctatg    5940
aaattctgaa ctctttgtaa gattagtgat agataaaaga atcttatcaa tttaatttat    6000
aaatacaaca ggattcaata aaaagatata gagatctata aataaagagc catactgttg    6060
tgaactttta tatctatcaa aacctttgca cattagacgt ggtataacta aatcaggctt    6120
atcgaaattt tttaaaattg ttttcattat agccccttta tatttagaag ttctaagatg    6180
attgcataga tagttgatgc accgttctgg tcgactttt taaacacttc ttttgataa    6240 attttttttt ttgtattcga atcattattt taggtgtata aagagctgca aatgatctag    6300
atgagattga tctcggtttc atttatatgc taatagtgtg ttagatacac actattaaaa    6360
aagtcatatg acttagagat tattatggaa aagggatagt gcaccgatat taatataatg    6420
gaaaatgaca cacgagttgt ccataataac atgtgaaaag tgaactattt aaaaggtttt    6480
tctgacctag tacatacaag gtgcgtaggt ttagctattt tagttttta gttttatttt    6540 ttaaagtgaa gttagttatt gatctgaaat catataacat gtacgtaccg tagatataaa    6600
aaactaccaa gtatatatca atttgaaata aacattattt taatatggca aaatcacaat    6660
tgttgactag acctaacact gaagaaaact atgtcatgtt tatcaattat gttgcataca    6720
gttaaaaaca aatatgttag agaaatcgtt atttgaaata gaaagttgc gcaaaatagt    6780 gattaacatc aaaatatgtt cagaaagttt ttataaatat gtgatcttgc attgtctgtt    6840
gactgtcgag gttatgata atttcccctt tttccaatgc aaaacttgtt gtgctatttt    6900
ctaatgatat atttttttcaa agtatggaga agatcctaga aaggtatgag aggtattctt    6960
acgcagaaag acggctagct tcaaatgatc cagactcata ggtagtgcat ttatgtaaat    7020
atagatatac tcttcatgcc caagaagcct gaattttta tcccactacg tactgcaaag    7080
ccaagtttaa ttgaataatt gtcctgttta aattatttag ttttcagtac aataatgtaa    7140
```

```
tcattagttt gcatgtttaa aaaagaaaag cacaagttct gatcaagtga aatataaatt      7200
gtaacgaaag agccaagcta gacaattacc tagctaggag ttatttgtta tcgtttttgt      7260
ttttaatttc tagttttttt ttttaaacta gaaaatatag tttcaatctt ttgttatcag      7320
ttttcaaaat gacatattta acataaatat gattgatttt aaattcattt attatatcat      7380
atttcatttc aaaataagtg aaacacttgt ctcaaaaagc tcactctcac ataaatgata      7440
aaagtgtttc acttatttta aaacggaaga attatgactt ttacttttca taaaacgaaa      7500
aactgaaata tgacaataat ctcaaatagc ttggagaaac cagatttcta tatatttccg      7560
tgatgaaatc acttttcatt atacgtaggt aaactggacc tttgacttcg caaaactgaa      7620
ggcgaagctt gaacttctac aaaggaatca taggtatgat ggcaatatgt cataattttt      7680
ctattattat ttttgcttcc aaaaccagac catatgtttg tatatttata tagtgatata      7740
ctccatccgt ttcattttaa tctatacatt tacacttatc aggtatgtca atgcaaaatt      7800
ttgaggatat atatctttag ttttgtattt ataaaaatta taaaaagtac atattaataa      7860
aatacatatt atgatgaatc taacaagatc ccacatgacg atatttccgt ccgcgtatga      7920
ataacaaata atggccaaag tgaaatttgt gaatagtgta aaatatcaaa gtgtaacaat      7980
taaaataaaa cggagggagt agtacttgtt tgtcacatac ttacttattt ttgttctctc      8040
cacaatgaaa ctgttctttc taataattaa aaaaagtgca tatgttgatg atttctctgt      8100
cactttaagt ggatattgaa tagtgataat ggattacttt gtgtataatt gcatttcaca      8160
tttgggtcta attttatacc cttttcgcat atcatgcttt gtgaatagta catatgatgt      8220
tcaagaatgt gagaagacat atcatacttt tgatatacct caaacatggg tgtatactgt      8280
atagtgaacg aaagtgttag tgtaatttta tttaggaggt ttagtggttt gtcctatata      8340
taatgctagt agttatacac catagttgtt gatgagcatc aactggcttt cctaacattt      8400
ttttctccat aacttacccc ttaccttaca ttagattact ctaggattac attctaccta      8460
aaatattatt actcccatca ttttaggtaa atatttttac tttgatttt  cgattatttt      8520 caagagttta aaataatgat taaaatttac catgatcagg cactacttag gacaagagct      8580
tgactcactt aacatgaagg aacttcagag tttagagcaa caacttgata ctgctctcaa      8640
aaatgttcga tctaggaagg taagaaattt tacttgtcta ccgtagtttc ataataaatt      8700
agtatttggg ctcgggcttt gccccagatt ggtattgtct tttcaaattt gatatgcatt      8760 ttttttccatt tccactaaaa tatattaaga aaattcaaca tttaaaggat acaaatataa      8820
taatgtggat acttaaagta tgattaaaat ttggttgaga tggtaattgt gtcatgtata      8880
atagcaagaa gtcacaagtt caaagctcgt tgcaagctaa atttattttt gttgattgac      8940
atgacttatc aacacactgg acaattctaa tcatctagtg gagtagcata tactagcaat      9000
ttatgcacgt gatgtgtgcc ttactttttt agaatataat ttataacttt tttgagcata      9060 aacaaggta aaatttgaac attagacata ttttttgggg ctagctaaat ttgttgttta      9120
aacctatatc acttaaccaa actcctcttt tattatttat tgatttatat tttatttaaa      9180 attttaaaa ttaaatgat gagcaataaa agaatgttaa gtagatttat taagtatttc        9240
ttatattttt atcaacaaag tattttgtgt taattaaatt atttcacttt gttaattgat      9300
tgtattttcc ttttaatttt attacttgat tgtgtattga ttgatcaaac ataattttttt     9360 tgttaatttt tttatgctat atttgaattt attttctttt catctgtttt tggtagagta      9420 gttgattttac taaagggtaa ttaaataaat ttattggggg acaccatagc tccccctcc      9480 cttatataat agagatttgt atagatttat tgtcttcctc aattattgat taactagtct      9540
```

```
tctatgcacg cgatgcgtgt gttgattgtt tgggtctatt cttaatataa atttcatcaa    9600
aatataatta tagtagtgtg atttacaatt attgctatac aaactactgt aatttataaa    9660
gttgttagaa attgagataa aaatttagat gtgaaatttt gtggtcaaat tatatttgta    9720 atttttaaa ctgagtaacc gttttctca tcatgtcaag ttactttgtt aatgcttatt      9780
taatttatta ttggaatttt tgacccatct ttaaattaga aaggatata atnnnnnnnn     9840 nnnnnnnnnn nnnnnnnnnn nnnnnnnnnn nnnnnnnnnn nnnnnnnnnn nnnnnnnnnn    9900
nnnnnnnnnn nnnnnnnnnn nnnnnnnnnn nnnnnnnnnn nnnnnnnnnn nnnnnnnnnn    9960
nnnnnnnnnn nnnnnnnnnn nnnnnnnnnn nnnnnnnnnn nnnnnnnnnn nnnnnnnnnn   10020
nnnnnnnnnn nnnnnnnnnn nnnnnnnnnn nnnnnnnnnn nnnnnnnnnn nnnnnnnnnn   10080
nnnnnnnnnn nnnnnnnnnn nnnnnnnnnn nnnnnnnnnn nnnnnnnnnn nnnnnnnnnn   10140
nnnnnnnnnn nnnnnnnnnn nnnnnnnnnn nnnnnnnnnn nnnnnnnnnn nnnnnnnnnn   10200
nnnnnnnnnn nnnnnnnnnn nnnnnnnnnn nnnnnnnnnn nnnnnnnnnn nnnnnnnnnn   10260
nnnnnnnnnn nnnnnnnnnn nnnnnnnnnn nnnnnnnnnn nnnnnnnnnn nnnnnnnnnn   10320
nnnnnnnnnn nnnnnnnnnn nnnnnnnnnn nnnnnnnnnn nnnnnnnnnn nnnnnnnnnn   10380
nnnnnnnnnn nnnnnnnnnn nnnnnnnnnn nnnnnnnnnn nnnnnnnnnn nnnnnnnnnn   10440
nnnnnnnnnn nnnnnnnnnn nnnnnnnnnn nnnnnnnnnn nnnnnnnnnn nnnnnnnnnn   10500
nnnnnnnnnn nnnnnnnnnn nnnnnnnnnn nnnnnnnnnn nnnnnnnnnn nnnnnnnnnn   10560
nnnnnnnnnn nnnnnnnnnn nnnnnnnnnn nnnnnnnnnn nnnnnnnnnn nnnnnnnnnn   10620
nnnnnnnnnn nnnnnnnnnn nnnnnnnnnn nnnnnnnnnn nnnnnnnnnn nnnnnnnnnn   10680
nnnnnnnnnn nnnnnnnnnn nnnnnnnnnn nnnnnnnnnn nnnnnnnnnn nnnnnnnnnn   10740
nnnnnnnnnn nnnnnnnnnn nnnnnnnnnn nnnnnnnnnn nnnnnnnnnn nnnnnnnnnn   10800
nnnnnnnnnn nnnnnnnnnn nnnnnnnnnn nnnnnnnnnn nnnnnnnnnn nnnnnnnnnn   10860
nnnnnnnnnn nnnnnnnnnn nnnnnnnnnn nnnnnnnnnn nnnnnnnnnn nnnnnnnnnn   10920
nnnnnnnnnn nnnnnnnnnn nnnnnnnnnn nnnnnnnnnn nnnnnnnnnn nnnnnnnnnn   10980
nnnnnnnnnn nnnnnnnnnn nnnnnnnnnn nnnnnnnnnn nnnnnnnnnn nnnnnnnnnn   11040
nnnnnnnnnn nnnnnnnnnn nnnnnnnnnn nnnnnnnnnn nnnnnnnnnn nnnnnnnnnn   11100
nnnnnnnnnn nnnnnnnnnn nnnnnnnnnn nnnnnnnnnn nnnnnnnnnn nnnnnnnnnn   11160
nnnnnnnnnn nnnnnnnnnn nnnnnnnnnn nnnnnnnnnn nnnnnnnnnn nnnnnnnnnn   11220
nnnnnnnnnn nnnnnnnnnn nnnnnnnnnn nnnnnnnnnn nnnnnnnnnn nnnnnnnnnn   11280
nnnnnnnnnn nnnnnnnnnn nnnnnnnnnn nnnnnnnnnn nnnnnnnnnn nnnnnnnnnn   11340
nnnnnnnnnn nnnnnnnnnn nnnnnnnnnn nnnnnnnnnn nnnnntatat atatatttag   11400
ctaagaaaaa aaagacattt cattgggga taccataact cccccttagc ttatataata    11460
gagatactat acttcttttc tgatagtgtc aaatttaatt ataaatcttt aacattggcc    11520
aattaataat tggacaagaa aaaatgaga caataataaa taaggcgatc ttcacagacg    11580
tattaacatg atggtaatta aaaatgttaa tcatagatct ttgtgttatc ttaataaat    11640 aaatttacta attagaatgt atcacataaa gtaagtatta atagcagcat aggataattc    11700
ttataatgga gattttatat ttttttatat aattatatga tttattgttg aaaatattag    11760
ttgattttaa ctggttgttt attcaatgac agaaccaact gatgcacgag tccatttctg    11820
aactccagaa gaaggtaata actccatttt ttactctcaa aggtttattg tttttaactt    11880
```

```
atttcttcta acctttata tatgagaagg tattgggtta gacgcgtctg accataatat    11940
taggtcggat gactttcagt tggtttcaat tttatttcag ttggtttcaa ttttgtcca    12000
gttggtttca atttttgttc agttggtttc aattttttt  agctggtttc aattttgtt    12060
cagttggttt caatatttt  tagttgatct tttttatttc agttggatgt cttttaagtt    12120
cagttactta tcttattgtt tcatttacgt gttttattgt aactgaaaac aaaacttaag    12180
taaatgaaat aaaataagtt ctaaataaaa gcaacttagg gcctgttctc cccagcttat    12240
tttcagttca gttcaattca gttcagttca attcaattca tttcagttca gttcagatca    12300
gatcagttca gttcagatca gatcagttct tgacaatact tttactctca catatcacta    12360
ttcatttcag ttcagttcaa ttcaattcag ttcagttcaa ttcagtttag ttcagttcag    12420
ttcagttcaa ttcagttgtt ttatgccgaa gagaacaggc ccttagnnnn nnnnnnnnn    12480
nnnnnnnnnn nnnnnnnnnn nnnnnnnnnn nnnnnnnnnn nnnnnnnnnn nnnnnnnnnn    12540
nnnnnnnnnn nnnnnnnnnn nnnnnnnnnn nnnnnnnnnn nnnnnnnnnn nnnnnnnnnn    12600
nnnnattca tttcagttca gttcaattca attcagttca gttcaattca gtttagttca    12660
gttcagttca gttcaattca gttgttttat gccgaagaga acaggcccct agttttcagt    12720
tacttatatt atcgtttcag ttagttttct tattctttca tttaacaact aactaaaata    12780
aaaaaaaaaa aactaactga aagcaaaact taattaaatg caaaaaatta agttctaaat    12840
gaaaccacat acgatcgaaa tttcaatcat ttcaaacatt atggtgtttt cgattctttc    12900
aaagaaggca agctgctccc gctattctac cctctttaga tcacaataaa gctcaggcct    12960
cacattcaaa gtttcctcaa agatggacgt tccaagtatc acatagacac atagtcctct    13020
tctccaaacg ctctccttcc tatcttgatg tcattagcaa acttcttgat ccagacggcg    13080
ccaacaaccg caccatgatc tccctctaaa gtactgacgg cccgtttggt tgttggtcat    13140
aaatgatggt aatgggaatg aagttgtgtg taaatttgtg aaaaatatca ttgtccattc    13200
ccatggtaat gctaatttat cttaatgtgt ccactttcct tctagaattt tcattctcat    13260
ccaataccac cttgtaaggt ggtaatgagt ggtaatgaaa attgcttccc cttggagaca    13320
aaaatacaag tttaggagtg agattgattg ctcatggaga aaaaaagtct ccccatggag    13380
atattaaggg tgattcccta ataaaattac acttaaaatt tattcccatt accgcaattt    13440
attaacatct accaaacggg ccgtgaaagt cttgaaacac atagtcgagt gagtagcttt    13500
gaggaaccat ctgtaaaaga acctgaggga gccaatgtgt gcgtaagtac caacggcgtg    13560
ttgtcagtgg aaaaggtggt gccgtggtgg cactcagtag tgatggagcc gccgtggtgt    13620
ttgagtgttg ccaaatacaa aggcggaatt tcgtaatctc taatttcttc tgtgaaattt    13680
ttgggatcag cctgtccgac caaacacatt ggatcaaacg gtctgaccca atagtttcaa    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
nnnnnnnnnn nnnnnnnnnn nnnnnnnnnn nnnnnnnnnn nnnnnnnnga tataaataga    14100
gatggaggac aagggtcttg gttttgtcat gttgtcaaag agttgaacaa tggtttttc    14160
gtattgttaa aaaattaaaa aaccagaggc cttcaatctc ttgatagata tagatagaaa    14220
aggaggacaa ggccgttctt ggttttgtta tattgtcaaa gagttgaaca atgattttt    14280
```

```
cgtgttgtca aaaaattaaa caatgaaaaa agatggcggg tgcttgatct aatagatcgg    14340
accatggatt gaaggtcttt taacttattt tatatatata ttgaacttat ctgaagatta    14400
tttaactctt tgaaattgta ttaacttccg aactttatga actttttaa ttcttcaaaa     14460 cttatctaca ttttatttga aaaaatattg aagacaaaaa aaccctcagt tggtttaaag    14520
ctgcggtaag atagagtgta aatgttattt ttttttatta aatcaagaaa taaaaagaaa    14580
tattaaataa aaagaattaa aaatggaaat gatgacagaa acttatggct tggaggagca    14640
atacttttaa gatagaccta aaccttaaat aagttaaaat ggaagtaatt tttcagtaga    14700
atcttattcc aatctatact ccgtgtttac tccatgtaat gcacatataa taaaaaaatt    14760
agaaattaca tagtataagg tttgatcctg tgactgtaag tttatatact aacttcttaa    14820
ccactagagc aagtgatatt tagtgttatc atttttaaagt ataattttaa caaatgaaat    14880
ttttttctta cccggaacat agctcggacc taataactag ttgaacaatt ataatctgta    14940
acttaaaatg atcctaatta ctgtactttc attacctata ataatagaat cttactatca    15000
ttggttcaga aaaaaaaaat cttattaaat gttaaccatt tatttgtaat tgaaacatac    15060
atgcacataa atgtaacttt tagtttatct taacttaaaa actgagaaaa tgttagttgg    15120
aaacttttgt atatatgttt ggataaacga cgctcaaaag tagggctaa aattttagta     15180 gataatataa gattatactc catctgttct agatagactt ctcatttttta attttggcag    15240 tattcataaa taaggaaat cttttcaaaaa aatttccaat atataagaaa aaaaataatc     15300
atgtgcggtt ttgtttgatt cgtctcattg tgtacattag gaaaattaaa cttatataat    15360
ttttactact atgtaattaa agatattaac gatacaaaat gtgtattgac aaacttatat    15420
tggagtaata ggaagtctat taagggaccg aagaaatatt acgtaaataa atctaataca    15480
aactaatata aattctactc cagacaataa agattctgtc ttatattgcc aagatatagt    15540
agctatttat tttatcttaa caaacataaa tgtttctaat gcttaaacat ggacatgtat    15600
tattttgtaa aatattatgt attatccaaa gttacatatt taaaggaagt tctattgctt    15660
gctctctttt agcactgccc aaaaaggtta aagtaatttt ttttctctgt ttaaaaaaaa    15720
aatgcattat atacagataa tttttgctag tcaataaagc tatccttatg acttatgagt    15780
gctacttgac tagggatgtg ttgtactcaa ttggaggtat acatacacca agattataga    15840
gcttttattt tgcctataaa aaatggaagc cggataggat accaaaaaag ctttgactta    15900
aatttgtaat gcataaaaat gatgatacct aacttattag ccatacttat ctaagcgtac    15960
gtcaatttaa atattgtgtt attgattaat aatgatcctt atatatccat attttgacaa    16020
ttaaacggta aattagagag aaaagtttga gaaaataatt atagcttacg taatgctata    16080
atccaaagtg tctccgcaca agcgtgggac aaaatagtac tttcggagaa gttacaatca    16140
acagctaggg agtcttcatt gttcttgaat agaaggatgg aaacaaagtt caccttcttt    16200
tattaaagta ttaaggtttg ttattagctc aatatccaat actttctctg cttttttatta   16260 cttcgtctgt ttcaaattaa atgatttttt ttttattta cactattttt aaatttcact    16320
tttaccatca tttatgattt atatgtgaat gaaaacatag ttacgtgtga tcttgttttt    16380
tttttttttt tttgtnnnnn nnnnnnnnnn nnnnnnnnnn nnnnnnnnnn nnnnnnnnnn    16440
nnnnnnnnnn nnnnnnnnnn nnnnnnnnnn nnnnnnnnnn nnnnnnnnnn nnnnnnnnnn    16500
nnnnnnnnnn nnnnnnnnnn nnnnnnnnnn nnnnnnnnnn nnnnnnnnnn nnnnnnnnnn    16560
nnnnnnnnnn nnnnnnnnnn nnnnnnnnnn nnnnnnnnnn nnnnnnnnnn nnnnnnnnnn    16620
```

```
nnnnnnnnnn nnnnnnnnnn nnnnnnnnnn nnnnnnnnnn nnnnnnnnnn nnnnnnnnnn    16680
nnnnnnnnnn nnnnnnnnnn nnnnnnnnnn nnnnnnnnnn nnnnnnnnnn nnnnnnnnnn    16740
nnnnnnnnnn nnnnnnnnnn nnnnnnnnnn nnnnnnnnnn nnnnnnnnnn nnnnnnnnnn    16800
nnnnnnnnnn nnnnnnnnnn nnnnnnnnnn nnnnnnnnnn nnnnnnnnnn nnnnnnnnnn    16860
nnnnnnnnnn nnnnnnnnnn nnnnnnnnnn nnnnnnnnnn nnnnnnnnnn nnnnnnnnnn    16920
nnnnnnnnnn nnnnnnnnnn nnnnnnnnnn nnnnnnnnnn nnnnnnnnnn nnnnnnnnnn    16980
nnnnnnnnnn nnnnnnnnnn nnnnnnnnnn nnnnnnnnnn nnnnnnnnnn nnnnnnnnnn    17040
nnnnnnnnnn nnnnnnnnnn nnnnnnnnnn nnnnnnnnnn nnnnnnnnnn nnnnnnnnnn    17100
nnnnnnnnnn nnnnnnnnnn nnnnnnnnnn nnnnnnnnnn nnnnnnnnnn nnnnnnnnnn    17160
nnnnnnnnnn nnnnnnnnnn nnnnnnnnnn nnnngtacat caaggaaatt tgcattaatg    17220
aaaaacggga gtacaaccta atggtaatac aaccaaacta acagaaaga agaaacaaca     17280 gacagtaaga aaacctctat aacgcgtaaa aacaatttaa cataaacact aactagaaaa    17340
agtccaggcc gaataacatt tgtcttgtgc gatggggagg gaagatgaag gagagtgaaa   17400
atctgttgaa agacacaact ctgacgatct tcatagagag attgtcgtac aactgctagt    17460
agatcctgtc cactaggcac gaaatcccaa ggtccttgat gagcctcctg ggattctcct   17520
gattcgttga acaaagaagt cactttcgag agtaacttcg gaccctgctg cgagggtctt    17580
cgaaaatcag tcacattaga ctgaaacccg aaaaacaagg tggaggtctt gacgtgcccc   17640
aaaacaagtt gggggcgtcc cacaagatgc gttttttagg tgtgatgaca catgatgtca    17700
tcacgagaaa ttggggcgag ttagtttgat gaactacgcc ccactgacgg atcctaagat    17760
ccaaagtgac aatctcgaaa ccagaagacc gacaaacaac agatctgaaa catacaaaca   17820
tgaaaataat gaaagcataa actgccaccc gacatataga gctccggcaa acaacaccat    17880
caagaacttg caccaaagac ttccttggca tactaaagac actgattcca actaacacta    17940 gcggggacg gggaagggac actcgactac acctaaacct aaccagggga cggggaaggg     18000
gaacttagac taaaccttcg taaaagggg gggatcgggg aggggaaaac cttgaccaag    18060
gaagctggtt ttaaaaacca cttagccgag ccaaaaaccg tgggtgggaa gaagaaacag    18120
accacaaaca gggggaaccg ggggatggga actcaccgaa caggggaggg ggagaaatcg    18180
cacagactcg gggaacgcct aaggactggg ggacgaccaa cgaacgaaag gttgggggtgg   18240 tgcgaaaaca agggaggggg acgcaccgac gaacaaaaaa accgacgaag aggccgaaaa    18300
agcgaaaggc cgacggagat aagattgaaa ggcgacgaaa aaagaaaaag gaacaaaacg    18360
aaagaaaaac gaactcgtcg gagacccgcc ggagacctac gcggcgccgg atctccggcg    18420
agttctaggg ttagagggtt tgttgtgttt gtttagggag aaggcagagg ttttttttt   18480 ttacgtgtga tcttgttaga tttgtcttaa catgtattct ttaatatact ttttttttta    18540 taattttgc aaatgcaaaa ttagagatat atgtcctcta aattttacat tcacatacgt    18600
gataaataag agtgctacaa ctaatttgaa acggataaag tatttgaatt gttttcatt    18660 taaaaagtt cgctatcatt tataatgtta tatatttgcc aatatgttat ctctttctct     18720
ctcttaccag agtttagatc cagtagagtt agtaaataat tctaccacgt agagttgaac    18780
aaatcatagc cattgatttt caaatcattg gtttatatat tctttcccaa aactccccc    18840 tattttcccc aaaaatcctc cccctcctta tctctttcca taaaatctga gtcgttgatt    18900
ttaaaatata aggtttggat tcaactccac tatgtagagt tttcatcaaa ctccaccgaa    18960
tccgagcccc tcctaccata gtacttcttg atttcccccat atttcttttcc tcatcttggt   19020
```

```
cctcaagcac attttaatat tatgggtatt aaacaataga gaaagtattt acttatagag    19080
aaagtatttt caatgattcc ctaaatttt ttttgaaaga aagaaaaggg atttcattaa    19140
tatttcgcca aacggcactt acaagtcatt tctgaaaaac ataaaattct aaaagaaata    19200
catatcaccc tagaaatgta aacatcgcag atttgactta attttgcctt aataaaaatc    19260
ttcatctgaa gcaatgcaat ctgtgagttc gctctggttc ggcatacgat ctgcagatgc    19320
ggaaattttg ggatgaacgt actccaatag tcttccataa ttttacagaa gttgtgaaac    19380
cctaattctt catgttgaat ctcgaacttc aaccaatgag aataatttct catacctaaa    19440
aacaaaagaa ccatactcac aactcccata ggggagaagg agatttccaa aacagaaact    19500
aaaaacccca taaagggt tgagaaaatc tcataaagag atactaattt attgaacaaa    19560
acaagaaaat gaactaaaaa ctgaaaataa aagggaaaaa ggggcttacc atggatgaaa    19620
acatccatgg cagcccccta attgatgaag aagggg̅taag ggaggctagg gttttagaga    19680
gagaaaagga gaggggaggc taggttttaa aaaaaaatat aatgattccc taaatttact    19740
tatatatatt taccaagatg acgtgatgtt ttacaaggcc catgattttt acgcgatcat    19800
gaaaaacaca gccaatttga atggagcaaa tatctacgcg tcatttagaa tattttgta    19860 tgggaaagtt ttttttgacc aatgtaatta ttaagaagca tcggccaccg ggtagataag    19920
atgtcactat acatccttt ccaaacttaa gtatgcctgt tgaactttg ttgcgtttgc    19980 agattcattt gaaattatat ttcctcagat cctctacttg taaaagaatg ttccattatt    20040
ttcttagttt acatgatatt tacaatagta tttgtctaca ttttgttcat attacttagt    20100
gatcagtgta tacgtcatat attagtttga actttgaaga catttatttt ctatatactt    20160
cctttgtctg ctaaattact ttggaaagct ttgtttttt tattaatata agaccctttg    20220
gagtttggaa atcactatct aatgaaatat ataattcatc attagaacaa aaatacaaat    20280
atcgtactat cacctatcat gttccttttg gatttcgctt cacaaaaata cattttaaaa    20340
aaaaataaaa taacaaatgg tagctaacaa cttattactt ttaaaagttt gtgtgcaccc    20400
taataagtac tcaaagtagt atgtaacaga gagagtataa tgctaaaata caaactaaat    20460
aaacaagaaa gtgtttctca acaataattt gctgcaggaa ttaggaaaca aagtaaataa    20520
attgcatgtt tatcatcaat acaatttact ggtagttaat tacaaacttc actcatgata    20580
attgaaagag gccactcaat ttcagctagg agttgtttat ttatttattt ttctttcagt    20640
taaattttga ctacccacaa aatcttcatc tggacctaat ctgcaatttg tggattttgg    20700
atgaaatttc taacctattt aagtagtctt attgtttaaa taacccatgc aattaaatta    20760
ggttatatgg gggtgattca tttaccaggc ccaagatttt atctcattct caattattat    20820
cgcaacaccc atgaacctaa gccaacatga cttatttacc aggccagcta gagaagaaca    20880
aggttgctga ttttcttgtc cgtgattgta gaagaaatgt tagaaatcta aatgttgtta    20940
gggatttacc cctcccccct actgagtgta tgaacttatt attgacggat tgttgtaggc    21000
ttccaagcca aaactctgat taagttttct tttatgccat tttaaccaaa aaaaaaaaa    21060 aagctaggaa gctagctcag cgcgctctaa ttatttcaca tgtgacatgt tttcacctta    21120
ttcatacttc tatatgcagg agagggcaat gcaggagcac aataacatcc tgtctaagaa    21180
ggtacttgca cttgaccagt ttgtgtaata ttgtaattta atttcttaga ttttggttgc    21240
atgctttgat gacgaatgac gattgacgaa tacatttta tgcagatcaa ggagagagga    21300
aaaaatctag agcaagtgca acagatgcag tggcagaacc agcaccagca ccagcaccag    21360
```

-continued

```
cagcagccgc caccgccgcc acaaaatcat caagttcctc ctgatgcatc aaatttcatg    21420
ctcccacctc caattccttc tttgaacacg gggtagttac ttcttcaact taatttcctc    21480
tattcaatat taagttaaga aacagatcac gtgattagtt cgttaatatt gctaattaat    21540
aatcatattg ttatatatca tgcattagtg ggtaccaagg acaatttggt ggagaagtaa    21600
ggaggaatga tcttgacctg acgctagaac cgatatactc atgtcacatg ggatgcttta    21660
caacatga                                                            21668

<210> SEQ ID NO 40
<211> LENGTH: 29237
<212> TYPE: DNA
<213> ORGANISM: Artificial Sequence
<220> FEATURE:
<223> OTHER INFORMATION: BvFUL genomic DNA showing  mutagenesis site at
      position 19552
<220> FEATURE:
<221> NAME/KEY: misc_feature
<222> LOCATION: (1029)..(1924)
<223> OTHER INFORMATION: n is a, c, g, or t
<220> FEATURE:
<221> NAME/KEY: mutation
<222> LOCATION: (19552)..(19552)
<223> OTHER INFORMATION: c to t
<220> FEATURE:
<221> NAME/KEY: misc_feature
<222> LOCATION: (20703)..(20722)
<223> OTHER INFORMATION: n is a, c, g, or t

<400> SEQUENCE: 40
atggggagag gtagggttca gctcaaaaga attgaaaaca agatcaaccg tcaagtgacc      60
ttctccaaac gtcggattgg attgttgaag aaagcgcacg agatctccat tctctgcgat     120
gccgatgtag ctctcatcat cttctccact aaaggcaagc tcttcgagta tgcttctgat     180
acctggtatg tctaatttta taacttcttc ttttgtacat caataatttt atcatcgact     240
caactaaaag cttaagcaga tggttagggt tctattatta ttgaattacc tcaaatttgt     300
catcgactca actaaaagta gagtatattt catgtagatc aggtgctttt tttgaatata     360
ttgtcagttt tagaactaca aaatgttgaa cacaagtatt tatacgcacg ctgacatgtg     420 aatttttttaa ttgacaactt tctaaattaa tactctaaat tactaatatg aagaacgtaa    480
tttattattt atcactttca gacaaaggca tgtttgtttt ttctattatt tttcccatga    540
aaattctcac caatatccga ttctgtatgt taattttagt aatttctaat tttgatgact    600
taataaattg taaaaagta taaaataaac aaatatccaa aacatctttg ttttcaagag     660
aaatatctta aaacttttg tttttttaaga gaaatatctt aaaacacttt ttatcatact    720
actatgatga tgtataaatc tattcaaaaa aaaaaaaaaa tgatgatgta taaataattt    780
aaagagttaa gtttattaga aattatagat atttatagag ctgagtaata aaataatact    840
ctacagatta tatgtagctg atgtagtgtg tctgctcctg taagatttcc tttttatctc    900
caaaaaaatt gcattgatat tcgagccttg ccgaccccct tttcctcttc aaccatttga    960
taagatccta tgcactgagt aatctagtat tatatgttag atgttatata ttaataagct   1020
aaaattgtnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnnnn nnnnnnnnnn   1320
```

```
nnnnnnnnnn nnnnnnnnnn nnnnnnnnnn nnnnnnnnnn nnnnnnnnnn nnnnnnnnnn      1380
nnnnnnnnnn nnnnnnnnnn nnnnnnnnnn nnnnnnnnnn nnnnnnnnnn nnnnnnnnnn      1440
nnnnnnnnnn nnnnnnnnnn nnnnnnnnnn nnnnnnnnnn nnnnnnnnnn nnnnnnnnnn      1500
nnnnnnnnnn nnnnnnnnnn nnnnnnnnnn nnnnnnnnnn nnnnnnnnnn nnnnnnnnnn      1560
nnnnnnnnnn nnnnnnnnnn nnnnnnnnnn nnnnnnnnnn nnnnnnnnnn nnnnnnnnnn      1620
nnnnnnnnnn nnnnnnnnnn nnnnnnnnnn nnnnnnnnnn nnnnnnnnnn nnnnnnnnnn      1680
nnnnnnnnnn nnnnnnnnnn nnnnnnnnnn nnnnnnnnnn nnnnnnnnnn nnnnnnnnnn      1740
nnnnnnnnnn nnnnnnnnnn nnnnnnnnnn nnnnnnnnnn nnnnnnnnnn nnnnnnnnnn      1800
nnnnnnnnnn nnnnnnnnnn nnnnnnnnnn nnnnnnnnnn nnnnnnnnnn nnnnnnnnnn      1860
nnnnnnnnnn nnnnnnnnnn nnnnnnnnnn nnnnnnnnnn nnnnnnnnnn nnnnnnnnnn      1920
nnnngatgat attatgtatc attattatca gtcatttatt attgatagat aatgttatta      1980
tttccataga tcatatataa tcttaccata tttactccct atgattatat atttctatct      2040
attaacatag taatagtgat atactaacaa cgagtatctt tcaagtaaat aaatcatata      2100
tatagggtta aaggtaaaa aagacaatat tttatttaca cccttcgtct      2160
cataaactcc tttctatttt tgtgttcac tcgttttcta aagttttttc tacttctttt      2220 acttttatt ggataaatac tttttccgtc tgtatgtgat ctacttatat tagtatttat      2280
agatagatta tactcttaaa gtattacatt cacaaaatca tgtgaattat taattaaagt      2340
aaaattatga gtatggtatt ataacttaaa cgaagtagtt gtattgttta aaccaataag      2400
tataataact tataaaactt aaaagttgat tctacactta tcatgcactt gtgttttgat      2460
gggttaaaaa ttagctagta cataagtaac ataacataaa cttatctctg tatagtatgt      2520
tgaattatta ctttatatt gaaaagaaca aagcacaat aagtccaaaa gatccgatct      2580
tttgattatc aactatgtaa gtgtcttttcc taaatgatca atcaccttaa ttagtatact      2640
aaacaggaca attatgacat ataacacttt tctatttgta caagttaatt aacccattga      2700
cattcattca gttagcctac attttttcaat aggtagtcat catcattctt tttttaacca      2760
atttttttac aataaccatt acctaccaac aacattttca ataatgaac tgaatgatgg      2820 attccgtcaa ggaaattgtt cgtggacagt ttgtttacct cccaaatttc ctttaatctc      2880
atgctttctc catcatccaa acaatctaat accaatcgtt ttctctaatt gcataaaccc      2940
taattgttga atcctttaat cttgccttt cacattgccc aattccttta gtatgatatt      3000
ttttattcga taatccctga taagtaaatt cactaatcta atttcagatg gattgttgta      3060
gagattgggg aattgaagat ttttgccctt ctttgttctt gtttacaatg aaggatgaag      3120
tttcatggaa tattgaagag aaatttgaga aagaaagaa agtgtgggct ttactgacga      3180
caaaaactgt cattttggtg gttttttttca ctaaggcatg tttggcacta gcgtttaagg      3240
tagcggttag cgatttgaca agatcaaaac gctacttaag aaaatgatga gtgtttggta      3300
agatagtggt tgttgtagca ggtagcaatt agagtagatt atgagtagcg gttgtggaat      3360
gttactacaa gtaacgtttg agatttagag gtagcagtcc agcaaagaaa cattgtataa      3420
tagcataagg tagaattaat taaccaatgt ttttttattt cttttttcctt ttattgttta      3480 ttaataattt tattttatgc caattcaatg tttatttac aatagcaaaa atgtaattta      3540
aatatttatt ttaaacataa taaatttta aagtattta gtaaaattgg taatataaat      3600
ttttcgaggg ttgaatattt tcttagatgt atacatttct ttgaatagtt aaaaaatcat      3660
atctcctttt tgtgtaactt ctttgaaaaa taaatcttga atttaactat tgaacgaaca      3720
```

```
tatgaaatta ttgtagttca tttcatatta taataaatgt taggtattgt cttttacaat   3780
ttcaactact tttggcaaac aattctgatt aaacagctat tttaatcgct gatcgttgac   3840
agcaaccgct aacagctact agaaccgcta cttttgccaa acatgcctaa accaagtaat   3900
atcggggatt cttattata taaaaagtta ataatgtgat tatttgaaaa aaaggttgac   3960
tttatatgtt gtttaaagaa aaaaaaacat ttattaatag aaaatatact ataggtct    4020
ctatataccc agggcgaaat gaatgtgtat cttttcaaat gagtatgcgt acatgttctg   4080
taaatgcata tttcatatga gcataatgtt tttactatta ttatgcacat ttgtgtttta   4140
attttttcaaa tgagtatgta aggaaaacat gtattcttgg catgtcagtg ttagtgattt   4200
ttgttgttat ataaatgttt tcgtgatttg tgaatgtggt acaaacattc atgtgccatg   4260
gcgtttagca aaacttttct agctcacatg atgcttcaag ctaattgcaa tgaactaata   4320
taagggagag acattttac gaattagttt tacattgata gtagtttgaa gaagatagtt    4380
taggagatag tttgttggaa tagaagctat gtgttagaat tagttatagt catcaattt    4440
tgaataagac tcattattat ttcaatcctt ctacctttta attactagtc caactctcac   4500
tctttggtat taaattacac cattcctacg gactatctaa caactctaac cacggcccat   4560
acttttctt cttaacataa aataatatta cgcttactaa ctactaactc ctatgacatc     4620
tacctttca ataaaataac aattgataac tatataacaa cttataatct aaaagtaagt    4680
gtcttgataa gtgtagagta ttgtgggacg aagggagtaa ttcatagcaa atactatcat   4740
agcaatacaa tactaggaga ctaagatgtg agttttgaac ttcaaaaaaa aatatacgcg   4800
acatagttca ccggaagaac tgcagcacaa caaatgcaaa tggggattaa atgaggagtt   4860
cacctacatc acacacaaga gcgattgagg attttcagat ctggaagaag agcgaaaaat   4920
caggcgagag cttcaacttt cggagtttaa tggaagagct aatgatgatt gaattattca   4980
gttggattta tcttttgtaa gatgaggga tgaagttgaa gattgccata ataaccttg     5040
agggcgacac aatggtggtg ggaatggaaa tatggaccac gaccgattta tgagtggaaa   5100
gaattgaagt ctctgataca atgacgtttt ggtatatcat cggtgctttc atggctgtca   5160
gatctaccga aaggaaaagt agtggtgaaa acaaatgtcg ttcaaaccaa ccaccttga    5220
ctttcaatat tgaagtgaca aggaaaactg gcaccttagc tagtgacttg gtggagtctt   5280
tgcgtaaacc ggtggaaaag aagcttatct ttgagttta gtgtggtctt ggtgcttgtt   5340
taagtggctt gactattag gaggaaaaaa atcaattgtg aacaattggt gagtaaccta    5400
aaaatcaatt gtgaacaatt ggtgagtaac ctaaaaatca attgtgaaca attggtgagt   5460
aacctttaaa ccagactcaa gagtgggaaa gaggcggtta gacaagtaga tttagaggaa   5520
gaggaggtag aaaatagatt agaattttt ttgggagttt tcaaatgtag tggtatcggc    5580
tcataacaag gtggtcaaat ggatggagag cttggtcgtt tgagtagtct catggtggtg   5640
attataacta cgttggcgat aaacaagttc gctttaccaa gaagttgatt ggtggaagag   5700
agattttcat aaagagggc tcgtatagca acagctttgt gtggtctcag tttcattgtc    5760
ggcaaagccg tggtggtaa atatggtgat tttggagatt gttatgatgg agggagttat   5820
ggtggtttca tgagacatgg atgctatggt ggtgctgtga tcggtggaga agaggagctc   5880
gtgaaaggtc actctgatgg agcgggtgta atggtggtct aggtttttc ggcatcggag     5940
gttgcgtatc tcgtgaaggt tcacatttgt acaccggtga atactatggt ggtgaactag   6000
gatgacagtc aaggtgacca tagtagaaaa aaaaaacata aaccatgtag cttagatgat   6060
```

| | | | | | |
|---|---|---|---|---|---|
| ttgaaaaaaa | atcatgtttt | tggagaagaa | tcttaaatat | tatgacagag | gcaaacttgt | 6120 |
| cattgaccaa | atagatgaca | tagcaattgc | acgtgtctcg | ttaaaatttg | aaaccataaa | 6180 |
| aaattcaaat | tgcacttcat | atgcctttct | tttggttgaa | aacttcatat | accctaatgc | 6240 |
| gtcaatatgg | ttcttttttcc | aaaaaaaaaa | gtaaattatt | tcggcgttag | taaaagcagg | 6300 |
| tccacctcca | taatccattt | tattaagcca | actcctctac | cctactttttg | caacctatca | 6360 |
| tttcttatttt | tctaaaatca | tatcaaaaaa | acaagtgtga | acccaaaact | aactatatta | 6420 |
| tacctaagtc | taatttcttc | atccaatgtg | ttcaaccccca | ttttttcaacc | cttccactca | 6480 |
| taaacccatc | ttcttttcact | cctaaaactt | tcagctcacg | ctcgtatcac | ctctttactc | 6540 |
| acatatcagc | ccaaacgatt | tcttattgaa | tccactaaat | tatgtatatc | gattttttca | 6600 |
| ccaagtactc | cgagttttca | aaaaatttac | ctggtacccc | caagttttca | aactacacgg | 6660 |
| gataccccta | agtttcaaac | taatacactc | agatacccttt | aatgactaac | gacattaatc | 6720 |
| gccgttagtc | attaacctta | atttttctaga | tttcaaccta | attaaccact | aaccctaacc | 6780 |
| ccaaccctaa | ccctaataat | aaccctaaac | ctaaccctaa | ccaccccctcc | ccaaccctcc | 6840 |
| caccacccct | gccccccatc | ctccactcct | gcgcagccag | caggccccccc | acccatttga | 6900 |
| ttttaaggaa | gaaacacgta | tcagggaagg | gggagaactt | agctctgaca | gcggcaacgg | 6960 |
| accaccgacg | agtctggact | gtaggacggc | agcgtcaagg | cgcgagccgg | ttgggctact | 7020 |
| gcagttcaaa | gcaaacaggg | gaggggaatc | gagccgagaa | gagagctaag | gaaagagggg | 7080 |
| tgatgggcgt | tgcggagatg | gtgcgcatag | tggtggtggt | gtgggggagc | tgtggtgggg | 7140 |
| gagaaatcga | atgggtgggg | gagagagggt | gggggggctgc | ggtgggggttg | gggctggagg | 7200 |
| gggtagggtg | ggtgggtgga | gggggtggtgg | ttgggtggta | gtgggacaac | tctcaaacat | 7260 |
| gattctttct | caaacatgat | tctttctcat | atccttttttt | ggatttcctt | aaaaaaatcc | 7320 |
| atatccaaat | aacgttgacc | ggtgagggac | aactcttttaa | cactattctt | tctcaaatct | 7380 |
| tatgaaatct | tcacatttaa | ctcgatctcc | ctttcaatga | acctaaagat | atatattaat | 7440 |
| agagttgcaa | attcctaaac | tctagaaaat | tcaaatacaa | cataagagtc | ctagattctt | 7500 |
| ccacaagatg | tattatatct | ttcaaagttt | cccagataaa | attagtaatt | aggaaactcc | 7560 |
| ttaacaagga | tacttaaagt | tttatctaaa | tcttgcataa | attgaaatcc | aaccataatt | 7620 |
| atgaataaat | aatcataaag | aatcctaaca | taaataacta | gaaaataaga | taataaagaa | 7680 |
| gcaacaaaag | aatctcataa | ccaccatttg | aatcccgcat | gagaacccaa | atagttgttg | 7740 |
| ttccttataa | aaacccacca | cctttcttcg | ggtattatga | cggtattgga | ctatagtatg | 7800 |
| agacgagatc | tcttaatcac | caatcaacta | ttgtaaactt | gtgagcctga | ataatttatt | 7860 |
| tgagatacaa | ttctaaggtt | gtttatgaac | gtgtttggta | aaattgttat | tgataactcg | 7920 |
| ttcgtggaaa | ataaatgcaa | aagtcaacat | gccaaaaaaa | gtgctaaaat | caactttcgg | 7980 |
| ctttgcttga | aatgttaagt | tttaagctat | ccaagagcca | ttagtcaaaa | tctattgaaa | 8040 |
| gcgtactcaa | aaaccattta | tcaaacaccc | ctacaaatcc | ctttagaaaa | cataggagt | 8100 |
| tgtacaatat | aagtattgag | ttataaagtt | gatcaagtga | tttaggaggt | tgttccaaat | 8160 |
| caatctacaa | gagtttgtat | acttatatccc | cttcgttttt | ttaattgtta | cacttaggcc | 8220 |
| ttgtttgaca | aatagagttt | agcggttaga | gtttagattt | tgctgttaga | gttttaactt | 8280 |
| tttgttaaat | agatttgact | gctgatttga | caacttcttc | ttataaatgt | gtttggtaat | 8340 |
| tattaacaga | ttgctaaaag | cttattaccc | tttatttatg | tgaaatgaca | tgtatagaca | 8400 |
| ttttaatcca | catgggtatt | attattatta | ttattcgagg | catacaagtc | attgaatata | 8460 |

```
tttttaccta atcctctaaa gaaaaagctc ctattaggag cttttcatt tcgagagttt    8520 ttattccaga actctcttca aaactctttt ttaccaaaga ataggagctt tttcatttca    8580
agagttttta ctccagaact ctctttaaaa ctctttttta ccaaacaccc cttttagagt    8640
ttttgactag tcaaaactct aaaagtggtc caaatttctc ttttaactcc aaaactctaa    8700
ttgccaaaca cccccttaca cttttcacgc ataccaatgc aacactttga cgattaacat    8760
ctccagtttt ttatttgtaa aaattataaa gagtgcatat taataagtag ggctgttcaa    8820
agtgcggtct ggaccgcacc aaaccgcaac ccaaaccgtt gtttcgcggt ttggtttggt    8880
ttgcggtttt aaaattgcgg tttgggttat gatttcaagc aaaccgcggt ttgcggtttg    8940
ggttgggttt ttatttttgt aaaccaaaac cgcaccgcaa accgcaatgt tacatttttt    9000
ttaaaaaaat aaattaaata catttatgaa ggtgacatac aattataaaa ttgaaaaaag    9060
aagtttgagg taaaaaactt taacacttat gataaatcat tatatatgtt taattatgaa    9120
ttcagcttca tatctatttg gactcttatt aacaattttc ttttaatctt aggaaacaaa    9180
agtaatgtcg cggaggaaat aatggttaaa ccgcaaccca aaccgcacca aaccgttttg    9240
cgcggtttgg gttgggttgg tttgggaaaa agtgcggtgc ggtttgggtt ggaaaatttt    9300
caaaccgtat atttgcggtt tgggttgggt tacatcccaa accgcacaaa cccaaaccgc    9360
gaacacccct attaataaga tacatattaa ttcgaatttg acaagatcca catgactatg    9420
tttttattcg cgtataaacc acaaaagaag gttcaagtaa aatttgtgta tggtgtaaca    9480
tgtcaatcaa agaacggagg taatatttgt caagacactt tagtcacttc taaattccta    9540
taaacaaaga aatatggaag aaaactggtg atgaaaattg aaaaggtggg tataataaga    9600
gagacacaat tctaaaataa gaaaatatta ataataaaat aataagttac gataggcctc    9660
atgtttgaaa acgaaaaaa taaggagata gttcgtgtaa aaaggaggga gtaaagggta    9720
atgcatactt tgtattgcaa gcttagtttt aaaaggcata agacgcaaag cgcatcgagg    9780
cacaagacga aggcgcatgc atctcgtagt tgaggcgtgt aatgatttta cttcacaacc    9840
acctgagcaa cccaatacag aacgaccaca agaaaaatag aaagaaagga atgatttttg    9900
attgatcagc agaaaataca gagcattcga gaggctcagt ctctcccaag gactacaaga    9960
tactactaaa tttcacaccc ccttcagtcc ccttacaccc ttatttatac tacttctgct   10020
ctcctatttt aacggctact gacattctct gagctggcct gctattcctc ttttttgtgct   10080 gacatttctg aatattctgt ggtagtggct ccattctcac atttggacag gtttacccct   10140
ccatttcttt cgtgcatacg tcagccacgg tttggggatt gaattcatta cattaccctg   10200
cccccaaaga ctcaccttgt cctcaaggtg gaaggaaggg aaacgttctt gcaccaaatc   10260
tgcatcttcc cacgtggctt caaaaggtgc taagtccttc catttcagta gcacttcagt   10320
ctgcgtatgc ctccctctct gtgtctgacg tacgtccaat aattcttcag gttccacaac   10380
tagttccaag tctgctgcta gttgagttgg tacagtggtt gctgcctggg catctccaat   10440
tgctcgtttg agctgggata cgtgaaatat aggatgtatt ttactggtgc ctggtaactg   10500
gagtttatag gcgaccttgc ccacctttg cagaacaggg aatgggccat agaagcgggc   10560
tgccagcttc tcaaatggtc gcttggccaa ggattgttga cggtatggct ggagctttaa   10620
gtaaaccaga tcccccactt caaaggactc atcgcgcctt cttgtgtcag cataggcttt   10680
catcttttgc tgggagcgta gtagatgaaa gcgtaaatca tcgaggatgg catcccgttc   10740
ttgcaacact tcctctaagt tatctactgg cgtttgccct ctgcctactc gccacaagtg   10800
```

```
tgtgggtcac gcccgtacaa caccctgaat ggagtcagct tagtagacat gtggggagag    10860
gtgttgtgtg agtattcagc ccaagggagc cactttgccc aagtcttcgg gtgcccgcc    10920
acgaaacatc tcagatatgt ctcaagtcct tgttcacaa tctcagtttg tccatcggtt    10980
tgcgggtgat aggcggtgct tctccttagt gttgtccctt ggagtcgaaa caactctttc    11040
caaaagtac tcagaaaaat tcgatccta tccgaaacga ttgatgccgg aaacccatga     11100
agttttacaa cctccctgat gaaagcttca gccacttgtg agagcactaa aaggatgacg    11160
aagcccaatg aaatgcgcat atttcgataa acggtccacc actactaaga tcgtgtccac    11220
cccccttggac aagggcaatc cttctatgaa atcaagagtg atatcctccc aaacctgagc   11280
tggaatggct aagggctgca gtaggcctgc tggcttttgt tgagagctct tatgctgttg    11340
acaaatgcta catcgctgca cgtacaatgc cacgtgcttc ctcataccta tccaatacca    11400
ctcagccgcc aacctaaggt acgttttttac ttcacctgca tgtcctcctt ctggggaatc   11460
atggtaagct atcatcaact taggaatgat gacggaagtg ttgggaatta ccattcgccc    11520
cttataccgc agcttgccat cctccaccgt gaaccccaca agtggtttat ctccctgcgc    11580
cacttcttcc ctgagccttt taaggaacca atcctcctct acctcttttt ggagctctgc    11640
ccagtccact ccttgggttg tgattatggt ccctagctcc atttcaccta cagttttttct   11700
agaaagcgca tccgcaacct tgttggttgc ccccggtttg tagtgtattt caaagtcaaa    11760
cccaattaat ttgcttaccc atttctgaaa atcagccccc acttcccgtt gttgtgtgat    11820
gaaacgcaaa ctttgttgat ccgtatggat cacaaatctt ctccccaaaa ggtaatgttt    11880
ccatttctgg accgcaaggc atatggcaat taattcctt tcataaacgg acttgtgttg     11940
tgctctcggt ccaaggagct tgctgtagaa tgcaatgggc ctgccctctt gcattaggac    12000
tgcccccacc ccatacccag acgcatccgt ctcaactacg aaaggcttat ggaaatcggg    12060
catagcaaga accggtggct gggtcatagc ttccttttaag tgagagaaag ctgaagtagc   12120
ttttctggac cagccaaagg agtccttacg caattgctcg gtaaggggct gggcaatttg    12180
cgcgtattgc ctgataaact tgcgataata cccggtcagc cctaaaaatc ctcgaagctc    12240
cctcaaattc ttgggaactt cccactccac catggcccctt atcttctcca tgtctactgc   12300
caccccatgc tgcgaaattt acatgcccca gtaggccac tgtcttcctc cccaagtcac     12360
atttcttctg gttagcgaac agtttgtgca atgctaacag ctgcaacacc aatcccatgt    12420
gtcgtgcgtg gtcctctttg gtcttactgt agaccagaat gtcgtcgaag aagaccagca    12480
caaacttcct cagatatgga cggaaaacgt tattcatgag tgactgaaaa gttgctgggg    12540
cattggtgag cccaaagggc attacgagaa attcgtaatg tccttcatgg gtgcgaaaag    12600
cagtcttatg ggtatcctcc gggcgaacta aaatttgatg gtatccggcc ttaaggtcga    12660
gtttagagaa gatggtagcg ccatgtaact cgtctagtag ctcatcaatg accggtatcg    12720
gatacttatc cggaaccgtc tccttgttca agcccgata atcgacacaa aacctccaag    12780
aaccatcttt tttcttcacc aataatacgg ggcttgaaaa tggactagtt gagggcttga    12840
tgatgcctgc ctccagcatc tctcggatga gtctctcgat ttcgtctttt tgaaattgag    12900
ggtaacggta tggcctaacc cccaccggat tactgccttc cttcaacgtg attgcatgct    12960
catgccccct ctttggtggc aggcccaccg gagtatcaaa aacttccgca aactgactaa    13020
ttaccttctg taaaaattcg ggtacttctt gtgcctcctt caactccgct tctcccttt    13080
tcccatcatc ctcaatctgg ttgagctcca agagaaaacc cccttttttct tttcggattg   13140
cctttatcat ggctctaagt gagatttag atcttgctaa ggaagggtcc cctctcaatg    13200
```

```
tcaccactct gccctccact tcaaactgca taacctgagt tttccagttg gtaatcactg    13260
accccaattt ctcgagccac tgcactccta atattaaatc tgagttaccc aggccgagag    13320
gtaaaaaatc ctctgttact tcgatttccc ccagctttaa agtcacccct tgacacaccc    13380
cagtaccatg gacagcttca ccattcccta aagacactcc aaatcccccct gcatctgaga   13440 tgaccaactc aagttcctca acagttaaca aggaaataaa attgtgagtg gcacccgggt    13500
caatcatgac caccacctct cttcctttaa tttttctagt gattttcatc gttttaggac    13560
tcatcaaacc aatcacagag ttgagagata cctcagtagg aagttccggt ggtggttcgg    13620
acggtggtgc acgagctgcg tcgctcacct cttcggtttc ttcctcctcg tcatgcatca    13680
gaatcacgct gatctctttt ctccggcaga tgtggccggc ggtccactta tcgtcacatt    13740
tatagcacaa ccctttgct ctcttctctt gatattcttt ctcggaaagt cgcttgaact     13800
ctacagattt ttttccttgc cccccagcaa ttggatacgt gttcaaggtg ttggaatttc    13860
cccctgggtt ttgggcccac attttgctgg caggtgggtt gaggctggtc gttggattga    13920
aggaagcccc tacactcctt gtcattcccc ctctgttata aatcgagtaa ggcccattct    13980
tagttggccc acttcttta taacccacaa tcctattcct ttcctcaatt cggcctgcta     14040
gttccattgc ttgctctagg tccataggat tgagtaacct gacctccact ttgatatcct    14100
cttccagccc attaatgaac tgacccatga gtatttcttc tggtactcta ctcaacggtg    14160
ccgccttctc aataaaagtg cgtcgatact catccaccgt ggtggtttgc tttgtggcca    14220
accaccgttc ccacaatgaa ccatagtggg ttggtcgaaa ctgacggagg aggtactcct    14280
tcagatctgc ccaccacctt atcggccgcc ttttattctc ccactggtac cacctgaggg    14340
catccccctc tatagacaca accgccgcct ccagggcttc actgctactc aggccataaa    14400
acgaaaaata tcgctcggct ctaaggatcc acccatccgg atcggaccca tggaaaatgg    14460
gcatctctaa ctttcgatat ttccagttcc ccccggaagt cgaacctcct ggccctccac    14520
ctgagccgcc atccccatac gatcggcccc cgagctggaa acctccatat tcgtcccctt    14580
ctcggccccc cagatttatc aggtcaggag ccctccgttc cggcggtcgg gggtgtccag    14640
tgacggtttc gggtgtctcc cgcgagggtt gtggcaaggt tgctcggatt tcaacctgaa    14700
atttcctctg ttcagcacgc aaccccttgaa tcgtcccatc ctgtgtctcc cttgaccggt   14760
taatccggtc ctccagccta acggccaaga cctccatctc ctcgcgactc ttcctcgccg    14820
cctcattctg gccttccaag atttgagcgg tcaacgattc ccccatggca ttaatggcag    14880
attccaccgc cctggacacc atggtggcca ctgacccttc gagggctgcc attctttctt    14940
ctaatgaatc caccctctgc acttcgtttc ttggtgccat ggatcgatgc tctgatacca    15000
agtgtaatga ttttacttac ttcacaacca cctgagcaac ccaatacaga acgaccacaa    15060
gaaaaataga aagaaaggaa atgattttga ttgatcagca gaaaatacag agcattcgag    15120
aggctcagtc tctcccaagg actacaagat actactaaat ttcacacccc cttcagtccc    15180
cttacaccct tatttatact acttctgctc tcctatttta acggctactg acattctctg    15240
agctggcctg ctattcctct ttttgtgctg acatttctga atattctgtg gtagtggctc    15300
cattctcaca tttggacagg tttacccctc catttcttc gtgcatacgt cagccacggt     15360
ttggggattg aattcattac aaggcgcacc tttggtacca agagacttag acatcaaata    15420
aagaagcatt gtaatactta gaataaacat tgtttttata ttctaaaaca catattttct    15480
ctaagacacc tagtaatctc atagtggatg tcatctagtt taggtggtaa ggttttattg    15540
```

```
agttggtact caagacctca gacttagagg tggcaaacgg atcatacggg tcgggtgaaa   15600
atgagtcggg tcataatcgg gtcacctttg tgtccaggtt acggtcaggt cgagttcgtt   15660
cgggtacgag ttcatattga gtccatgagg tttcatgtca tatcgggtcg ggttagattg   15720
gatttacaat ttcgcaaata aataaaacgc atataatact aaagagagta aattaaataa   15780
ttaacggaca ctagctaaat catatattag tattttatga tgtattttcc ttaaatttat   15840
ttaaaaaata actaatatga caattttcg ggccgggttc gggttgtggt catcattatc   15900
gggtcaattt agtatcgggt aggctcgggt tcatgtcata ttcgggtcta ttttaattcg   15960
agtcgggtta tttcggattt aagctctatt tcgggtcagt attttcgatg aagaacgggt   16020
ttcggatcgg gtcaccggat acggatctat tttgccgagt cagactgctt ttcaaaccta   16080
ataatctcag tttttccacc tattcagatt tgcctatgat ctctatttag ataaatgagt   16140
acaatattgt gtctatccat gaaaatgaat atctcacaat gtaaaaggat atctctaaat   16200
ttcactaatc actctatctg ttttgaataa taatattcta ttttattgca tgtagtaaag   16260
atcgagtatt tagtgagatt tggagaaaag aggaggctag agagaaacta ggatttagag   16320
aggagaaggg ggctctgtaa cacatacaag atagatactc ttttacacta acttttcaag   16380
atactcaaca tataaaatca gcatcatctt ccaaacaaca actttaagcc acccatgaat   16440
cttaattaga taataaaaca taatcgtgaa tcatctatcc tttgtttggg gggatcctaa   16500
agcaattgag gaaaagcttt gatgcaaata tcaattgtgt aaaaaagcaa gtattcgttc   16560
gtgatgttgc tatactaggt tattttttgg atccaaaagt cattcctact agaatcattt   16620
aggaaaattg tcagtatgaa ttttaaattc aggttataac caaagataat tgaaaattgt   16680
caaacttttc aaataattcc gaaataaaca tgtttgtaac atggataaac ttttcattgc   16740
ttttcaaata attccaaaat aaacatgtta taacatagat aacctttca gataattcca   16800 aaataaacat gttgtatcat ggataaactt tcattgttt ctagtcactt aaaattctaa   16860
aaaaatcttt cctccctact gttactctct ctagcaccaa atctatcaca tgagaaggca   16920
gaggttttca aaataaaccg ttacttaatt tggtacttat ttcttgatcg gtgttcatat   16980
catatgagtt cctactctat atctctctac tcttctaaat ccttgtgtca cttcctgtgt   17040
ttcataaata aaaaggagga agtattagtt ttgaaacgaa aggagtatgg tgcatacatt   17100
gatagaaaaa agaagttatt tgtccttatt tcactcatat aacaacacca aattctgtat   17160
tgttatcaca aaataaaact tggattatct ttgtttcata gcccaaattt agaattagtt   17220
tgtcagattt ccaatcatct aattacaata ttagagctag acctaggaca aaaggtgggt   17280
ttggctactt ggtaatagct atgtctagtg ctaggatatg tcattgtcgt agaaccatgt   17340
tatggacatc ttaagaaaca aggttaacct aattggttgg agatcctact ttcacttta   17400 taataaagtt tcgattcttg cctatttgta aagtagaatt cctaaatttc ccttcactga   17460
tatttatctt aacataaaaa aatgttataa acattgggat tgtatataag tcaaaataaa   17520
ttgacaatct tggtaacaac taagttaaca ttaattttat aagtaaatga ttaatcccaa   17580
tataatctct tatttagtaa atgagacaaa cttgtacacc ttcgtgttag actcgttaat   17640
gttcgctaac aattcattca gtagtcaaca gcattttaaa tttgaaataa gtgttcttgt   17700 ggttttgag agatcaagca agaaaacatg tctctcccct ttgaccaact aattgggatt   17760
aagaatacta gttttaagat tttaagaatg agttatagtc tttcttagac cgctacaatc   17820
cccttgttga tatgaaccag atatattttg tgttcaaata gtagatcaat gcattgttga   17880
taatcctttg ttaatgtact tgttgatctt attttgtact tttggtagat gcgctatact   17940
```

```
ttctttcgat tgctcatttt gaactcttaa ctacatatgt tagtttaagt agatgattta   18000
gaattgctat ttcaatcttc aataagcaat ttaagttgtc aaaccttgtt tcacatcatt   18060
agggtgaaag ttatttggat aaagacctat atctaattca atccaaagca aattagtaat   18120
gcggattgga ctcaaactat gtttagattg gattcgaatt gagtttcttt tcttttttctt  18180 aaaaaaattg gattttccga tcgaattgag ggtgattaga tccaaaataa ccgaatagta   18240
gataggattt gtgttgtata ttagaattgg gcttaaggat ttccatttta acaaaaaaac   18300
caaatggtcc gactatcaaa aactataatt tgatagtcat gcctatcgaa aactttatt    18360 tcattctcgc acctaattat gggcttgtat aaattagttc tactatcgaa aactaatttt   18420
gatgctcgtg cctaatttaa attttcgaaa aaatgaagtt aagaaaattg gatatttcgg   18480
attggatcca atatatcttg tgaattatta atttggatta gtttggactc aaattcttat   18540
tggattggat tcaaattaaa agattaaaat tcaaattttg ttcgaatcaa attggagtag   18600
gcttaagttt aaatcataca ccgaactttc accactaccc atcatgctta agcttctaat   18660
gtaagagagt gtttgggagt tgagctcgaa caactaaatt tctaaaagaa ccaagttcaa   18720
acaagaaatc taaaagctcg attaaacttg agtcaagctc aaacacctat attccttatt   18780
ggagcttgac tgaagattga acacttattc cttattaagc tttacgctaa aacattgctc   18840
gactcaactc ttctacatcc ctatagttca aaagaaatag ttgtgggctg tggtgctctt   18900
gtagaccaac gcactagttt aacaaagcta agtgcctgac tgcaattcca tacacattac   18960
gatcaccatg acctagtttc agctcacact ttggaagtct aatttgaact tgttctctac   19020
ctccaattca ttgtggggta ggaggcgata gttaagggat caaaatctta tgatataact   19080
tgcataggct atgccactat ataatgcgtc ttgtgtccca ttagtttta atcaaattga    19140 aatgttttac catttatatc ttcaattatg tatggatact aatatttgat ttgacgtttg   19200
atatgatatt aaatgtggac tgttattctt gatgtgcttg agaagctttt ttggggccag   19260
ttagaaacta tattccttt atggtcctaa ctaggttgtt gttggtgtgt tcccaaataa    19320
cagcatggaa aggatactcg agcgctatga aagacactca tatgcagaga gacaactgac   19380
tgctccagat cctggatccc atgtaatcca gctaggcaac tatcttttct aagcatttaa   19440
atcgttgaga tttcaatttt aaatgtgttt taactgataa ttcatgcatt atatgcttag   19500
gtaagtttga ctctggaaca cgcaaaactt aaggctaggc tggacattct ttagaaaaat   19560
caaaggtaat aagatccaga ccaaatataa tttgtataat aaccaccttcatgaggaaaat  19620 ttaagatcct tgataatttc aggcattaca tgggagaaga acttgatacc ttgagtctca   19680
aggagcttca gaatttagag catcaaattg acagtgctct taaacacatc aggtcaaaga   19740
aggtagtttc acagttgcat tagatcatct tatggatcaa ttggatcact tgtttgtatt   19800
ttagcgttgc tcaacacggt cgtctaatat agtgtgcaaa acgacctaca gggcaacacc   19860
ttttataggg ctcgaaaata cgaaaaatta atgtttgtt ttagtcatat tgttcaaacc    19920
caagctttat cttgtcaaaa atattttata atgattattt tttagaatac attatttaca   19980
tttttgcaat ttatgcataa tacttctaag gtccaacttt ataattgaaa tagaagtcct   20040 taaatttaa agacgacctt gaggaaacct aatttcttct catatataat taaatcaatt    20100
attctacaag ttagtagaac aaatactaca ataacaacaa tattgaagcc ctaatctcag   20160
taggattgga ttgattgtat gaagtcttat tagtggccgt taaatgtttc ttgtaggtca   20220
agatgacatg gctcatatag taaggttact tgactaaaag acgaggattt gtttcgactt   20280
```

```
agattttaac aagtttccct catttgttaa cacctaagcg tactaaatca aattctaggt    20340
tttactcact caaatttccg atttaggaag ggcttgagga tagttgtatt atcgtaactg    20400
actaatcaaa ggagcctctc ttagatcagg tttcacttgc caattctaac aacttgtttg    20460
gtaaaaggaa tttggaatga aaagaaagga attgaaaaga acattctac ttttcaatgt     20520 ttcattcaaa ataacatttt aagtgatag gaaatggaaa gaagtgaaac gaaagcctct     20580
ttacaaaatt atcatttttc tacccccccc ccccccccaaa aaaaaaaaaa aaaataagta   20640
gtaagtagta gaagaagaaa taataacta acaagagtag taagttttta cgttttcttt    20700
ctnnnnnnnn nnnnnnnnnn nnattcaaat cagaactgaa tagtcataac cggaagatta    20760
gtttctctct agcgtgacta gggtttgagt aaaaagagaa aacttaaatc aaacatggga    20820
tattaaggtt tttttttcctt tcttcagttc ttttctcttc ccaatccttt cctaaaaatg   20880
aaccaaacag gctgcaaggt tttcacttgc ttaacacaag atttattttt aaaaataatt    20940
acactccaaa cttttaagct taaaccaat tttaattcaa atcagaactg aatagtcata     21000 actgaagat tagtttctct ctagcgtgac tagggtttga gtgaaaaagt ctagggtttc    21060
atgtcattct tcttgcttcg agtcccttct tgggattgtt gttagccatt atggctaccg    21120
aaatcgttat taaatgtcta aatcttagaa ttactgctga agaaaacaac ttggtgtttc    21180
tcgaagatgt tgatgataac tcgcagcacc atacgctcgc actggcgatt gttggaaagg    21240
ttctttcgtc aagaccatac aatttcgagg cacttaaatg aaccttaaac tagatatggg    21300
tgatatccaa aggagcccta cttcacccta ttgaaaacgg acttttttgtg gtacaatttg    21360 cgacaattaa ggaccgatct aaggttctag tcagcagacc atggaccttc gatataaacc    21420
ttgttctctt agatgctatt gaaggggta ctcaatcttg acccattgcc cgttttggac     21480
tcgcttgtat aaccttccta tggactgccg atatgagaag ttcatcaaaa actattgttg    21540
gtgtattggg ggaggtattg gaagttgatt ttgacaggat tgtttgggat aaatctgcaa    21600
gagtaaaggt gaagattgac attacaaaat cgttttgtcg tgtgcagatg atcaagacta    21660 acagggtga ggctgtgatg atcaatgtta agtatgaaag acttcctaca atttgttatg     21720
tgtggaattc tggccatatt gaaagagatt gtgtgaagac ccaggaagaa gagaaacaag    21780
tggagagaca atagggggtc ttggaggcct ctccgcgtag gggacgatta aagatggtga    21840
aagagtcgaa agccttcctt cagtgtgctc gtacactcca cttaataac aaggaagaag     21900 taagggtga ggaaccacgg gattatgtgg agccgagggg ttattgtcgg ctatcttagg     21960
gggtaaaact ttggtggtcc aggagatagt ggacggctct aaggatgcca tcgaggaagt    22020
tcgtgctgaa ggtgcaccac tctagccccc ttgtaccctt tgggtaatgc catgctacct    22080
tttacttttg ctgttgggag tgctaatcct actccctccc accgaaaagt taaaattaaa    22140
aacaaggcaa gggttcaggg tgttttgaac caagttaatg ttgtgggtgt tgggggggttg    22200 gctaataatg ggggttgtga gaaaaggata ttccccaacc cgatggtgtt agaaaaagaa    22260 aagggggttca atgaagaggg tttaagatag caaaacgaga ggattgtatg taacctatca    22320
gtagggaggt aactattgag gtggaggtgg gcgagaccca ccccgcccg acattatgaa     22380 tatcctatgt tgcaactgtt ggggattggg caaccccgg gaagttcgga tgcttcgtag     22440
gtggagcaat agtgctacac tgagttcggt ttttatttct aaaactatga ttagtggtcg    22500
tgatgtggaa agggtgcaaa gcgggtaggg ttttgattgg gcaattgggg tggatagcgt    22560
tggaacttca agagtttggt gcatttattg gaaagctggg gaagtggact ttactctagt    22620
ctctctatca agtcatcata tttgtgggaa tgtgaagctt gttgatggga aggtatgatg    22680
```

```
cttagtgagt atttatggtt gggcggatac aattcaaaag tataaaacat gggagcttat    22740
gcaatccttt cactcatatc atgggccgat attgtttggt tgggacttca atgagatttt    22800
gacaatcgga gaaattgaag gagggtccga aactcaatga agtaacatgc ataattttct    22860
agaaacttta gatgacatga agcttaggga ccttggctat tcgggaactt ggtatacata    22920
agagagaggc tttaagccac ggaagagaat gagggagaaa cttgatcatt tgttgcatc     22980 ttcatcatgg tgtgacttct ttccgaaagc tacagttgag cacttgatgc gctacaaatc    23040
ggaccacact cctattttgg ttcgccttgt aggccatcag tgaagacata agaagaaaaa    23100
gacgtagttt tgttttgaga ctgcttgggt gcttgaggaa ggttgtgagg cccaatgggt    23160
gagtcatggg ccgggtttac tcgcgaggta tttatcgagc gctttaaagc cgtggaaggt    23220
gggttcaaag caaggagtga tgggtctctt agtaatctgg gcccgcgtgt gagggagatt    23280
gaggaggcca ttatagatgg gaggcagcga agcagataag gactatgagg ctctatgaga    23340
ctcctctccc acgaaagtta gacgaggtgt tggacaagca ggagcgtttt tggtttttga    23400
ggtctcgtgt gagttagata aaggatggtg atcgtaatac acaatatttc caccacaaag    23460
cttcccaaca caaacgtcgc aactacatag cggggatgta tgataataaa ggggtgtggc    23520
aagataacga agaggatatt gaagggaata tttcagagta ttaccaaacc tcgttcggtt    23580
cgtgctcccc ctctaggaag aacgtcgcgg ttgtccttga ggttgtgagc ccggtgataa    23640
ctgatgatat gaatatggcg gttatgaaat cttacactaa agatgaggtg tgggaagcac    23700
taaaccacat gaagcctaac ggaatgcatg ccatcccttta tagaggttct ggaatacctt   23760
ggagatgata ttacatctgt catttttaggt attattcatg gcacccgacc ccagatgttt   23820
ttaacaagac taatattgtg ctcattccta aagtcaaatc cccaaatctt gtttctgagt    23880
ttcgcccgat tagcctctgt gatgttatct ataaacttgc ctcaaaagta cttgctaaca    23940
gattaaaaca ggtttgcctg acattgttta tgataaccag agtgcatttg tgtccggaag    24000
ctatattacg aacaatgctt tgatttctct tgaattattt gactctatga aaaaatgata    24060
cagagctagg aaaggttttg tgtcgatgaa attggatatg agtaaagcct ataaaagagt    24120
tgagtggtgt tttttcagta gtgtgttgga gaagttggat tttgctgaat catgagtgaa    24180
tgttgttatg agatgtgtgt cttttgtgca gtactcttt gtggttaatg ataatatatg      24240
tggagctctg acaccctcaa gggggctttg acagggagac cctatatccc cgtatttgtt   24300
tatacttgtt gcagataccg tttagctct tcttagcaag gcattcaaca atgcgtggct     24360
atacttgata ttctcaacaa atatgaggca gcatcaggct agaaaataaa tattgacaag    24420
tcaggaatct ctttcaataa aagatttgac gtatttatg gccatgaaac aagttgagaa     24480
gcatcagaaa gacttggtat cccaactttg gctaggagtt cgaaaaagt catatttgct     24540 gacattcaag agcgaatttg gaagaagctg cacggatgga gagaaaaact tctcgcgggc    24600
ttgaaaagaa actctcttaa aagttgtggt tcaagcaatt ctaacctatt tggtgggcgt    24660
ttacagattc ctaaccagta ttatccaggc cattcatttg gccatggtaa agttttggtg    24720
ggggtcgaaa agggcccaca attcgatgca tctgggggga tatgtgctca ccaaaatgtt   24780
taaggagcct tagctttaaa gacttagggg tgttcaatga acctaaacta aggaggaatg    24840
cgtggcattt gattcctgct ggtgagtccc tttcgggtcg agtgttctcg gccaagtact    24900
attcgaagtc aaccttttg gactcatttc taggtccggt aggtagcttc tcttggaaga     24960
gtatttgggg ggccaaggca ttagttaagg gtgttttatg gtgcgtaggc aatggcagac    25020
```

```
aaatcaacat atggcgtgac tcgcgggtgt tgaatggtga tagtaggttc atccccggag    25080
agcgcgtttc aggccttgag gatgtttgtg atctaataga ttttgcacaa tggagtgcga    25140
tgtggacctt gtcacgattg cttcaatgaa gatgatgctc aagccatttt agtcatacct    25200
ctaagtaagc gccttctgaa ggacatggtc tcttgggctt tcactaagga tgaattttt     25260 ttgtaaaaac aacctatatg gccggttggt cgaggaattt gaatttgttt cacaaagcat    25320
ggctgcaaat ctggggcctt aacgtgtctc gaaggtctg ccacttcctt tggcgtttat     25380
gctcggtacc cttcctgttc gagctctttt aaaacgacgc cacataactg atgatgattc    25440
atgtcctttg tctaaaggag cccggaaagc atatcacacg cgttgttcta ttgcccatat    25500
gtagccgaag catgggagag tgcgggcctc acaaattgtt tgcctttgtt tgatgggct     25560 ggtatgcttg atgcgtgggg ggagtgggaa acaatcgatg actagtccct tgtaagactt    25620
agcttcttgg cttatcactt gtggtttagg cgaaataaat gtgttttga  aggggtggtg    25680 agagcgaatg agagtgttgt ggaatatgcc actaaagcta ctgttgatca tggtttgtat    25740
agtgcccgca tttatggtgg gtcgaaggct accgcatcca aaagctcgaa ggtatgggtt    25800 cccctccag cttgtcgtac gatctaaagg ttgatgcatc agtggggaat ggtggatggg     25860
tggggctagg agtaatcgcc tgaaactaga aggggaggt gctcgtggct gcaactagga     25920
gggtcagagc ttgtggcccg tggaaatggc tgaaggaag gctctttgtc ttgctcttag     25980
gcttgcctcg ctcatacaac ttgcaagaag tgatcgtgga gtttgactgt caatcttggt    26040
gaaccatctc tccaagggtg ctatttactt tgcatttta agtcaaagct tgaaccttga     26100 taaaaaatc ccgttcgaca tgaaaagtgc cttgattttg cgggtttggg agtgccttat     26160
tgattctggg gtttgattttg taacacccttt agtaaaaaca tgtaagctaa ctgtaaaacg    26220
aacattaatc aaactaggat atgtaaaatt cctaaatcaa gaagaatttc cacttgtgct    26280
gaatttgtcc accttgcatg acacccaata aaagcccatg tctcctagaa ccccttatgc    26340
cgccttattc atcttttctc aagttgagtt ggagtcctct atggtccact cgacttcttt    26400
agcacactct cggtaaaaac ttttaatatt attttatttt agactccacc atcttgacat    26460
ttattccttc ttaaacttgc ttcacacaaa catctaacac tagaattcta tatagaatag    26520
cttgaatctc tcttaggata accttatagt aaatgcaact acgccatcc ttaaaccttt     26580 ctaagaggag ctttatcgta tttacattcg cttcactttg aaacgtcgct aagtgtatgt    26640
tgcactttcc aaaccatgtg ttagctaaga ccaagttata tgactgcata acctaaatag    26700
tcttcctcga gaaattcac tagttggatc ggaagagttt gtgtaaatct atggcggcgc     26760
gggactgggc cttcacgatt tcaagtgttt taatgcagct cttctaggta aacaagtttc    26820
ctaatagcgt ggtgactcaa atattgagga cttgttgtta tactaatgct attcctggcg    26880
gcacttaagg ggtgaaatag gtggtacaaa ggagtgcttg atggcgtgtg ggtagtagtt    26940
gaatatatca gtatgatcaa gtccatggat ccctcgtact tattcgtgca agattatttt    27000
tccacgaggc aaagcgagcg agaatcttaa ggtttatgat catattcatc ttgtacgtgc    27060
taagggtaat gtccctttca ataatgagct atttctcctt ttgagcaaga gcgtatctta    27120
agcattcctc gtagttctcg tctcccaac gatgttttat gttggaatct gaatttggag     27180
aaagacggag acttttcgtt cggtctatcg agccattctt ttgagttgga tggcgagagc    27240
gtgatttcat cgtcaatacg ctctaattta tggagtataa tatggcagga tagtaccttt    27300
caacgtgtta agcttttatc tgcattgtcg acacaaaggg gattgagtaa gcctgtgccg    27360
agtatggaac cattgtgtaa tctttatgcg ttggaggatc aatggagcta cacttcttac    27420
```

```
gagactttgt tattggaagg gcttatatgg gatccaacta gggtagtcaa aacattggtc    27480
ggggctgcgc tgcaattttg gggacttggc accggcgttt ttggagtagc tccctcatgt    27540
ggaacatagg cttttgatga cgatatacta ggctagatgg aatataagag agaggtgttt    27600
gtttgaggag gaggtttgtg atccctatca aaccacatgc ataatctcat ggcgtagctt    27660
catgtggaac actgacatat tgcatgtgta gggttaggtg cttgcctagg acaccacatg    27720
ggaagagctc cgttaagctt aatgtggatg gagggtgtgt ggaagggttg ggtgcgtcca    27780
ctggagtggt gattagggggg atggatgaaa aagcgttgta gttgcaacat agaaaggtgg    27840
aggactgcga ggaaccgtta aaaaggctat atttttatggt gttcatttgg ttgtggaagt    27900 cgattttttga aatatggttg ttggaagtga ctatcttcac ctcgttgaag caacttcttc    27960
aaaagtggaa ggcaaaaata gcttccatgt tattgttgat gacattgttc atggtagtga    28020
tatgttaaat acttcgtctt gtagttttgt tcgtagggat gggaataggg tttctcacga    28080
actcccccat ggaaatatca taatggctca tgctcatagg taaatgaata agctaacaaa    28140
attgttcatc tttgcagaac caactcatgc atgaatcgat ttctcagctt cagcgaaagg    28200
tagacagctc tagagagagc atctagtctc aaaaatacca tgagattctg tagtgtcctg    28260
acatgtttta tatgacagga caaagcgtta aaggagcaca acaacttgct atccaagaag    28320
gtataagttc agcaagattg tttagtaaca ttgttaatct tgctgattgc tttgaaacat    28380
gtcttgctat ggttaacaat gttgactgaa ccaaaatagg tgaaggagag ggagaaggtg    28440
ctggctcagc aggcagaatt ggatcagcaa aatcatgaca ataactcatc tggctttgtg    28500
atgtctcaag ctttgccctc actgaataca gggtcagtcc tcaataacct ctaatcattt    28560
ttccaagatc caaagtaaac atggtttcat aatttaatta agatttttt gaaccatgtc    28620 tccatacaac cttactagga ctaatactac taatttaaga ccccaacgat aaacaacaat    28680
aattagccat atctggctag cacctttttgg acaacacacc acatgagact cttggccaac    28740
ttctttgatt tccttcagtc tgatagatat gaatatcttc tgaagagctc tttggttcat    28800
aattattgat ttagaaaaga attcagcaag gtgagtcatt tggtaacctt aaggtcatta    28860
tgggggtact aaatcaaagt gaagatatat ttaggtggca tcagaagaga tgatatagat    28920
aggttgtatc ctgtcgatag gttatttgga tatgtatcaa aagtttcttt tataatatat    28980
ctatactgat tggttgatgt atcaaatatc cctacagatt gtgaaaaaat ccctacaga    29040 ttgtgaaaat atccctagaa cctgtgatga tataagatgt gctccgcatg ctttattgaa    29100
cataatgtat tcaattcttg aaatgcagag gaacaagcag cagtgcagtg gaagatgaag    29160
caacacaacc accaaatcta aacagcaact ctgcacaaat accgtcctgg atgcttcaac    29220
acatccaaga gcagtaa                                                    29237
```

<210> SEQ ID NO 41
<211> LENGTH: 256
<212> TYPE: PRT
<213> ORGANISM: Arabidopsis thaliana

<400> SEQUENCE: 41

Met Gly Arg Gly Arg Val Gln Leu Lys Arg Ile Glu Asn Lys Ile Asn
1               5                   10                  15

Arg Gln Val Thr Phe Ser Lys Arg Arg Ala Gly Leu Leu Lys Lys Ala
            20                  25                  30

His Glu Ile Ser Val Leu Cys Asp Ala Glu Val Ala Leu Val Val Phe
        35                  40                  45

```
Ser His Lys Gly Lys Leu Phe Glu Tyr Ser Thr Asp Ser Cys Met Glu
         50                  55                  60

Lys Ile Leu Glu Arg Tyr Glu Arg Tyr Ser Tyr Ala Glu Arg Gln Leu
 65                  70                  75                  80

Ile Ala Pro Glu Ser Asp Val Asn Thr Asn Trp Ser Met Glu Tyr Asn
                 85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Thr Arg Lys Asn
130                 135                 140

Gln Leu Met Tyr Glu Ser Ile Asn Glu Leu Gln Lys Lys Glu Lys Ala
145                 150                 155                 160

Ile Gln Glu Gln Asn Ser Met Leu Ser Lys Gln Ile Lys Glu Arg Glu
                165                 170                 175

Lys Ile Leu Arg Ala Gln Glu Gln Trp Asp Gln Asn Gln Gly
            180                 185                 190

His Asn Met Pro Pro Leu Pro Pro Gln His Gln Ile Gln His
        195                 200                 205

Pro Tyr Met Leu Ser His Gln Pro Ser Pro Phe Leu Asn Met Gly Gly
210                 215                 220

Leu Tyr Gln Glu Asp Asp Pro Met Ala Met Arg Arg Asn Asp Leu Glu
225                 230                 235                 240

Leu Thr Leu Glu Pro Val Tyr Asn Cys Asn Leu Gly Cys Phe Ala Ala
                245                 250                 255

<210> SEQ ID NO 42
<211> LENGTH: 242
<212> TYPE: PRT
<213> ORGANISM: Arabidopsis thaliana

<400> SEQUENCE: 42

Met Gly Arg Gly Arg Val Gln Leu Lys Arg Ile Glu Asn Lys Ile Asn
 1               5                  10                  15

Arg Gln Val Thr Phe Ser Lys Arg Arg Ser Gly Leu Leu Lys Lys Ala
             20                  25                  30

His Glu Ile Ser Val Leu Cys Asp Ala Glu Val Ala Leu Ile Val Phe
         35                  40                  45

Ser Ser Lys Gly Lys Leu Phe Glu Tyr Ser Thr Asp Ser Cys Met Glu
     50                  55                  60

Arg Ile Leu Glu Arg Tyr Asp Arg Tyr Leu Tyr Ser Asp Lys Gln Leu
 65                  70                  75                  80

Val Gly Arg Asp Val Ser Gln Ser Glu Asn Trp Val Leu Glu His Ala
                 85                  90                  95

Lys Leu Lys Ala Arg Val Glu Val Leu Glu Lys Asn Lys Arg Asn Phe
            100                 105                 110

Met Gly Glu Asp Leu Asp Ser Leu Ser Leu Lys Glu Leu Gln Ser Leu
        115                 120                 125

Glu His Gln Leu Asp Ala Ala Ile Lys Ser Ile Arg Ser Arg Lys Asn
130                 135                 140

Gln Ala Met Phe Glu Ser Ile Ser Ala Leu Gln Lys Lys Asp Lys Ala
145                 150                 155                 160

Leu Gln Asp His Asn Asn Ser Leu Leu Lys Lys Ile Lys Glu Arg Glu
```

```
                165                 170                  175
Lys Lys Thr Gly Gln Gln Glu Gly Gln Leu Val Gln Cys Ser Asn Ser
            180                 185                 190

Ser Ser Val Leu Leu Pro Gln Tyr Cys Val Thr Ser Ser Arg Asp Gly
        195                 200                 205

Phe Val Glu Arg Val Gly Gly Glu Asn Gly Gly Ala Ser Ser Leu Thr
        210                 215                 220

Glu Pro Asn Ser Leu Leu Pro Ala Trp Met Leu Arg Pro Thr Thr Thr
225                 230                 235                 240

Asn Glu
```

The invention claimed is:

1. A method for producing a *Beta vulgaris* plant, where the bolting and flowering is inhibited after vernalization, comprising
either the following steps (I), (II) and (III):
(I) mutagenizing one or more parts of a *Beta vulgaris* plant and subsequently regenerating one or more *Beta vulgaris* plants from the one or more parts to yield a regenerated plant, or mutagenizing one or more *Beta vulgaris* plants to yield a mutagenized plant;
(II) identifying a regenerated or mutagenized plant of (I) that exhibits one or more mutations in a first endogenous DNA sequence and exhibits one or more mutations in a second endogenous DNA sequence; and
(III) generating a *Beta vulgaris* plant in which the one or more mutations in the first endogenous DNA sequence and the one or more mutations in the second endogenous DNA sequence are homozygous,
or the following steps (IV), (V), (VI) and (VII):
(IV) mutagenizing one or more parts of a *Beta vulgaris* plant and subsequently regenerating one or more *Beta vulgaris* plants from the one or more parts to yield a regenerated plant, or mutagenizing one or more *Beta vulgaris* plants to yield a mutagenized plant;
(V) identifying a first regenerated or mutagenized plant of (III) that exhibits one or more mutations in a first endogenous DNA sequence and a second regenerated or mutagenized plant of (III) that exhibits one or more mutations in a second endogenous DNA sequence;
(VI) crossing the first regenerated or mutagenized plant with the second regenerated or mutagenized plant and selecting a progeny comprising the one or more mutations in the first endogenous DNA sequence and/or in a regulatory sequence thereof and the one or more mutations in the second endogenous DNA sequence; and
(VII) generating from the progeny of (VI) a *Beta vulgaris* plant in which the one or more mutations in the first endogenous DNA sequence and the one or more mutations in the second endogenous DNA sequence are homozygous;
wherein the first endogenous DNA sequence has a nucleic acid sequence identical to a sequence that
a) exhibits a sequence comprising nucleotides 1-185, 6923-7001, 7589-7653, 8561-8659, 11792-11834, 21139-21181, 21286-21453, and 21569-21668 of SEQ ID NO: 1 or comprising the coding sequence of SEQ ID NO: 2,
b) comprises a nucleotide sequence exhibiting at least 98% identity to nucleotides 1-185, 6923-7001, 7589-7653, 8561-8659, 11792-11834, 21139-21181, 21286-21453, and 21569-21668 of SEQ ID NO: 1 or comprises a nucleotide sequence exhibiting at least 98% identity to the coding sequence of SEQ ID NO: 2,
c) is complementary to any one of the sequences recited in (a) and (b) above
d) encodes a protein comprising an amino acid sequence exhibiting at least 98% sequence identity to SEQ ID NO: 5;
wherein the second endogenous DNA sequence has a nucleic acid sequence identical to a sequence that
A) exhibits a sequence comprising SEQ ID NO: 3 or comprising the coding sequence of SEQ ID NO: 4,
B) comprises a nucleotide sequence exhibiting at least 98% identity to nucleotides 1-185, 19324-19462, 19501-19565, 19643-19742, 28158-28199, 28279-28320, 28420-28532, and 29128-29237 of SEQ ID NO: 3 or comprises a nucleotide sequence exhibiting at least 98% identity to the coding sequence of SEQ ID NO: 4,
C) is complementary to any one of the sequences recited in (A) and (B) above, or
D) encodes a protein comprising an amino acid sequence exhibiting at least 98% sequence identity to SEQ ID NO: 6.

2. A *Beta vulgaris* plant, produced by the method of claim 1, or a part thereof,
wherein the part is selected from the group consisting of a stem, a root, and a seed, and
wherein the bolting and flowering of the plant is inhibited after vernalization.

3. A *Beta vulgaris* plant, where the bolting and flowering is inhibited after vernalization, wherein the plant comprises one or more mutations in a first endogenous DNA sequence and comprises one or more mutations in a second endogenous DNA sequence,
wherein the first endogenous DNA sequence comprises a nucleic acid sequence identical to a sequence that
a) comprises a sequence comprising nucleotides 1-185, 6923-7001, 7589-7653, 8561-8659, 11792-11834, 21139-21181, 21286-21453, and 21569-21668 of SEQ ID NO: 1 or comprising the coding sequence of SEQ ID NO: 2, b) comprises a nucleotide sequence exhibiting at least 98% identity to nucleotides 1-185, 6923-7001, 7589-7653, 8561-8659, 11792-11834, 21139-21181, 21286-21453, and 21569-21668 of SEQ ID NO: 1 or comprises a nucleotide sequence exhibiting at least 98% identity to the coding sequence of SEQ ID NO: 2, c) is complementary to any one of the sequences recited in (a) and (b) above d) encodes a protein comprising an amino acid sequence exhibiting at least 98% sequence identity to SEQ ID NO: 5;

wherein the second endogenous DNA sequence comprises a nucleic acid sequence identical to a sequence that A) comprises a sequence comprising SEQ ID NO: 3 or comprising the coding sequence of SEQ ID NO: 4, B) comprises a nucleotide sequence exhibiting at least 98% identity to nucleotides 1-185, 19324-19462, 19501-19565, 19643-19742, 28158-28199, 28279-28320, 28420-28532, and 29128-29237 of SEQ ID NO: 3 or comprises a nucleotide sequence exhibiting at least 98% identity to the coding sequence of SEQ ID NO: 4, C) is complementary to any one of the sequences recited in (A) and (B) above, or D) encodes a protein comprising an amino acid sequence exhibiting at least 98% sequence identity to SEQ ID NO: 6;

wherein the one or more mutations cause a reduction of the activity or stability of the protein or polypeptide encoded by the endogenous DNA sequence compared to a non-mutagenized wildtype plant.

* * * * *